US012534731B2

(12) United States Patent
Bostwick et al.

(10) Patent No.: US 12,534,731 B2
(45) Date of Patent: Jan. 27, 2026

(54) ALPHA-2A ADRENERGIC RECEPTOR (ADRA2A) IRNA AGENT COMPOSITIONS AND METHODS OF USE THEREOF

(71) Applicant: ALNYLAM PHARMACEUTICALS, INC., Cambridge, MA (US)

(72) Inventors: Bret L. Bostwick, Cambridge, MA (US); James D. Mcininch, Burlington, MA (US); Adam Castoreno, Framingham, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 659 days.

(21) Appl. No.: 17/907,741

(22) PCT Filed: Apr. 1, 2021

(86) PCT No.: PCT/US2021/025420
§ 371 (c)(1),
(2) Date: Sep. 29, 2022

(87) PCT Pub. No.: WO2021/202902
PCT Pub. Date: Oct. 7, 2021

(65) Prior Publication Data

US 2023/0138507 A1 May 4, 2023

Related U.S. Application Data

(60) Provisional application No. 63/003,702, filed on Apr. 1, 2020.

(51) Int. Cl.
*C12N 15/113* (2010.01)
*A61K 47/54* (2017.01)

(52) U.S. Cl.
CPC ........ *C12N 15/1138* (2013.01); *A61K 47/549* (2017.08); *C12N 2310/14* (2013.01); *C12N 2310/314* (2013.01); *C12N 2310/315* (2013.01); *C12N 2310/3183* (2013.01); *C12N 2310/321* (2013.01); *C12N 2310/322* (2013.01); *C12N 2310/3515* (2013.01); *C12N 2320/30* (2013.01)

(58) Field of Classification Search
CPC ............ C12N 15/1138; C12N 2310/14; C12N 2310/314; C12N 2310/315; C12N 2310/321; C12N 2310/322; C12N 2310/3515; C12N 2320/30; A61K 47/549
See application file for complete search history.

(56) References Cited

U.S. PATENT DOCUMENTS

| | | | |
|---|---|---|---|
| 3,228,831 | A | 1/1966 | Nicholson et al. |
| 3,687,808 | A | 8/1972 | Merigan, Jr. et al. |
| 3,904,682 | A | 9/1975 | Fried et al. |
| 4,009,197 | A | 2/1977 | Fried et al. |
| 4,469,863 | A | 9/1984 | Ts'O et al. |
| 4,476,301 | A | 10/1984 | Imbach et al. |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,683,202 | A | 7/1987 | Mullis |
| 4,762,779 | A | 8/1988 | Snitman |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,837,028 | A | 6/1989 | Allen |
| 4,845,205 | A | 7/1989 | Huynh Dinh et al. |
| 4,876,335 | A | 10/1989 | Yamane et al. |
| 4,897,355 | A | 1/1990 | Eppstein et al. |
| 4,904,582 | A | 2/1990 | Tullis |
| 4,948,882 | A | 8/1990 | Ruth |
| 4,958,013 | A | 9/1990 | Letsinger |
| 4,981,957 | A | 1/1991 | Lebleu et al. |
| 5,023,243 | A | 6/1991 | Tullis |
| 5,034,506 | A | 7/1991 | Summerton et al. |
| 5,082,830 | A | 1/1992 | Brakel et al. |
| 5,109,124 | A | 4/1992 | Ramachandran et al. |
| 5,112,963 | A | 5/1992 | Pieles et al. |
| 5,118,800 | A | 6/1992 | Smith et al. |
| 5,118,802 | A | 6/1992 | Smith et al. |
| 5,130,302 | A | 7/1992 | Spielvogel et al. |
| 5,134,066 | A | 7/1992 | Rogers et al. |
| 5,138,045 | A | 8/1992 | Cook et al. |
| 5,166,315 | A | 11/1992 | Summerton et al. |
| 5,171,678 | A | 12/1992 | Behr et al. |

(Continued)

FOREIGN PATENT DOCUMENTS

| | | |
|---|---|---|
| WO | WO 1988/04924 | 7/1988 |
| WO | WO 1991/16024 | 10/1991 |

(Continued)

OTHER PUBLICATIONS

Aigner, "Delivery Systems for the Direct Application of siRNAs to Induce RNA Interference (RNAi) In Vivo," J. Biomed. Biotechnol., 2006, 2006:71659, 15 pp.
Akaneya et al., "RNAi-Induced Gene Silencing by Local Electroporation in Targeting Brain Region," J. Neurophysiol., 2005, 93:594-602.
Akhtar & Juliano, "Cellular uptake and intracellular fate of antisense oligonucleotides," Trends Cell. Biol., 1992, 2(5):139-144.
Allen & Chonn, "Large unilamellar liposomes with low uptake into the reticuloendothelial system," FEBS Letters, 1987, 223(1):42-46.

(Continued)

*Primary Examiner* — Terra C Gibbs
(74) *Attorney, Agent, or Firm* — Womble Bond Dickinson (US) LLP

(57) ABSTRACT

The disclosure relates to double stranded ribonucleic acid (dsRNAi) agents and compositions targeting an alpha-2A adrenergic receptor (ADRA2A) gene, as well as methods of inhibiting expression of an ADRA2A gene and methods of treating subjects having an ADRA2A-associated disease or disorder, e.g., a primary tauopathy or Alzheimer's disease, using such dsRNAi agents and compositions.

20 Claims, No Drawings

Specification includes a Sequence Listing.

(56) References Cited

U.S. PATENT DOCUMENTS

| | | | |
|---|---|---|---|
| 5,175,273 | A | 12/1992 | Bischofberger et al. |
| 5,177,195 | A | 1/1993 | Gregory et al. |
| 5,185,444 | A | 2/1993 | Summerton et al. |
| 5,188,897 | A | 2/1993 | Suhadolnik et al. |
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,235,033 | A | 8/1993 | Summerton et al. |
| 5,245,022 | A | 9/1993 | Weis et al. |
| 5,254,469 | A | 10/1993 | Warren, III et al. |
| 5,258,506 | A | 11/1993 | Urdea et al. |
| 5,262,536 | A | 11/1993 | Hobbs, Jr. |
| 5,264,423 | A | 11/1993 | Cohen et al. |
| 5,264,562 | A | 11/1993 | Matteucci |
| 5,264,564 | A | 11/1993 | Matteucci |
| 5,272,250 | A | 12/1993 | Spielvogel et al. |
| 5,276,019 | A | 1/1994 | Cohen et al. |
| 5,278,302 | A | 1/1994 | Caruthers et al. |
| 5,283,185 | A | 2/1994 | Epand et al. |
| 5,286,717 | A | 2/1994 | Cohen et al. |
| 5,292,873 | A | 3/1994 | Rokita et al. |
| 5,317,098 | A | 5/1994 | Shizuya et al. |
| 5,319,080 | A | 6/1994 | Leumann |
| 5,321,131 | A | 6/1994 | Agrawal et al. |
| 5,359,044 | A | 10/1994 | Cook et al. |
| 5,367,066 | A | 11/1994 | Urdea et al. |
| 5,371,241 | A | 12/1994 | Brush |
| 5,391,723 | A | 2/1995 | Priest |
| 5,393,878 | A | 2/1995 | Leumann |
| 5,399,676 | A | 3/1995 | Froehler |
| 5,405,938 | A | 4/1995 | Summerton et al. |
| 5,405,939 | A | 4/1995 | Suhadolnik et al. |
| 5,414,077 | A | 5/1995 | Lin et al. |
| 5,416,203 | A | 5/1995 | Letsinger |
| 5,432,272 | A | 7/1995 | Benner |
| 5,434,257 | A | 7/1995 | Matteucci et al. |
| 5,445,934 | A | 8/1995 | Fodor et al. |
| 5,446,137 | A | 8/1995 | Maag et al. |
| 5,451,463 | A | 9/1995 | Nelson et al. |
| 5,453,496 | A | 9/1995 | Caruthers et al. |
| 5,455,233 | A | 10/1995 | Spielvogel et al. |
| 5,457,187 | A | 10/1995 | Gmeiner et al. |
| 5,459,255 | A | 10/1995 | Cook et al. |
| 5,466,677 | A | 11/1995 | Baxter et al. |
| 5,466,786 | A | 11/1995 | Buhr et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,486,603 | A | 1/1996 | Buhr |
| 5,489,677 | A | 2/1996 | Sanghvi et al. |
| 5,502,177 | A | 3/1996 | Matteucci et al. |
| 5,510,475 | A | 4/1996 | Agrawal et al. |
| 5,512,439 | A | 4/1996 | Hornes et al. |
| 5,512,667 | A | 4/1996 | Reed et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,465 | A | 6/1996 | Haralambidis et al. |
| 5,525,711 | A | 6/1996 | Hawkins et al. |
| 5,536,821 | A | 7/1996 | Agrawal et al. |
| 5,539,082 | A | 7/1996 | Nielsen et al. |
| 5,541,307 | A | 7/1996 | Cook et al. |
| 5,541,313 | A | 7/1996 | Ruth |
| 5,541,316 | A | 7/1996 | Engelskirchen et al. |
| 5,543,152 | A | 8/1996 | Webb et al. |
| 5,545,730 | A | 8/1996 | Urdea et al. |
| 5,550,111 | A | 8/1996 | Suhadolnik et al. |
| 5,552,538 | A | 9/1996 | Urdea et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,552 | A | 10/1996 | Magda et al. |
| 5,567,810 | A | 10/1996 | Weis et al. |
| 5,567,811 | A | 10/1996 | Misiura et al. |
| 5,571,799 | A | 11/1996 | Tkachuk et al. |
| 5,574,142 | A | 11/1996 | Meyer, Jr. et al. |
| 5,576,427 | A | 11/1996 | Cook et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,361 | A | 12/1996 | Cook et al. |
| 5,587,371 | A | 12/1996 | Sessler et al. |
| 5,587,469 | A | 12/1996 | Cook et al. |
| 5,591,584 | A | 1/1997 | Chang et al. |
| 5,591,722 | A | 1/1997 | Montgomery et al. |
| 5,594,121 | A | 1/1997 | Froehler et al. |
| 5,595,726 | A | 1/1997 | Magda et al. |
| 5,596,086 | A | 1/1997 | Matteucci et al. |
| 5,596,091 | A | 1/1997 | Switzer |
| 5,597,696 | A | 1/1997 | Linn et al. |
| 5,597,909 | A | 1/1997 | Urdea et al. |
| 5,599,923 | A | 2/1997 | Sessler et al. |
| 5,599,928 | A | 2/1997 | Hemmi et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bischofberger et al. |
| 5,639,873 | A | 6/1997 | Barascut et al. |
| 5,646,265 | A | 7/1997 | Mcgee |
| 5,658,873 | A | 8/1997 | Bertsch-Frank et al. |
| 5,663,312 | A | 9/1997 | Chaturvedula |
| 5,670,633 | A | 9/1997 | Cook et al. |
| 5,677,195 | A | 10/1997 | Winkler et al. |
| 5,677,437 | A | 10/1997 | Teng et al. |
| 5,677,439 | A | 10/1997 | Weis et al. |
| 5,681,941 | A | 10/1997 | Cook et al. |
| 5,688,941 | A | 11/1997 | Cook et al. |
| 5,700,920 | A | 12/1997 | Altmann et al. |
| 5,705,188 | A | 1/1998 | Junichi et al. |
| 5,714,331 | A | 2/1998 | Buchardt et al. |
| 5,719,262 | A | 2/1998 | Buchardt et al. |
| 5,744,305 | A | 4/1998 | Fodor et al. |
| 5,750,692 | A | 5/1998 | Cook et al. |
| 5,770,722 | A | 6/1998 | Lockhart et al. |
| 5,854,033 | A | 12/1998 | Lizardi |
| 5,874,219 | A | 2/1999 | Rava et al. |
| 5,976,567 | A | 11/1999 | Wheeler et al. |
| 5,981,501 | A | 11/1999 | Wheeler et al. |
| 6,015,886 | A | 1/2000 | Dale et al. |
| 6,028,188 | A | 2/2000 | Arnold, Jr. et al. |
| 6,054,299 | A | 4/2000 | Conrad |
| 6,124,445 | A | 9/2000 | Imbach et al. |
| 6,147,200 | A | 11/2000 | Manoharan et al. |
| 6,160,109 | A | 12/2000 | Just et al. |
| 6,166,197 | A | 12/2000 | Cook et al. |
| 6,169,170 | B1 | 1/2001 | Gryaznov et al. |
| 6,172,209 | B1 | 1/2001 | Manoharan et al. |
| 6,191,105 | B1 | 2/2001 | Ekwuribe et al. |
| 6,222,025 | B1 | 4/2001 | Cook et al. |
| 6,235,887 | B1 | 5/2001 | Froehler et al. |
| 6,239,265 | B1 | 5/2001 | Cook |
| 6,268,490 | B1 | 7/2001 | Imanishi et al. |
| 6,277,603 | B1 | 8/2001 | Cook |
| 6,294,664 | B1 | 9/2001 | Ravikumar et al. |
| 6,320,017 | B1 | 11/2001 | Ansell |
| 6,326,199 | B1 | 12/2001 | Cook et al. |
| 6,346,614 | B1 | 2/2002 | Metelev et al. |
| 6,380,368 | B1 | 4/2002 | Froehler et al. |
| 6,444,423 | B1 | 9/2002 | Meade et al. |
| 6,525,191 | B1 | 2/2003 | Ramasamy |
| 6,528,640 | B1 | 3/2003 | Beigelman et al. |
| 6,531,590 | B1 | 3/2003 | Manoharan et al. |
| 6,534,484 | B1 | 3/2003 | Wheeler et al. |
| 6,534,639 | B1 | 3/2003 | Manoharan et al. |
| 6,576,752 | B1 | 6/2003 | Manoharan et al. |
| 6,586,410 | B1 | 7/2003 | Wheeler et al. |

(56) References Cited

U.S. PATENT DOCUMENTS

| | | | |
|---|---|---|---|
| 6,608,035 | B1 | 8/2003 | Agrawal et al. |
| 6,617,438 | B1 | 9/2003 | Beigelman et al. |
| 6,639,062 | B2 | 10/2003 | Manoharan et al. |
| 6,670,461 | B1 | 12/2003 | Wengel et al. |
| 6,683,167 | B2 | 1/2004 | Metelev et al. |
| 6,747,014 | B2 | 6/2004 | Teng et al. |
| 6,770,748 | B2 | 8/2004 | Imanishi et al. |
| 6,783,931 | B1 | 8/2004 | Cook et al. |
| 6,794,499 | B2 | 9/2004 | Wengel et al. |
| 6,815,432 | B2 | 11/2004 | Wheeler et al. |
| 6,858,225 | B2 | 2/2005 | Semple et al. |
| 6,858,715 | B2 | 2/2005 | Ravikumar et al. |
| 6,867,294 | B1 | 3/2005 | Sanghvi et al. |
| 6,878,805 | B2 | 4/2005 | Manoharan et al. |
| 6,887,906 | B1 | 5/2005 | Teng et al. |
| 6,900,297 | B1 | 5/2005 | Cook et al. |
| 6,998,484 | B2 | 2/2006 | Koch et al. |
| 7,015,315 | B1 | 3/2006 | Cook et al. |
| 7,034,133 | B2 | 4/2006 | Wengel et al. |
| 7,037,646 | B1 | 5/2006 | Cook et al. |
| 7,041,816 | B2 | 5/2006 | Ravikumar et al. |
| 7,045,610 | B2 | 5/2006 | Dempcy et al. |
| 7,053,207 | B2 | 5/2006 | Wengel |
| 7,063,860 | B2 | 6/2006 | Chancellor et al. |
| 7,070,802 | B1 | 7/2006 | Bhalani et al. |
| 7,084,125 | B2 | 8/2006 | Wengel |
| RE39,464 | E | 1/2007 | Cook et al. |
| 7,157,099 | B2 | 1/2007 | Autuori et al. |
| 7,273,933 | B1 | 9/2007 | Krotz et al. |
| 7,321,029 | B2 | 1/2008 | Gryaznov et al. |
| 7,399,845 | B2 | 7/2008 | Seth et al. |
| 7,427,605 | B2 | 9/2008 | Davis et al. |
| 7,427,672 | B2 | 9/2008 | Imanishi et al. |
| 7,495,088 | B1 | 2/2009 | Brakel et al. |
| 7,569,686 | B1 | 8/2009 | Bhat et al. |
| 7,626,014 | B2 | 12/2009 | Manoharan et al. |
| 7,741,457 | B2 | 6/2010 | Seth et al. |
| 7,858,769 | B2 | 12/2010 | Jadhav et al. |
| 8,022,193 | B2 | 9/2011 | Seth et al. |
| 8,030,467 | B2 | 10/2011 | Seth et al. |
| 8,058,069 | B2 | 11/2011 | Yaworski et al. |
| 8,101,348 | B2 | 1/2012 | Tuschl et al. |
| 8,106,022 | B2 | 1/2012 | Manoharan et al. |
| 8,158,601 | B2 | 4/2012 | Chen et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,314,227 | B2 | 11/2012 | Wengel |
| 2003/0027780 | A1 | 2/2003 | Hardee et al. |
| 2004/0171570 | A1 | 9/2004 | Allerson et al. |
| 2005/0244858 | A1 | 11/2005 | Rossi et al. |
| 2008/0039618 | A1 | 2/2008 | Allerson et al. |
| 2009/0012281 | A1 | 1/2009 | Swayze et al. |
| 2010/0173973 | A1 | 7/2010 | Brown |
| 2010/0324120 | A1 | 12/2010 | Chen et al. |
| 2011/0313020 | A1 | 12/2011 | Templin et al. |
| 2012/0157511 | A1 | 6/2012 | Manoharan et al. |
| 2013/0011922 | A1 | 1/2013 | Quay et al. |
| 2013/0096289 | A1 | 4/2013 | Wengel |
| 2013/0190383 | A1 | 7/2013 | Vaish et al. |
| 2013/0237557 | A1 | 9/2013 | Mookerjee et al. |
| 2015/0292023 | A1 | 10/2015 | Fishel et al. |
| 2016/0282365 | A1 | 9/2016 | Gaitanaris et al. |

FOREIGN PATENT DOCUMENTS

| | | |
|---|---|---|
| WO | WO 1993/24640 | 12/1993 |
| WO | WO 1994/00569 | 1/1994 |
| WO | WO 1994/02595 | 2/1994 |
| WO | WO 1996/37194 | 11/1996 |
| WO | WO 1996/40964 | 12/1996 |
| WO | WO 1997/13499 | 4/1997 |
| WO | WO 1997/30731 | 8/1997 |
| WO | WO 1998/39359 | 9/1998 |
| WO | WO 1999/14226 | 3/1999 |
| WO | WO 2000/03683 | 1/2000 |
| WO | WO 2000/22114 | 4/2000 |
| WO | WO 2005/095984 | 10/2005 |
| WO | WO 2007/091269 | 8/2007 |
| WO | WO 2007/117686 | 10/2007 |
| WO | WO 2008/042973 | 4/2008 |
| WO | WO 2009/014887 | 1/2009 |
| WO | WO 2009/088891 | 7/2009 |
| WO | WO 2009/088892 | 7/2009 |
| WO | WO 2009/127060 | 10/2009 |
| WO | WO 2009/132131 | 10/2009 |
| WO | WO 2010/011895 | 1/2010 |
| WO | WO 2010/054406 | 5/2010 |
| WO | WO 2010/088537 | 8/2010 |
| WO | WO 2010/129709 | 11/2010 |
| WO | WO 2010/141511 | 12/2010 |
| WO | WO 2011/005861 | 1/2011 |
| WO | WO 2011/031520 | 3/2011 |
| WO | WO 2011/133876 | 10/2011 |
| WO | WO 2012/177906 | 12/2012 |
| WO | WO 2013/036868 | 3/2013 |
| WO | WO 2013/075035 | 5/2013 |
| WO | WO 2014/179620 | 11/2014 |
| WO | WO 2014/179627 | 11/2014 |
| WO | WO 2015/116658 | 8/2015 |
| WO | WO 2019/055633 | 3/2019 |
| WO | WO 2019/186160 | 10/2019 |
| WO | WO 2019/217459 | 11/2019 |
| WO | WO 2000/22113 | 4/2022 |

OTHER PUBLICATIONS

Aoki et al., "Potential tumor-targeting peptide vector of histidylated oligolysine conjugated to a tumor-homing RGD motif," Cancer Gene Therapy, 2001, 8(10):783-787.

Arnold et al., "Specific beta1-adrenergic receptor silencing with small interfering RNA lowers high blood pressure and improves cardiac function in myocardial ischemia," J. Hypertens., 2007, 25(1):197-205.

Bangham et al., "Diffusion of Univalent Ions Across the Lamellae of Swollen Phospholipids," J. Mol. Biol., 1965, 13:238-252.

Bernstein et al., "Role for a bidentate ribonuclease in the initiation step of RNA interference," Nature, 2001, 409:363-366.

Bitko et al., "Inhibition of respiratory viruses by nasally administered siRNA," Nat. Med., 2005, 11:50-55; published online Dec. 26, 2004.

Bonnet et al., "Systemic Delivery of DNA or siRNA Mediated by Linear Polyethylenimine (L-PEI) Does Not Induce an Inflammatory Response," Pharm. Res., 2008, 25(12):2972-2982; Epub Aug. 16, 2008.

Buur et al., "Penetration of 5-Fluorouracil and Prodrugs Across the Intestine of the Albino Rabbit: Evidence for Shift in Absorption Site from the Upper to the Lower Region of the Gastrointestinal Tract by Prodrugs," J. Control Rel., 1990, 14:43-51.

Chien et al., "Novel cationic cardiolipin analogue-based liposome for efficient DNA and small interfering RNA delivery in vitro and in vivo," Cancer Gene Ther., 2005, 12:321-328.

Choi et al., "A three-dimensional human neural cell culture model of Alzheimer's disease," Nature, 2014, 515(7526):274-278.

Chu & Rana, "Potent RNAi by short RNA triggers," RNA, 2008, 14:1714-1719.

Constantinides et al., "Formulation and Intestinal Absorption Enhancement Evaluation of Water-in-Oil Microemulsions Incorporating Medium-Chain Glycerides," Pharmaceutical Research, 1994, 11(10):1385-1390.

Couture & Stinchcomb, "Anti-gene therapy: the use of ribozymes to inhibit gene function," Trends in Genetics, 1996, 12(12):510-515.

Crooke et al., "Pharmacokinetic Properties of Several Novel Oligonucleotide Analogs in mice," J. Pharmacol. Exp. Ther., 1996, 277:923-937.

Dorn et al., "siRNA relieves chronic neuropathic pain," Nucleic Acids, 2004, 32:e49, 6 pp.

Du Plessis et al., "Topical delivery of liposomally encapsulated gamma-interferon," Antiviral Research, 1992, 18:259-265.

(56) References Cited

OTHER PUBLICATIONS

Elbashir et al., "Functional anatomy of siRNAs for mediating efficient RNAi in *Drosophila melanogaster* embryo lysate," EMBO J., 2001, 20(23):6877-6888.
Elbashir et al., "RNA interference is mediated by 21-and 22-nucleotide RNAs," Genes Dev., 2001, 15:188-200.
El-Hariri et al., "The Mitigating Effects of Phosphatidylcholines on Bile Salt- and Lysophosphatidylcholine-induced Membrane Damage," J. Pharm. Pharmacol., 1992, 44:651-654.
Elmén et al., "Locked nucleic acid (LNA) mediated improvements in siRNA stability and functionality," Nucleic Acids Research, 2005, 33(1):439-447.
Esquerda-Canals et al., "Mouse Models of Alzheimer's Disease," J, Alzheimer's Dis., 2017, 57:1171-1183.
Felgner et al., "Lipofection: A highly efficient, lipid-mediated DNA-transfection procedure," Proc. Natl. Acad. Sci. USA, 1987, 84:7413-7417.
Felgner et al., "Enhanced Gene Delivery and Mechanism Studies with a Novel Series of Cationic Lipid Formulations," J. Biol. Chem., 1994, 269(4):2550-2561.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., 2009, 5:838-843.
Fukunaga et al., "Liposome Entrapment Enhances the Hypocalcemic Action of Parenterally Administered Calcitonin," Endocrinol., 1984, 115(2):757-761.
Gabizon & Papahadjopoulos, "Liposome formulations with prolonged circulation time in blood and enhanced uptake by tumors," Proc. Natl. Acad. Sci. USA, 1988, 85:6949-6953.
Gao et al, "A Novel Cationic Liposome Reagent for Efficient Transfection of Mammalian Cells," Biochim. Biophys. Res. Commun., 1991, 179(1):280-285.
Gassmann et al., "Maintenance of an extrachromosomal plasmid vector in mouse embryonic stem cells," Proc. Natl. Acad. Sci. USA, 1995, 92:1292-1296.
Genome Reference Consortium Human Build 38, "Genome assembly GRCh38," Dec. 17, 2013.
Gershon et al., "Mode of Formation and Structural Features of DNA-Cationic Liposome Complexes Used for Transfection," Biochem., 1993, 32:7143-7151.
Grünweller et al., "Comparison of different antisense strategies in mammalian cells using locked nucleic acids, 2'-O-methyl RNA, phosphorothioates and small interfering RNA," Nucleic Acids Research, 2003, 31(12):3185-3193.
Guatelli et al., "Isothermal, in vitro amplification of nucleic acids by a multienzyme reaction modeled after retroviral replication," Proc. Natl. Acad. Sci. USA, 1990, 87:1874-1878.
Haubner et al., "Glycosylated RGD-Containing Peptides: Tracer for Tumor Targeting and Angiogenesis Imaging with Improved Biokinetics," J Nucl Med, 2001, 42:326-336.
Ho et al., "Preparation of Microemulsions Using Polyglycerol Fatty Acid Esters as Surfactant for the Delivery of Protein Drugs," J. Pharm. Sci., 1996, 85(2):138-143.
Howard et al., "RNA Interference in Vitro and in Vivo Using a Chitosan/siRNA Nanoparticle System," Mol. Ther., 2006, 14(4):476-484.
Hu et al., "Topical delivery of cyclosporin A from non-ionic liposomal systems : an in vivo/in vitro correlation study using hairless mouse skin," S.T.P. Pharma. Sci., 1994, 4(6):466-469.
Itani et al., "A simple and efficient liposome method for transfection of DNA into mammalian cells grown in suspension," Gene, 1987, 56:267-276.
Jarrett, "Affinity chromatography with nucleic acid polymers," Chromatogr., 1993, 618:315-339.
Jensen et al., "Unlocked nucleic acid (UNA) and UNA derivatives: Thermal denaturation studies," Nuc. Acids Symp. Series, 2008, 52(1):133-134.
Kabanov et al., "A new class of antivirals: antisense oligonucleotides combined with a hydrophobic substituent effectively inhibit influenza virus reproduction and synthesis of virus-specific proteins in MDCK cells," FEBS Lett., 1990, 259(2):327-330.
Kim et al., "Preparation of Multivesicular Liposomes," Biochim. Biophys. Acta, 1983, 728:339-348.
Kim et al., "Synthetic dsRNA Dicer substrates enhance RNAi potency and efficacy," Nat Biotech, 2005, 23(2):222-226.
Kim et al., "Cholesteryl Oligoarginine Delivering Vascular Endothelial Growth Factor siRNA Effectively Inhibits Tumor Growth in Colon Adenocarcinoma," Mol. Ther., 2006, 14(3):343-350.
Kim et al., "Local and systemic delivery of VEGF siRNA using polyelectrolyte complex micelles for effective treatment of cancer," Journal of Controlled Release, 2008, 129:107-116.
Kubo et al., "Chemically modified symmetric and asymmetric duplex RNAs: an enhanced stability to nuclease degradation and gene silencing effect," Biochem. Biophys. Res. Comm., 2008, 365:54-61; available online Oct. 29, 2007.
Kwoh et al., "Transcription-based amplification system and detection of amplified human immunodeficiency virus type 1 with a bead-based sandwich hybridization format," Proc. Natl. Acad. Sci. USA, 1989, 86:1173-1177.
Lam et al., "A new type of synthetic peptide library for identifying ligand-binding activity," Nature, 1991, 354:82-84.
Lee et al., "Mucosal Penetration Enhancers For Facilitation of Peptide and Protein Drug Absorption," Critical Reviews in Therapeutic Drug Carrier Systems, 1991, 8(2):91-192.
Letsinger et al., "Cholesteryl-conjugated oligonucleotides: Synthesis, properties, and activity as inhibitors of replication of human immunodeficiency virus in cell culture," Proc. Natl. Acid. Sci. USA, 1989, 86:6553-6556.
Li et al., "Polyethylenimine-complexed Plasmid Particles Targeting Focal Adhesion Kinase Function as Melanoma Tumor Therapeutics," Mol. Ther., 2007, 15(3):515-523.
Lima et al., "Single-Stranded siRNAs Activate RNAi in Animals," Cell, 2012, 150:883-894.
Liu, "Radiolabeled Multimeric Cyclic RGD Peptides as Integrin $\alpha v\beta 3$ Targeted Radiotracers for Tumor Imaging," Mol. Pharm., 2006, 3(5):472-487.
Lizardi et al., "Exponential Amplification of Recombinant-RNA Hybridization Probes," Bio/Technology, 1988, 6:1197-1202.
Makimura et al., "Reducing hypothalamic AGRP by RNA interference increases metabolic rate and decreases body weight without influencing food intake," BMC Neurosci., 2002, 3:18, 6 pp.
Mannino & Gould-Fogerite, "Liposome Mediated Gene Transfer," Biotechniques, 1988, 6(7):682-690.
Manoharan et al., "Chemical Modifications to Improve Uptake and Bioavailability of Antisense Oligonucleotides," Ann. N. Y. Acad. Sci., 1992, 660:306-309.
Manoharan et al., "Introduction of a Lipophilic Thioether Tether in the Minor Groove of Nucleic Acids for Antisense Applications," Biorg. Med. Chem. Let., 1993, 3(12):2765-2770.
Manoharan et al., "Cholic Acid-Oligonucleotide Conjugates for Antisense Applications," Biorg. Med. Chem. Let., 1994, 4(8):1053-1060.
Manoharan et al., "Lipidic Nucleic Acids," Tetrahedron Lett., 1995, 36(21):3651-3654.
Manoharan et al., "Oligonucleotide Conjugates: Alteration of the Pharmacokinetic Properties of Antisense Agents," Nucleosides & Nucleotides, 1995, 14(3-5):969-973.
Martin et al., "A New Access to 2'-O-alkylated Ribonucleosides and Properties of 2'-O-Alkylated Oligoribonucleotides," Helv. Chim. Acta, 1995, 78:486-504 (including machine translation).
Matsumoto et al., "Tau Fibril Formation in Cultured Cells Compatible with a Mouse Model of Tauopathy," Int. J. Mol. Sci., 2018, 19:e1497, 14 pp.
Mayer et al., "Vesicles of variable sizes produced by a rapid extrusion procedure," Biochim. Biophys. Acta, 1986, 858:161-168.
Mayhew et al., "Characterization of Liposomes Prepared by Using a Microemulsifier," Biochim. Biophys. Acta, 1984, 775:169-174.
Mcnamara et al., "Cell type-specific delivery of siRNAs with aptamer-siRNA chimeras," Nat. Biotechnol., 2006, 24(8):1005-1015.

(56) References Cited

OTHER PUBLICATIONS

Mikhailov et al., "Synthesis of a New Class of Acyclic 2',5'- and 3',5'-Oligonucleotide Analogs Based on 9-[1,5-dihydroxy-4(S)-hydroxymethyl-3-oxapent-2(R)-yl]-adenine," Tetrahedron Letters, 1985, 26(17):2059-2062.
Mishra et al., "Improved leishmanicidal effect of phosphorotioate antisense oligonucleotides by LDL-mediated delivery," Biochim. Biophys. Acta, 1995, 1264:229-237.
Mook et al., "Evaluation of locked nucleic acid-modified small interfering RNA in vitro and in vivo," Mol Canc Ther, 2007, 6(3):833-843.
Muranishi, "Absorption Enhancers," Critical Reviews in Therapeutic Drug Carrier Systems, 1990, 7(1):1-33.
Nabel et al., "Direct gene transfer wit DNA-liposome complexes in melanoma: Expression, biologic activity, and lack of toxicity in humans," Proc. Natl. Acad. Sci. USA, 1993, 90:11307-11311.
Nabel et al., "Gene Transfer In Vivo with DNA-Liposome Complexes: Lack of Autoimmunity and Gonadal Localization," Human Gene Ther., 1992, 3:649-656.
NCBI Gene 150, "ADRA2A adrenoceptor alpha 2A [ *Homo sapiens* (human) ]," Jun. 21, 2023.
NCBI Reference Sequence: NC_000010.11, "*Homo sapiens* chromosome 10, GRCh38.p14 Primary Assembly," Mar. 20, 2023.
NCBI Reference Sequence: NG_012020.1, "*Homo sapiens* adrenoceptor alpha 2A (ADRA2A), RefSeqGene (LRG_545) on chromosome 10," Apr. 18, 2021.
NCBI Reference Sequence: NM_000681.4, "*Homo sapiens* adrenoceptor alpha 2A (ADRA2A), mRNA," Dec. 25, 2022.
NCBI Reference Sequence: NM_007417.5, "Mus musculus adrenergic receptor, alpha 2a (Adra2a), mRNA," Jun. 20, 2023.
NCBI Reference Sequence: NM_012739.3, "Rattus norvegicus adrenoceptor alpha 2A (Adra2a), mRNA," Aug. 14, 2023.
NCBI Reference Sequence: XM_015148184.2, "Predicted: Macaca mulatta adrenoceptor alpha 2A (ADRA2A), mRNA," Apr. 26, 2019.
Nicolau et al., "Liposomes as Carriers for in Vivo Gene Transfer and Expression," Meth. Enzymol., 1987, 149:157-176.
Nielsen et al., "Sequence-Selective Recognition of DNA by Strand Displacement with a Thymine-Substituted Polyamide," Science, 1991, 254(5037)1497-1500.
Nykänen et al., "ATP Requirements and Small Interfering RNA Structure in the RNA Interference Pathway," Cell, 2001, 107(3):309-321.
Oberhauser & Wagner, "Effective incorporation of 2'-O-methyl-oligoribonucleotides into liposomes and enhanced cell association through modification with thiocholesterol," Nucl. Acids Res., 1992, 20(3):533-538.
Olson et al., "Preparation of liposomes of defined size distribution by extrusion through polycarbonate membranes," Biochim. Biophys. Acta, 1979, 557(1):9-23.
Pal et al., "Systemic delivery of RafsiRNA using cationic cardiolipin liposomes silences Raf-1 expression and inhibits tumor growth in xenograft model of human prostate cancer," Int J. Oncol., 2005, 26:1087-1091.
Papahadjopoulos & Gabizon, "Targeting of Liposomes to Tumor Cells in Vivo," Ann. N.Y. Acad. Sci., 1987, 507(1):64-74.
Philipp et al., "Physiological significance of alpha2-adrenergic receptor subtype diversity: one receptor is not enough," Am J Physiol Regulatory Integrative Comp Physiol, 2002, 283(2):R287-R295.
Pillé et al., "Anti-RhoA and Anti-RhoC siRNAs Inhibit the Proliferation and Invasiveness of MDA-MB-231 Breast Cancer Cells in Vitro and in Vivo," Mol. Ther., 2005, 11(2):267-274.
Raza et al., "Parkinson's disease: Mechanisms, translational models and management strategies," Life Sci., 2019, 226:77-90.
Reich et al., "Small interfering RNA (siRNA) targeting VEGF effectively inhibits ocular neovascularization in a mouse model," Mol. Vis., 2003, 9:210-216.
Ritschel, "Microemulsions for Improved Peptide Absorption from the Gastrointestinal Tract," Meth. Find. Exp. Clin. Pharmacol., 1991, 13(3):205-220.
Saison-Behmoaras et al., "Short modified antisense oligonucleotides directed against Ha-ras point mutation induce selective cleavage of the mRNA and inhibit T24 cells proliferation," EMBO J, 1991, 10(5):1111-1118.
Sharp, "RNA interference—2001," Genes Dev., 2001, 15:485-490.
Shea et al., "Synthesis, hybridization properties and antiviral activity of lipid-oligodeoxynucleotide conjugates," Nucl. Acids Res., 1990, 18(13):3777-3783.
Shishkina et al., "Attenuation of α2A-Adrenergic Receptor Expression in Neonatal Rat Brain by RNA Interference or Antisense Oligonucleotide Reduced Anxiety in Adulthood," Neuroscience, 2004, 129:521-528.
Simeoni et al., "Insight into the mechanism of the peptide-based gene delivery system MPG: implications for delivery of siRNA into mammalian cells," Nucl. Acids Res., 2003, 31(11):2717-2724.
Sørensen et al., "Gene Silencing by Systemic Delivery of Synthetic siRNAs in Adult Mice," J. Mol. Biol., 2003, 327:761-766.
Soutschek et al., "Therapeutic silencing of an endogenous gene by systemic administration of modified siRNAs," Nature, 2004, 432:173-178.
Straubinger & Papahadjopoulos, "Liposomes as Carriers for Intracellular Delivery of Nucleic Acids," Meth. Enzymol., 1983, 101:512-527.
Strauss & Jaenisch, "Molecular complementation of a collagen mutation in mammalian cells using yeast artificial chromosomes," EMBO J., 1992, 11(2):417-422.
Svinarchuk et al., "Inhibition of HIV proliferation in MT-4 cells by antisense oligonucleotide conjugated to lipophilic groups," Biochimie, 1993, 75:49-54.
Szoka & Papahadjopoulos, "Procedure for preparation of liposomes with large internal aqueous space and high capture by reverse-phase evaporation," Proc. Natl. Acad. Sci., 1978, 75(9):4194-4198.
Takahashi et al., "The Use of a Perfluorochemical Emulsion as a Vascular Perfusate in Drug Absorption," J. Pharm. Pharmacol., 1988, 40:252-257.
Tan et al., "Gene knockdown with intrathecal siRNA of NMDA receptor NR2B subunit reduces formalin-induced nociception in the rat," Gene Ther., 2005, 12:59-66.
Tetko et al., "Prediction of n-Octanol/Water Partition Coefficients from PHYSPROP Database Using Artificial Neural Networks and E-State Indices," J. Chem. Inf. Comput. Sci., 2001, 41:1407-1421.
Thakker et al., "Neurochemical and behavioral consequences of widespread gene knockdown in the adult mouse brain by using nonviral RNA interference," Proc. Natl. Acad. Sci. U.S.A., 2004, 101(49):17270-17275.
Tolentino et al., "Intravitreal Injection of Vascular Endothelial Growth Factor Small Interfering RNA Inhibits Growth and Leakage in a Nonhuman Primate, Laser-Induced Model of Choroidal Neovascularization," Retina, 2004, 24(1):132-138.
Tomalia et al., "Dendrimers as multi-purpose nanodevices for oncology drug delivery and diagnostic imaging," Biochem. Soc. Trans., 2007, 35(1):61-67.
Verma et al., "Small Interfering RNAs Directed against—Catenin Inhibit the in Vitro and in Vivo Growth of Colon Cancer Cells," Clin. Cancer Res., 2003, 9:1291-1300.
Wang & Huang, "pH-sensitive immunoliposomes mediate target-cell-specific delivery and controlled expression of a foreign gene in mouse," Proc. Natl Acad. Sci. USA, 1987, 84:7851-7855.
Wang & Huang, "Plasmid DNA Adsorbed to pH-sensitive Liposomes Efficiently Transforms the Target Cells," Biochem. Biophys. Res. Commun., 1987, 147(3):980-985.
Weiner et al., "Liposomes: A Novel Topical Delivery System for Pharmaceutical and Cosmetic Applications," Journal of Drug Targeting, 1994, 2:405-410.
Wu et al., "Increased Microvascular Permeability Contributes to Preferential Accumulation of Stealth Liposomes in Tumor Tissue," Cancer Research, 1993, 53:3765-3770.
Yamamoto et al., "A Mechanistic Study on Enhancement of Rectal Permeability to Insulin in the Albino Rabbit," J. Pharm. Exp. Ther., 1992, 263(1):25-31.
Yamashita et al., "Effects of diclofenac sodium and disodium ethylenediaminetetraacetate on electrical parameters of the mucosal

(56) References Cited

OTHER PUBLICATIONS membrane and their relation to the permeability enhancing effects in the rat jejunum," J. Pharm. Pharmacol., 1987, 39:621-626.
Yamashita et al., "Effect of Adjuvants on Charge-Selective Permeability and Electrical Resistance of Rat Jejunal Membrane," J. Pharm. Sci., 1990, 79(7):579-583.
Yoo et al., "PAMAM Dendrimers as Delivery Agents for Antisense Oligonucleotides, " Pharm. Res., 1999, 16:1799-1804.
Zhang et al., "Small Interfering RNA Targeting Heme Oxygenase-1 Enhances Ischemia-Reperfusion-induced Lung Apoptosis," J. Biol. Chem., 2004, 279(11):10677-10684.
Zhang et al., "Amyloid β redirects norepinephrine signaling to activate the pathogenic GSK3B/tau cascade," Sci Transl Med, 2020, 12(526):eaay6931, 23 pp.
Zhou et al., "Lipophilic polylysines mediate efficient DNA transfection in mammalian cells," Biochim. Biophys. Acta, 1991, 1065:8-14.
Zhou & Huang, "Targeted delivery of DNA by liposomes and polymers," Journal of Controlled Release, 1992, 19:269-274.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties," J. Org. Chem., 2009, 74:118-134.
Zimmermann et al., "RNAi-mediated gene silencing in non-human primates," Nature, 2006, 441:111-114.
Zitzmann et al., "Arginine-glycine-aspartic acid (RGD)-peptide binds to both tumor and tumor endothelial cells in vivo.," Cancer Res., 2002, 62:5139-5143.
International Search Report and Written Opinion issued Aug. 23, 2021 in PCT/US2021/025420.
Rosengren et al., Supporting Online Material for "Overexpression of Alpha2A-Adrenergic Receptors Contributes to Type 2 Diabetes," Nov. 19, 2009, 29 pp.
Rosengren et al., "Overexpression of Alpha2A-Adrenergic Receptors Contributes to Type 2 Diabetes," Science, Jan. 8, 2010, 327:217-220.
Partial Supplementary Search Report issued Apr. 9, 2024, in European Patent Application No. 21781935.8.
Extended European Search Report issued Jul. 1, 2024, in European Patent Application No. 21781935.8.

ALPHA-2A ADRENERGIC RECEPTOR (ADRA2A) IRNA AGENT COMPOSITIONS AND METHODS OF USE THEREOF

CROSS-REFERENCE TO RELATED APPLICATIONS

This application claims the benefit of priority to U.S. Provisional Application No. 63/003,702, filed on Apr. 1, 2020. The entire contents of the foregoing application are hereby incorporated herein by reference.

SEQUENCE LISTING

The instant application contains a Sequence Listing which has been submitted electronically in ASCII format and is hereby incorporated by reference in its entirety. The ASCII copy, created on Mar. 23, 2021, is named A108868_1090WO_SL.txt and is 186,727 bytes in size.

BACKGROUND OF THE INVENTION

The alpha-2A adrenergic receptor (ADRA2A) gene encoding the alpha-2A adrenergic receptor protein is located in the chromosomal region 10q25.2. ADRA2A belongs to the G Protein-Coupled Receptor (GPCR) superfamily. The ADRA2A protein has only 1 exon with a total of 465 amino acids.

ADRA2A is involved in regulating neurotransmitter release in sympathetic nerves and neurons in the central nervous system. ADRA2A has been implicated in the hyperphosphorylation of tau protein. Hyperphosphorylation of tau protein is known to result in insoluble aggregates of tau protein in neurons (neurofibrillary tangles) and other cells which result in tauopathies, a class of progressive neurodegenerative diseases defined by deposits of tau protein in the brain. Tauopathies include, for example, primary tauopathies such as frontotemporal dementia (FTD), frontotemporal dementia and parkinsonism linked to chromosome 17 (FTDP-17), frontotemporal lobar degeneration (FTLD), progressive supranuclear palsy (PSP), corticobasal degeneration (CBD), chronic traumatic encephalopathy (CTE), Pick's disease (PiD), globular glial tauopathies (GGTs), argyrophilic grain disease (AGD), and primary age-related tauopathy (PART), and secondary tauopathies such as Alzheimer's disease.

Presently, there is no disease-modifying therapy for tauopathies such as Alzheimer's disease, and treatments are only aimed at alleviating the symptoms of disease and improving the patient's quality of life as the neurodegenerative disease progresses. Accordingly, there is a need for agents that can treat, prevent, and/or inhibit the progression of the formation of the neurofibrillary tangles that result in tauopathies.

BRIEF SUMMARY OF THE INVENTION

The present disclosure provides RNAi compositions, which effect the RNA-induced silencing complex (RISC)-mediated cleavage of RNA transcripts of an ADRA2A gene. The ADRA2A gene may be within a cell, e.g., a cell within a subject, such as a human. The use of these iRNAs enables the targeted degradation of mRNAs of the corresponding gene (ADRA2A gene) in mammals.

The iRNAs of the invention have been designed to target an ADRA2A gene, e.g., an ADRA2A gene having a missense and/or deletion mutations in the exon of the gene and/or a wild type gene in a subject having a tauopathy, and having a combination of nucleotide modifications. The iRNAs of the invention inhibit the expression of the ADRA2A gene by at least about 30%, 35%, 40%, 45%, 50%, 55%, 60%, 65%, 70%, 75%, 80%, 85%, 90%, 95%, or 99%. Without intending to be limited by theory, it is believed that a combination or sub-combination of the foregoing properties and the specific target sites, or the specific modifications in these iRNAs confer to the iRNAs of the invention improved efficacy, stability, potency, durability, and safety. In one aspect, the present invention provides double stranded ribonucleic acid (dsRNA) agent for inhibiting expression of ADRA2A, wherein the dsRNA agent comprises a sense strand and an antisense strand forming a double stranded region, wherein the sense strand comprises at least 15 contiguous nucleotides differing by no more than 3 nucleotides from the nucleotide sequence of SEQ ID NO: 1 and the antisense strand comprises at least 15 contiguous nucleotides differing by no more than 3 nucleotides from the nucleotide sequence of SEQ ID NO: 2.

In another aspect, the present invention provides a double stranded ribonucleic acid (dsRNA) agent for inhibiting expression of ADRA2A, wherein the dsRNA agent comprises a sense strand and an antisense strand forming a double stranded region, wherein the antisense strand comprises a region of complementarity to an mRNA encoding ADRA2A, and wherein the region of complementarity comprises at least 15 contiguous nucleotides differing by no more than 3 nucleotides from the nucleotide sequence of SEQ ID NO:2.

In yet another aspect, the present invention provides a double stranded ribonucleic acid (dsRNA) agent for inhibiting expression of ADRA2A, wherein the dsRNA agent comprises a sense strand and an antisense strand forming a double stranded region, wherein the antisense strand comprises a region of complementarity to an mRNA encoding ADRA2A, and wherein the region of complementarity comprises at least 15 contiguous nucleotides differing by no more than 3 nucleotides from any one of the antisense nucleotide sequences in Table 3 or 4.

In one embodiment, the sense strand comprises at least 15 contiguous nucleotides differing by no more than three nucleotides from any one of the nucleotide sequence of nucleotides 193-213, 323-343, 422-442, 440-460, 528-548, 540-560, 555-575, 594-614, 607-627, 621-641, 641-661, 657-677, 679-699, 702-722, 716-736, 729-749, 965-985, 1090-1110, 1148-1168, 1167-1187, 1212-1232, 1224-1244, 1266-1286, 1287-1307, 1304-1324, 1325-1345, 1340-1360, 1352-1372, 1367-1387, 1404-1424, 1416-1436, 1428-1448, 1460-1480, 1478-1498, 1493-1513, 1505-1525, 1517-1537, 1575-1595, 1589-1609, 1601-1621, 1619-1639, 1641-1661, 1653-1673, 1665-1685, 1896-1916, 2117-2137, 2129-2149, 2145-2165, 2163-2183, 2177-2197, 2189-2209, 2223-2243, 2235-2255, 2258-2278, 2280-2300, 2292-2312, 2306-2326, 2318-2338, 2357-2377, 2385-2405, 2432-2452, 2466-2486, 2525-2545, 2538-2558, 2564-2584, 2580-2600, 2595-2615, 2610-2630, 2622-2642, 2635-2655, 2650-2670, 2667-2687, 2679-2699, 2694-2714, 2717-2737, 2750-2770, 2771-2791, 2837-2857, 2881-2901, 2893-2913, 2919-2939, 2936-2956, 2948-2968, 2971-2991, 2988-3008, 3011-3031, 3026-3046, 3043-3063, 3060-3080, 3072-3092, 3084-3104, 3117-3137, 3132-3152, 3147-3167, 3167-3187, 3180-3200, 3198-3218, 3210-3230, 3222-3242, 3237-3257, 3249-3269, 3262-3282, 3286-3306, 3298-3318, 3316-3336, 3329-3349, 3354-3374, 3375-3395, 3398-3418, 3410-3430, 3430-3450, 3445-3465, 3457-3477, 3470-3490, 3485-3505, 3497-3517, 3509-3529, 3521-3541, 3554-3574, 3566-3586, 3582-3602, 3608-3628, 3625-3645, 3642-3662, 3654-3674, 3666-3686, 3695-3715, 3708-3728, 3746-3766, 759-3779, 3771-3791, 3786-3806, 3798-3818, 3811-3831, and 3830-3850 of SEQ ID NO: 1, and the antisense strand comprises at least 15 contiguous nucleotides from the corresponding nucleotide sequence of SEQ ID NO: 2.

In one embodiment, the sense strand comprises at least 15 contiguous nucleotides differing by no more than three nucleotides from any one of the nucleotide sequence of nucleotides 193-213, 528-548, 540-560, 555-575, 594-614, 607-627, 621-641, 641-661, 657-677, 2771-2791, and 3375-3395 of SEQ ID NO: 1, and the antisense strand comprises at least 15 contiguous nucleotides from the corresponding nucleotide sequence of SEQ ID NO: 2.

In one embodiment, the sense strand comprises at least 15 contiguous nucleotides differing by no more than three nucleotides from any one of the nucleotide sequence of nucleotides 528-677 of SEQ ID NO: 1, and the antisense strand comprises at least 15 contiguous nucleotides from the corresponding nucleotide sequence of SEQ ID NO: 2.

In one embodiment, the sense strand comprises at least 15 contiguous nucleotides differing by no more than three nucleotides from any one of the nucleotide sequence of nucleotides 555-677, 555-627, 594-627, and 641-677 of SEQ ID NO: 1, and the antisense strand comprises at least 15 contiguous nucleotides from the corresponding nucleotide sequence of SEQ ID NO: 2.

In one embodiment, the sense strand comprises at least 15 contiguous nucleotides differing by no more than three nucleotides from any one of the nucleotide sequence of nucleotides 528-548, 555-575, 594-614, 607-627, 641-661, 657-677, 679-699, 702-722, 1266-1286, 1460-1480, 1478-1498, 1619-1639, 1641-1661, 2145-2165, 2292-2312, 2622-2642, 2635-2655, 2667-2687, 2717-2737, 2771-2791, 2837-2857, 2893-2913, 2971-2991, 2988-3008, 3060-3080, 3084-3104, 3117-3137, 3132-3152, 3167-3187, 3180-3200, 3198-3218, 3210-3230, 3222-3242, 3237-3257, 3249-3269, 3262-3282, 3298-3316, 3316-3336, 3375-3395, 3398-3418, 3410-3430, 3430-3450, 3497-3517, 3509-3529, 3521-3541, 3554-3574, 3566-3586, 3608-3628, 3625-3645, 3642-3662, 3654-3674, 3666-3686, 3708-3728, 3746-3766, and 3759-3779 of SEQ ID NO: 1, and the antisense strand comprises at least 15 contiguous nucleotides from the corresponding nucleotide sequence of SEQ ID NO: 2.

In one embodiment, the sense strand comprises at least 15 contiguous nucleotides differing by no more than three nucleotides from any one of the nucleotide sequence of nucleotides 555-627, 641-722, 641-677, 1460-1498, 1619-1661, 2622-2655, 2771-2857, 2971-3008, 3084-3152, 3167-3282, 3180-3218, 3237-3269, 3298-3336, 3375-3450, 3410-3450, 3497-3586, 3509-3574, 3521-3574, 3608-3686, 3642-3686, 3654-3686, 3708-3779, and 3708-3766 of SEQ ID NO: 1, and the antisense strand comprises at least 15 contiguous nucleotides from the corresponding nucleotide sequence of SEQ ID NO: 2.

In one embodiment, the sense strand comprises at least 15 contiguous nucleotides differing by no more than three nucleotides from any one of the nucleotide sequence of nucleotides 528-548, 555-575, 594-614, 607-627, 641-661, 657-677, 2771-2791, 3375-3395, 555-627, 594-627, 555-614, 641-677 of SEQ ID NO: 1, and the antisense strand comprises at least 15 contiguous nucleotides from the corresponding nucleotide sequence of SEQ ID NO: 2.

In one embodiment, the antisense strand comprises at least 15 contiguous nucleotides differing by no more than three nucleotides from any one of the antisense strand nucleotide sequences of a duplex selected from the group consisting of AD-1201748, AD-1201749, AD-1201750, AD-1201751, AD-1201752, AD-1201753, AD-1201754, AD-1201755, AD-1201756, AD-1201757, AD-1201758, AD-1201759, AD-1201760, AD-1201761, AD-1201762, AD-1201763, AD-1201764, AD-1201765, AD-1201766, AD-1201767, AD-1201768, AD-1201769, AD-1201770, AD-1201771, AD-1201772, AD-1201773, AD-1201774, AD-1201775, AD-1201776, AD-1201777, AD-1201778, AD-1201779, AD-1201780, AD-1201781, AD-1201782, AD-1201783, AD-4201784, AD-1201785, AD-1201786, AD-1201787, AD-1201788, AD-1201789, AD-1201790, AD-1201791, AD-1201792, AD-1201793, AD-1201794, AD-1201795, AD-1201796, AD-1201797, AD-1201798, AD-1201799, AD-1201800, AD-1201801, AD-1201802, AD-1201803, AD-1201804, AD-1201805, AD-1201806, AD-1201807, AD-1201808, AD-1201809, AD-1201810, AD-1201811, AD-1201812, AD-1201813, AD-1201814, AD-1201815, AD-1201816, AD-1201817, AD-1201818, AD-4201819, AD-1201820, AD-1201821, AD-1201822, AD-1201823, AD-1201824, AD-1201825, AD-1201826, AD-1201827, AD-1201828, AD-1201829, AD-1201830, AD-1201831, AD-1201832, AD-1201833, AD-1201834, AD-1201835, AD-1201836, AD-1201837, AD-1201838, AD-1201839, AD-1201840, AD-1201841, AD-1201842, AD-1201843, AD-1201844, AD-1201845, AD-1201846, AD-1201847, AD-1201848, AD-1201849, AD-1201850, AD-1201851, AD-1201852, AD-1201853, AD-1201854, AD-1201855, AD-1201856, AD-1201857, AD-1201858, AD-1201859, AD-1201860, AD-1201861, AD-1201862, AD-1201863, AD-1201864, AD-1201865, AD-1201866, AD-1201867, AD-1201868, AD-1201869, AD-1201870, AD-1201871, AD-1201872, AD-1201873, AD-1201874, AD-1201875, AD-1201876, AD-1201877, AD-1201878, AD-1201879, AD-1201880, AD-1201881, and AD-1201882.

In some embodiments, the nucleotide sequence of the sense and antisense strand comprises any one of the sense strand nucleotide sequences in Table 3 or 4.

In one embodiment, the sense strand, the antisense strand, or both the sense strand and the antisense strand is conjugated to one or more lipophilic moieties.

In one embodiment, the lipophilic moiety is conjugated to one or more internal positions in the double stranded region of the dsRNA agent.

In one embodiment, the lipophilic moiety is conjugated via a linker or carrier.

In one embodiment, the lipophilicity of the lipophilic moiety, measured by log Kow, exceeds 0.

In one embodiment, the hydrophobicity of the double-stranded RNAi agent, measured by the unbound fraction in a plasma protein binding assay of the double-stranded RNAi agent, exceeds 0.2.

In one embodiment, the plasma protein binding assay is an electrophoretic mobility shift assay using human serum albumin protein.

In some embodiments, the dsRNA agent comprises at least one modified nucleotide.

In one embodiment, no more than five of the sense strand nucleotides and no more than five of the nucleotides of the antisense strand are unmodified nucleotides In one embodiment, all of the nucleotides of the sense strand and all of the nucleotides of the antisense strand are modified nucleotides.

In one embodiment, at least one of the modified nucleotides is selected from the group a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a 5'-phosphorothioate group, a nucleotide comprising a 5'-methylphosphonate group, a nucleotide comprising a 5' phosphate or 5' phosphate mimic, a nucleotide comprising vinyl phosphonate, a nucleotide comprising adenosine-glycol nucleic acid (GNA), a nucleotide comprising thymidine-glycol nucleic acid (GNA) S-Isomer, a nucleotide comprising 2-hydroxymethyl-tetrahydrofurane-5-phosphate, a nucleotide comprising 2'-deoxythymidine-3'phosphate, a nucleotide comprising 2'-deoxyguanosine-3'-phosphate, and a terminal nucleotide linked to a cholesteryl derivative and a dodecanoic acid bisdecylamide group; and combinations thereof.

In one embodiment, the modified nucleotide is selected from the group consisting of a 2'-deoxy-2-fluoro modified nucleotide, a 2'-deoxy-modified nucleotide, 3'-terminal deoxy-thymine nucleotides (dT), a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

In one embodiment, the modified nucleotide comprises a short sequence of 3'-terminal deoxy-thymine nucleotides (dT).

In one embodiment, the modifications on the nucleotides are 2'-O-methyl. GNA and 2'fluoro modifications.

In some embodiments, the dsRNA agent further comprises at least one phosphorothioate internucleotide linkage.

In one embodiment, the dsRNA agent comprises 6-8 phosphorothioate internucleotide linkages.

In one embodiment, each strand is no more than 30 nucleotides in length.

In one embodiment, at least one strand comprises a 3' overhang of at least 1 nucleotide. In another embodiment, at least one strand comprises a 3' overhang of at least 2 nucleotides.

The double stranded region may be 15-30 nucleotide pairs in length; 17-23 nucleotide pairs in length; 17-25 nucleotide pairs in length: 23-27 nucleotide pairs in length; 19-21 nucleotide pairs in length; or 21-23 nucleotide pairs in length.

Each strand may have 19-30 nucleotides; 19-23 nucleotides; or 21-23 nucleotides.

In one embodiment, one or more lipophilic moieties are conjugated to one or more internal positions on at least one strand, such as via a linker or carrier.

In one embodiment, the internal positions include all positions except the terminal two positions from each end of the at least one strand.

In another embodiment, the internal positions include all positions except the terminal three positions from each end of the at least one strand.

In one embodiment, the internal positions exclude a cleavage site region of the sense strand.

In one embodiment, the internal positions include all positions except positions 9-12, counting from the 5'-end of the sense strand.

In another embodiment, the internal positions include all positions except positions 11-13, counting from the 3'-end of the sense strand.

In one embodiment, the internal positions exclude a cleavage site region of the antisense strand.

In one embodiment, the internal positions include all positions except positions 12-14, counting from the 5'-end of the antisense strand.

In one embodiment, the internal positions include all positions except positions 11-13 on the sense strand, counting from the 3'-end, and positions 12-14 on the antisense strand, counting from the 5'-end.

In one embodiment, the one or more lipophilic moieties are conjugated to one or more of the internal positions selected from the group consisting of positions 4-8 and 13-18 on the sense strand, and positions 6-10 and 15-18 on the antisense strand, counting from the 5'end of each strand.

In another embodiment, the one or more lipophilic moieties are conjugated to one or more of the internal positions selected from the group consisting of positions 5, 6, 7, 15, and 17 on the sense strand, and positions 15 and 17 on the antisense strand, counting from the 5'-end of each strand.

In one embodiment, the internal positions in the double stranded region exclude a cleavage site region of the sense strand.

In one embodiment, the sense strand is 21 nucleotides in length, the antisense strand is 23 nucleotides in length, and the lipophilic moiety is conjugated to position 21, position 20, position 15, position 1, position 7, position 6, or position 2 of the sense strand or position 16 of the antisense strand.

In one embodiment, the lipophilic moiety is conjugated to position 21, position 20, position 15, position 1, or position 7 of the sense strand.

In another embodiment, the lipophilic moiety is conjugated to position 21, position 20, or position 15 of the sense strand.

In yet another embodiment, the lipophilic moiety is conjugated to position 20 or position 15 of the sense strand.

In one embodiment, the lipophilic moiety is conjugated to position 16 of the antisense strand.

In one embodiment, the lipophilic moiety is an aliphatic, alicyclic, or polyalicyclic compound.

In one embodiment, the lipophilic moiety is selected from the group consisting of lipid, cholesterol, retinoic acid, cholic acid, adamantane acetic acid, 1-pyrene butyric acid, dihydrotestosterone, 1,3-bis-O(hexadecyl)glycerol, geranyloxyhexyanol, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine.

In one embodiment, the lipophilic moiety contains a saturated or unsaturated C4-C30 hydrocarbon chain, and an optional functional group selected from the group consisting of hydroxyl, amine, carboxylic acid, sulfonate, phosphate, thiol, azide, and alkyne.

In one embodiment, the lipophilic moiety contains a saturated or unsaturated C6-C18 hydrocarbon chain.

In one embodiment, the lipophilic moiety contains a saturated or unsaturated C16 hydrocarbon chain.

In one embodiment, the saturated or unsaturated C16 hydrocarbon chain is conjugated to position 6, counting from the 5'-end of the strand.

In one embodiment, the lipophilic moiety is conjugated via a carrier that replaces one or more nucleotide(s) in the internal position(s) or the double stranded region.

In one embodiment, the carrier is a cyclic group selected from the group consisting of pyrrolidinyl, pyrazolinyl, pyrazolidinyl, imidazolinyl, imidazolidinyl, piperidinyl, piperazinyl, [1,3]dioxolanyl, oxazolidinyl, isoxazolidinyl, morpholinyl, thiazolidinyl, isothiazolidinyl, quinoxalinyl, pyridazinonyl, tetrahydrofuranyl, and decalinyl; or is an acyclic moiety based on a serinol backbone or a diethanolamine backbone.

In one embodiment, the lipophilic moiety is conjugated to the double-stranded iRNA agent via a linker containing an ether, thioether, urea, carbonate, amine, amide, maleimide-thioether, disulfide, phosphodiester, sulfonamide linkage, a product of a click reaction, or carbamate.

In one embodiment, the lipophilic moiety is conjugated to a nucleobase, sugar moiety, or internucleosidic linkage.

In one embodiment, the lipophilic moiety or targeting ligand is conjugated via a bio-cleavable linker selected from the group consisting of DNA, RNA, disulfide, amide, functionalized monosaccharides or oligosaccharides of galactosamine, glucosamine, glucose, galactose, mannose, and combinations thereof.

In one embodiment, the 3' end of the sense strand is protected via an end cap which is a cyclic group having an amine, said cyclic group being selected from the group consisting of pyrrolidinyl, pyrazolinyl, pyrazolidinyl, imidazolinyl, imidazolidinyl, piperidinyl, piperazinyl, 11.31 dioxolanyl, oxazolidinyl, isoxazolidinyl, morpholinyl, thiazolidinyl, isothiazolidinyl, quinoxalinyl, pyridazinonyl, tetrahydrofuranyl, and decalinyl.

In one embodiment, the targeting ligand is a GalNAc conjugate.

In one embodiment, the dsRNA agent further comprises a terminal, chiral modification occurring at the first internucleotide linkage at the 3' end of the antisense strand, having the linkage phosphorus atom in Sp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp configuration or Sp configuration.

In another embodiment, the dsRNA agent further comprises a terminal, chiral modification occurring at the first and second internucleotide linkages at the 3' end of the antisense strand, having the linkage phosphorus atom in Sp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration.

In yet another embodiment, the dsRNA agent further comprises a terminal, chiral modification occurring at the first, second and third internucleotide linkages at the 3' end of the antisense strand, having the linkage phosphorus atom in Sp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration.

In another embodiment, the dsRNA agent further comprises a terminal, chiral modification occurring at the first, and second internucleotide linkages at the 3' end of the antisense strand, having the linkage phosphorus atom in Sp configuration, a terminal, chiral modification occurring at the third internucleotide linkages at the 3' end of the antisense strand, having the linkage phosphorus atom in Rp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration.

In another embodiment, the dsRNA agent further comprises a terminal, chiral modification occurring at the first, and second internucleotide linkages at the 3' end of the antisense strand, having the linkage phosphorus atom in Sp configuration, a terminal, chiral modification occurring at the first, and second internucleotide linkages at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration.

In one embodiment, the dsRNA agent further comprises a phosphate or phosphate mimic at the 5'-end of the antisense strand.

In one embodiment, the phosphate mimic is a 5'-vinyl phosphonate (VP).

In one embodiment, the base pair at the 1 position of the 5'-end of the antisense strand of the duplex is an AU base pair.

In one embodiment, the sense strand has a total of 21 nucleotides and the antisense strand has a total of 23 nucleotides.

The present invention also provides cells and pharmaceutical compositions for inhibiting expression of a gene encoding ADRA2A comprising the dsRNA agents of the invention, such.

In one embodiment, the dsRNA agent is in an unbuffered solution, such as saline or water.

In another embodiment, the dsRNA agent is in a buffer solution, such as a buffer solution comprising acetate, citrate, prolamine, carbonate, or phosphate or any combination thereof; or phosphate buffered saline (PBS).

In one aspect, the present invention provides a method of inhibiting expression of an ADRA2A gene in a cell, the method comprising contacting the cell with a dsRNA agent of the invention, or a pharmaceutical composition of the invention, thereby inhibiting expression of the ADRA2A gene in the cell.

In one embodiment, cell is within a subject.

In one embodiment, the subject is a human.

In one embodiment, the subject has an ADRA2A-associated disorder.

In one embodiment, the ADRA2A-associated disorder in the subject is a neurodegenerative disorder.

In one embodiment, the neurodegenerative disorder is a tauopathy.

In one embodiment, the neurodegenerative disorder/tauopathy is Alzheimer's disease.

In another embodiment, the neurodegenerative disorder/tauopathy is a primary tauopathy.

In one embodiment, the primary tauopathy is selected from the group consisting of frontotemporal dementia (FTD), frontotemporal dementia and parkinsonism linked to chromosome 17 (FTDP-17), frontotemporal lobar degeneration (FTLD), progressive supranuclear palsy (PSP), corticobasal degeneration (CBD), chronic traumatic encephalopathy (CTE), Pick's disease (PiD), globular glial tauopathies (GGTs), argyrophilic grain disease (AGD), and primary age-related tauopathy (PART).

In one embodiment, contacting the cell with the dsRNA agent inhibits the expression of ADRA2A by at least 30%.

In one embodiment, inhibiting expression of ADRA2A decreases ADRA2A protein level in serum of the subject by at least 30%.

In one aspect, the present invention provides method of treating a subject having a disorder that would benefit from reduction in ADRA2A expression, comprising administering to the subject a therapeutically effective amount of a dsRNA agent of the invention, or a pharmaceutical composition of the invention, thereby treating the subject having the disorder that would benefit from reduction in ADRA2A expression.

In another aspect, the present invention provides a method of preventing at least one symptom in a subject having a disorder that would benefit from reduction in ADRA2A expression, comprising administering to the subject a prophylactically effective amount of a dsRNA agent of the invention, or a pharmaceutical composition of the invention, thereby preventing at least one symptom in the subject having the disorder that would benefit from reduction in ADRA2A expression.

In one embodiment, the disorder is an ADRA2A-associated disorder.

In one embodiment, the ADRA2A-associated disorder is selected from the group consisting of Alzheimer's disease, frontotemporal dementia (FTD), frontotemporal dementia and parkinsonism linked to chromosome 17 (FTDP-17), frontotemporal lobar degeneration (FTLD), progressive supranuclear palsy (PSP), corticobasal degeneration (CBD), chronic traumatic encephalopathy (CTE), Pick's disease (PiD), globular glial tauopathies (GGTs), argyrophilic grain disease (AGD), and primary age-related tauopathy (PART).

In one embodiment, the ADRA2A-associated disorder is Alzheimer's disease.

In one embodiment, the ADRA2A-associated disorder is a primary tauopathy.

In one embodiment, the subject is human.

In one embodiment, the administration of the agent to the subject causes a decrease in ADRA2A protein accumulation.

In one embodiment, the dsRNA agent is administered to the subject at a dose of about 0.01 mg/kg to about 50 mg/kg.

In one embodiment, the dsRNA agent is administered to the subject subcutaneously.

In another embodiment, the dsRNA agent is administered to the subject intrathecally.

In one embodiment, the methods of the invention further comprise determining the level of ADRA2A in a sample(s) from the subject.

In one embodiment, the level of ADRA2A in the subject sample(s) is an ADRA2A protein level in a blood, serum, or cerebrospinal fluid sample(s).

In one embodiment, the methods of the invention further comprise administering to the subject an additional therapeutic agent.

In one aspect, the present invention provides a kit comprising a dsRNA agent of the invention, or a pharmaceutical composition of the invention.

In another aspect, the present invention provides a vial comprising a dsRNA agent of the invention, or a pharmaceutical composition of the invention.

In yet another aspect, the present invention provides a syringe comprising a dsRNA agent of the invention, or a pharmaceutical composition of the invention.

In another aspect, the present invention provides an intrathecal pump comprising a dsRNA agent of the invention, or a pharmaceutical composition of the invention.

DETAILED DESCRIPTION OF THE INVENTION

The present disclosure provides RNAi compositions, which effect the RNA-induced silencing complex (RISC)-mediated cleavage of RNA transcripts of an ADRA2A gene. The ADRA2A gene may be within a cell, e.g., a cell within a subject, such as a human. The use of these iRNAs enables the targeted degradation of mRNAs of the corresponding gene (ADRA2A gene) in mammals.

The iRNAs of the invention have been designed to target an ADRA2A gene, e.g., an ADRA2A gene either with or without nucleotide modifications. The iRNAs of the invention inhibit the expression of the ADRA2A gene by at least about 30%, 35%, 40%, 45%, 50%, 55%, 60%, 65%, 70%, 75%, 80%, 85%, 90%, 95%, or 99%. Without intending to be limited by theory, it is believed that a combination or sub-combination of the foregoing properties and the specific target sites, or the specific modifications in these iRNAs confer to the iRNAs of the invention improved efficacy, stability, potency, durability, and safety.

Accordingly, the present disclosure also provides methods of using the RNAi compositions of the disclosure for inhibiting the expression of an ADRA2A gene or for treating a subject having a disorder that would benefit from inhibiting or reducing the expression of an ADRA2A gene, e.g., an ADRA2A-associated disease, for example, a neurodegenerative disease such as a tauopathy, including primary tauopathies and Alzheimer's disease.

The RNAi agents of the disclosure include an RNA strand (the antisense strand) having a region which is about 30 nucleotides or less in length, e.g., 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of an ADRA2A gene, e.g., an ADRA2A exon. In certain embodiments, the RNAi agents of the disclosure include an RNA strand (the antisense strand) having a region which is about 21-23 nucleotides in length, which region is substantially complementary to at least part of an mRNA transcript of an ADRA2A gene.

In certain embodiments, the RNAi agents of the disclosure include an RNA strand (the antisense strand) which can include longer lengths, for example up to 66 nucleotides, e.g., 36-66, 26-36, 25-36, 31-60, 2243, 27-53 nucleotides in length with a region of at least 19 contiguous nucleotides that is substantially complementary to at least a part of an mRNA transcript of an ADRA2A gene. These RNAi agents with the longer length antisense strands preferably include a second RNA strand (the sense strand) of 20-60 nucleotides in length wherein the sense and antisense strands form a duplex of 18-30 contiguous nucleotides.

The use of these RNAi agents enables the targeted degradation and/or inhibition of mRNAs of an ADRA2A gene in mammals. Thus, methods and compositions including these RNAi agents are useful for treating a subject who would benefit by a reduction in the levels or activity of an ADRA2A protein, such as a subject having an ADRA2A-associated disease, such as, a tauopathy.

The following detailed description discloses how to make and use compositions containing RNAi agents to inhibit the expression of an ADRA2A gene, as well as compositions and methods for treating subjects having diseases and disorders that would benefit from inhibition or reduction of the expression of the genes.

I. Definitions

In order that the present disclosure may be more readily understood, certain terms are first defined. In addition, it should be noted that whenever a value or range of values of a parameter are recited, it is intended that values and ranges intermediate to the recited values are also intended to be part of this disclosure.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to". The term "or" is used herein to mean, and is used interchangeably with, the term "and/or," unless context clearly indicates otherwise.

The term "about" is used herein to mean within the typical ranges of tolerances in the art. For example. "about" can be understood as about 2 standard deviations from the mean. In certain embodiments, about means±10%. In certain embodiments, about means±5%. When about is present before a series of numbers or a range, it is understood that "about" can modify, each of the numbers in the series or range.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 18 nucleotides of a 21 nucleotide nucleic acid molecule" means that 18, 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range.

As used herein, methods of detection can include determination that the amount of analyte present is below the level of detection of the method.

In the event of a conflict between an indicated target site and the nucleotide sequence for a sense or antisense strand, the indicated sequence takes precedence.

In the event of a conflict between a chemical structure and a chemical name, the chemical structure takes precedence.

As used herein, the term "alpha-2A adrenergic receptor" (i.e. "$\alpha_{2A}$ adrenergic receptor") used interchangeably with the term "ADRA2A," refers to the well-known gene and polypeptide encoded by that gene, also known in the art as "alpha-2A adrenoceptor" (i.e. "$\alpha_{2A}$ adrenoceptor"), "ADRA2," "ADRA2R," "ADRAR," "ALPHA2AAR," and "ZNF32." The ADRA2A gene is active in the brain and other tissues throughout the body. ADRA2A is expressed in various regions of the central nervous system, including the brainstem (particularly in the locus coeruleus of the pons), midbrain, hypothalamus, hippocampus, cerebral cortex (particularly, the pre-frontal cortex), cerebellum, septum, and spinal cord as well as the peripheral nervous system, such as in the paravertebral ganglia (i.e. sympathetic chain ganglia), particularly, the superior cervical ganglia. ADRA2A is located in both pre-synaptic and post-synaptic locations.

ADRA2A encodes for a protein known as alpha-2A adrenergic receptor, a G-protein coupled receptor which binds epinephrine (i.e. adrenaline) and norepinephrine (i.e. noradrenaline). Alpha-2A adrenergic receptor is one of three highly homologous subtypes, including alpha-2A-, alpha-2B-, and alpha-2C-adrenergic receptors. These receptors are all involved in regulating neurotransmitter release from sympathetic nerves and adrenergic neurons in the central nervous system. Given the high degree of homology between the alpha-2A, alpha-2B, and alpha-2C-adrenergic receptors, most ligands are not specific to any particular subtype. Alpha-2 type adrenergic receptors also regulate pain perception, body temperature, seizure thresholds, suppression of insulin release from pancreatic beta cells, and activation of platelet aggregation.

Alpha-2A adrenergic receptor controls pre-synaptic negative feedback inhibition of norepinephrine and regulates noradrenergic input to the cerebrum and the resulting response in that region of the brain. In addition, it serves as the primary autoreceptor in sympathetic neurons, controlling norepinephrine release. Alpha-2A adrenergic receptor is believed to operate at high stimulation frequencies and to regulate norepinephrine release during maximal sympathetic activation. Alpha-2A adrenergic receptor regulates physiological responses including lowering blood pressure, evoking sedation, reducing pain perception, and decreasing epileptogenesis and anxiety. Alpha-2A adrenergic receptor is involved in controlling vascular tone via arteriolar smooth muscle cell contraction and mediates many responses to administration of alpha-2-type adrenergic receptor agonists.

Alpha-2A adrenergic receptor allosterically inhibits adenylyl cyclase (decreasing cAMP) and reduces cytoplasmic calcium via ion channel effectors. Upon activation, alpha-2A adrenergic receptor binds the universal GPCR regulator, arrestin 3, which mediates agonist-induced endocytosis and desensitization of the alpha-2A adrenergic receptor. The intracellular domain of amyloid precursor protein (APP) binds the intracellular domain of alpha-2A adrenergic receptor, antagonistically competing with arrestin-3 and attenuating the arrestin-3-dependent endocytosis and desensitization of the alpha-2A adrenergic receptor. β-amyloid oligomers allosterically bind Alpha-2A adrenergic receptors to redirect norepinephrine signaling to glycogen synthase kinase 3β (GSK3β) and tau hyperphosphorylation. The norepinephrine-dependent signaling sensitize GSK3β/tau activation to nanomolar amounts of extracellular μ-amyloid aggregates, which is 50-100 fold lower than the amount required to induce GSK3β/tau activation absent the norepinephrine-dependent mechanism. Norepinephrine signaling via alpha-2A adrenergic receptor couples β-amyloid proteotoxicity to tauopathies, such as Alzheimer's disease. (Zhang, et al. (2002) *Sci Transl Med Vol.* 12, Issue 526: eaay6931)

ADRA2A polymorphisms have been associated with various phenotypes relating, for instance, to platelet function, plasma von Willebrand factor levels, blood pressure, body fat distribution, bone density, generalized anxiety disorder, attention deficit hyperactivity disorder (ADHD)-like behaviors, symptom expression of gastrointestinal disorders, decision making in chronic drug users, and ADRA2A-induced response to various therapeutic drugs.

Mice lacking functional ADRA2A appear to develop normally. Mutations in the ADRA2A gene have been associated with deficient ion channel coupling/activation in mice. Presynaptic inhibition of neurotransmitter release remained normal or only slightly attenuated in mice having mutations resulting in functional knockout of ADRA2A. (Philipp, et al. (2002) *Am J Physiol Regulatory Integrative Comp Physiol* Vol. 283, Issue 2: R287-R295)

Exemplary nucleotide and amino acid sequences of ADRA2A can be found, for example, at GenBank Accession No. NM_000681.4 (*Homo sapiens* ADRA2A, SEQ ID NO: 1, reverse complement. SEQ ID NO: 2); GenBank Accession No.: XM_015148184.2 (*Macaca mulatta* ADRA2A, SEQ ID NO: 3, reverse complement, SEQ ID NO: 4); GenBank Accession No. NM_007417.5 (*Mus musculus* ADRA2A, SEQ ID NO: 5; reverse complement, SEQ ID NO: 6); and GenBank Accession No.: NM_012739.3 (*Rattus norvegicus* ADRA2A, SEQ ID NO: 7, reverse complement, SEQ ID NO: 8).

The nucleotide sequence of the genomic region of human chromosome harboring the ADRA2A gene may be found in, for example, the Genome Reference Consortium Human Build 38 (also referred to as Human Genome build 38 or GRCh38) available at GenBank. The nucleotide sequence of the genomic region of human chromosome 10 harboring the ADRA2A gene may also be found at, for example, GenBank Accession No. NC_000010.11, corresponding to nucleotides 111077029-111080907 of human chromosome 10. The nucleotide sequence of the human ADRA2A gene may be found in, for example, GenBank Accession No. NG_012020.1.

Further examples of ADRA2A sequences can be found in publically available databases, for example, GenBank, OMIM, and UniProt.

Additional information on ADRA2A can be found, for example, at https://www.ncbi.nim.nih.gov/gene/150. The term ADRA2A as used herein also refers to variations of the ADRA2A gene including variants provided in the clinical variant database, for example, at https://www.ncbi.nln.nih.gov/clinvar/?term=NM_000681.4.

The entire contents of each of the foregoing GenBank Accession numbers and the Gene database numbers are incorporated herein by reference as of the date of filing this application.

As used herein, "target sequence" refers to a contiguous portion of the nucleotide sequence of an mRNA molecule formed during the transcription of an ADRA2A gene, including mRNA that is a product of RNA processing of a primary transcription product. In one embodiment, the target portion of the sequence will be at least long enough to serve as a substrate for RNAi-directed cleavage at or near that portion of the nucleotide sequence of an mRNA molecule formed during the transcription of an ADRA2A gene.

The target sequence is about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. In certain embodiments, the target sequence is 19-23 nucleotides in length, optionally 21-23 nucleotides in length. Ranges and lengths intermediate to the above recited ranges and lengths are also contemplated to be part of the disclosure.

As used herein, the term "strand comprising a sequence" refers to an oligonucleotide comprising a chain of nucleotides that is described by the sequence referred to using the standard nucleotide nomenclature. "G," "C," "A," "T", and "U" each generally stand for a nucleotide that contains guanine, cytosine, adenine, thymidine, and uracil as a base, respectively in the context of a modified or unmodified nucleotide. However, it will be understood that the term "ribonucleotide" or "nucleotide" can also refer to a modified nucleotide, as further detailed below, or a surrogate replacement moiety (see, e.g., Table 2). The skilled person is well aware that guanine, cytosine, adenine, thymidine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the disclosure by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the disclosure.

The terms "iRNA", "RNAi agent," "iRNA agent," "RNA interference agent" as used interchangeably herein, refer to an agent that contains RNA as that term is defined herein, and which mediates the targeted cleavage of an RNA transcript via an RNA-induced silencing complex (RISC) pathway. RNA interference (RNAi) is a process that directs the sequence-specific degradation of mRNA. RNAi modulates, e.g., inhibits, the expression of ADRA2A in a cell, e.g., a cell within a subject, such as a mammalian subject.

In one embodiment, an RNAi agent of the disclosure includes a single stranded RNAi that interacts with a target RNA sequence, e.g., an ADRA2A target mRNA sequence, to direct the cleavage of the target RNA. Without wishing to be bound by theory it is believed that long double stranded RNA introduced into cells is broken down into double-stranded short interfering RNAs (siRNAs) comprising a sense strand and an antisense strand by a Type III endonuclease known as Dicer (Sharp et al. (2001) *Genes Dev.* 15:485). Dicer, a ribonuclease-III-like enzyme, processes this dsRNA into 19-23 base pair short interfering RNAs with characteristic two base 3' overhangs (Bernstein, et al., (2001) *Nature* 409:363). These siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the disclosure relates to a single stranded RNA (ssRNA) (the antisense strand of a siRNA duplex) generated within a cell and which promotes the formation of a RISC complex to effect silencing of the target gene, i.e., an ADRA2A gene. Accordingly, the term "siRNA" is also used herein to refer to an RNAi as described above.

In another embodiment, the RNAi agent may be a single-stranded RNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded RNAs are described in U.S. Pat. No. 8,101,348 and in Lima et al., (2012) *Cell* 150:883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150:883-894.

In another embodiment, a "RNAi agent" for use in the compositions and methods of the disclosure is a double stranded RNA and is referred to herein as a "double stranded RNAi agent," "double stranded RNA (dsRNA) molecule," "dsRNA agent," or "dsRNA". The term "dsRNA" refers to a complex of ribonucleic acid molecules, having a duplex structure comprising two anti-parallel and substantially complementary nucleic acid strands, referred to as having "sense" and "antisense" orientations with respect to a target RNA, i.e., an ADRA2A gene. In some embodiments of the disclosure, a double stranded RNA (dsRNA) triggers the degradation of a target RNA, e.g., an mRNA, through a post-transcriptional gene-silencing mechanism referred to herein as RNA interference or RNAi.

In general, a dsRNA molecule can include ribonucleotides, but as described in detail herein, each or both strands can also include one or more non-ribonucleotides, e.g., a deoxyribonucleotide, a modified nucleotide. In addition, as used in this specification, an "RNAi agent" may include ribonucleotides with chemical modifications; an RNAi agent may include substantial modifications at multiple nucleotides. As used herein, the term "modified nucleotide" refers to a nucleotide having, independently, a modified sugar moiety, a modified internucleotide linkage, or a modified nucleobase. Thus, the term modified nucleotide encompasses substitutions, additions or removal of, e.g., a functional group or atom, to internucleoside linkages, sugar moieties, or nucleobases. The modifications suitable for use in the agents of the disclosure include all types of modifications disclosed herein or known in the art. Any such modifications, as used in a siRNA type molecule, are encompassed by "RNAi agent" for the purposes of this specification and claims.

In certain embodiments of the instant disclosure, inclusion of a deoxy-nucleotide if present within an RNAi agent can be considered to constitute a modified nucleotide.

The duplex region may be of any length that permits specific degradation of a desired target RNA through a RISC pathway, and may range from about 15-36 base pairs in length, for example, about 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. In certain embodiments, the duplex region is 19-21 base pairs in length, e.g., 21 base pairs in length. Ranges and lengths intermediate to the above recited ranges and lengths are also contemplated to be part of the disclosure.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 4, at least 5, at least 6, at least 7, at least 8, at least 9, at least 10, at least 20, at least 23 or more unpaired nucleotides or nucleotides not directed to the target site of the dsRNA. In some embodiments, the hairpin loop can be 10 or fewer nucleotides. In some embodiments, the hairpin loop can be 8 or fewer unpaired nucleotides. In some embodiments, the hairpin loop can be 4-10 unpaired nucleotides. In some embodiments, the hairpin loop can be 4-8 nucleotides.

Where the two substantially complementary strands of a dsRNA are comprised by separate RNA molecules, those molecules need not, but can be covalently connected. In certain embodiments where the two strands are connected covalently by means other than an uninterrupted chain of nucleotides between the 3'-end of one strand and the 5'-end of the respective other strand forming the duplex structure, the connecting structure is referred to as a "linker" (though it is noted that certain other structures defined elsewhere herein can also be referred to as a "linker"). The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs. In one embodiment of the RNAi agent, at least one strand comprises a 3' overhang of at least 1 nucleotide. In another embodiment, at least one strand comprises a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In one embodiment, an RNAi agent of the disclosure is a dsRNA, each strand of which independently comprises 19-23 nucleotides, that interacts with a target RNA sequence, e.g., an ADRA2A target mRNA sequence, to direct the cleavage of the target RNA.

In some embodiments, an iRNA of the invention is a dsRNA of 24-30 nucleotides that interacts with a target RNA sequence, e.g., an ADRA2A target mRNA sequence, to direct the cleavage of the target RNA.

As used herein, the term "nucleotide overhang" refers to at least one unpaired nucleotide that protrudes from the duplex structure of an RNAi agent, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively, the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end or the 5'-end. In another embodiment, one or more of the nucleotides in the overhang is replaced with a nucleoside thiophosphate.

In certain embodiments, the antisense strand of a dsRNA has a 1-10 nucleotide, e.g., 0-3, 1-3, 2-4, 2-5, 4-10, 5-10, e.g., a 1, 2, 3, 4, 5, 6, 7, 8, 9, or 10 nucleotide, overhang at the 3'-end or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end or the 5'-end. In another embodiment, one or more of the nucleotides in the overhang is replaced with a nucleoside thiophosphate.

In certain embodiments, the overhang on the sense strand or the antisense strand, can include extended lengths longer than 10 nucleotides, e.g., 1-30 nucleotides, 2-30 nucleotides, 10-30 nucleotides, or 10-15 nucleotides in length. In certain embodiments, an extended overhang is on the sense strand of the duplex. In certain embodiments, an extended overhang is present on the 3'end of the sense strand of the duplex. In certain embodiments, an extended overhang is present on the 5'end of the sense strand of the duplex. In certain embodiments, an extended overhang is on the antisense strand of the duplex. In certain embodiments, an extended overhang is present on the 3'end of the antisense strand of the duplex. In certain embodiments, an extended overhang is present on the 5'end of the antisense strand of the duplex. In certain embodiments, one or more of the nucleotides in the overhang is replaced with a nucleoside thiophosphate. In certain embodiments, the overhang includes a self-complementary portion such that the overhang is capable of forming a hairpin structure that is stable under physiological conditions.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double stranded over its entire length.

The term "antisense strand" or "guide strand" refers to the strand of an RNAi agent, e.g., a dsRNA, which includes a region that is substantially complementary to a target sequence, e.g., an ADRA2A mRNA.

As used herein, the term "region of complementarity" refers to the region on the antisense strand that is substantially complementary to a sequence, for example a target sequence, e.g., an ADRA2A nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- or 3'-terminus of the RNAi agent. In some embodiments, a double stranded RNA agent of the invention includes a nucleotide mismatch in the antisense strand. In some embodiments, the antisense strand of the double stranded RNA agent of the invention includes no more than 4 mismatches with the target mRNA, e.g., the antisense strand includes 4, 3, 2, 1, or 0 mismatches with the target mRNA. In some embodiments, the antisense strand double stranded RNA agent of the invention includes no more than 4 mismatches with the sense strand, e.g., the antisense strand includes 4, 3, 2, 1, or 0 mismatches with the sense strand. In some embodiments, a double stranded RNA agent of the invention includes a nucleotide mismatch in the sense strand. In some embodiments, the sense strand of the double stranded RNA agent of the invention includes no more than 4 mismatches with the antisense strand, e.g., the sense strand includes 4, 3, 2, 1, or 0 mismatches with the antisense strand. In some embodiments, the nucleotide mismatch is, for example, within 5, 4, 3 nucleotides from the 3'-end of the iRNA. In another embodiment, the nucleotide mismatch is, for example, in the 3'-terminal nucleotide of the iRNA agent. In some embodiments, the mismatch(s) is not in the seed region.

Thus, an RNAi agent as described herein can contain one or more mismatches to the target sequence. In one embodiment, an RNAi agent as described herein contains no more than 3 mismatches (i.e., 3, 2, 1, or 0 mismatches). In one embodiment, an RNAi agent as described herein contains no more than 2 mismatches. In one embodiment, an RNAi agent as described herein contains no more than 1 mismatch. In one embodiment, an RNAi agent as described herein contains 0 mismatches. In certain embodiments, if the antisense strand of the RNAi agent contains mismatches to the target sequence, the mismatch can optionally be restricted to be within the last 5 nucleotides from either the 5'- or 3'-end of the region of complementarity. For example, in such embodiments, for a 23 nucleotide RNAi agent, the strand which is complementary to a region of an ADRA2A gene, generally does not contain any mismatch within the central 13 nucleotides. The methods described herein or methods known in the art can be used to determine whether an RNAi agent containing a mismatch to a target sequence is effective in inhibiting the expression of an ADRA2A gene. Consideration of the efficacy of RNAi agents with mismatches in inhibiting expression of an ADRA2A gene is important, especially if the particular region of complementarity in an ADRA2A gene is known to have polymorphic sequence variation within the population.

As used herein, "substantially all of the nucleotides are modified" are largely but not wholly modified and can include not more than 5, 4, 3, 2, or 1 unmodified nucleotides.

The term "sense strand" or "passenger strand" as used herein, refers to the strand of an RNAi agent that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary." when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an RNAi agent, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an RNAi agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding ADRA2A). For example, a polynucleotide is complementary to at least a part of an ADRA2A mRNA if the sequence is substantially complementary to a non-interrupted portion of an mRNA encoding ADRA2A.

Accordingly, in some embodiments, the antisense polynucleotides disclosed herein are fully complementary to the target ADRA2A sequence. In other embodiments, the antisense polynucleotides disclosed herein are substantially complementary to the target ADRA2A sequence and comprise a contiguous nucleotide sequence which is at least 80% complementary over its entire length to the equivalent region of the nucleotide sequence of any one of SEQ ID NOs:1, 3, 5 and 7, or a fragment of any one of SEQ ID NOs: 1, 3, 5 and 7, such as about 85%, about 90%, about 91%, about 92%, about 93%, about 94%, about 95%, about 96%, about 97%, about 98%, or about 99% complementary.

In some embodiments, the antisense polynucleotides disclosed herein are substantially complementary to a fragment of a target ADRA2A sequence and comprise a contiguous nucleotide sequence which is at least 80% complementary over its entire length to a fragment of SEQ ID NO: 1 selected from the group of nucleotides 191-213, 321-343, 420-442, 438-460, 526-548, 538-560, 553-575, 592-614, 605-627, 619-641, 639-661, 655-677, 677-699, 700-722, 714-736, 727-749, 963-985, 1088-1110, 1146-1168, 1165-1187, 1210-1232, 1222-1244, 1264-1286, 1285-1307, 1302-1324, 1323-1345, 1338-1360, 1350-1372, 1365-1387, 1402-1424, 1414-1436, 1426-1448, 1458-1480, 1476-1498, 1491-1513, 1503-1525, 1515-1537, 1573-1595, 1587-1609, 1599-1621, 1617-1639, 1639-1661, 1651-1673, 1663-1685, 1894-1916, 2115-2137, 2127-2149, 2143-2165, 2161-2183, 2175-2197, 2187-2209, 2221-2243, 2233-2255, 2256-2278, 2278-2300, 2290-2312, 2304-2326, 2316-2338, 2355-2377, 2383-2405, 2430-2452, 2464-2486, 2523-2545, 2536-2558, 2562-2584, 2578-2600, 2593-2615, 2608-2630, 2620-2642, 2633-2655, 2648-2670, 2665-2687, 2677-2699, 2692-2714, 2715-2737, 2748-2770, 2769-2791, 2835-2857, 2879-2901, 2891-2913, 2917-2939, 2934-2956, 2946-2968, 2969-2991, 2986-3008, 3009-3031, 3024-3046, 3041-3063, 3058-3080, 3070-3092, 3082-3104, 3115-3137, 3130-3152, 3145-3167, 3165-3187, 3178-3200, 3196-, 3218, 3208-3230, 3220-3242, 3235-3257, 3247-3269, 3260-3282, 3284-3306, 3296-3318, 3314-3336, 3327-3349, 3352-3374, 3373-3395, 3396-3418, 3408-3430, 3428-3450, 3443-3465, 3455-3477, 3468-3490, 3483-3505, 3495-3517, 3507-3529, 3519-3541, 3552-3574, 3564-3586, 3580-3602, 3606-3628, 3623-3645, 3640-3662, 3652-3674, 3664-3686, 3693-3715, 3706-3728, 3744-3766, 3757-3779, 3769-3791, 3784-3806, 3796-3818, 3809-3831, and 3828-3850 of SEQ ID NO: 1, such as about 85%, about 90%, about 91%, about 92%, about 93%, about 94%, about 95%, about 96%, about 97%, about 98%, or about 99% complementary. Ranges intermediate to the above recited ranges are also contemplated to be part of the disclosure.

In other embodiments, the antisense polynucleotides disclosed herein are substantially complementary to the target ADRA2A sequence and comprise a contiguous nucleotide sequence which is at least about 80% complementary over its entire length to any one of the sense strand nucleotide sequences in Table 3 or 4, or a fragment of any one of the sense strand nucleotide sequences in Table 3 or 4, such as about 85%, about 90%, about 91%, about 92%, about 93%, about 94%, about 95%, about 96%, about 97%, about 98%, about 99%, or 100% complementary.

In one embodiment, an RNAi agent of the disclosure includes a sense strand that is substantially complementary to an antisense polynucleotide which, in turn, is the same as a target ADRA2A sequence, and wherein the sense strand polynucleotide comprises a contiguous nucleotide sequence which is at least about 80% complementary over its entire length to the equivalent region of the nucleotide sequence of SEQ ID NOs:1, 3, 5 and 7, or a fragment of any one of SEQ ID NOs:1, 3, 5 and 7, such as about 85%, about 90%, about 91%, about 92%, about 93%, about 94%, about 95%, about 96%, about 97%, about 98%, about 99%, or 100% complementary.

In some embodiments, an iRNA of the invention includes a sense strand that is substantially complementary to an antisense polynucleotide which, in turn, is complementary to a target ADRA2A sequence, and wherein the sense strand polynucleotide comprises a contiguous nucleotide sequence which is at least about 80% complementary over its entire length to any one of the antisense strand nucleotide sequences in Table 3 or 4, or a fragment of any one of the antisense strand nucleotide sequences in Table 3 or 4, such as about 85%, about 90%, about 91%, about 92%, about 93%, about 94%, about 95%, about 96%, about 97%, about 98%, about 99%, or 100% complementary.

In certain embodiments, the sense and antisense strands are selected from any one of duplexes AD-1201748, AD-1201749, AD-1201750, AD-1201751, AD-1201752, AD-1201753, AD-1201754, AD-1201755, AD-1201756, AD-1201757, AD-1201758, AD-1201759, AD-1201760, AD-1201761, AD-1201762, AD-1201763, AD-1201764, AD-1201765, AD-1201766, AD-1201767, AD-1201768, AD-1201769, AD-1201770, AD-1201771, AD-1201772, AD-1201773, AD-1201774, AD-1201775, AD-1201776, AD-1201777, AD-1201778, AD-1201779, AD-1201780, AD-1201781, AD-1201782, AD-1201783, AD-1201784, AD-1201785, AD-1201786, AD-1201787, AD-1201788, AD-1201789, AD-1201790, AD-1201791, AD-1201792, AD-1201793, AD-1201794, AD-1201795, AD-1201796, AD-1201797, AD-1201798, AD-1201799, AD-1201800, AD-1201801, AD-1201802, AD-1201803, AD-1201804, AD-1201805, AD-1201806, AD-1201807, AD-1201808, AD-1201809, AD-1201810, AD-1201811, AD-1201812, AD-1201813, AD-1201814, AD-1201815, AD-1201816, AD-1201817, AD-1201818, AD-1201819, AD-1201820, AD-1201821, AD-1201822, AD-1201823, AD-1201824, AD-1201825, AD-1201826, AD-1201827, AD-1201828, AD-1201829, AD-1201830, AD-1201831, AD-1201832, AD-1201833, AD-1201834, AD-1201835, AD-1201836, AD-1201837, AD-1201838, AD-1201839, AD-1201840, AD-1201841, AD-1201842, AD-1201843, AD-1201844, AD-1201845, AD-1201846, AD-1201847, AD-1201848, AD-1201849, AD-1201850, AD-1201851, AD-1201852, AD-1201853, AD-1201854, AD-1201855, AD-1201856, AD-1201857, AD-1201858, AD-1201859, AD-1201860, AD-1201861, AD-1201862, AD-1201863, AD-1201864, AD-1201865, AD-1201866, AD-1201867, AD-1201868, AD-1201869, AD-1201870, AD-1201871, AD-1201872, AD-1201873, AD-1201874, AD-1201875, AD-1201876, AD-1201877, AD-1201878, AD-1201879, AD-1201880, AD-1201881, and AD-1201882.

In one embodiment, at least partial suppression of the expression of an ADRA2A gene, is assessed by a reduction of the amount of ADRA2A mRNA, e.g., sense mRNA, antisense mRNA, total ADRA2A mRNA, which can be isolated from or detected in a first cell or group of cells in which an ADRA2A gene is transcribed and which has or have been treated such that the expression of an ADRA2A gene is inhibited, as compared to a second cell or group of cells substantially identical to the first cell or group of cells but which has or have not been so treated (control cells). The degree of inhibition may be expressed in terms of:

$$\frac{(mRNA\text{ in control cells}) - (mRNA\text{ in treated cells})}{(mRNA\text{ in control cells})} \cdot 100\%$$

The phrase "contacting a cell with an RNAi agent," such as a dsRNA, as used herein, includes contacting a cell by any possible means. Contacting a cell with an RNAi agent includes contacting a cell in vitro with the RNAi agent or contacting a cell in vivo with the RNAi agent. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the central nervous system (CNS), optionally via intrathecal, intravitreal or other injection, or to the bloodstream or the subcutaneous space, such that the agent will subsequently reach the tissue where the cell to be contacted is located. For example, the RNAi agent may contain or be coupled to a ligand, e.g., a lipophilic moiety or moieties as described below and further detailed, e.g., in PCT/US2019/031170, which is incorporated herein by reference, that directs or otherwise stabilizes the RNAi agent at a site of interest, e.g., the CNS. Combinations of in vitro and in vivo methods of contacting are also possible. For example, a cell may also be contacted in vitro with an RNAi agent and subsequently transplanted into a subject.

In one embodiment, contacting a cell with an RNAi agent includes "introducing" or "delivering the RNAi agent into the cell" by facilitating or effecting uptake or absorption into the cell. Absorption or uptake of an RNAi agent can occur through unaided diffusive or active cellular processes, or by auxiliary agents or devices. Introducing an RNAi agent into a cell may be in vitro or in vivo. For example, for in vivo introduction, an RNAi agent can be injected into a tissue site or administered systemically. In vitro introduction into a cell includes methods known in the art such as electroporation and lipofection. Further approaches are described herein below or are known in the art.

The term "lipophile" or "lipophilic moiety" broadly refers to any compound or chemical moiety having an affinity for lipids. One way to characterize the lipophilicity of the lipophilic moiety is by the octanol-water partition coefficient, log $K_{ow}$, where $K_{ow}$ is the ratio of a chemical's concentration in the octanol-phase to its concentration in the aqueous phase of a two-phase system at equilibrium. The octanol-water partition coefficient is a laboratory-measured property of a substance. However, it may also be predicted by using coefficients attributed to the structural components of a chemical which are calculated using first-principle or empirical methods (see, for example, Tetko et al., *J. Chem. Inf. Comput. Sci.* 41:1407-21 (2001), which is incorporated herein by reference in its entirety). It provides a thermodynamic measure of the tendency of the substance to prefer a non-aqueous or oily milieu rather than water (i.e. its hydrophilic/lipophilic balance). In principle, a chemical substance is lipophilic in character when its log $K_{ow}$ exceeds 0. Typically, the lipophilic moiety possesses a log $K_{ow}$ exceeding 1, exceeding 1.5, exceeding 2, exceeding 3, exceeding 4, exceeding 5, or exceeding 10. For instance, the log $K_{ow}$ of 6-amino hexanol, for instance, is predicted to be approximately 0.7. Using the same method, the log $K_{ow}$ of cholesteryl N-(hexan-6-ol) carbamate is predicted to be 10.7.

The lipophilicity of a molecule can change with respect to the functional group it carries. For instance, adding a hydroxyl group or amine group to the end of a lipophilic moiety can increase or decrease the partition coefficient (e.g., log $K_{ow}$) value of the lipophilic moiety.

Alternatively, the hydrophobicity of the double-stranded RNAi agent, conjugated to one or more lipophilic moieties, can be measured by its protein binding characteristics. For instance, in certain embodiments, the unbound fraction in the plasma protein binding assay of the double-stranded RNAi agent could be determined to positively correlate to the relative hydrophobicity of the double-stranded RNAi agent, which could then positively correlate to the silencing activity of the double-stranded RNAi agent.

In one embodiment, the plasma protein binding assay determined is an electrophoretic mobility shift assay (EMSA) using human serum albumin protein. An exemplary protocol of this binding assay is illustrated in detail in, e.g., PCT/US2019/031170. The hydrophobicity of the double-stranded RNAi agent, measured by fraction of unbound siRNA in the binding assay, exceeds 0.15, exceeds 0.2, exceeds 0.25, exceeds 0.3, exceeds 0.35, exceeds 0.4, exceeds 0.45, or exceeds 0.5 for an enhanced in vivo delivery of siRNA.

Accordingly, conjugating the lipophilic moieties to the internal position(s) of the double-stranded RNAi agent provides optimal hydrophobicity for the enhanced in vivo delivery of siRNA.

The term "lipid nanoparticle" or "LNP" is a vesicle comprising a lipid layer encapsulating a pharmaceutically active molecule, such as a nucleic acid molecule, e.g., a rNAi agent or a plasmid from which an RNAi agent is transcribed. LNPs are described in, for example, U.S. Pat. Nos. 6,858,225, 6,815,432, 8,158,601, and 8,058,069, the entire contents of which are hereby incorporated herein by reference.

As used herein, a "subject" is an animal, such as a mammal, including a primate (such as a human, a non-human primate, e.g., a monkey, and a chimpanzee), or a non-primate (such as a rat, or a mouse). In a preferred embodiment, the subject is a human, such as a human being treated or assessed for a disease, disorder, or condition that would benefit from reduction in ADRA2A expression; a human at risk for a disease, disorder, or condition that would benefit from reduction in ADRA2A expression; a human having a disease, disorder, or condition that would benefit from reduction in ADRA2A expression; or human being treated for a disease, disorder, or condition that would benefit from reduction in ADRA2A expression as described herein. In some embodiments, the subject is a female human. In other embodiments, the subject is a male human. In one embodiment, the subject is an adult subject. In one embodiment, the subject is a pediatric subject. In another embodiment, the subject is a juvenile subject, i.e., a subject below 20 years of age.

As used herein, the terms "treating" or "treatment" refer to a beneficial or desired result including, but not limited to, alleviation or amelioration of one or more signs or symptoms associated with ADRA2A gene expression or ADRA2A protein production, e.g., ADRA2A-associated diseases, such as ADRA2A-associated disease. "Treatment" can also mean prolonging survival as compared to expected survival in the absence of treatment.

The term "lower" in the context of the level of ADRA2A in a subject or a disease marker or symptom refers to a statistically significant decrease in such level. The decrease can be, for example, at least 10%, 15%, 20%, 25%, 30%, %, 40%, 45%, 50%, 55%, 60%, 65%, 70%, 75%, 80%, 85%, 90%, 95%, or more. In certain embodiments, a decrease is at least about 20%. In certain embodiments, the decrease is at least about 30% in a disease marker, e.g., a decrease of 30%, 35%, 40%, 45%, 50%, 55%, 60%, 65%, 70%, 75%, 80%, 85%, 90%, 95%, 99%, or more. In certain embodiments, the decrease is at least about 50% in a disease marker. "Lower" in the context of the level of ADRA2A in a subject is preferably down to a level accepted as within the range of normal for an individual without such disorder. In certain embodiments. "lower" is the decrease in the difference between the level of a marker or symptom for a subject suffering from a disease and a level accepted within the range of normal for an individual, e.g., the level of decrease in bodyweight between an obese individual and an individual having a weight accepted within the range of normal.

As used herein, "prevention" or "preventing," when used in reference to a disease, disorder, or condition thereof, that would benefit from a reduction in expression of an ADRA2A gene or production of an ADRA2A protein, refers to a reduction in the likelihood that a subject will develop a symptom associated with such a disease, disorder, or condition, e.g., a symptom of an ADRA2A-associated disease. The failure to develop a disease, disorder, or condition, or the reduction in the development of a symptom associated with such a disease, disorder, or condition (e.g., by at least about 10% on a clinically accepted scale for that disease or disorder), or the exhibition of delayed symptoms delayed (e.g., by days, weeks, months or years) is considered effective prevention.

As used herein, the term "ADRA2A-associated disease" or "ADRA2A-associated disorder" includes any disease or disorder that would benefit from reduction in the expression and/or activity of ADRA2A. Exemplary ADRA2A-associated diseases include those diseases in which subjects carry missense mutations and/or deletions in the ADRA2A gene and/or tauopathies. A tauopathy is a neurodegenerative disease associated with the aggregation of tau protein into neurofibrillary or gliofibrillary tangles in the human brain. Tauopathies may be a primary tauopathy, in which the tauopathy plays a predominant role in the neurodegenerative disease pathology, or a secondary tauopathy, in which additional pathologies play major roles in the neurodegenerative disease. Tauopathies that would benefit from reduction in the expression and/or activity of ADRA2A are generally primary tauopathies, but may include secondary tauopathies in which the tauopathy plays a significant role, particularly Alzheimer's disease. Six isoforms of tau proteins can be produced from alternative splicing of the microtubule-associate protein tau (MAPT) gene. Tau proteins are abundantly expressed in neurons of the central nervous system and maintain the stability of microtubules, particularly in axons, but are also expressed at lower levels in astrocytes and oligodendrocytes of the central nervous system. Changes in ratios of tau isoforms and/or hyperphosphonylation of tau proteins can result in tau proteins becoming insoluble and misfolding, leading to intracellular aggregation, disruption of axonal transport, and cell loss. Neurofibrillary tangles may be particularly abundant in the frontal and temporal neocortex and the limbic structures of subjects with tauopathies. Aggregated tau generally has a beta-pleated sheet conformation. It has been contemplated that tau aggregation may result from an increased number of phosphorylated sites on each tau protein and/or from an increased number of the proportion of phosphorylated tau proteins. It is believed that neurofibrillary tangles may propagate between neurons.

Primary tauopathies can include, but are not limited to, at least some forms of: frontotemporal dementia (FTD), frontotemporal dementia and parkinsonism linked to chromosome 17 (FTDP-17), frontotemporal lobar degeneration (FTLD), progressive supranuclear palsy (PSP), corticobasal degeneration (CBD), chronic traumatic encephalopathy (CTE), Pick's disease (PiD), globular glial tauopathies (GGTs), argyrophilic grain disease (AGD), and primary age-related tauopathy (PART). Alzheimer's disease, which is classified as a secondary tauopathy, is another example of an ADRA2A-associated disease. ADRA2A-associated diseases or disorders may also include diseases in which subjects carry missense mutations and/or deletions in the MAPT gene or another gene in which the mutation and/or deletion is associated with a tauopathy. Over 40 MAPT mutations are known which cause tauopathy. Some clinical syndromes may be associated with multiple tauopathies. In many instances, additional pathologies are present in the disease or disorder beyond the tauopathy, even amongst primary tauopathies.

"Therapeutically effective amount." as used herein, is intended to include the amount of an RNAi agent that, when administered to a subject having an ADRA2A-associated disease, is sufficient to effect treatment of the disease (e.g., by diminishing, ameliorating, or maintaining the existing disease or one or more symptoms of disease). The "therapeutically effective amount" may vary depending on the RNAi agent, how the agent is administered, the disease and its severity and the history, age, weight, family history, genetic makeup, the types of preceding or concomitant treatments, if any, and other individual characteristics of the subject to be treated.

"Prophylactically effective amount." as used herein, is intended to include the amount of an RNAi agent that, when administered to a subject having an ADRA2A-associated disorder, is sufficient to prevent or ameliorate the disease or one or more symptoms of the disease. Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylactically effective amount" also includes an amount of an RNAi agent that produces some desired local or systemic effect at a reasonable benefit/risk ratio applicable to any treatment. An RNAi agent employed in the methods of the present disclosure may be administered in a sufficient amount to produce a reasonable benefit/risk ratio applicable to such treatment.

The phrase "pharmaceutically acceptable" is employed herein to refer to those compounds, materials, compositions, or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates or polyanhydrides; (22) bulking agents, such as polypeptides and amino acids (23) serum component, such as serum albumin, HDL and LDL; and (22) other non-toxic compatible substances employed in pharmaceutical formulations.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the brain (e.g., whole brain or certain segments of brain, e.g., striatum, or certain types of cells in the brain, such as, e.g., neurons and glial cells (astrocytes, oligodendrocytes, microglial cells)). In some embodiments, a "sample derived from a subject" refers to blood drawn from the subject or plasma or serum derived therefrom. In further embodiments, a "sample derived from a subject" refers to brain tissue (or subcomponents thereof) or retinal tissue (or subcomponents thereof) derived from the subject.

II. RNAi Agents of the Disclosure

Described herein are RNAi agents which inhibit the expression of an ADRA2A gene. In one embodiment, the RNAi agent includes double stranded ribonucleic acid (dsRNA) molecules for inhibiting the expression of an ADRA2A gene in a cell, such as a cell within a subject, e.g., a mammal, such as a human having an ADRA2A-associated disease, e.g., ADRA2A-associated disease. The dsRNA includes an antisense strand having a region of complementarity which is complementary to at least a part of an mRNA formed in the expression of an ADRA2A gene. The region of complementarity is about 15-30 nucleotides or less in length. Upon contact with a cell expressing the ADRA2A gene, the RNAi agent inhibits the expression of the ADRA2A gene (e.g., a human gene, a primate gene, a non-primate gene) by at least 30% as assayed by, for example, a PCR or branched DNA (bDNA)-based method, or by a protein-based method, such as by immunofluorescence analysis, using, for example, western blotting or flowcytometric techniques. In one embodiment, the level of knockdown is assayed in monkey Cos-7 cells using an assay method provided in Example 2 below. In another embodiment, the level of knockdown is assayed in human BE(2)-C cells. In some embodiments, the level of knockdown is assayed in mouse Neuro-2a cells.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of an ADRA2A gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is 15 to 30 base pairs in length, e.g., 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. In certain preferred embodiments, the duplex structure is 18 to 25 base pairs in length, e.g., 18-25, 18-24, 18-23, 18-22, 18-21, 18-20, 19-25, 19-24, 19-23, 19-22, 19-21, 19-20, 20-25, 20-24, 20-23, 20-22, 20-21, 21-25, 21-24, 21-23, 21-22, 22-25, 22-24, 22-23, 23-25, 23-24 or 24-25 base pairs in length, for example, 19-21 basepairs in length. Ranges and lengths intermediate to the above recited ranges and lengths are also contemplated to be part of the disclosure.

Similarly, the region of complementarity to the target sequence is 15 to 30 nucleotides in length, e.g., 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, for example 19-23 nucleotides in length or 21-23 nucleotides in length. Ranges and lengths intermediate to the above recited ranges and lengths are also contemplated to be part of the disclosure.

In some embodiments, the duplex structure is 19 to 30 base pairs in length. Similarly, the region of complementarity to the target sequence is 19 to 30 nucleotides in length.

In some embodiments, the dsRNA is 15 to 23 nucleotides in length, 19 to 23 nucleotides in length, or 25 to 30 nucleotides in length. In general, the dsRNA is long enough to serve as a substrate for the Dicer enzyme. For example, it is well known in the art that dsRNAs longer than about 21-23 nucleotides can serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 15 to 36 base pairs, e.g., 15-36, 15-35, 15-34, 15-33, 15-32, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 base pairs, for example, 19-21 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an RNAi agent useful to target ADRA2A expression is not generated in the target cell by cleavage of a larger dsRNA.

A dsRNA as described herein can further include one or more single-stranded nucleotide overhangs e.g., 1, 2, 3, or 4 nucleotides. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

A dsRNA can be synthesized by standard methods known in the art. Double stranded RNAi compounds of the invention may be prepared using a two-step procedure. First, the individual strands of the double stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Similarly, single-stranded oligonucleotides of the invention can be prepared using solution-phase or solid-phase organic synthesis or both.

In one aspect, a dsRNA of the disclosure includes at least two nucleotide sequences, a sense sequence and an antisense sequence. The sense strand sequence for ADRA2A may be selected from the group of sequences provided in Table 3 or 4, and the corresponding nucleotide sequence of the antisense strand of the sense strand may be selected from the group of sequences of Table 3 or 4. In this aspect, one of the two sequences is complementary to the other of the two sequences, with one of the sequences being substantially complementary to a sequence of an mRNA generated in the expression of an ADRA2A gene. As such, in this aspect, a dsRNA will include two oligonucleotides, where one oligonucleotide is described as the sense strand (passenger strand) in Table 3 or 4, and the second oligonucleotide is described as the corresponding antisense strand (guide strand) of the sense strand in Table 3 or 4.

In one embodiment, the substantially complementary sequences of the dsRNA are contained on separate oligonucleotides. In another embodiment, the substantially complementary sequences of the dsRNA are contained on a single oligonucleotide.

It will be understood that, although the sequences in Tables 3 and 4 are described as modified or conjugated sequences, the RNA of the RNAi agent of the disclosure e.g., a dsRNA of the disclosure, may comprise any one of the sequences set forth in Table 3 or 4 that is un-modified, un-conjugated, or modified or conjugated differently than described therein. For example, although the sense strands of the agents of the invention may be conjugated to a GalNAc ligand, these agents may be conjugated to a moiety that directs delivery to the CNS, e.g., a C16 ligand, as described herein. A lipophilic ligand can be included in any of the positions provided in the instant application.

The skilled person is well aware that dsRNAs having a duplex structure of about 20 to 23 base pairs, e.g., 21, base pairs have been hailed as particularly effective in inducing RNA interference (Elbashir et al., (2001) *EMBO J.*, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided herein, dsRNAs described herein can include at least one strand of a length of minimally 21 nucleotides. It can be reasonably expected that shorter duplexes minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences provided herein, and differing in their ability to inhibit the expression of an ADRA2A gene by not more than 10, 15, 20, 25, 30, 35, 40, 45 or 50% inhibition from a dsRNA comprising the full sequence using the in vitro assay with, e.g., A549 cells and a 10 nM concentration of the RNA agent and the PCR assay as provided in the examples herein, are contemplated to be within the scope of the present disclosure. In some embodiments, inhibition from a dsRNA comprising the full sequence was measured using the in vitro assay with primary mouse hepatocytes.

In addition, the RNAs described herein identify a site(s) in an ADRA2A transcript that is susceptible to RISC-mediated cleavage. As such, the present disclosure further features RNAi agents that target within this site(s). As used herein, an RNAi agent is said to target within a particular site of an RNA transcript if the RNAi agent promotes cleavage of the transcript anywhere within that particular site. Such an RNAi agent will generally include at least about 15 contiguous nucleotides, preferably at least 19 nucleotides, from one of the sequences provided herein coupled to additional nucleotide sequences taken from the region contiguous to the selected sequence in an ADRA2A gene.

III. Modified RNAi Agents of the Disclosure

In one embodiment, the RNA of the RNAi agent of the disclosure e.g., a dsRNA, is un-modified, and does not comprise, e.g., chemical modifications or conjugations known in the art and described herein. In preferred embodiments, the RNA of an RNAi agent of the disclosure, e.g., a dsRNA, is chemically modified to enhance stability or other beneficial characteristics. In certain embodiments of the disclosure, substantially all of the nucleotides of an RNAi agent of the disclosure are modified. In other embodiments of the disclosure, all of the nucleotides of an RNAi agent of the disclosure are modified. RNAi agents of the disclosure in which "substantially all of the nucleotides are modified" are largely but not wholly modified and can include not more than 5, 4, 3, 2, or unmodified nucleotides. In still other embodiments of the disclosure, RNAi agents of the disclosure can include not more than 5, 4, 3, 2 or 1 modified nucleotides.

The nucleic acids featured in the disclosure can be synthesized or modified by methods well established in the art, such as those described in "Current protocols in nucleic acid chemistry." Beaucage, S. L. et al. (Edrs.), John Wiley & Sons, Inc., New York, NY, USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; or backbone modifications, including modification or replacement of the phosphodiester linkages. Specific examples of RNAi agents useful in the embodiments described herein include, but are not limited to, RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified RNAi agent will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3-amino phosphoramidate and aminoalkylphosphoramidates, thionophosphoramidates, thionoalkylphosphonates, thionoalkylphosphotriesters, and boranophosphates having normal 3'-5 linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments of the invention, the dsRNA agents of the invention are in a free acid form. In other embodiments of the invention, the dsRNA agents of the invention are in a salt form. In one embodiment, the dsRNA agents of the invention are in a sodium salt form. In certain embodiments, when the dsRNA agents of the invention are in the sodium salt form, sodium ions are present in the agent as counterions for substantially all of the phosphodiester and/or phosphorothioate groups present in the agent. Agents in which substantially all of the phosphodiester and/or phosphorothioate linkages have a sodium counterion include not more than 5, 4, 3, 2, or 1 phosphodiester and/or phosphorothioate linkages without a sodium counterion. In some embodiments, when the dsRNA agents of the invention are in the sodium salt form, sodium ions are present in the agent as counterions for all of the phosphodiester and/or phosphorothioate groups present in the agent.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in RNAi agents, in which both the sugar and the internucleoside linkage, i.e., the backbone, of the nucleotide units are replaced with novel groups. The base units are maintained for hybridization with an appropriate nucleic acid target compound. One such oligomeric compound, a RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the RNAi agents of the disclosure are described in, for example, in Nielsen et al., *Science,* 1991, 254, 1497-1500.

Some embodiments featured in the disclosure include RNAs with phosphorothioate backbones and oligonucleosides with heteroatom backbones, and in particular $—CH_2—NH—CH_2—$, $—CH_2—N(CH_3)—O—CH_2—$[known as a methylene (methylimino) or MMI backbone], $—CH_2—O—N(CH_3)—CH_2—$, $—CH_2—N(CH_3)—N(CH_3)—CH_2—$ and $—N(CH_3)—CH_2—CH_2$-[wherein the native phosphodiester backbone is represented as $—O—PO—CH_2—$] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The RNAi agents, e.g., dsRNAs, featured herein can include one of the following at the 2-position: OH; F; O—, S—, or N-alkyl; O—, S—, or N-alkenyl; O—, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an RNAi agent, or a group for improving the pharmacodynamic properties of an RNAi agent, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-$OCH_3$), 2-aminopropoxy (2'-$OCH_2CH_2CH_2NH_2$), 2'-O-hexadecyl, and 2'-fluoro (2'-F). Similar modifications can also be made at other positions on the RNA of an RNAi agent, particularly the 3' position of the sugar on the 3' terminal nucleotide or in 2'-5' linked dsRNAs and the 5' position of 5' terminal nucleotide. RNAi agents can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An RNAi agent of the disclosure can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L. ed. John Wiley & Sons, 1990, these disclosed by Englisch et al., (1991) *Angewandte Chemie, International Edition,* 30:613, and those disclosed by Sanghvi. Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the disclosure. These include 5-substituted pyrimidines, 6-azapyrimidines and N-2, N-6 and 0-6 substituted purines, including 2-aminopropyladenine, 5-propynyluracil and 5-propynylcytosine, 5-methylcytosine substitutions have been shown to increase nucleic acid duplex stability by 0.6-1.2° C. (Sanghvi. Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

An RNAi agent of the disclosure can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen. J. et al., (2005) *Nucleic Acids Research* 33(1):439-447; Mook, O R, et al., (2007) *Mol Canc Ther* 6(3):833-843; Grunweller, A. et al., (2003) *Nucleic Acids Research* 31(12):3185-3193).

An RNAi agent of the disclosure can also be modified to include one or more bicyclic sugar moieties. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the disclosure may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-$CH_2$—O-2' bridge. This structure effectively "locks" the ribose in the 3'-endo structural conformation. The addition of locked nucleic acids to siRNAs has been shown to increase siRNA stability in serum, and to reduce off-target effects (Elnen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the disclosure include without limitation nucleosides comprising a bridge between the 4' and the 2' ribosyl ring atoms. In certain embodiments, the antisense polynucleotide agents of the disclosure include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2'; 4'-(CH2)2-O-2' (ENA); 4'-CH(CH3)-O-2' (also referred to as "constrained ethyl" or "cEt") and 4'-CH(CH2OCH3)-4)-2' (and analogs thereof; see, e.g., U.S. Pat. No. 7,399,845); 4'-C(CH3)(CH3)-O-2' (and analogs thereof, see e.g., U.S. Pat. No. 8,278,283); 4'-CH2-N(OCH3)-2' (and analogs thereof; see e.g., U.S. Pat. No. 8,278,425); 4'-CH2-O—N(CH3)-2' (see, e.g., U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., *J. Org. Chem.,* 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative US patents and US patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

An RNAi agent of the disclosure can also be modified to include one or more constrained ethyl nucleotides. As used herein, a "constrained ethyl nucleotide" or "cEt" is a locked nucleic acid comprising a bicyclic sugar moiety comprising a 4'-CH(CH3)-0-2' bridge. In one embodiment, a constrained ethyl nucleotide is in the S conformation referred to herein as "S-cEt."

An RNAi agent of the disclosure may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US 2013/0190383; and WO 2013/036868, the entire contents of each of which are hereby incorporated herein by reference.

In some embodiments, an RNAi agent of the disclosure comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C F and C4' carbons). In another example, the C2'-C3' bond (i.e. the covalent carbon-carbon bond between the C2' and C3' carbons) of the sugar has been removed (see *Nuc. Acids Symp. Series,* 52, 133-134 (2008) and Fluiter et al., *Mol. Biosyst.,* 2009, 10, 1039 hereby incorporated by reference).

Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6). N-(acetyl-4-hydroxyprolinol (Hyp-NHAc), thymidine-2-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in WO 2011/005861.

Other modifications of an RNAi agent of the disclosure include a 5' phosphate or 5' phosphate mimic, e.g., a 5'-terminal phosphate or phosphate mimic on the antisense strand of an RNAi agent. Suitable phosphate mimics are disclosed in, for example US 2012/0157511, the entire contents of which are incorporated herein by reference.

A. Modified RNAi Agents Comprising Motifs of the Disclosure

In certain aspects of the disclosure, the double-stranded RNAi agents of the disclosure include agents with chemical modifications as disclosed, for example, in WO 2013/075035, the entire contents of which are incorporated herein by reference. As shown herein and in WO 2013/075035, a superior result may be obtained by introducing one or more motifs of three identical modifications on three consecutive nucleotides into a sense strand or antisense strand of an RNAi agent, particularly at or near the cleavage site. In some embodiments, the sense strand and antisense strand of the RNAi agent may otherwise be completely modified. The introduction of these motifs interrupts the modification pattern, if present, of the sense or antisense strand. The RNAi agent may be optionally conjugated with a lipophilic ligand, e.g., a C16 ligand, for instance on the sense strand. The RNAi agent may be optionally modified with a (S)-glycol nucleic acid (GNA) modification, for instance on one or more residues of the antisense strand. The resulting RNAi agents present superior gene silencing activity.

Accordingly, the disclosure provides double stranded RNAi agents capable of inhibiting the expression of a target gene (i.e., an ADRA2A gene) in vivo. The RNAi agent comprises a sense strand and an antisense strand. Each strand of the RNAi agent may be 15-30 nucleotides in length. For example, each strand may be 16-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length. In certain embodiments, each strand is 19-23 nucleotides in length.

The sense strand and antisense strand typically form a duplex double stranded RNA ("dsRNA"), also referred to herein as an "RNAi agent." The duplex region of an RNAi agent may be 15-30 nucleotide pairs in length. For example, the duplex region can be 16-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length. In preferred embodiments, the duplex region is 19-21 nucleotide pairs in length.

In one embodiment, the RNAi agent may contain one or more overhang regions or capping groups at the 3-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 24 nucleotides in length, 1-3 nucleotides in length, 2-3 nucleotides in length, or 1-2 nucleotides in length. In preferred embodiments, the nucleotide overhang region is 2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one embodiment, the nucleotides in the overhang region of the RNAi agent can each independently be a modified or unmodified nucleotide including, but no limited to 2'-sugar modified, such as, 2-F, 2'-O-methyl, thymidine (T), and any combinations thereof.

For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3'-terminal end of the sense strand or, alternatively, at the 3'-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In one embodiment, the RNAi agent is a double ended bluntmer of 19 nucleotides in length, wherein the sense strand contains at least one motif of three 2'-F modifications on three consecutive nucleotides at positions 7, 8, 9 from the 5'end. The antisense strand contains at least one motif of three 2'-O-methyl modifications on three consecutive nucleotides at positions 11, 12, 13 from the 5'end.

In another embodiment, the RNAi agent is a double ended bluntmer of 20 nucleotides in length, wherein the sense strand contains at least one motif of three 2'-F modifications on three consecutive nucleotides at positions 8, 9, 10 from the 5'end. The antisense strand contains at least one motif of three 2'-O-methyl modifications on three consecutive nucleotides at positions 11, 12, 13 from the 5'end.

In yet another embodiment, the RNAi agent is a double ended bluntmer of 21 nucleotides in length, wherein the sense strand contains at least one motif of three 2'-F modifications on three consecutive nucleotides at positions 9, 10, 11 from the 5'end. The antisense strand contains at least one motif of three 2'-O-methyl modifications on three consecutive nucleotides at positions 11, 12, 13 from the 5'end.

In one embodiment, the RNAi agent comprises a 21 nucleotide sense strand and a 23 nucleotide antisense strand, wherein the sense strand contains at least one motif of three 2'-F modifications on three consecutive nucleotides at positions 9, 10, 11 from the 5'end; the antisense strand contains at least one motif of three 2'-O-methyl modifications on three consecutive nucleotides at positions 11, 12, 13 from the 5'end, wherein one end of the RNAi agent is blunt, while the other end comprises a 2 nucleotide overhang. Preferably, the 2 nucleotide overhang is at the 3'-end of the antisense strand. When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In one embodiment, every nucleotide in the sense strand and the antisense strand of the RNAi agent, including the nucleotides that are part of the motifs are modified nucleotides. In one embodiment each residue is independently modified with a 2'-O-methyl or 3'-fluoro, e.g., in an alternating motif. Optionally, the RNAi agent further comprises a ligand (e.g., a lipophilic ligand, optionally a C16 ligand).

In one embodiment, the RNAi agent comprises a sense and an antisense strand, wherein the sense strand is 25-30 nucleotide residues in length, wherein starting from the 5' terminal nucleotide (position 1) positions 1 to 23 of the first strand comprise at least 8 ribonucleotides; the antisense strand is 36-66 nucleotide residues in length and, starting from the 3' terminal nucleotide, comprises at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when the double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In one embodiment, the RNAi agent comprises sense and antisense strands, wherein the RNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region which is at least 25 nucleotides in length, and the second strand is sufficiently complementary to a target mRNA along at least 19 nucleotide of the second strand length to reduce target gene expression when the RNAi agent is introduced into a mammalian cell, and wherein dicer cleavage of the RNAi agent preferentially results in an siRNA comprising the 3' end of the second strand, thereby reducing expression of the target gene in the mammal. Optionally, the RNAi agent further comprises a ligand.

In one embodiment, the sense strand of the RNAi agent contains at least one motif of three identical modifications on three consecutive nucleotides, where one of the motifs occurs at the cleavage site in the sense strand.

In one embodiment, the antisense strand of the RNAi agent can also contain at least one motif of three identical modifications on three consecutive nucleotides, where one of the motifs occurs at or near the cleavage site in the antisense strand.

For an RNAi agent having a duplex region of 17-23 nucleotide in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the $1^{st}$ nucleotide from the 5'-end of the antisense strand, or, the count starting from the $1^{st}$ paired nucleotide within the duplex region from the 5'-end of the antisense strand. The cleavage site in the antisense strand may also change according to the length of the duplex region of the RNAi from the 5'-end.

The sense strand of the RNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In one embodiment, the sense strand of the RNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistry of the motifs are distinct from each other and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the RNAi agent may contain more than one motif of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In one embodiment, the wing modification on the sense strand or antisense strand of the RNAi agent typically does not include the first one or two terminal nucleotides at the 3'-end, 5'-end or both ends of the strand.

In another embodiment, the wing modification on the sense strand or antisense strand of the RNAi agent typically does not include the first one or two paired nucleotides within the duplex region at the 3'-end, 5'-end or both ends of the strand.

When the sense strand and the antisense strand of the RNAi agent each contain at least one wing modification, the wing modifications may fall on the same end of the duplex region, and have an overlap of one, two or three nucleotides.

When the sense strand and the antisense strand of the RNAi agent each contain at least two wing modifications, the sense strand and the antisense strand can be so aligned that two modifications each from one strand fall on one end of the duplex region, having an overlap of one, two or three nucleotides; two modifications each from one strand fall on the other end of the duplex region, having an overlap of one, two or three nucleotides; two modifications one strand fall on each side of the lead motif, having an overlap of one, two, or three nucleotides in the duplex region.

In one embodiment, the RNAi agent comprises mismatch(es) with the target, within the duplex, or combinations thereof. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the RNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In another embodiment, the nucleotide at the 3'-end of the sense strand is deoxy-thymine (dT). In another embodiment, the nucleotide at the 3'-end of the antisense strand is deoxy-thymine (dT). In one embodiment, there is a short sequence of deoxy-thymine nucleotides, for example, two dT nucleotides on the 3'-end of the sense or antisense strand.

In one embodiment, the sense strand sequence may be represented by formula (I):

$$5'n_p\text{-}N_a\text{—}(XXX)_i\text{—}N_b\text{—}YYY\text{—}N_b\text{—}(ZZZ)_j\text{—}N_a\text{-}n_q3' \quad (I)$$

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein Nb and Y do not have the same modification; and

XXX, YYY and ZZZ each independently represent one motif of three identical modifications on three consecutive nucleotides. Preferably YYY is all 2'-F modified nucleotides.

In one embodiment, the $N_a$ or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8, 7, 8, 9, 8, 9, 10, 9, 10, 11, 10, 11, 12 or 11, 12, 13) of—the sense strand, the count starting from the $1^{st}$ nucleotide, from the 5'-end; or optionally, the count starting at the $1^{st}$ paired nucleotide within the duplex region, from the 5'-end.

In one embodiment, i is 1 and j is 0, or i is 0 and j is 1, or both i and j are 1. The sense strand can therefore be represented by the following formulas:

$$5'n_p\text{-}N_a\text{—}YYY\text{—}N_b\text{—}ZZZ\text{—}N_a\text{-}n_q3' \quad (Ib);$$

$$5'n_p\text{-}N_a\text{—}XXX\text{—}N_b\text{—}YYY\text{—}N_a\text{-}n_q3' \quad (Ic); \text{ or}$$

$$5'n_p\text{-}N_a\text{—}XXX\text{—}N_b\text{—}YYY\text{—}N_b\text{—}ZZZ\text{—}N_a\text{-}n_q3' \quad (Id).$$

When the sense strand is represented by formula (Ib), $N_b$ represents an oligonucleotide sequence comprising 0-10, 0-7, 0-5, 0-4, 0-2 or 0 modified nucleotides.

Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6. Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

$$5'n_p\text{-}N_a\text{—}YYY\text{—}N_a\text{-}n_q3' \quad (Ia).$$

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

$$5'n_q\text{-}N_a'\text{—}(Z'Z'Z')_k\text{—}N_b'\text{—}Y'Y'Y'\text{—}N_b'\text{—}(X'X'X')_l\text{—}N'_a\text{-}n_p'3' \quad (II)$$

wherein:

k and l are each independently 0 or 1;

p' and q' are each independently 0-6;

each $N_a'$ independently represents an oligonucleotide sequence comprising 0-25 modified nucleotides, each sequence comprising at least two differently modified nucleotides;

each $N_b$' independently represents an oligonucleotide sequence comprising 0-10 modified nucleotides;

each $n_p$' and $n_q$' independently represent an overhang nucleotide;

wherein $N_b$' and Y' do not have the same modification;

and X'X'X', Y'Y'Y' and Z'Z'Z' each independently represent one motif of three identical modifications on three consecutive nucleotides.

In one embodiment, the $N_a$' or $N_b$' comprise modifications of alternating pattern.

The Y'Y'Y' motif occurs at or near the cleavage site of the antisense strand. For example, when the RNAi agent has a duplex region of 17-23 nucleotide in length, the Y'Y'Y' motif can occur at positions 9, 10, 11; 10, 11, 12; 11, 12, 13; 12, 13, 14; or 13, 14, 15 of the antisense strand, with the count starting from the $1^{st}$ nucleotide, from the 5'-end; or optionally, the count starting at the $1^{st}$ paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1.

The antisense strand can therefore be represented by the following formulas:

$$5'n_q\text{-}N_a'\text{—Z'Z'Z'—}N_b'\text{—Y'Y'Y'—}N_a'\text{-}n_p3' \quad \text{(IIb);}$$

$$5'n_q\text{-}N_a'\text{—Y'Y'Y'—}N_b'\text{—X'X'X'-}n_p3' \quad \text{(IIc); or}$$

$$5'n_q\text{-}N_a'\text{—Z'Z'Z'—}N_b'\text{—Y'Y'Y'—}N_b'\text{—X'X'X'—}N_a'\text{-}n_p3' \quad \text{(IId).}$$

When the antisense strand is represented by formula (IIb). $N_b$' represents an oligonucleotide sequence comprising 0-10, 0-7, 0-10, 0-7, 0-5, 0-4, 0-2 or 0 modified nucleotides. Each $N_a$'independently represents an oligonucleotide sequence comprising 2-20, 2-15, or 2-10 modified nucleotides.

When the antisense strand is represented as formula (IIc), $N_b$' represents an oligonucleotide sequence comprising 0-10, 0-7, 0-10, 0-7, 0-5, 0-4, 0-2 or 0 modified nucleotides. Each $N_a$'independently represents an oligonucleotide sequence comprising 2-20, 2-15, or 2-10 modified nucleotides.

When the antisense strand is represented as formula (IId), each $N_b$' independently represents an oligonucleotide sequence comprising 0-10, 0-7, 0-10, 0-7, 0-5, 0-4, 0-2 or 0 modified nucleotides. Each $N_a$' independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and l is 0 and the antisense strand may be represented by the formula:

$$5'n_p\text{-}N_a'\text{—Y'Y'Y'—}N_a'\text{-}n_q3' \quad \text{(Ia).}$$

When the antisense strand is represented as formula (IIa), each $N_a$' independently represents an oligonucleotide sequence comprising 2-20, 2-15, or 2-10 modified nucleotides.

Each of X', Y' and Z' may be the same or different from each other.

Each nucleotide of the sense strand and antisense strand may be independently modified with LNA, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the 1 nucleotide from the 5'-end, or optionally, the count starting at the $1^{st}$ paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the $1^{st}$ nucleotide from the 5'-end, or optionally, the count starting at the $1^{st}$ paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with an antisense strand being represented by any one of formulas (IIa), (IIb), (IIc), and (IId), respectively.

Accordingly, the RNAi agents for use in the methods of the disclosure may comprise a sense strand and an antisense strand, each strand having 14 to 30 nucleotides, the RNAi duplex represented by formula (III):

$$\text{sense: } 5'n_p\text{-}N_a\text{—(XXX)}_i\text{—}N_b\text{—YYY—}N_b\text{—(ZZZ)}_j\text{—}N_a\text{-}n_q3'$$

$$\text{antisense: } 3'n_p'\text{—}N_a'\text{—(X'X'X')}_k\text{—}N_b'\text{—Y'Y'Y'—}N_b'\text{—(Z'Z'Z')}_l\text{—}N_a'\text{-}n_q'5' \quad \text{(III)}$$

wherein:

i, j, k, and l are each independently 0 or 1;

p, p', q, and q' are each independently 0-6;

each $N_a$ and $N_a$' independently represents an oligonucleotide sequence comprising 0-25 modified nucleotides, each sequence comprising at least two differently modified nucleotides;

each $N_b$ and $N_b$' independently represents an oligonucleotide sequence comprising 0-10 modified nucleotides: wherein each $n_p$', $n_p$, $n_q$', and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and is 0; k is 0 and l is 1; or both k and l are 0; or both k and l are 1.

Exemplary combinations of the sense strand and antisense strand forming an RNAi duplex include the formulas below:

$$5'n_p\text{-}N_a\text{—YYY—}N_a\text{-}n_q3'$$

$$3'n_p'\text{—}N_a'\text{—Y'Y'Y'—}N_a'n_q'5' \quad \text{(IIIa)}$$

$$5'n_p\text{-}N_a\text{—YYY—}N_b\text{—ZZZ—}N_a\text{-}n_q3'$$

$$3'n_p\text{-}N_a'\text{—Y'Y'Y'—}N_b'\text{—Z'Z'Z'—}N_a'n_q'5' \quad \text{(IIIb)}$$

$$5'n_p\text{-}N_a\text{—XXX—}N_b\text{—YYY—}N_a\text{-}n_q3'$$

$$3'n_p'\text{—}N_a'\text{—X'X'X'—}N_b'\text{—Y'Y'Y'—}N_a'\text{-}n_q'5' \quad \text{(IIIc)}$$

$5'n_p\text{-}N_a\text{—XXX—}N_b\text{—YYY—}N_b\text{—ZZZ—}N_a\text{-}n_q3'$ $3'n_p'\text{—}N_a'\text{—X'X'X'—}N_b'\text{—Y'Y'Y'—}N_b'\text{—Z'Z'Z'—}N_a\text{-}n_q'5'$ (IIId)

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each $N_b$, $N_b'$ independently represents an oligonucleotide sequence comprising 0-10, 0-7, 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b'$ independently represents an oligonucleotide sequence comprising 0-10, 0-7, 0-10, 0-7, 0-5, 0-4, 0-2 or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$ and $N_b'$ independently comprises modifications of alternating pattern.

In one embodiment, when the RNAi agent is represented by formula (IId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'>0$ and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more C16 (or related) moieties attached through a bivalent or trivalent branched linker (described below). In another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more lipophilic, e.g., C16 (or related) moieties, optionally attached through a bivalent or trivalent branched linker.

In one embodiment, when the RNAi agent is represented by formula (IIIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more lipophilic, e.g., C16 (or related) moieties attached through a bivalent or trivalent branched linker.

In one embodiment, the RNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, the RNAi agent is a multimer containing three, four, five, six or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two RNAi agents represented by formula (III), (IIIa), (IIIb), (IIIc), and (IIId) are linked to each other at the 5' end, and one or both of the 3' ends and are optionally conjugated to a ligand. Each of the agents can target the same gene or two different genes; or each of the agents can target same gene at two different target sites.

Various publications describe multimeric RNAi agents that can be used in the methods of the disclosure. Such publications include WO2007/091269. WO2010/141511, WO2007/117686, WO2009/014887, and WO2011/031520; and U.S. Pat. No. 7,858,769, the entire contents of each of which are hereby incorporated herein by reference.

In certain embodiments, the compositions and methods of the disclosure include a vinyl phosphonate (VP) modification of an RNAi agent as described herein. In exemplary embodiments, a vinyl phosphonate of the disclosure has the following structure:

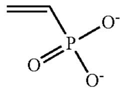

A vinyl phosphonate of the instant disclosure may be attached to either the antisense or the sense strand of a dsRNA of the disclosure. In certain preferred embodiments, a vinyl phosphonate of the instant disclosure is attached to the antisense strand of a dsRNA, optionally at the 5' end of the antisense strand of the dsRNA.

Vinyl phosphate modifications are also contemplated for the compositions and methods of the instant disclosure. An exemplary vinyl phosphate structure is:

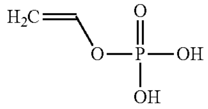

i. Thermally Destabilizing Modifications

In certain embodiments, a dsRNA molecule can be optimized for RNA interference by incorporating thermally destabilizing modifications in the seed region of the antisense strand (i.e., at positions 2-9 of the 5'-end of the antisense strand) to reduce or inhibit off-target gene silencing. It has been discovered that dsRNAs with an antisense strand comprising at least one thermally destabilizing modification of the duplex within the first 9 nucleotide positions, counting from the 5' end, of the antisense strand have reduced off-target gene silencing activity. Accordingly, in some embodiments, the antisense strand comprises at least one (e.g., one, two, three, four, five or more) thermally destabilizing modification of the duplex within the first 9 nucleotide positions of the 5' region of the antisense strand. In some embodiments, one or more thermally destabilizing modification(s) of the duplex is/are located in positions 2-9, or preferably positions 4-8, from the 5'-end of the antisense strand. In some further embodiments, the thermally destabilizing modification(s) of the duplex is/are located at position 6, 7 or 8 from the 5'-end of the antisense strand. In still some further embodiments, the thermally destabilizing modification of the duplex is located at position 7 from the 5'-end of the antisense strand. The term "thermally destabilizing modification(s)" includes modification(s) that would result with a dsRNA with a lower overall melting temperature (Tm) (preferably a Tm with one, two, three or four degrees lower than the Tm of the dsRNA without having such modification(s). In some embodiments, the thermally destabilizing modification of the duplex is located at position 2, 3, 4, 5 or 9 from the 5'-end of the antisense strand.

The thermally destabilizing modifications can include, but are not limited to, abasic modification, mismatch with the opposing nucleotide in the opposing strand; and sugar modification such as 2'-deoxy modification or acyclic nucleotide, e.g., unlocked nucleic acids (UNA) or glycol nucleic acid (GNA).

Exemplified abasic modifications include, but are not limited to the following:

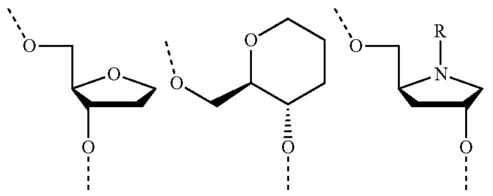

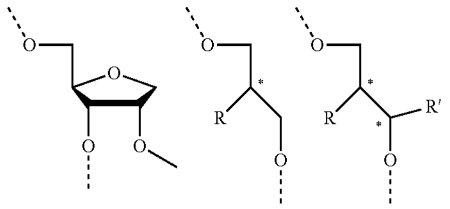

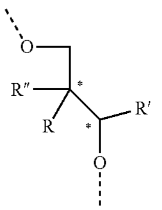

Wherein R=H, Me, Et or OMe; R'=H, Me, Et or OMe; R"=H, Me, Et or OMe

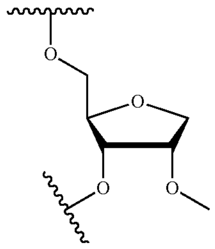

Mod2
(2'-OMe Abasic Spacer)

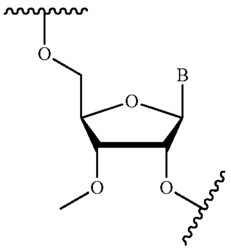

Mod3
(3'-OMe)

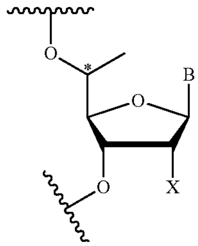

Mod4
(5'-Me)

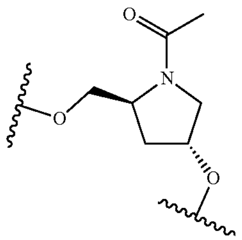

Mod6
(Hyp-spacer)

X = OMe, F wherein B is a modified or unmodified nucleobase.

Exemplified sugar modifications include, but are not limited to the following:

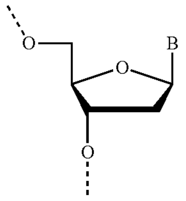

2'-deoxy

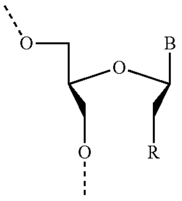

unlocked nucleic acid
R = H, OH, O-alkyl

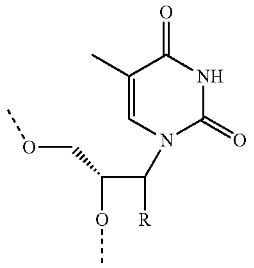

glycol nucleic acid
R = H, OH, O-alkyl

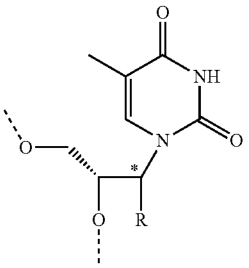

glycol nucleic acid
R = H, OH, O-alkyl

-continued

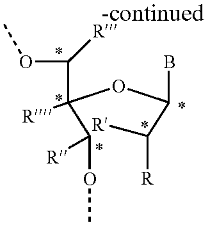

unlocked nucleic acid

R = H, OH, $CH_3$, $CH_2CH_3$, O-alkyl, $NH_2$, NHMe, $NMe_2$

R′ = H, OH, $CH_3$, $CH_2CH_3$, O-alkyl, $NH_2$, NHMe, $NMe_2$

R″ = H, OH, $CH_3$, $CH_2CH_3$, O-alkyl, $NH_2$, NHMe, $NMe_2$

R‴ = H, OH, $CH_3$, $CH_2CH_3$, O-alkyl, $NH_2$, NHMe, $NMe_2$

R⁗ = H, OH, $CH_3$, $CH_2CH_3$, O-alkyl, $NH_2$, NHMe, $NMe_2$

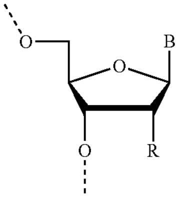

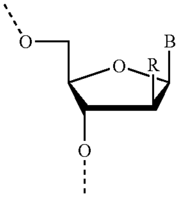

R = H, methyl, ethyl wherein B is a modified or unmodified nucleobase.

In some embodiments the thermally destabilizing modification of the duplex is selected from the group consisting of:

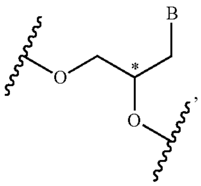

,

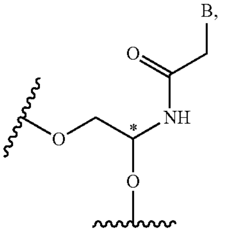

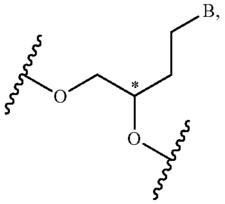

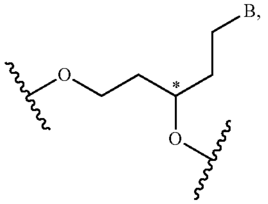

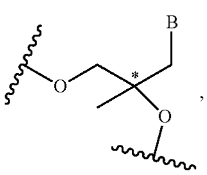

, and

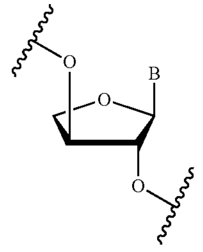

wherein B is a modified or unmodified nucleobase and the asterisk on each structure represents either R, S or racemic.

The term "acyclic nucleotide" refers to any nucleotide having an acyclic ribose sugar, for example, where any of bonds between the ribose carbons (e.g., C1'-C2', C2'-C3', C3'-C4', C4'-O4', or C1'-O4') is absent or at least one of ribose carbons or oxygen (e.g., C1', C2', C3', C4' or O4') are independently or in combination absent from the nucleotide. In some embodiments, acyclic nucleotide is

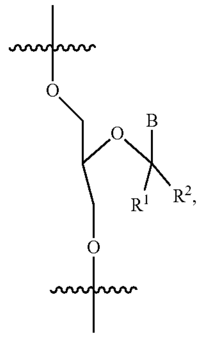

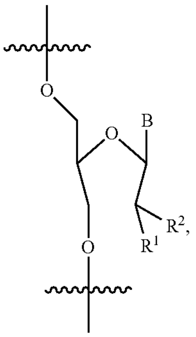

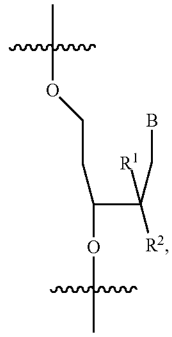

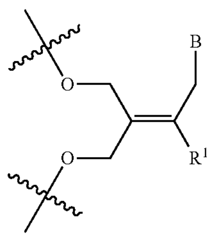

or

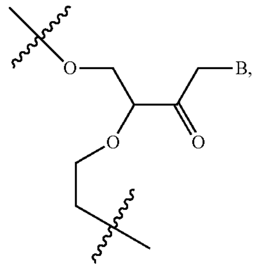

wherein B is a modified or unmodified nucleobase. $R^1$ and $R^2$ independently are H, halogen, $OR_3$, or alkyl; and $R_3$ is H, alkyl, cycloalkyl, aryl, aralkyl, heteroaryl or sugar). The term "UNA" refers to unlocked acyclic nucleic acid, wherein any of the bonds of the sugar has been removed, forming an unlocked "sugar" residue. In one example, UNA also encompasses monomers with bonds between C1'-C4' being removed (i.e. the covalent carbon-oxygen-carbon bond between the C1' and C4' carbons). In another example, the C2'-C3' bond (i.e. the covalent carbon-carbon bond between the C2 and C3' carbons) of the sugar is removed (see Mikhailov et. al., Tetrahedron Letters, 26 (17): 2059 (1985); and Fluiter et al., Mol. Biosyst., 10: 1039 (2009), which are hereby incorporated by reference in their entirety). The acyclic derivative provides greater backbone flexibility without affecting the Watson-Crick pairings. The acyclic nucleotide can be linked via 2'-5' or 3'-5' linkage.

The term 'GNA' refers to glycol nucleic acid which is a polymer similar to DNA or RNA but differing in the composition of its "backbone" in that is composed of repeating glycerol units linked by phosphodiester bonds:

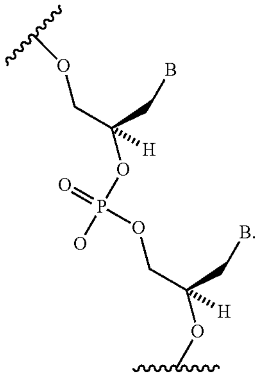

(R)-GNA

The thermally destabilizing modification of the duplex can be mismatches (i.e., noncomplementary base pairs) between the thermally destabilizing nucleotide and the opposing nucleotide in the opposite strand within the dsRNA duplex. Exemplary mismatch base pairs include G:G, G:A, G:U, G:T, A:A, A:C, C:C, C:U, C:T, U:U, T:T, U:T, or a combination thereof. Other mismatch base pairings known in the art are also amenable to the present invention. A mismatch can occur between nucleotides that are either naturally occurring nucleotides or modified nucleotides, i.e., the mismatch base pairing can occur between the nucleobases from respective nucleotides independent of the modifications on the ribose sugars of the nucleotides. In certain embodiments, the dsRNA molecule contains at least one nucleobase in the mismatch pairing that is a 2'-deoxy nucleobase; e.g., the 2'-deoxy nucleobase is in the sense strand.

In some embodiments, the thermally destabilizing modification of the duplex in the seed region of the antisense strand includes nucleotides with impaired W—C H-bonding to complementary base on the target mRNA, such as:

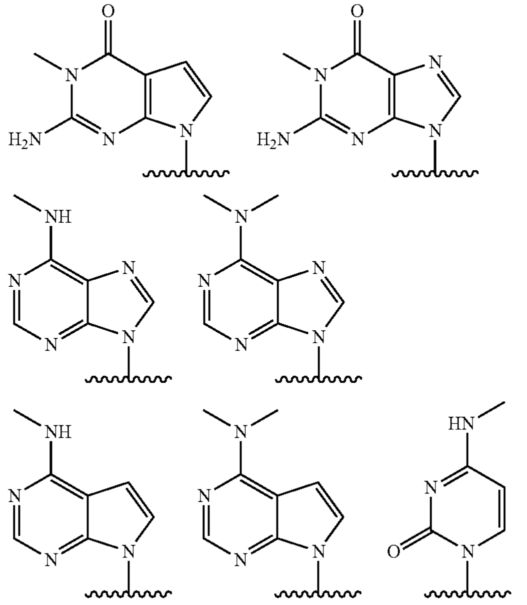

-continued

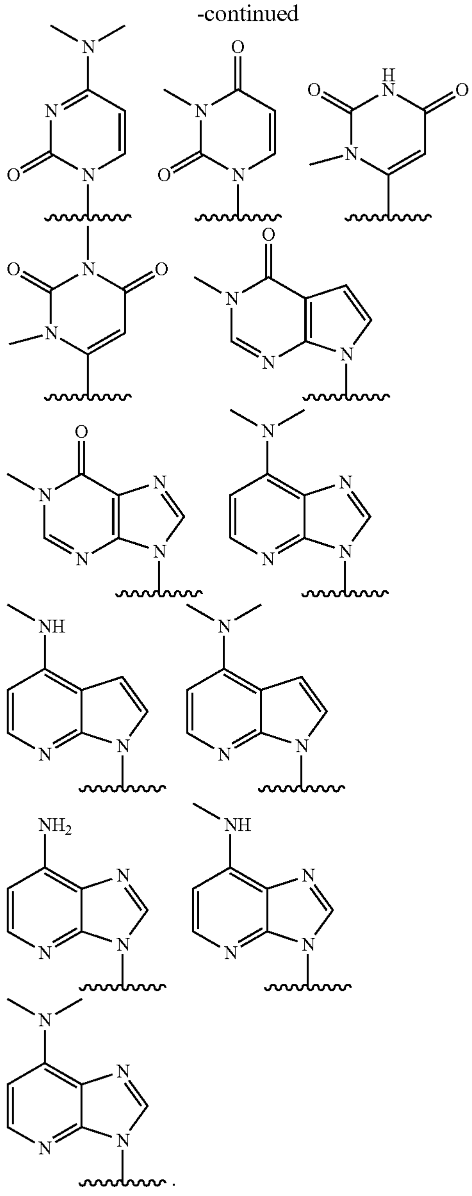

More examples of abasic nucleotide, acyclic nucleotide modifications (including UNA and GNA), and mismatch modifications have been described in detail in WO 2011/133876, which is herein incorporated by reference in its entirety.

The thermally destabilizing modifications may also include universal base with reduced or abolished capability to form hydrogen bonds with the opposing bases, and phosphate modifications.

In some embodiments, the thermally destabilizing modification of the duplex includes nucleotides with non-canonical bases such as, but not limited to, nucleobase modifications with impaired or completely abolished capability to form hydrogen bonds with bases in the opposite strand. These nucleobase modifications have been evaluated for destabilization of the central region of the dsRNA duplex as described in WO 2010/0011895, which is herein incorporated by reference in its entirety. Exemplary nucleobase modifications are:

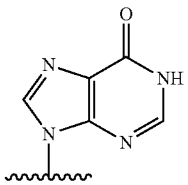

inosine

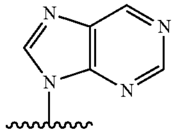

nebularine

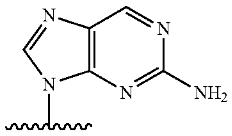

2-aminopurine

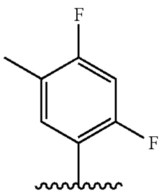

2,4-difluorotoluene

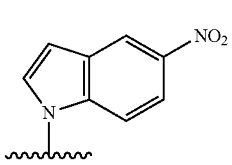

5-nitroindole

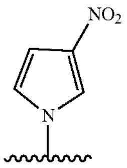

3-nitropyrrole

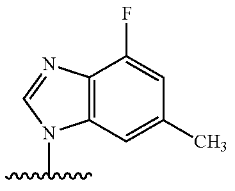

4-Fluoro-6-methylbenzimidazole

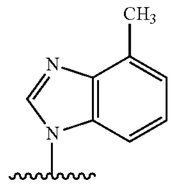

4-Methylbenzimidazole

In some embodiments, the thermally destabilizing modification of the duplex in the seed region of the antisense strand includes one or more α-nucleotide complementary to the base on the target mRNA, such as:

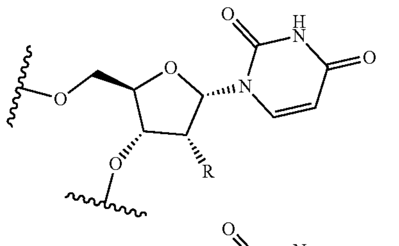

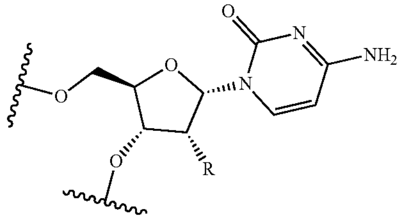

-continued

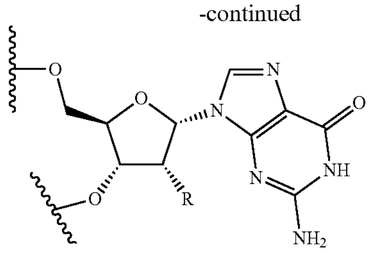

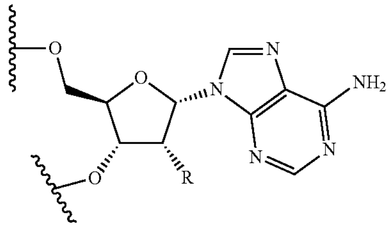

wherein R is H, OH, $OCH_3$, F, $NH_2$, NHMe, $NMe_2$ or O-alkyl.

Exemplary phosphate modifications known to decrease the thermal stability of dsRNA duplexes compared to natural phosphodiester linkages are:

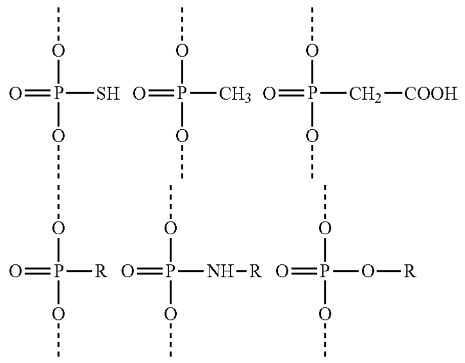

R = alkyl

The alkyl for the R group can be a $C_1$-$C_6$alkyl. Specific alkyls for the R group include, but are not limited to methyl, ethyl, propyl, isopropyl, butyl, pentyl and hexyl.

As the skilled artisan will recognize, in view of the functional role of nucleobases is defining specificity of an RNAi agent of the disclosure, while nucleobase modifications can be performed in the various manners as described herein, e.g., to introduce destabilizing modifications into an RNAi agent of the disclosure, e.g., for purpose of enhancing on-target effect relative to off-target effect, the range of modifications available and, in general, present upon RNAi agents of the disclosure tends to be much greater for non-nucleobase modifications, e.g., modifications to sugar groups or phosphate backbones of polyribonucleotides. Such modifications are described in greater detail in other sections of the instant disclosure and are expressly contemplated for RNAi agents of the disclosure, either possessing native nucleobases or modified nucleobases as described above or elsewhere herein.

In addition to the antisense strand comprising a thermally destabilizing modification, the dsRNA can also comprise one or more stabilizing modifications. For example, the dsRNA can comprise at least two (e.g., two, three, four, five, six, seven, eight, nine, ten or more) stabilizing modifications. Without limitations, the stabilizing modifications all can be present in one strand. In some embodiments, both the sense and the antisense strands comprise at least two stabilizing modifications. The stabilizing modification can occur on any nucleotide of the sense strand or antisense strand. For instance, the stabilizing modification can occur on every nucleotide on the sense strand or antisense strand; each stabilizing modification can occur in an alternating pattern on the sense strand or antisense strand; or the sense strand or antisense strand comprises both stabilizing modification in an alternating pattern. The alternating pattern of the stabilizing modifications on the sense strand may be the same or different from the antisense strand, and the alternating pattern of the stabilizing modifications on the sense strand can have a shift relative to the alternating pattern of the stabilizing modifications on the antisense strand.

In some embodiments, the antisense strand comprises at least two (e.g., two, three, four, five, six, seven, eight, nine, ten or more) stabilizing modifications. Without limitations, a stabilizing modification in the antisense strand can be present at any positions. In some embodiments, the antisense comprises stabilizing modifications at positions 2, 6, 8, 9, 14, and 16 from the 5'-end. In some other embodiments, the antisense comprises stabilizing modifications at positions 2, 6, 14, and 16 from the 5'-end. In still some other embodiments, the antisense comprises stabilizing modifications at positions 2, 14, and 16 from the 5'-end.

In some embodiments, the antisense strand comprises at least one stabilizing modification adjacent to the destabilizing modification. For example, the stabilizing modification can be the nucleotide at the 5'-end or the 3'-end of the destabilizing modification, i.e., at position −1 or +1 from the position of the destabilizing modification. In some embodiments, the antisense strand comprises a stabilizing modification at each of the 5'-end and the 3'-end of the destabilizing modification, i.e., positions −1 and +1 from the position of the destabilizing modification.

In some embodiments, the antisense strand comprises at least two stabilizing modifications at the 3'-end of the destabilizing modification, i.e., at positions +1 and +2 from the position of the destabilizing modification.

In some embodiments, the sense strand comprises at least two (e.g., two, three, four, five, six, seven, eight, nine, ten or more) stabilizing modifications. Without limitations, a stabilizing modification in the sense strand can be present at any positions. In some embodiments, the sense strand comprises stabilizing modifications at positions 7, 10, and 11 from the 5'-end. In some other embodiments, the sense strand comprises stabilizing modifications at positions 7, 9, 10, and 11 from the 5'-end. In some embodiments, the sense strand comprises stabilizing modifications at positions opposite or complimentary to positions 11, 12, and 15 of the antisense strand, counting from the 5'-end of the antisense strand. In some other embodiments, the sense strand comprises stabilizing modifications at positions opposite or complimentary to positions 11, 12, 13, and 15 of the antisense strand, counting from the 5'-end of the antisense strand. In some embodiments, the sense strand comprises a block of two, three, or four stabilizing modifications.

In some embodiments, the sense strand does not comprise a stabilizing modification in position opposite or complimentary to the thermally destabilizing modification of the duplex in the antisense strand.

Exemplary thermally stabilizing modifications include, but are not limited to, 2'-fluoro modifications. Other thermally stabilizing modifications include, but are not limited to, LNA.

In some embodiments, the dsRNA of the disclosure comprises at least four (e.g., four, five, six, seven, eight, nine, ten, or more) 2'-fluoro nucleotides. Without limitations, the 2'-fluoro nucleotides all can be present in one strand. In some embodiments, both the sense and the antisense strands comprise at least two 2'-fluoro nucleotides. The 2'-fluoro modification can occur on any nucleotide of the sense strand or antisense strand. For instance, the 2'-fluoro modification can occur on every nucleotide on the sense strand or antisense strand; each 2'-fluoro modification can occur in an alternating pattern on the sense strand or antisense strand; or the sense strand or antisense strand comprises both 2'-fluoro modifications in an alternating pattern. The alternating pattern of the 2'-fluoro modifications on the sense strand may be the same or different from the antisense strand, and the alternating pattern of the 2'-fluoro modifications on the sense strand can have a shift relative to the alternating pattern of the 2'-fluoro modifications on the antisense strand.

In some embodiments, the antisense strand comprises at least two (e.g., two, three, four, five, six, seven, eight, nine, ten, or more) 2'-fluoro nucleotides. Without limitations, a 2'-fluoro modification in the antisense strand can be present at any positions. In some embodiments, the antisense comprises 2'-fluoro nucleotides at positions 2, 6, 8, 9, 14, and 16 from the 5'-end. In some other embodiments, the antisense comprises 2'-fluoro nucleotides at positions 2, 6, 14, and 16 from the 5'-end. In still some other embodiments, the antisense comprises 2'-fluoro nucleotides at positions 2, 14, and 16 from the 5'-end.

In some embodiments, the antisense strand comprises at least one 2'-fluoro nucleotide adjacent to the destabilizing modification. For example, the 2'-fluoro nucleotide can be the nucleotide at the 5'-end or the 3'-end of the destabilizing modification, i.e., at position −1 or +1 from the position of the destabilizing modification. In some embodiments, the antisense strand comprises a 2'-fluoro nucleotide at each of the 5'-end and the 3'-end of the destabilizing modification, i.e., positions −1 and +1 from the position of the destabilizing modification.

In some embodiments, the antisense strand comprises at least two 2'-fluoro nucleotides at the 3'-end of the destabilizing modification, i.e., at positions +1 and +2 from the position of the destabilizing modification.

In some embodiments, the sense strand comprises at least two (e.g., two, three, four, five, six, seven, eight, nine, ten or more) 2'-fluoro nucleotides. Without limitations, a 2'-fluoro modification in the sense strand can be present at any positions. In some embodiments, the antisense comprises 2'-fluoro nucleotides at positions 7, 10, and 11 from the 5'-end. In some other embodiments, the sense strand comprises 2'-fluoro nucleotides at positions 7, 9, 10, and 11 from the 5'-end. In some embodiments, the sense strand comprises 2'-fluoro nucleotides at positions opposite or complimentary to positions 11, 12, and 15 of the antisense strand, counting from the 5'-end of the antisense strand. In some other embodiments, the sense strand comprises 2'-fluoro nucleotides at positions opposite or complimentary to positions 11, 12, 13, and 15 of the antisense strand, counting from the 5'-end of the antisense strand. In some embodiments, the sense strand comprises a block of two, three or four 2'-fluoro nucleotides.

In some embodiments, the sense strand does not comprise a 2'-fluoro nucleotide in position opposite or complimentary to the thermally destabilizing modification of the duplex in the antisense strand.

In some embodiments, the dsRNA molecule of the disclosure comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a blunt end at 5'-end of the antisense strand. Preferably, the 2 nt overhang is at the 3'-end of the antisense.

In some embodiments, the dsRNA molecule of the disclosure comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand). For example, the thermally destabilizing nucleotide occurs between positions opposite or complimentary to positions 14-17 of the 5'-end of the sense strand, and wherein the dsRNA optionally further has at least one (e.g., one, two, three, four, five, six or all seven) of the following characteristics: (i) the antisense comprises 2, 3, 4, 5, or 6 2'-fluoro modifications; (ii) the antisense comprises 1, 2, 3, 4, or 5 phosphorothioate internucleotide linkages; (iii) the sense strand is conjugated with a ligand; (iv) the sense strand comprises 2, 3, 4, or 5 2'-fluoro modifications; (v) the sense strand comprises 1, 2, 3, 4, or 5 phosphorothioate internucleotide linkages; and (vi) the dsRNA comprises at least four 2'-fluoro modifications; and (vii) the dsRNA comprises a duplex region of 12-30 nucleotide pairs in length.

In some embodiments, the dsRNA molecule of the disclosure comprises a sense and antisense strands, wherein said dsRNA molecule comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5'end, wherein the 3' end of said sense strand and the 5' end of said antisense strand form a blunt end and said antisense strand is 1-4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said dsRNA molecule is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5, or 6 2'-fluoro modifications; (ii) the antisense comprises 1, 2, 3, 4, or 5 phosphorothioate internucleotide linkages; (iii) the sense strand is conjugated with a ligand; (iv) the sense strand comprises 2, 3, 4, or 5 2'-fluoro modifications; (v) the sense strand comprises 1, 2, 3, 4, or 5 phosphorothioate internucleotide linkages; and (vi) the dsRNA comprises at least four 2'-fluoro modifications; and (vii) the dsRNA has a duplex region of 12-29 nucleotide pairs in length.

In some embodiments, every nucleotide in the sense strand and antisense strand of the dsRNA molecule may be modified. Each nucleotide may be modified with the same or different modification which can include one or more alteration of one or both of the non-linking phosphate oxygens or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases, the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of an RNA. E.g., a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA. HNA, CeNA, 2'-methoxyethyl, 2'-O-methyl, 2'-O-allyl, 2'-C-allyl, 2'-deoxy, or 2'-fluoro. The strands can contain more than one modification. In some embodiments, each residue of the sense strand and antisense strand is independently modified with 2'-O-methyl or 2'-fluoro. It is to be understood that these modifications are in addition to the at least one thermally destabilizing modification of the duplex present in the antisense strand.

At least two different modifications are typically present on the sense strand and antisense strand. Those two modifications may be the 2'-deoxy, 2'-O-methyl or 2'-fluoro modifications, acyclic nucleotides or others. In some embodiments, the sense strand and antisense strand each comprises two differently modified nucleotides selected from 2'-O-methyl or 2'-deoxy. In some embodiments, each residue of the sense strand and antisense strand is independently modified with 2'-O-methyl nucleotide, 2'-deoxy nucleotide, 2'-deoxy-2'-fluoro nucleotide, 2'-O—N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, or 2'-ara-F nucleotide. Again, it is to be understood that these modifications are in addition to the at least one thermally destabilizing modification of the duplex present in the antisense strand.

In some embodiments, the dsRNA molecule of the disclosure comprises modifications of an alternating pattern, particular in the B1, B2, B3, B1', B2', B3', B4' regions. The term "alternating motif" or "alternative pattern" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAABBAABB . . . ," "AABAABAABAAB . . . ," "AAABAAABAAAB . . . ," "AAABBBAAABBB . . . ," or "ABCABCABCABC . . . ," etc.
The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In some embodiments, the dsRNA molecule of the disclosure comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 3'-5' of the strand within the duplex region. As another example, the alternating motif in the sense strand may start with "AABBAABB" from 5'-3' of the strand and the alternating motif in the antisense strand may start with "BBAABBAA" from 3'-5' of the strand within the duplex region, so that there is a complete or partial shift of the modification patterns between the sense strand and the antisense strand.

The dsRNA molecule of the disclosure may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In some embodiments, the dsRNA molecule comprises the phosphorothioate or methylphosphonate internucleotide linkage modification in the overhang region. For example, the overhang region comprises two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. Preferably, these terminal three nucleotides may be at the 3'-end of the antisense strand.

In some embodiments, the sense strand of the dsRNA molecule comprises 1-10 blocks of two to ten phosphorothioate or methylphosphonate internucleotide linkages separated by 1, 2, 3, 4, 5, 6, 7, 8, 9, 10, 11, 12, 13, 14, 15, or 16 phosphate internucleotide linkages, wherein one of the phosphorothioate or methylphosphonate internucleotide linkages is placed at any position in the oligonucleotide sequence and the said sense strand is paired with an antisense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of two phosphorothioate or methylphosphonate internucleotide linkages separated by 1, 2, 3, 4, 5, 6, 7, 8, 9, 10, 11, 12, 13, 14, 15, 16, 17, or 18 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of three phosphorothioate or methylphosphonate internucleotide linkages separated by 1, 2, 3, 4, 5, 6, 7, 8, 9, 10, 11, 12, 13, 14, 15, or 16 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of four phosphorothioate or methylphosphonate internucleotide linkages separated by 1, 2, 3, 4, 5, 6, 7, 8, 9, 10, 11, 12, 13, or 14 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of five phosphorothioate or methylphosphonate internucleotide linkages separated by 1, 2, 3, 4, 5, 6, 7, 8, 9, 10, 11, or 12 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of six phosphorothioate or methylphosphonate internucleotide linkages separated by 1, 2, 3, 4, 5, 6, 7, 8, 9, or 10 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of seven phosphorothioate or methylphosphonate internucleotide linkages separated by 1, 2, 3, 4, 5, 6, 7, or 8 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of eight phosphorothioate or methylphosphonate internucleotide linkages separated by 1, 2, 3, 4, 5, or 6 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of nine phosphorothioate or methylphosphonate internucleotide linkages separated by 1, 2, 3, or 4 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the dsRNA molecule of the disclosure further comprises one or more phosphorothioate or methylphosphonate internucleotide linkage modification within 1-10 of the termini position(s) of the sense or antisense strand. For example, at least 2, 3, 4, 5, 6, 7, 8, 9, or 10 nucleotides may be linked through phosphorothioate or methylphosphonate internucleotide linkage at one end or both ends of the sense or antisense strand.

In some embodiments, the dsRNA molecule of the disclosure further comprises one or more phosphorothioate or methylphosphonate internucleotide linkage modification within 1-10 of the internal region of the duplex of each of the sense or antisense strand. For example, at least 2, 3, 4, 5, 6, 7, 8, 9, or 10 nucleotides may be linked through phosphorothioate methylphosphonate internucleotide linkage at position 8-16 of the duplex region counting from the 5'-end of the sense strand; the dsRNA molecule can optionally further comprise one or more phosphorothioate or methylphosphonate internucleotide linkage modification within 1-10 of the termini position(s).

In some embodiments, the dsRNA molecule of the disclosure further comprises one to five phosphorothioate or methylphosphonate internucleotide linkage modification(s) within position 1-5 and one to five phosphorothioate or methylphosphonate internucleotide linkage modification(s) within position 18-23 of the sense strand (counting from the 5'-end), and one to five phosphorothioate or methylphosphonate internucleotide linkage modification at positions 1 and 2 and one to five within positions 18-23 of the antisense strand (counting from the 5'-end).

In some embodiments, the dsRNA molecule of the disclosure further comprises one phosphorothioate internucleotide linkage modification within position 1-5 and one phosphorothioate or methylphosphonate internucleotide linkage modification within position 18-23 of the sense strand (counting from the 5'-end), and one phosphorothioate internucleotide linkage modification at positions 1 and 2 and two phosphorothioate or methylphosphonate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the disclosure further comprises one phosphorothioate internucleotide linkage modification within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the disclosure further comprises one phosphorothioate internucleotide linkage modification within position 1-5 and one within position 18-23 of the sense strand (counting from the 5'-end), and two phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the disclosure further comprises one phosphorothioate internucleotide linkage modification within position 1-5 (counting from the 5'-end) of the sense strand, and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the disclosure further comprises two phosphorothioate internucleotide linkage modifications within position 1-5 (counting from the 5'-end) of the sense strand, and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and one within position 18-23 of the sense strand (counting from the 5'-end), and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the disclosure further comprises two phosphorothioate internucleotide linkage modifications within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the disclosure further comprises two phosphorothioate internucleotide linkage modifications at position 1 and 2, and two phosphorothioate internucleotide linkage modifications at position 20 and 21 of the sense strand (counting from the 5'-end), and one phosphorothioate internucleotide linkage modification at positions 1 and one at position 21 of the antisense strand (counting from the 5'-end).

In some embodiments, the dsRNA molecule of the disclosure further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 20 and 21 the antisense strand (counting from the 5'-end).

In some embodiments, the dsRNA molecule of the disclosure further comprises two phosphorothioate internucleotide linkage modifications at position 1 and 2, and two phosphorothioate internucleotide linkage modifications at position 21 and 22 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the disclosure further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 21 and 22 the antisense strand (counting from the 5'-end).

In some embodiments, the dsRNA molecule of the disclosure further comprises two phosphorothioate internucleotide linkage modifications at position 1 and 2, and two phosphorothioate internucleotide linkage modifications at position 22 and 23 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the disclosure further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 23 and 23 the antisense strand (counting from the 5'-end).

In some embodiments, compound of the disclosure comprises a pattern of backbone chiral centers. In some embodiments, a common pattern of backbone chiral centers comprises at least 5 internucleotidic linkages in the Sp configuration. In some embodiments, a common pattern of backbone chiral centers comprises at least 6 internucleotidic linkages in the Sp configuration. In some embodiments, a common pattern of backbone chiral centers comprises at least 7 internucleotidic linkages in the Sp configuration. In some embodiments, a common pattern of backbone chiral centers comprises at least 8 internucleotidic linkages in the Sp configuration. In some embodiments, a common pattern of backbone chiral centers comprises at least 9 internucleotidic linkages in the Sp configuration. In some embodiments, a common pattern of backbone chiral centers comprises at least 10 internucleotidic linkages in the Sp configuration. In some embodiments, a common pattern of backbone chiral centers comprises at least 11 internucleotidic linkages in the Sp configuration. In some embodiments, a common pattern of backbone chiral centers comprises at least 12 internucleotidic linkages in the Sp configuration. In some embodiments, a common pattern of backbone chiral centers comprises at least 13 internucleotidic linkages in the Sp configuration. In some embodiments, a common pattern of backbone chiral centers comprises at least 14 internucleotidic linkages in the Sp configuration. In some embodiments, a common pattern of backbone chiral centers comprises at least 15 internucleotidic linkages in the Sp configuration. In some embodiments, a common pattern of backbone chiral centers comprises at least 16 internucleotidic linkages in the Sp configuration. In some embodiments, a common pattern of backbone chiral centers comprises at least 17 internucleotidic linkages in the Sp configuration. In some embodiments, a common pattern of backbone chiral centers comprises at least 18 internucleotidic linkages in the Sp configuration. In some embodiments, a common pattern of backbone chiral centers comprises at least 19 internucleotidic linkages in the Sp configuration. In some embodiments, a common pattern of backbone chiral centers comprises no more than 8 internucleotidic linkages in the Rp configuration. In some embodiments, a common pattern of backbone chiral centers comprises no more than 7 internucleotidic linkages in the Rp configuration. In some embodiments, a common pattern of backbone chiral centers comprises no more than 6 internucleotidic linkages in the Rp configuration. In some embodiments, a common pattern of backbone chiral centers comprises no more than 5 internucleotidic linkages in the Rp configuration. In some embodiments, a common pattern of backbone chiral centers comprises no more than 4 internucleotidic linkages in the Rp configuration. In some embodiments, a common pattern of backbone chiral centers comprises no more than 3 internucleotidic linkages in the Rp configuration. In some embodiments, a common pattern of backbone chiral centers comprises no more than 2 internucleotidic linkages in the Rp configuration. In some embodiments, a common pattern of backbone chiral centers comprises no more than 1 internucleotidic linkages in the Rp configuration. In some embodiments, a common pattern of backbone chiral centers comprises no more than 8 internucleotidic linkages which are not chiral (as a non-limiting example, a phosphodiester). In some embodiments, a common pattern of backbone chiral centers comprises no more than 7 internucleotidic linkages which are not chiral. In some embodiments, a common pattern of backbone chiral centers comprises no more than 6 internucleotidic linkages which are not chiral. In some embodiments, a common pattern of backbone chiral centers comprises no more than 5 internucleotidic linkages which are not chiral. In some embodiments, a common pattern of backbone chiral centers comprises no more than 4 internucleotidic linkages which are not chiral. In some embodiments, a common pattern of backbone chiral centers comprises no more than 3 internucleotidic linkages which are not chiral. In some embodiments, a common pattern of backbone chiral centers comprises no more than 2 internucleotidic linkages which are not chiral. In some embodiments, a common pattern of backbone chiral centers comprises no more than 1 internucleotidic linkages which are not chiral. In some embodiments, a common pattern of backbone chiral centers comprises at least 10 internucleotidic linkages in the Sp configuration, and no more than 8 internucleotidic linkages which are not chiral. In some embodiments, a common pattern of backbone chiral centers comprises at least 11 internucleotidic linkages in the Sp configuration, and no more than 7 internucleotidic linkages which are not chiral. In some embodiments, a common pattern of backbone chiral centers comprises at least 12 internucleotidic linkages in the Sp configuration, and no more than 6 internucleotidic linkages which are not chiral. In some embodiments, a common pattern of backbone chiral centers comprises at least 13 internucleotidic linkages in the Sp configuration, and no more than 6 internucleotidic linkages which are not chiral. In some embodiments, a common pattern of backbone chiral centers comprises at least 14 internucleotidic linkages in the Sp configuration, and no more than 5 internucleotidic linkages which are not chiral. In some embodiments, a common pattern of backbone chiral centers comprises at least 15 internucleotidic linkages in the Sp configuration, and no more than 4 internucleotidic linkages which are not chiral. In some embodiments, the internucleotidic linkages in the Sp configuration are optionally contiguous or not contiguous. In some embodiments, the internucleotidic linkages in the Rp configuration are optionally contiguous or not contiguous. In some embodiments, the internucleotidic linkages which are not chiral are optionally contiguous or not contiguous.

In some embodiments, compound of the disclosure comprises a block is a stereochemistry block. In some embodiments, a block is an Rp block in that each internucleotidic linkage of the block is Rp. In some embodiments, a 5'-block is an Rp block. In some embodiments, a 3'-block is an Rp block. In some embodiments, a block is an Sp block in that each internucleotidic linkage of the block is Sp. In some embodiments, a 5'-block is an Sp block. In some embodiments, a 3'-block is an Sp block. In some embodiments, provided oligonucleotides comprise both Rp and Sp blocks. In some embodiments, provided oligonucleotides comprise one or more Rp but no Sp blocks. In some embodiments, provided oligonucleotides comprise one or more Sp but no Rp blocks. In some embodiments, provided oligonucleotides comprise one or more PO blocks wherein each internucleotidic linkage in a natural phosphate linkage.

In some embodiments, compound of the disclosure comprises a 5'-block is an Sp block wherein each sugar moiety comprises a 2'-F modification. In some embodiments, a 5'-block is an Sp block wherein each of internucleotidic linkage is a modified internucleotidic linkage and each sugar moiety comprises a 2'-F modification. In some embodiments, a 5'-block is an Sp block wherein each of internucleotidic linkage is a phosphorothioate linkage and each sugar moiety comprises a 2'-F modification. In some embodiments, a 5'-block comprises 4 or more nucleoside units. In some embodiments, a 5'-block comprises 5 or more nucleoside units. In some embodiments, a 5'-block comprises 6 or more nucleoside units. In some embodiments, a 5'-block comprises 7 or more nucleoside units. In some embodiments, a 3'-block is an Sp block wherein each sugar moiety comprises a 2'-F modification. In some embodiments, a 3'-block is an Sp block wherein each of internucleotidic linkage is a modified internucleotidic linkage and each sugar moiety comprises a 2'-F modification. In some embodiments, a 3'-block is an Sp block wherein each of internucleotidic linkage is a phosphorothioate linkage and each sugar moiety comprises a 2'-F modification. In some embodiments, a 3'-block comprises 4 or more nucleoside units. In some embodiments, a 3'-block comprises 5 or more nucleoside units. In some embodiments, a 3'-block comprises 6 or more nucleoside units. In some embodiments, a 3'-block comprises 7 or more nucleoside units.

In some embodiments, compound of the disclosure comprises a type of nucleoside in a region or an oligonucleotide is followed by a specific type of internucleotidic linkage, e.g., natural phosphate linkage, modified internucleotidic linkage, Rp chiral internucleotidic linkage, Sp chiral internucleotidic linkage, etc. In some embodiments, A is followed by Sp. In some embodiments, A is followed by Rp. In some embodiments, A is followed by natural phosphate linkage (PO). In some embodiments, U is followed by Sp. In some embodiments, U is followed by Rp. In some embodiments, U is followed by natural phosphate linkage (PO). In some embodiments. C is followed by Sp. In some embodiments, C is followed by Rp. In some embodiments. C is followed by natural phosphate linkage (PO). In some embodiments, G is followed by Sp. In some embodiments, G is followed by Rp. In some embodiments, G is followed by natural phosphate linkage (PO). In some embodiments, C and U are followed by Sp. In some embodiments, C and U are followed by Rp. In some embodiments. C and U are followed by natural phosphate linkage (PO). In some embodiments. A and G are followed by Sp. In some embodiments, A and G are followed by Rp.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 3, 4 or 5 phosphorothioate internucleotide linkages; (v) the dsRNA comprises at least four 2'-fluoro modifications; (vi) the dsRNA comprises a duplex region of 1240 nucleotide pairs in length; and (vii) the dsRNA has a blunt end at 5'-end of the antisense strand.

In some embodiments, the dsRNA molecule of the disclosure comprises mismatch(es) with the target, within the duplex, or combinations thereof. The mismatch can occur in the overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In some embodiments, the dsRNA molecule of the disclosure comprises at least one of the first 1, 2, 3, 4, or 5 base pairs within the duplex regions from the 5'-end of the antisense strand can be chosen independently from the group of: A:U, G:U, I:C, and mismatched pairs, e.g., non-canonical or other than canonical pairings or pairings which include a universal base, to promote the dissociation of the antisense strand at the 5'-end of the duplex.

In some embodiments, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

It was found that introducing 4'-modified or 5'-modified nucleotide to the 3'-end of a phosphodiester (PO), phosphorothioate (PS), or phosphorodithioate (PS2) linkage of a dinucleotide at any position of single stranded or double stranded oligonucleotide can exert steric effect to the internucleotide linkage and, hence, protecting or stabilizing it against nucleases.

In some embodiments, 5'-modified nucleoside is introduced at the 3'-end of a dinucleotide at any position of single stranded or double stranded siRNA. For instance, a 5'-alkylated nucleoside may be introduced at the 3'-end of a dinucleotide at any position of single stranded or double stranded siRNA. The alkyl group at the 5' position of the ribose sugar can be racemic or chirally pure R or S isomer. An exemplary 5'-alkylated nucleoside is 5'-methyl nucleoside. The 5'-methyl can be either racemic or chirally pure R or S isomer.

In some embodiments, 4'-modified nucleoside is introduced at the 3'-end of a dinucleotide at any position of single stranded or double stranded siRNA. For instance, a 4'-alkylated nucleoside may be introduced at the 3'-end of a dinucleotide at any position of single stranded or double stranded siRNA. The alkyl group at the 4' position of the ribose sugar can be racemic or chirally pure R or S isomer. An exemplary 4'-alkylated nucleoside is 4'-methyl nucleoside. The 4'-methyl can be either racemic or chirally pure R or S isomer. Alternatively, a 4'-O-alkylated nucleoside may be introduced at the 3'-end of a dinucleotide at any position of single stranded or double stranded siRNA. The 4'-(O-alkyl of the ribose sugar can be racemic or chirally pure R or S isomer. An exemplary 4-O-alkylated nucleoside is 4'-O-methyl nucleoside. The 4'-O-methyl can be either racemic or chirally pure R or S isomer.

In some embodiments, 5'-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 5'-alkylated nucleoside is 5'-methyl nucleoside. The 5'-methyl can be either racemic or chirally pure R or S isomer.

In some embodiments, 4'-alkylated nucleoside is introduced at any position on the sense strand or antisense strand of a dsRNA, and such modification maintains or improves potency of the dsRNA. The 4'-alkyl can be either racemic or chirally pure R or S isomer. An exemplary 4'-alkylated nucleoside is 4'-methyl nucleoside. The 4'-methyl can be either racemic or chirally pure R or S isomer.

In some embodiments, 4'-O-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 4'-O-alkylated nucleoside is 4'-O-methyl nucleoside. The 4'-O-methyl can be either racemic or chirally pure R or S isomer.

In some embodiments, the dsRNA molecule of the disclosure can comprise 2'-5' linkages (with 2'-H, 2'-OH and 2'-OMe and with P═O or P═S). For example, the 2'-5' linkages modifications can be used to promote nuclease resistance or to inhibit binding of the sense to the antisense strand, or can be used at the 5' end of the sense strand to avoid sense strand activation by RISC.

In another embodiment, the dsRNA molecule of the disclosure can comprise L sugars (e.g., L ribose, L-arabinose with 2'-H, 2'-OH and 2'-OMe). For example, these L sugars modifications can be used to promote nuclease resistance or to inhibit binding of the sense to the antisense strand, or can be used at the 5' end of the sense strand to avoid sense strand activation by RISC.

Various publications describe multimeric siRNA which can all be used with the dsRNA of the disclosure. Such publications include WO2007/091269, U.S. Pat. No. 7,858,769, WO2010/141511, WO2007/117686, WO2009/014887, and WO2011/031520 which are hereby incorporated by their entirely.

As described in more detail below, the RNAi agent that contains conjugations of one or more carbohydrate moieties to an RNAi agent can optimize one or more properties of the RNAi agent. In many cases, the carbohydrate moiety will be attached to a modified subunit of the RNAi agent. For example, the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The RNAi agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

In certain specific embodiments, the RNAi agent for use in the methods of the disclosure is an agent selected from the group of agents listed in Table 3 or 4. These agents may further comprise a ligand.

IV. iRNAs Conjugated to Ligands

Another modification of the RNA of an iRNA of the invention involves chemically linking to the iRNA one or more ligands, moieties or conjugates that enhance the activity, cellular distribution or cellular uptake of the iRNA, e.g., into a cell. Such moieties include but are not limited to lipid moieties such as a cholesterol moiety (Letsinger et al., *Proc. Natl. Acid. Sci. USA,* 1989, 86: 6553-6556), cholic acid (Manoharan et al., *Biorg. Med. Chem. Let.,* 1994, 4:1053-1060), a thioether, e.g., beryl-S-tritylthiol (Manoharan et al., *Ann. N.Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J.* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylamino-carbonyloxycholesterol moiety (Crooke et al., *J. Pharmacol. Exp. Ther.,* 1996, 277:923-937).

In certain embodiments, a ligand alters the distribution, targeting or lifetime of an iRNA agent into which it is incorporated. In some embodiments, a ligand provides an enhanced affinity for a selected target, e.g., molecule, cell or cell type, compartment, e.g., a cellular or organ compartment, tissue, organ or region of the body, as, e.g., compared to a species absent such a ligand. Typical ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dexran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an α helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. In certain embodiments, the ligand is a multivalent galactose, e.g., an N-acetyl-galactosamine.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents. PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated iRNAs of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems™ (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In certain embodiments, the ligand or conjugate is a lipid or lipid-based molecule. Such a lipid or lipid-based molecule can typically bind a serum protein, such as human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, or (c) can be used to adjust binding to a serum protein, e.g., HSA.

A lipid-based ligand can be used to modulate, e.g., control (e.g., inhibit) the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In certain embodiments, the lipid-based ligand binds HSA. For example, the ligand can bind HSA with a sufficient affinity such that distribution of the conjugate to a non-kidney tissue is enhanced. However, the affinity is typically not so strong that the HSA-ligand binding cannot be reversed.

In certain embodiments, the lipid-based ligand binds HSA weakly or not at all, such that distribution of the conjugate to the kidney is enhanced. Other moieties that target to kidney cells can also be used in place of or in addition to the lipid-based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

B. Cell Permeation Agents

In another aspect, the ligand is a cell-permeation agent, such as a helical cell-permeation agent. In certain embodiments, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is typically an α-helical agent and can have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 9). An RFGF analogue (e.g., amino acid sequence AALLPVLLAAP (SEQ ID NO: 10)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 11)) and the *Drosophila* Antennapedia protein (RQIKIWFQNRRMKWKK (SEQ ID NO: 12)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., *Nature,* 354:82-84, 1991).

Typically, the peptide or peptidomimetic tethered to a dsRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidomimetics may include D-amino acids, as well as synthetic RGD mimics. In addition to RGD, one can use other moieties that target the integrin ligand. Preferred conjugates of this ligand target PECAM-1 or VEGF.

An RGD peptide moiety can be used to target a particular cell type, e.g., a tumor cell, such as an endothelial tumor cell or a breast cancer tumor cell (Zitzmann et al., *Cancer Res.,* 62:513943, 2002). An RGD peptide can facilitate targeting of an dsRNA agent to tumors of a variety of other tissues, including the lung, kidney, spleen, or liver (Aoki et al., (*Cancer Gene Therapy* 8:783-787, 2001). Typically, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., *Jour. Nucl. Med.,* 42:326-336, 2001).

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., *Nucl. Acids Res.* 31:2717-2724, 2003).

C. Carbohydrate Conjugates

In some embodiments of the compositions and methods of the invention, an iRNA further comprises a carbohydrate. The carbohydrate conjugated iRNA are advantageous for the in vivo delivery of nucleic acids, as well as compositions suitable for in vivo therapeutic use, as described herein. As used herein. "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and tri-saccharides include sugars having two or three monosaccharide units (e.g., C5, C6, C7, or C8).

In certain embodiments, a carbohydrate conjugate comprises a monosaccharide.

In certain embodiments, the monosaccharide is an N-acetylgalactosamine (GalNAc). GalNAc conjugates, which comprise one or more N-acetylgalactosamine (GalNAc) derivatives, are described, for example, in U.S. Pat. No. 8,106,022, the entire content of which is hereby incorporated herein by reference. In some embodiments, the GalNAc conjugate serves as a ligand that targets the iRNA to particular cells. In some embodiments, the GalNAc conjugate targets the iRNA to liver cells, e.g., by serving as a ligand for the asialoglycoprotein receptor of liver cells (e.g., hepatocytes).

In some embodiments, the carbohydrate conjugate comprises one or more GalNAc derivatives. The GalNAc derivatives may be attached via a linker, e.g., a bivalent or trivalent branched linker. In some embodiments the GalNAc conjugate is conjugated to the 3' end of the sense strand. In some embodiments, the GalNAc conjugate is conjugated to the iRNA agent (e.g., to the 3' end of the sense strand) via a linker, e.g., a linker as described herein. In some embodiments the GalNAc conjugate is conjugated to the 5' end of the sense strand. In some embodiments, the GalNAc conjugate is conjugated to the iRNA agent (e.g., to the 5' end of the sense strand) via a linker, e.g., a linker as described herein.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker. In other embodiments of the invention, the GalNAc or GalNAc derivative is attached to an iRNA agent of the invention via a tetravalent linker.

In certain embodiments, the double stranded RNAi agents of the invention comprise one GalNAc or GalNAc derivative attached to the iRNA agent. In certain embodiments, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker. The hairpin loop may also be formed by an extended overhang in one strand of the duplex.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker. The hairpin loop may also be formed by an extended overhang in one strand of the duplex.

In some embodiments, the GalNAc conjugate is
Formula I
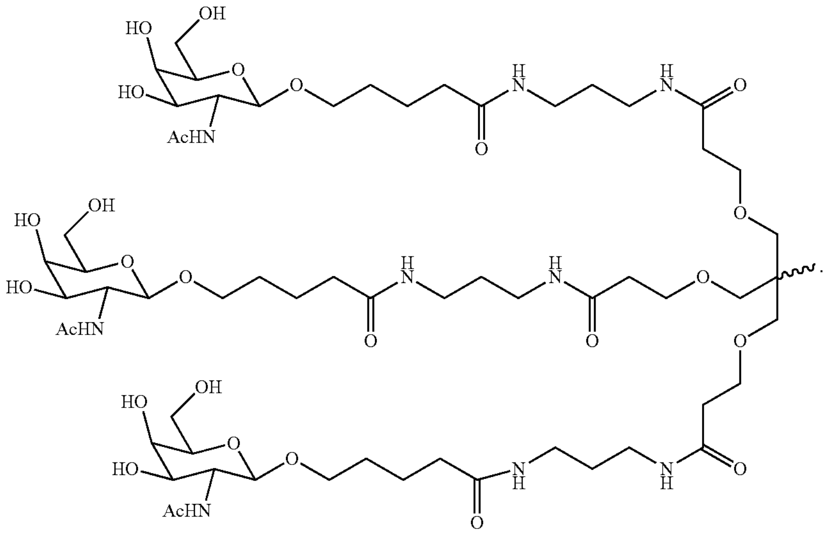
In some embodiments, the RNAi agent is attached to the carbohydrate conjugate via a linker as shown in the following schematic, wherein X is O or S
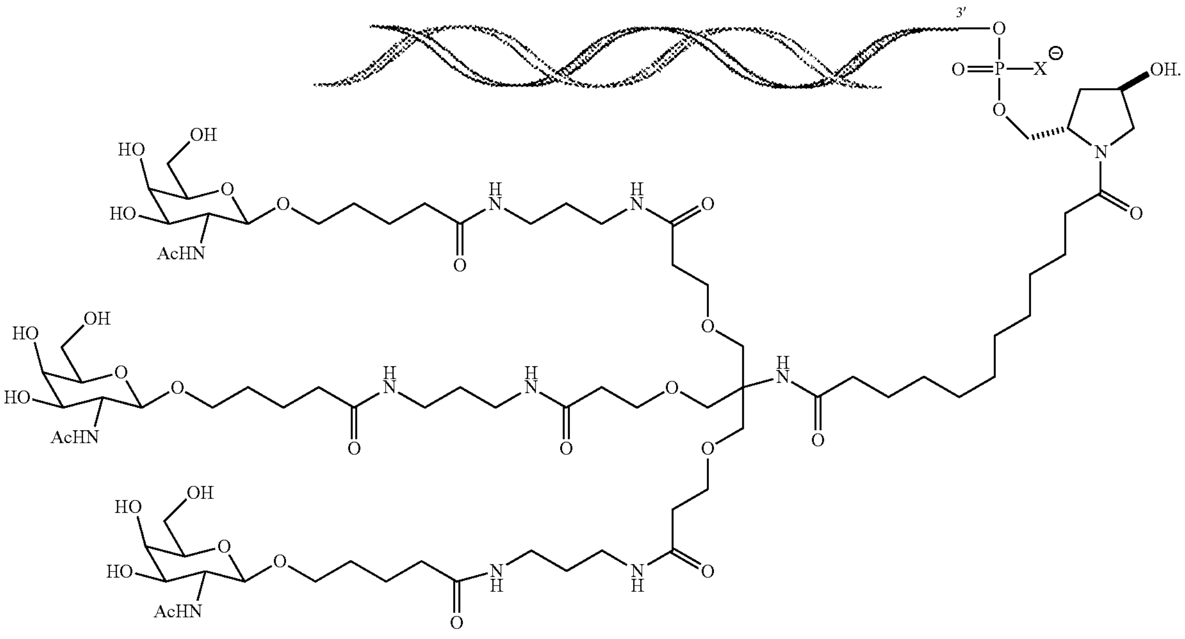

In some embodiments, the RNAi agent is conjugated to L96 as defined in Table 2 and shown below:
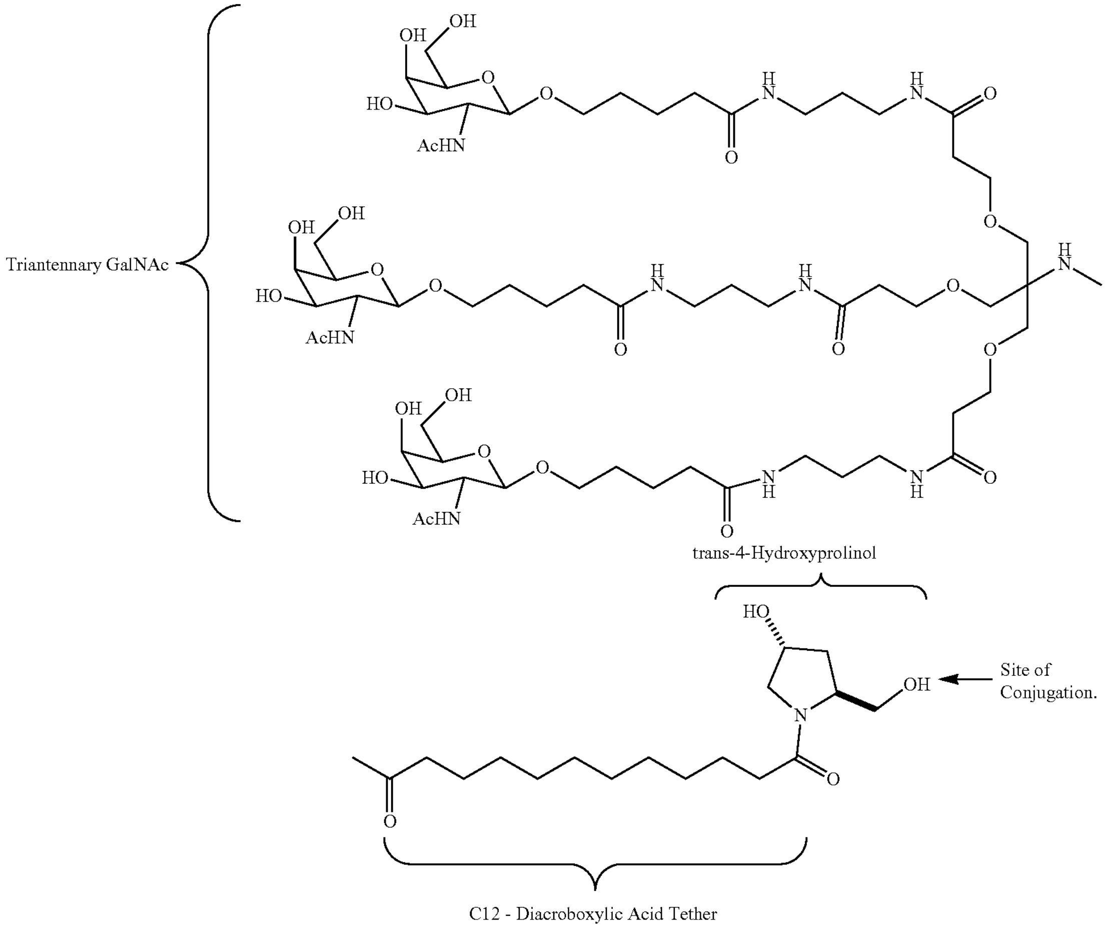
In certain embodiments, a carbohydrate conjugate for use in the compositions and methods of the invention is selected from the group consisting of:
Formula I
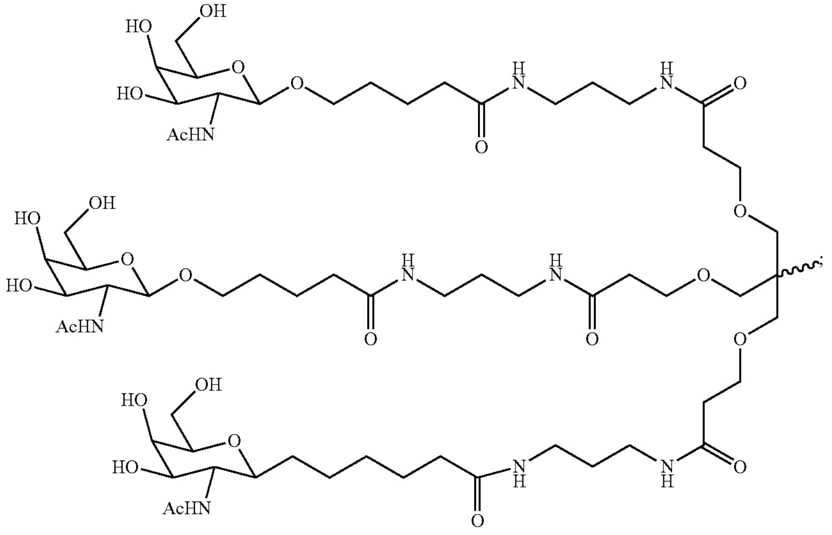

-continued
Formula II
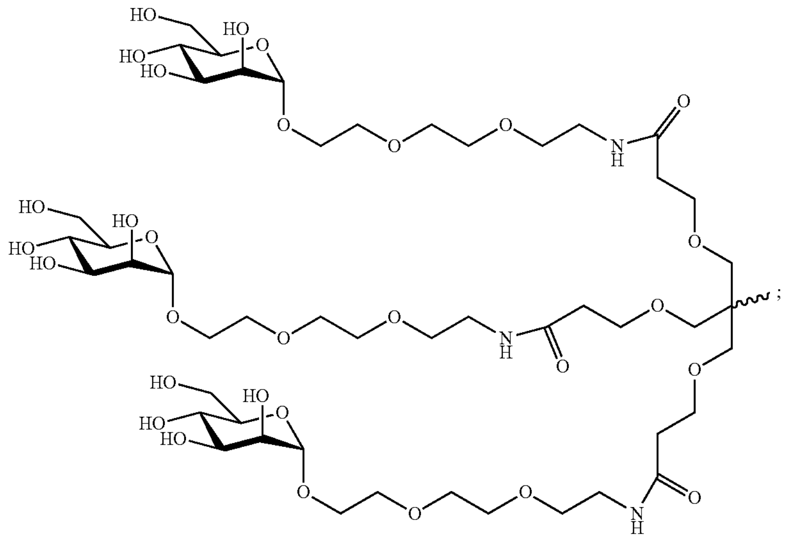
Formula III
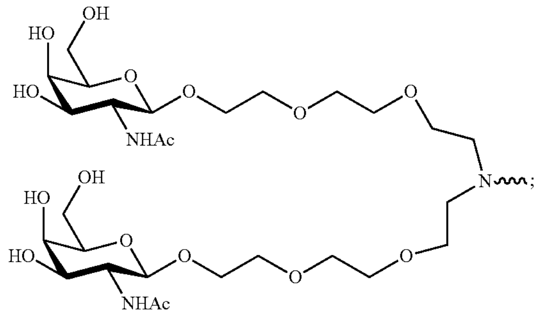
Formula IV
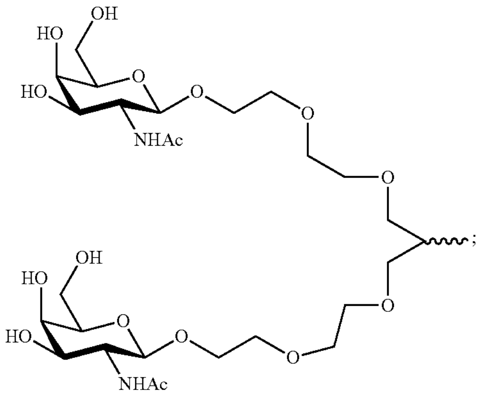
Formula V
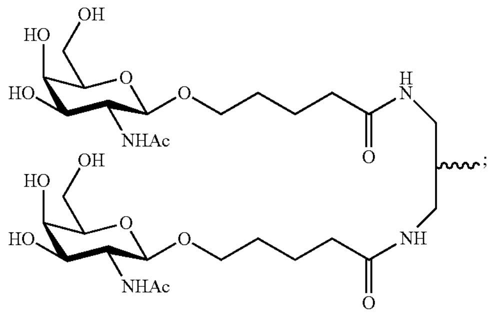
Formula VI
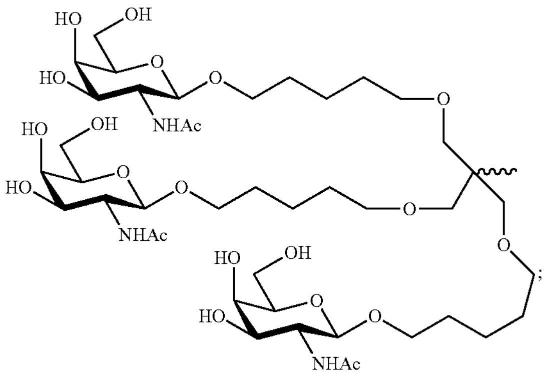
Formula VII
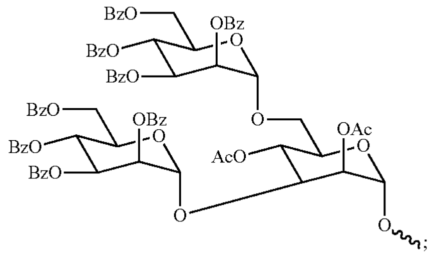

-continued
Formula VIII
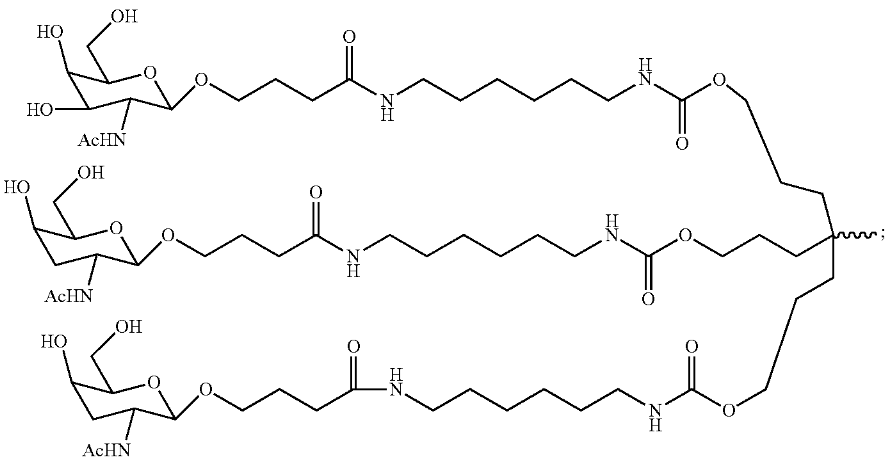
Formula IX
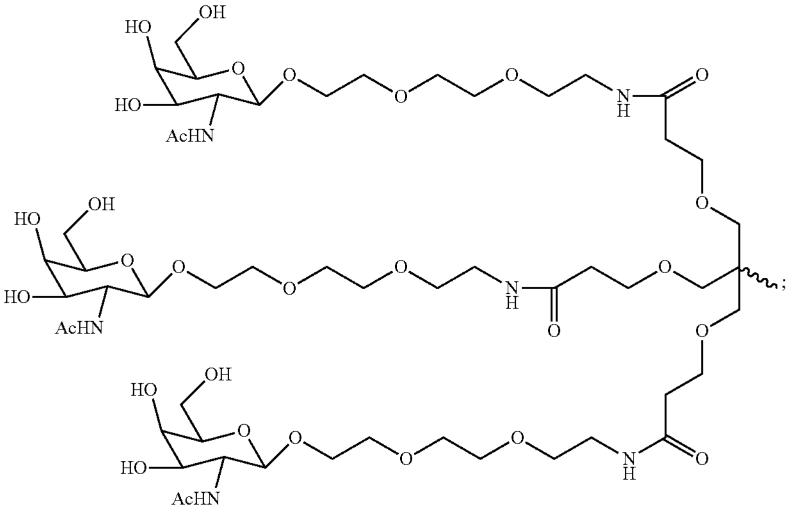
Formula X
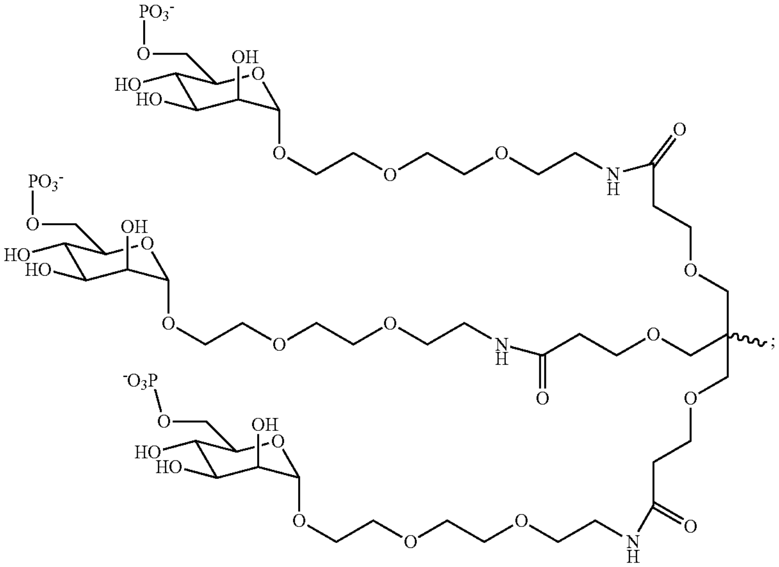

-continued
Formula XI
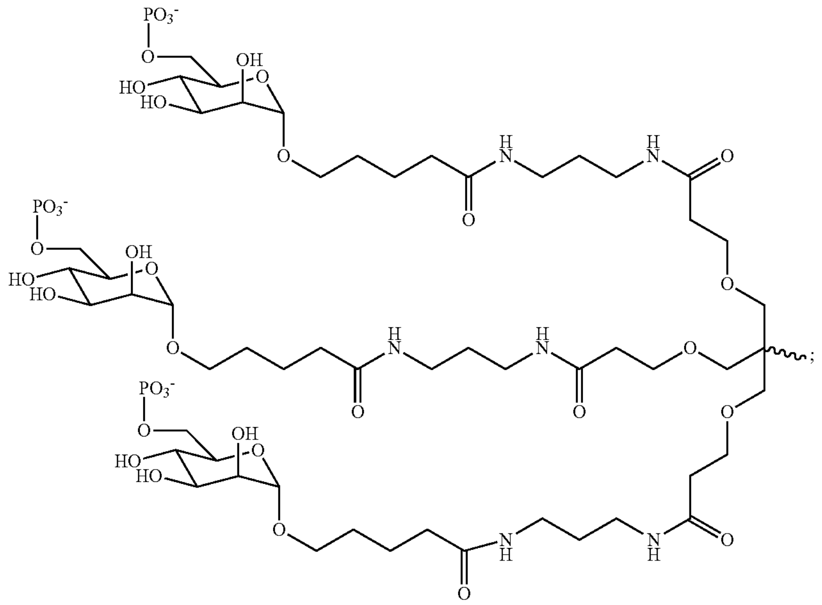
Formula XII
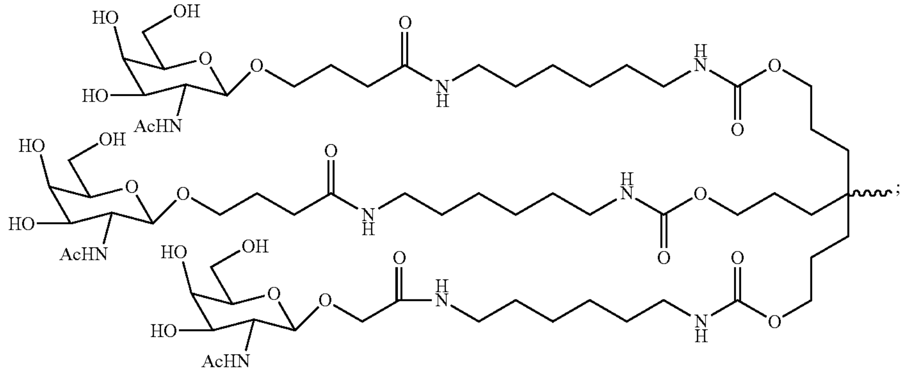
Formula XIII
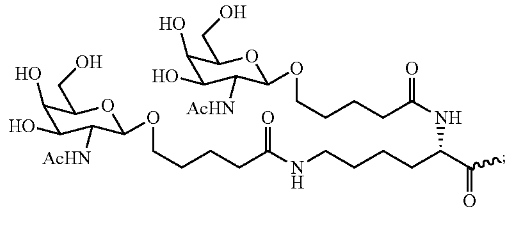
Formula XIV
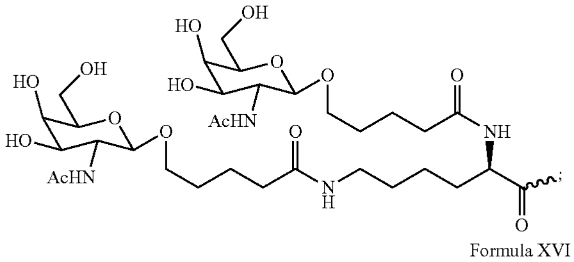
Formula XV
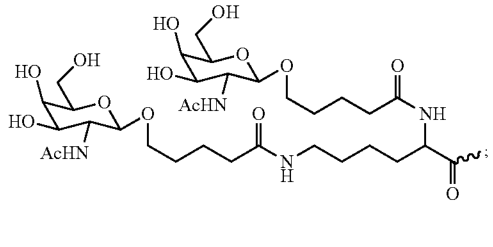
Formula XVI
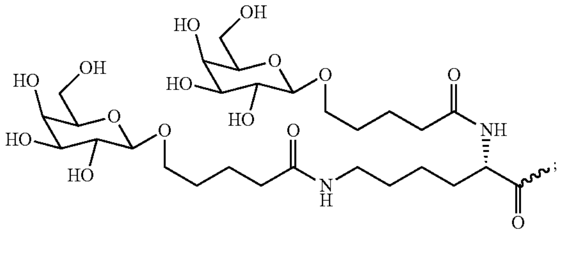

-continued
Formula XVII
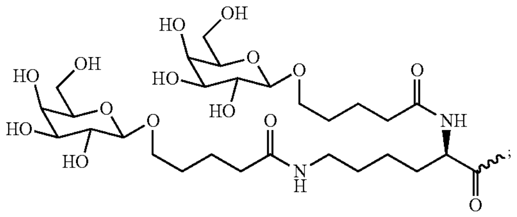
Formula XVIII
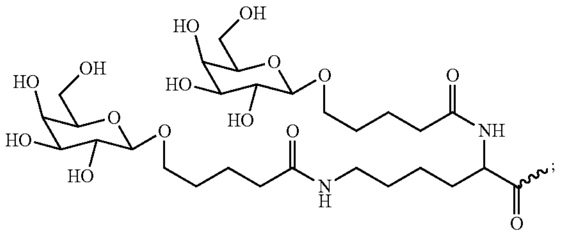
Formula XIX
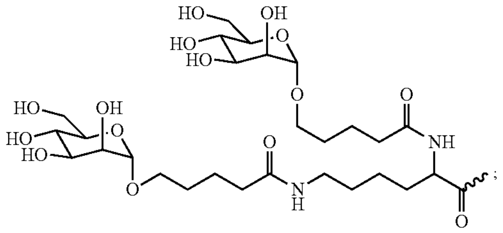
Formula XX
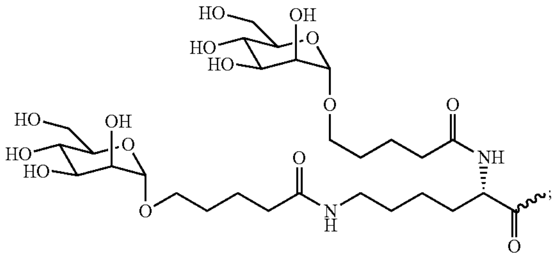
Formula XXI
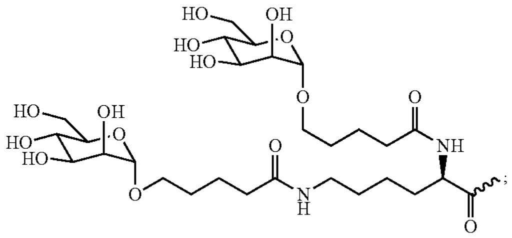
Formula XXII
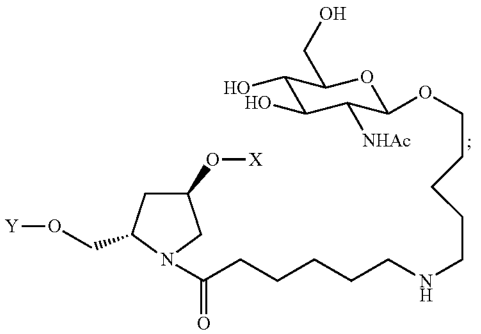
(Formula XXIII)
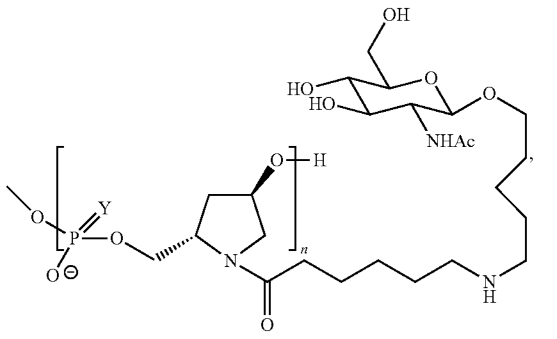
wherein Y is O or S and n is 3 -6;

-continued
(Formula XXIV)
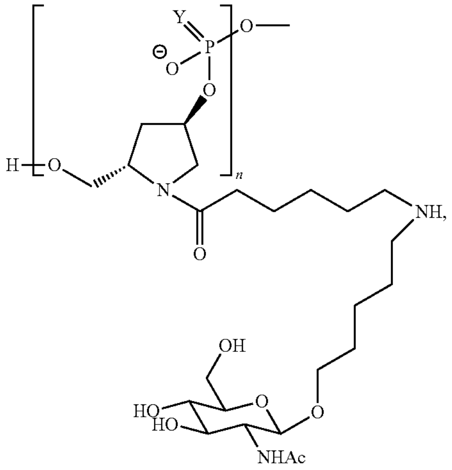
wherein Y is O or S and n is 3-6;
Formula XXV
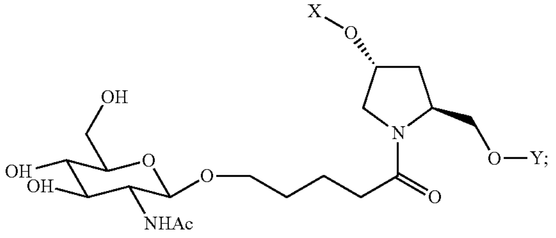
(Formula XXVI)
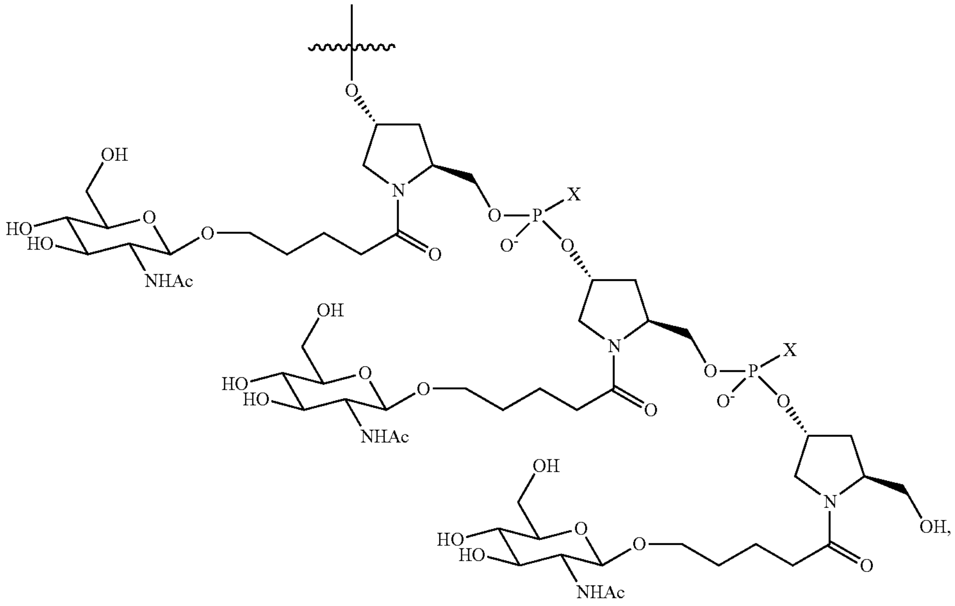
wherein X is O or S;

-continued
Formula XXVII
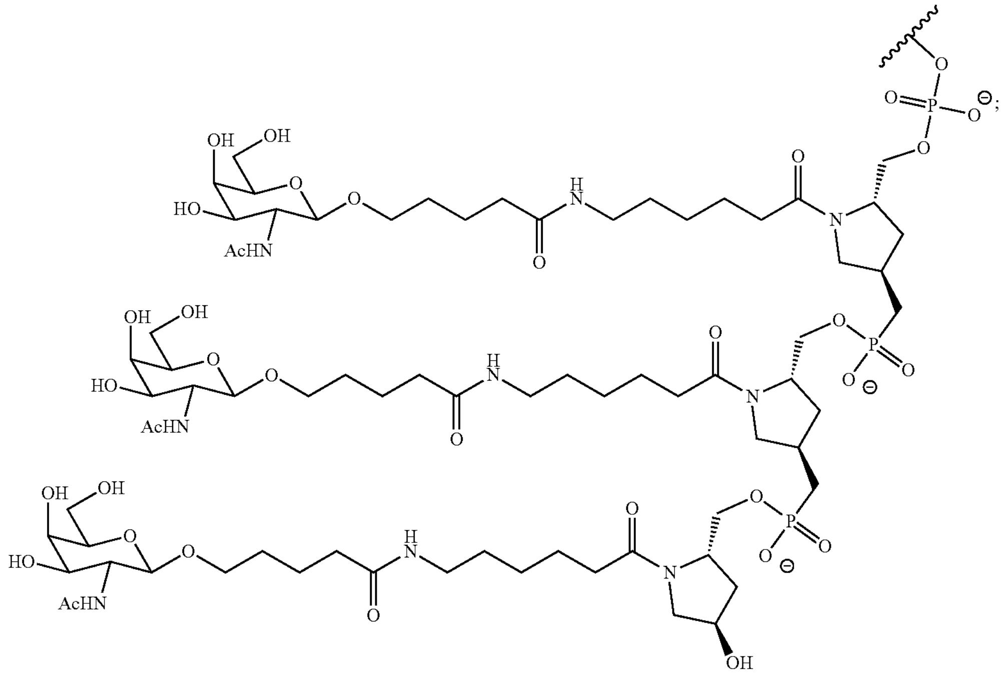
Formula XXVIII
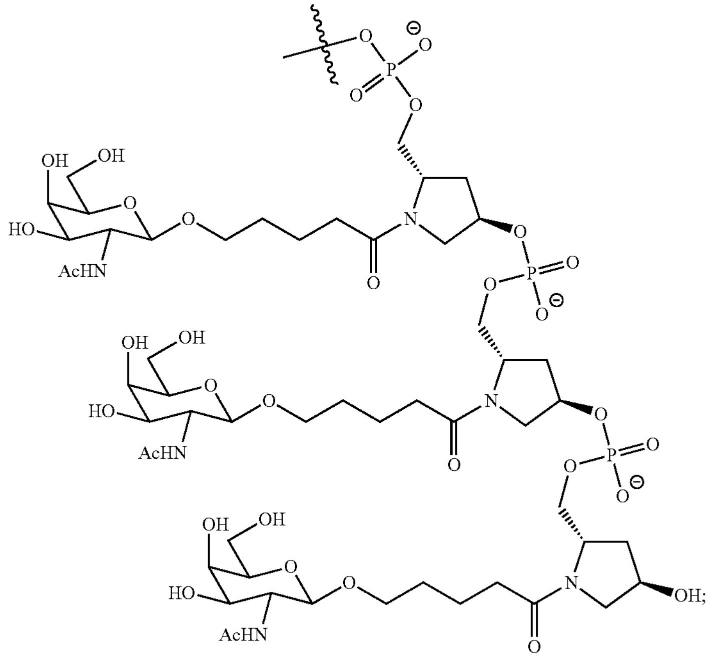

-continued
Formula XXIX
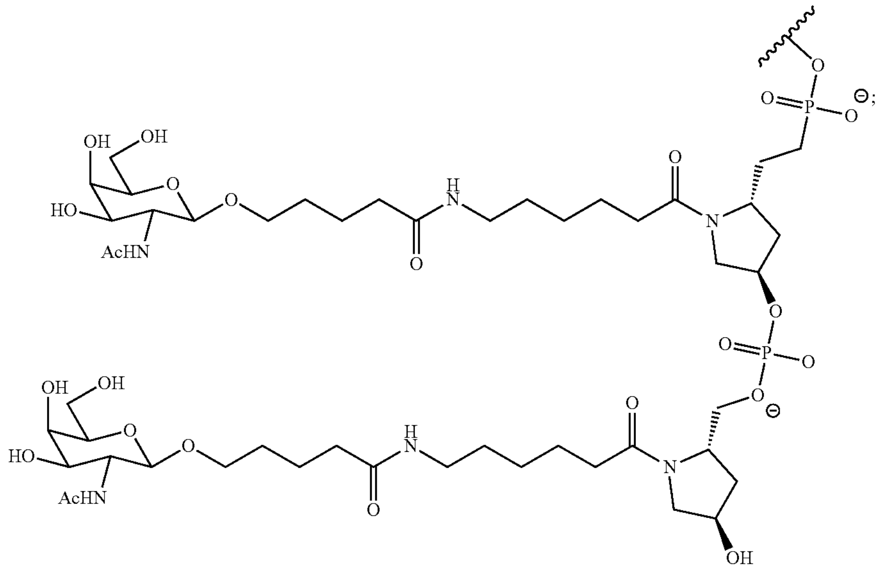
Formula XXX
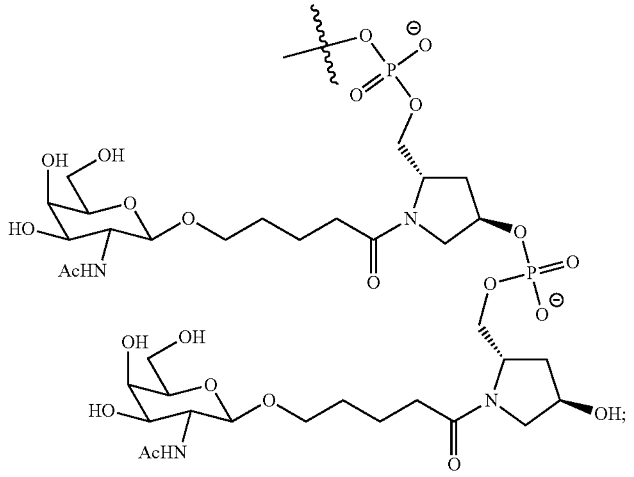
Formula XXXI
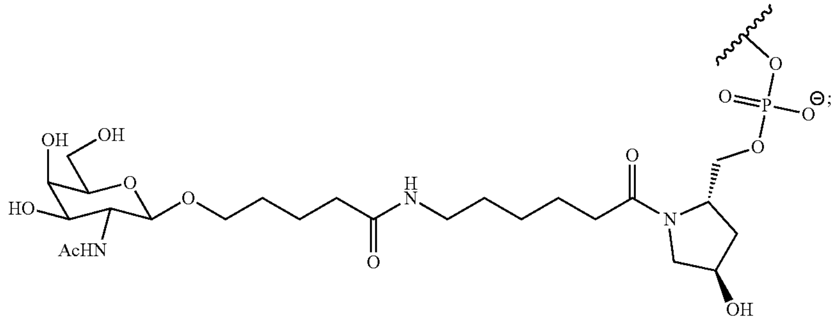
Formula XXXII
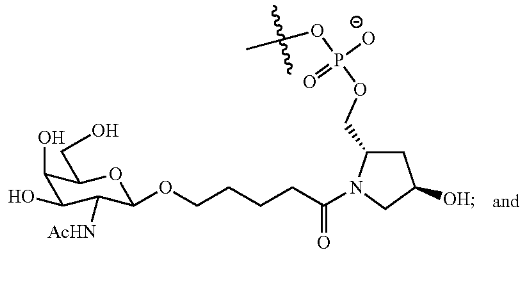
and -continued
Formula XXXIII
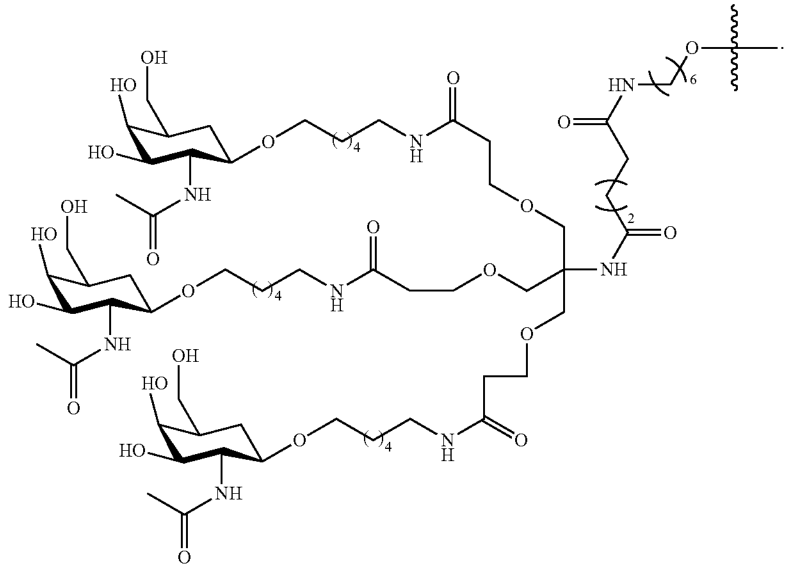
In certain embodiments, a carbohydrate conjugate for use in the compositions and methods of the invention is a monosaccharide. In certain embodiments, the monosaccharide is an N-acetylgalactosamine, such as
Formula I
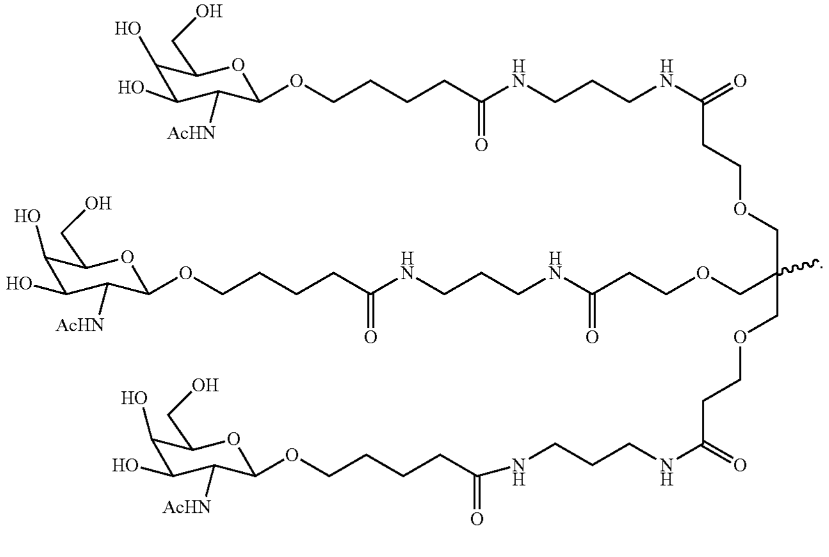

Another representative carbohydrate conjugate for use in the embodiments described herein includes, but is not limited to,
(Formula XXXIV)
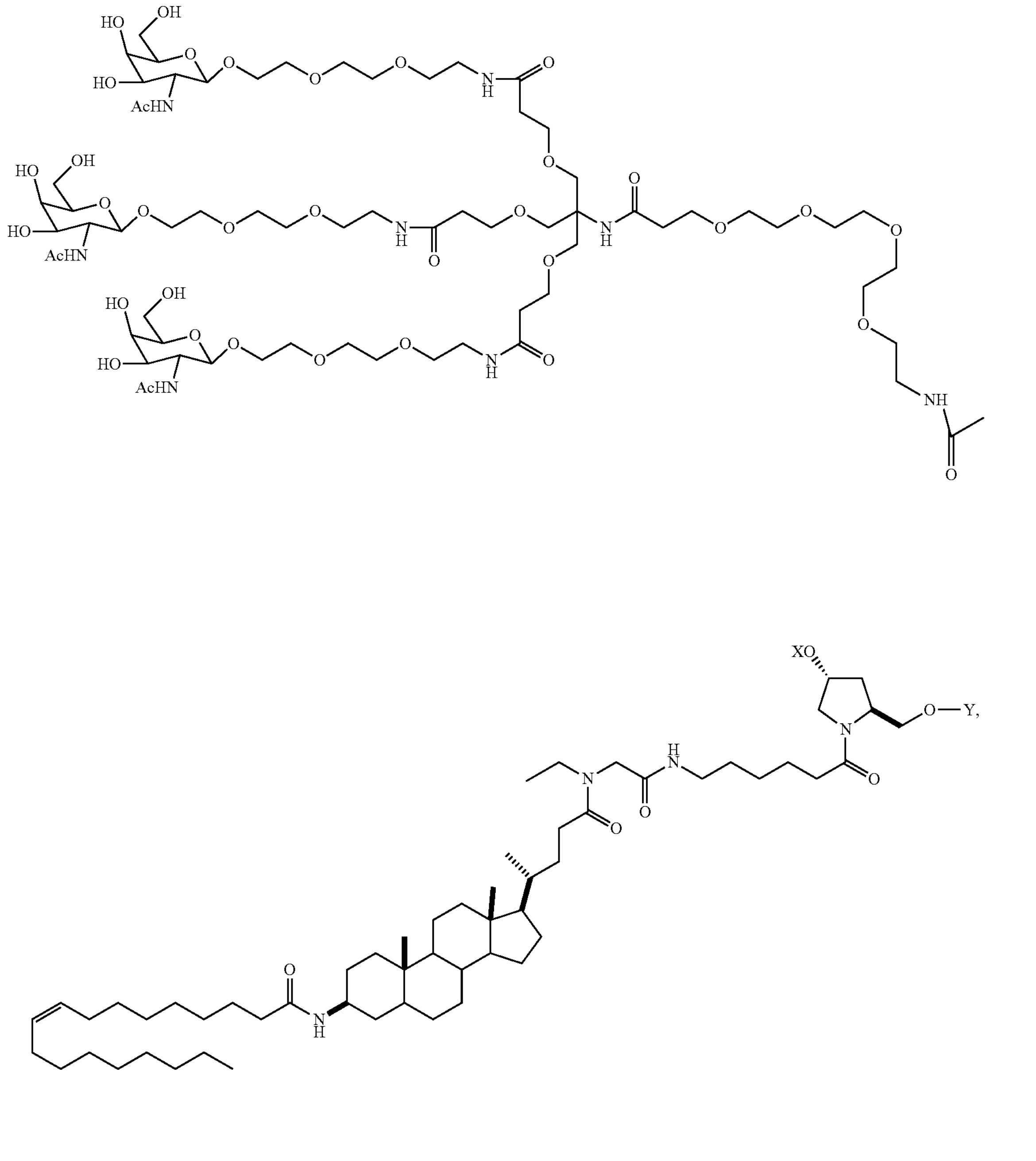
when one of X or Y is an oligonucleotide, the other is a hydrogen.

In some embodiments, a suitable ligand is a ligand disclosed in WO 2019/055633, the entire contents of which are incorporated herein by reference. In one embodiment the ligand comprises the structure below:

Formula XXXV

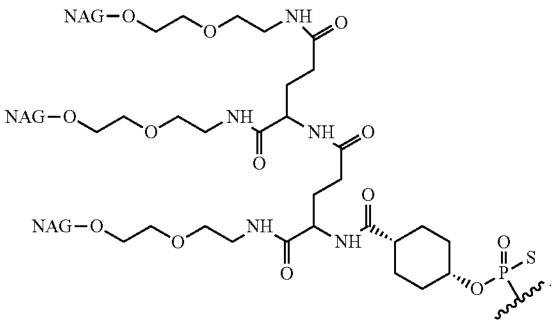

(NAG37)s

In certain embodiments, the RNAi agents of the disclosure may include GalNAc ligands, even if such GalNAc ligands are currently projected to be of limited value for the preferred intrathecal/CNS delivery route(s) of the instant disclosure.

In certain embodiments of the invention, the GalNAc or GalNAc derivative is attached to an iRNA agent of the invention ria a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one or more GalNAc or GalNAc derivative attached to the iRNA agent. The GalNAc may be attached to any nucleotide via a linker on the sense strand or antisense strand. The GalNac may be attached to the 5'-end of the sense strand, the 3' end of the sense strand, the 5'-end of the antisense strand, or the 3'-end of the antisense strand. In one embodiment, the GalNAc is attached to the 3' end of the sense strand, e.g., via a trivalent linker.

In other embodiments, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of linkers, e.g., monovalent linkers.

In some embodiments, for example, when the two strands of an iRNA agent of the invention is part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker.

In some embodiments, the carbohydrate conjugate further comprises one or more additional ligands as described above, such as, but not limited to, a PK modulator or a cell permeation peptide.

Additional carbohydrate conjugates and linkers suitable for use in the present invention include those described in WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic, where R8 is hydrogen, acyl, aliphatic or substituted aliphatic. In certain embodiments, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower, enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In certain embodiments, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In certain embodiments, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—. —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—. —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

iii. Acid Cleavable Linking Groups

In certain embodiments, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Cleavable Linking Groups

In certain embodiments, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleavable Linking Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —$NHCHR^{A}C(O)NHCHR^{B}C(O)$—, where $R^A$ and $R^B$ are the R groups of the two adjacent amino acids. These candidates can be evaluated using methods analogous to those described above.

In some embodiments, an iRNA of the invention is conjugated to a carbohydrate through a linker. Non-limiting examples of iRNA carbohydrate conjugates with linkers of the compositions and methods of the invention include, but are not limited to, (Formula XXXVI)

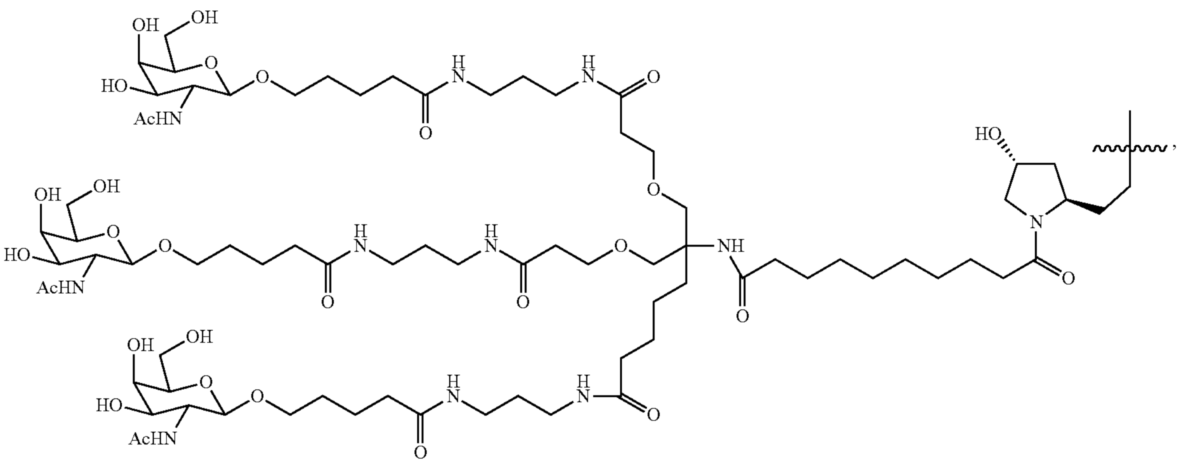

(Formula XXXVII)

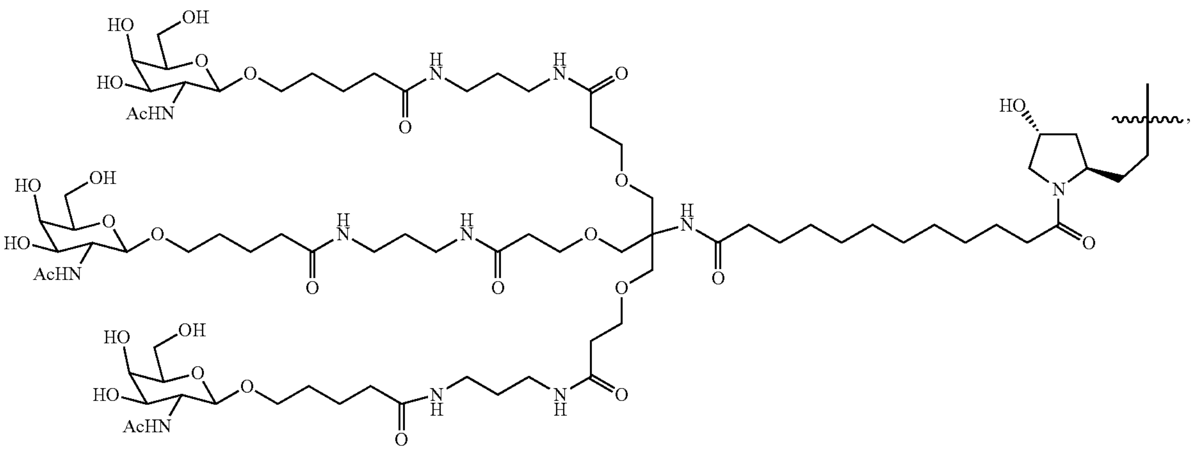

(Formula XXXVIII)

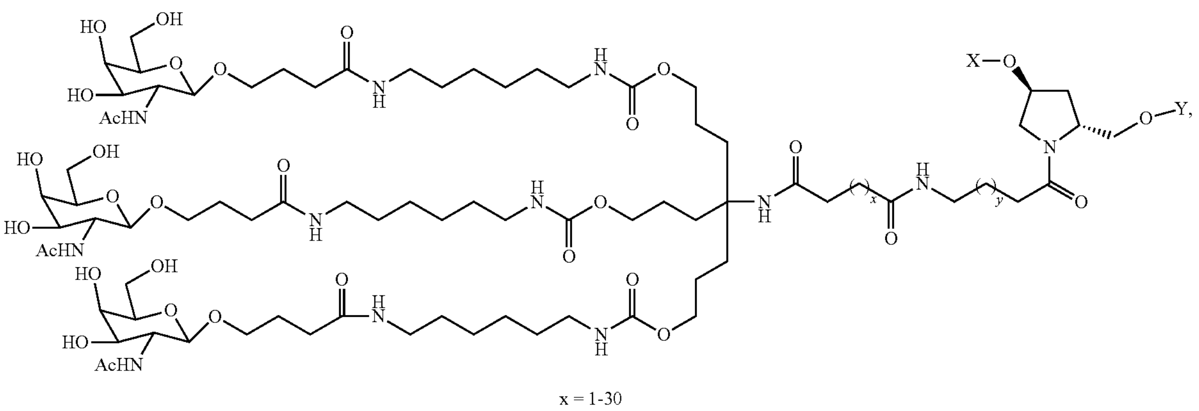

x = 1-30
y = 1-15

-continued
(Formula XXXIX)
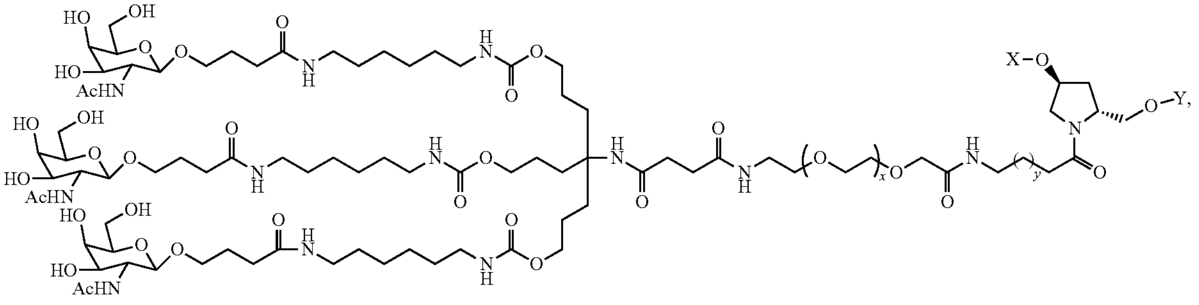
x = 1-30
y = 1-15
(Formula XL)
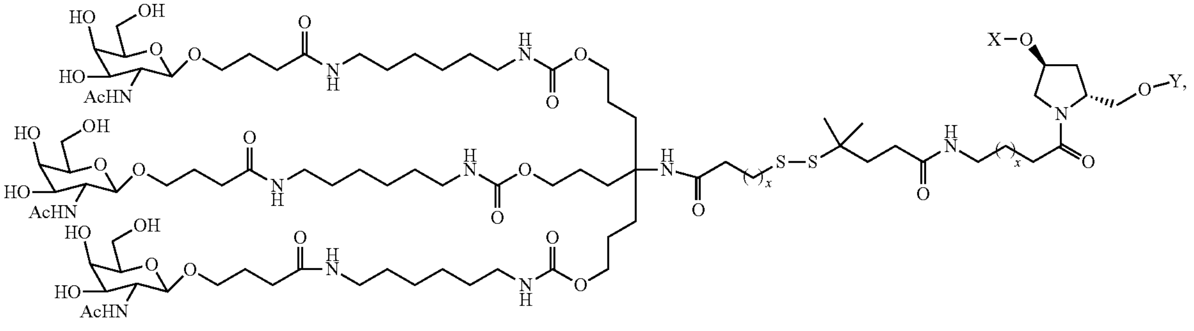
x = 0-30
y = 1-15
(Formula XLI)
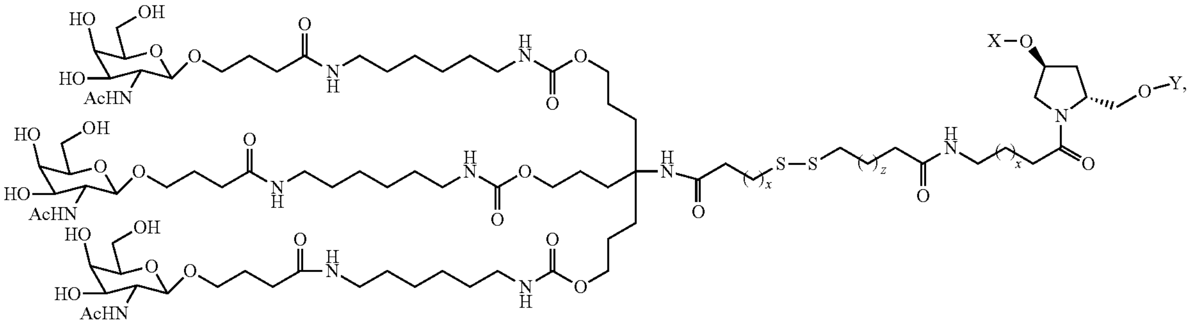
x = 0-30
y = 1-15
z = 1-20
(Formula XLII)
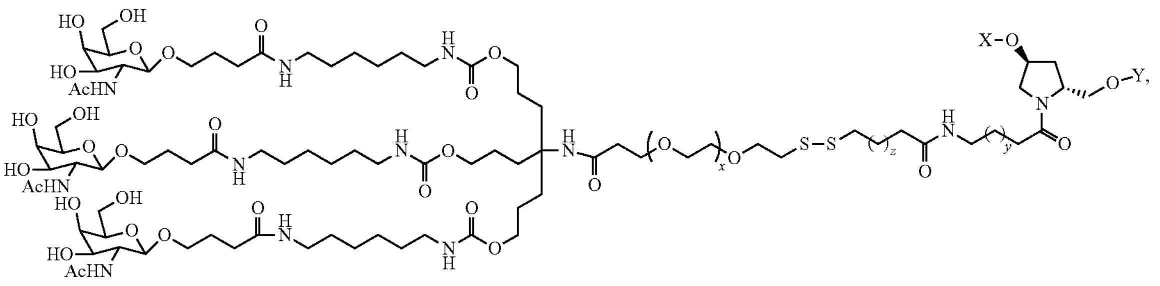
and
x = 1-30
y = 1-15
z = 1-20

-continued (Formula XLIII)

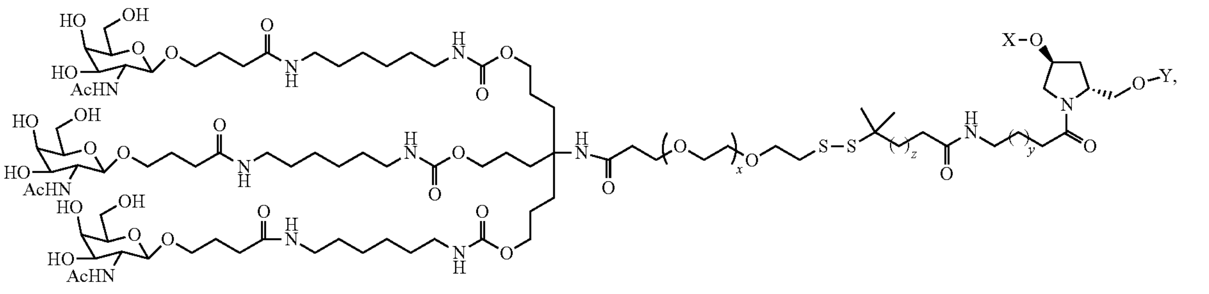

x = 1-30
y = 1-15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In certain embodiments, a dsRNA of the invention is conjugated to a bivalent or trivalent branched linker selected from the group of structures shown in any of formula (XLIV)-(XLVII):

Formula XLIV

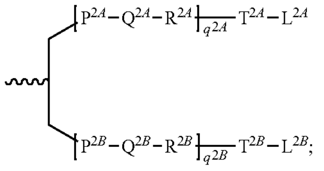

Formula XLV

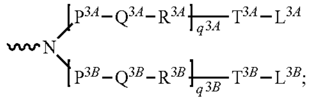

Formula XLVI

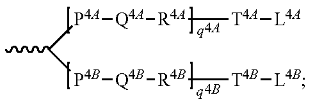

or

Formula XLVII

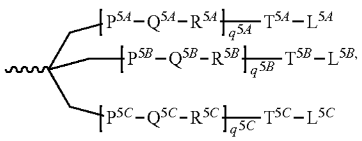

wherein:

q2A, q2B, q3A, q3B, q4A, q4B, q5A, q5B and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{4B}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')═C(R"), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)(O)$, —C(O)—CH$(R^a)$—NH—, CO, CH═N—O,

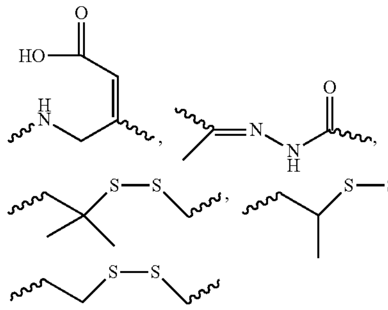

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain.

Trivalent conjugating GalNAc derivatives are particularly useful for use with RNAi agents for inhibiting the expression of a target gene, such as those of formula (XLVIII):

Formula XLVIII

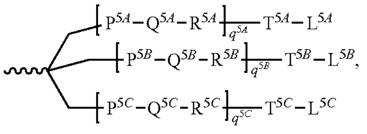

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas I, VI, IX, X, and XI.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591, 584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941; 6,294,664; 6,320,017; 6,576,752; 6,783,931; 6,900,297; 7,037,646; and 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNA agents, that contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.,* 2007, 365(1):54-61; Letsinger et al., *Proc. Natl. Acad Sci. USA,* 1989, 86:6553), cholic acid (Manoharan et al., *Bioorg. Med. Chem. Lett.,* 1994, 4:1053), a thioether, e.g., hexyl-S-tritylthiol (Manoharan et al., *Ann. N. Y. Acad Sci.,* 1992, 660:306; Manoharan et al., *Bioorg. Med Chem. Let.,* 1993, 3:2765), a thiocholesterol (Oberhauser et al., *Nucl. Acids Res.,* 1992, 20:533), an aliphatic chain, e.g., dodecandiol or undecyl residues (Saison-Behmoaras et al., *EMBO J.,* 1991, 10:111; Kabanov et al., *FEBS Lett.,* 1990, 259:327; Svinarchuk et al., *Biochimie,* 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Representative United States patents that teach the preparation of such RNA conjugates have been listed above. Typical conjugation protocols involve the synthesis of RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

V. Delivery of an RNAi Agent of the Disclosure

The delivery of an RNAi agent of the disclosure to a cell e.g., a cell within a subject, such as a human subject (e.g., a subject in need thereof, such as a subject having an ADRA2A-associated disorder, e.g., ADRA2A-associated disease, can be achieved in a number of different ways. For example, delivery may be performed by contacting a cell with an RNAi agent of the disclosure either in vitro or in vivo. In vivo delivery may also be performed directly by administering a composition comprising an RNAi agent, e.g., a dsRNA, to a subject. Alternatively, in vivo delivery may be performed indirectly by administering one or more vectors that encode and direct the expression of the RNAi agent. These alternatives are discussed further below.

In general, any method of delivering a nucleic acid molecule (in vitro or in vivo) can be adapted for use with an RNAi agent of the disclosure (see e.g., Akhtar S. and Julian R L., (1992) *Trends Cell. Biol.* 2(5):139-144 and WO94/02595, which are incorporated herein by reference in their entireties). For in vivo delivery, factors to consider in order to deliver an RNAi agent include, for example, biological stability of the delivered agent, prevention of non-specific effects, and accumulation of the delivered agent in the target tissue. The non-specific effects of an RNAi agent can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the RNAi agent to be administered. Several studies have shown successful knockdown of gene products when an RNAi agent is administered locally. For example, intraocular delivery of a VEGF dsRNA by intravitreal injection in cynomolgus monkeys (Tolentino, M J. et al., (2004) *Retina* 24:132-138) and subretinal injections in mice (Reich. S J. et al. (2003) *Mol. Vis.* 9:210-216) were both shown to prevent neovascularization in an experimental model of age-related macular degeneration. In addition, direct intratumoral injection of a dsRNA in mice reduces tumor volume (Pille, J. et al. (2005) *Mol. Ther.* 11:267-274) and can prolong survival of tumor-bearing mice (Kim, W J. et al., (2006) *Mol. Ther.* 14:343-350; Li. S. et al., (2007) *Mol. Ther.* 15:515-523). RNA interference has also shown success with local delivery to the CNS by direct injection (Dom, G. et al., (2004) *Nucleic Acids* 32:e49; Tan, P H. et al. (2005) *Gene Ther.* 12:59-66; Makimura, H. et al. (2002) *BMC Neurosci.* 3:18; Shishkina, G T., et al. (2004) *Neuroscience* 129:521-528; Thakker, E R., et al. (2004) *Proc. Natl. Acad. Sr. U.S.A.* 101:17270-17275; Akaneya, Y., et al. (2005) *J. Neurophysiol.* 93:594602) and to the lungs by intranasal administration (Howard, K A. et al., (2006) *Mol. Ther.* 14:476-484; Zhang, X. et al., (2004) *J. Biol. Chem.* 279:10677-10684; Bitko, V. et al., (2005) *Nat. Med.* 11:50-55). For administering an RNAi agent systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the RNAi agent to the target tissue and avoid undesirable off-target effects (e.g., without wishing to be bound by theory, use of GNAs as described herein has been identified to destabilize the seed region of a dsRNA, resulting in enhanced preference of such dsRNAs for on-target effectiveness, relative to off-target effects, as such off-target effects are significantly weakened by such seed region destabilization). RNAi agents can be modified by chemical conjugation to lipophilic groups such as cholesterol to enhance cellular uptake and prevent degradation. For example, an RNAi agent directed against ApoB conjugated to a lipophilic cholesterol moiety was injected systemically into mice and resulted in knockdown of apoB mRNA in both the liver and jejunum (Soutschek, J. et al., (2004) *Nature* 432:173-178). Conjugation of an RNAi agent to an aptamer has been shown to inhibit tumor growth and mediate tumor regression in a mouse model of prostate cancer (McNamara, J O. et al., (2006) *Nat. Biotechnol.* 24:1005-1015). In an alternative embodiment, the RNAi agent can be delivered using drug delivery systems such as a nanoparticle, a dendrimer, a polymer, liposomes, or a cationic delivery system. Positively charged cationic delivery systems facilitate binding of molecule RNAi agent (negatively charged) and also enhance interactions at the negatively charged cell membrane to permit efficient uptake of an RNAi agent by the cell. Cationic lipids, dendrimers, or polymers can either be bound to an RNAi agent, or induced to form a vesicle or micelle (see e.g., Kim S H. et al., (2008) *Journal of Controlled Release* 129(2):107-116) that encases an RNAi agent. The formation of vesicles or micelles further prevents degradation of the RNAi agent when administered systemically. Methods for making and administering cationic-RNAi agent complexes are well within the abilities of one skilled in the art (see e.g., Sorensen, D R., et al. (2003) *J. Mol. Biol* 327:761-766; Verma, U N. et al., (2003) *Clin. Cancer Res.* 9:1291-1300; Arnold. A S et al. (2007) *J. Hypertens.* 25:197-205, which are incorporated herein by reference in their entirety). Some non-limiting examples of drug delivery systems useful for systemic delivery of RNAi agents include DOTAP (Sorensen, D R., et al (2003), supra; Verma, U N. et al., (2003), supra). Oligofectamine, "solid nucleic acid lipid particles" (Zimmermann, T S. et al., (2006) *Nature* 441:111-114), cardiolipin (Chien, P Y. et al., (2005) *Cancer Gene Ther.* 12:321-328; Pal, A. et al., (2005) *Int J. Oncol.* 26:1087-1091), polyethyleneimine (Bonnet M E, et al., (2008) *Pharm. Res.* August 16 Epub ahead of print; Aigner, A. (2006) *J. Biomed. Biotechnol.* 71659). Arg-Gly-Asp (RGD) peptides (Liu, S. (2006) *Mol. Pharm.* 3:472-487), and polyamidoamines (Tomalia, D A. et al., (2007) *Biochem. Soc. Trans.* 35:61-67; Yoo, H, et al., (1999) *Pharm. Res.* 16:1799-1804). In some embodiments, an RNAi agent forms a complex with cyclodextrin for systemic administration. Methods for administration and pharmaceutical compositions of RNAi agents and cyclodextrins can be found in U.S. Pat. No. 7,427,605, which is herein incorporated by reference in its entirety.

Certain aspects of the instant disclosure relate to a method of reducing the expression of an ADRA2A target gene in a cell, comprising contacting said cell with the double-stranded RNAi agent of the disclosure. In one embodiment, the cell is an extraheptic cell, optionally a CNS cell. In other embodiment, the cell is an extraheptic cell, optionally an ocular cell.

Another aspect of the disclosure relates to a method of reducing the expression of an ADRA2A target gene in a subject, comprising administering to the subject the double-stranded RNAi agent of the disclosure.

Another aspect of the disclosure relates to a method of treating a subject having a CNS disorder (neurodegenerative disorder), comprising administering to the subject a therapeutically effective amount of the double-stranded ADRA2A-targeting RNAi agent of the disclosure, thereby treating the subject. Exemplary CNS disorders that can be treated by the method of the disclosure include ADRA2A-associated disease CNS disorders such as tauopathies (including, e.g., primary tauopathies and Alzheimer's disease).

Another aspect of the disclosure relates to a method of treating a subject having an ocular system disorder, comprising administering to the subject a therapeutically effective amount of the double-stranded ADRA2A-targeting RNAi agent of the disclosure, thereby treating the subject.

In one embodiment, the double-stranded RNAi agent is administered intrathecally. By intrathecal administration of the double-stranded RNAi agent, the method can reduce the expression of an ADRA2A target gene in a brain (e.g., striatum) or spine tissue, for instance, cortex, cerebellum, cervical spine, lumbar spine, and thoracic spine, immune cells such as monocytes and T-cells.

For ease of exposition the formulations, compositions and methods in this section are discussed largely with regard to modified siRNA compounds. It may be understood, however, that these formulations, compositions and methods can be practiced with other siRNA compounds, e.g., unmodified siRNA compounds, and such practice is within the disclosure. A composition that includes an RNAi agent can be delivered to a subject by a variety of routes. Exemplary routes include: intrathecal, intravenous, topical, rectal, anal, vaginal, nasal, pulmonary, and ocular.

The RNAi agents of the disclosure can be incorporated into pharmaceutical compositions suitable for administration. Such compositions typically include one or more species of RNAi agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present disclosure may be administered in a number of ways depending upon whether local or systemic treatment is desired and upon the area to be treated. Administration may be topical (including ophthalmic, vaginal, rectal, intranasal, transdermal), intrathecal, oral, or parenteral. Parenteral administration includes intravenous drip, subcutaneous, intraperitoneal or intramuscular injection, or intrathecal or intraventricular administration.

The route and site of administration may be chosen to enhance targeting. For example, to target neural or spinal tissue, intrathecal injection would be a logical choice. Lung cells might be targeted by administering the RNAi agent in aerosol form. The vascular endothelial cells could be targeted by coating a balloon catheter with the RNAi agent and mechanically introducing the RNA.

Formulations for topical administration may include transdermal patches, ointments, lotions, creams, gels, drops, suppositories, sprays, liquids, and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water, syrups, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening or flavoring agents can be added.

Compositions for intrathecal or intraventricular administration may include sterile aqueous solutions which may also contain buffers, diluents, and other suitable additives.

Formulations for parenteral administration may include sterile aqueous solutions which may also contain buffers, diluents, and other suitable additives. Intraventricular injection may be facilitated by an intraventricular catheter, for example, attached to a reservoir. For intravenous use, the total concentration of solutes may be controlled to render the preparation isotonic.

In one embodiment, the administration of the siRNA compound, e.g., a double-stranded siRNA compound, or ssiRNA compound, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral, or ocular. Administration can be provided by the subject or by another person, e.g., a health care provider. The medication can be provided in measured doses or in a dispenser which delivers a metered dose. Selected modes of delivery are discussed in more detail below.

A. Intrathecal Administration.

In one embodiment, the double-stranded RNAi agent is delivered by intrathecal injection (i.e., injection into the spinal fluid which bathes the brain and spinal cord tissue). Intrathecal injection of RNAi agents into the spinal fluid can be performed as a bolus injection or via minipumps which can be implanted beneath the skin, providing a regular and constant delivery of siRNA into the spinal fluid. The circulation of the spinal fluid from the choroid plexus, where it is produced, down around the spinal chord and dorsal root ganglia and subsequently up past the cerebellum and over the cortex to the arachnoid granulations, where the fluid can exit the CNS, that, depending upon size, stability, and solubility of the compounds injected, molecules delivered intrathecally could hit targets throughout the entire CNS.

In some embodiments, the intrathecal administration is via a pump. The pump may be a surgically implanted osmotic pump. In one embodiment, the osmotic pump is implanted into the subarachnoid space of the spinal canal to facilitate intrathecal administration.

In some embodiments, the intrathecal administration is via an intrathecal delivery system for a pharmaceutical including a reservoir containing a volume of the pharmaceutical agent, and a pump configured to deliver a portion of the pharmaceutical agent contained in the reservoir. More details about this intrathecal delivery system may be found in WO 2015/116658, which is incorporated by reference in its entirety.

The amount of intrathecally injected RNAi agents may vary from one target gene to another target gene and the appropriate amount that has to be applied may have to be determined individually for each target gene. Typically, this amount ranges from 10 μg to 2 mg, preferably 50 μg to 1500 μg, more preferably 100 μg to 1000 μg.

B. Vector Encoded RNAi Agents of the Disclosure

RNAi agents targeting the ADRA2A gene can be expressed from transcription units inserted into DNA or RNA vectors (see, e.g., Couture, A, et al., *TIG.* (1996), 12:5-10; WO 00/22113. WO 00/22114, and U.S. Pat. No. 6,054,299). Expression is preferably sustained (months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., (1995) *Proc. Natl. Acad Sci. USA* 92:1292).

The individual strand or strands of an RNAi agent can be transcribed from a promoter on an expression vector. Where two separate strands are to be expressed to generate, for example, a dsRNA, two separate expression vectors can be co-introduced (e.g., by transfection or infection) into a target cell. Alternatively, each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

RNAi agent expression vectors are generally DNA plasmids or viral vectors. Expression vectors compatible with eukaryotic cells, preferably those compatible with vertebrate cells, can be used to produce recombinant constructs for the expression of an RNAi agent as described herein. Delivery of RNAi agent expressing vectors can be systemic, such as by intravenous or intramuscular administration, by administration to target cells ex-planted from the patient followed by reintroduction into the patient, or by any other means that allows for introduction into a desired target cell.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an RNAi agent will generally require regulatory elements, e.g., promoters, enhancers, etc., to ensure the expression of the RNAi agent in target cells. Other aspects to consider for vectors and constructs are known in the art.

VI. Pharmaceutical Compositions of the Invention

The present disclosure also includes pharmaceutical compositions and formulations which include the RNAi agents of the disclosure. In one embodiment, provided herein are pharmaceutical compositions containing an RNAi agent, as described herein, and a pharmaceutically acceptable carrier. The pharmaceutical compositions containing the RNAi agent are useful for treating a disease or disorder associated with the expression or activity of ADRA2A, e.g., ADRA2A-associated disease.

In some embodiments, the pharmaceutical compositions of the invention are sterile. In another embodiment, the pharmaceutical compositions of the invention are pyrogen free.

Such pharmaceutical compositions are formulated based on the mode of delivery. One example is compositions that are formulated for systemic administration via parenteral delivery, e.g., by intravenous (IV), intramuscular (IM), or for subcutaneous (subQ) delivery. Another example is compositions that are formulated for direct delivery into the CNS, e.g., by intrathecal or intravitreal routes of injection, optionally by infusion into the brain (e.g., striatum), such as by continuous pump infusion.

The pharmaceutical compositions of the disclosure may be administered in dosages sufficient to inhibit expression of an ADRA2A gene. In general, a suitable dose of an RNAi agent of the disclosure will be in the range of about 0.001 to about 200.0 milligrams per kilogram body weight of the recipient per day, generally in the range of about 1 to 50 mg per kilogram body weight per day.

A repeat-dose regimen may include administration of a therapeutic amount of an RNAi agent on a regular basis, such as monthly to once every six months. In certain embodiments, the RNAi agent is administered about once per quarter (i.e., about once every three months) to about twice per year.

After an initial treatment regimen (e.g., loading dose), the treatments can be administered on a less frequent basis.

In other embodiments, a single dose of the pharmaceutical compositions can be long lasting, such that subsequent doses are administered at not more than 1, 2, 3, or 4 or more month intervals. In some embodiments of the disclosure, a single dose of the pharmaceutical compositions of the disclosure is administered once per month. In other embodiments of the disclosure, a single dose of the pharmaceutical compositions of the disclosure is administered once per quarter to twice per year.

The skilled artisan will appreciate that certain factors can influence the dosage and timing required to effectively treat a subject, including but not limited to the severity of the disease or disorder, previous treatments, the general health or age of the subject, and other diseases present. Moreover, treatment of a subject with a therapeutically effective amount of a composition can include a single treatment or a series of treatments.

Advances in mouse genetics have generated a number of mouse models for the study of various human diseases, including tauopathies such as Alzheimer's disease that would benefit from reduction in the expression of ADRA2A. Such models can be used for in vivo testing of RNAi agents, as well as for determining a therapeutically effective dose. Suitable rodent models are known in the art and include, for example, those described in, for example, Esquerda-Canals, et al. (*J Alzheimers Dis* (2017) 15(4): 1171-1183) and Raza, et al. (*Life Sci* (2019) 1:226: 77-90). Additionally, cell culture models which include human cells and are suitable for in vitro testing are known in the art and include, for example, Matsumoto, et al, (*Int J Mol Sci* (2018) 19:5: pii: E 1497) and Choi, et al. (Nature (2014) 515(7526): 274-8).

The pharmaceutical compositions of the present disclosure can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The RNAi agents can be delivered in a manner to target a particular tissue, such as the CNS (e.g., neuronal, glial or vascular tissue of the brain).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the RNAi agents featured in the disclosure are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). RNAi agents featured in the disclosure can be encapsulated within liposomes or can form complexes thereto, in particular to cationic liposomes. Alternatively, RNAi agents can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

A. RNAi Agent Formulations Comprising Membranous Molecular Assemblies

An RNAi agent for use in the compositions and methods of the disclosure can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the RNAi agent composition. The lipophilic material isolates the aqueous interior from an aqueous exterior, which typically does not include the RNAi agent composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the RNAi agent are delivered into the cell where the RNAi agent can specifically bind to a target RNA and can mediate RNAi. In some cases the liposomes are also specifically targeted, e.g., to direct the RNAi agent to particular cell types.

A liposome containing an RNAi agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The RNAi agent preparation is then added to the micelles that include the lipid component. The cationic groups on the lipid interact with the RNAi agent and condense around the RNAi agent to form a liposome. After condensation, the detergent is removed, e.g., by dialysis, to yield a liposomal preparation of RNAi agent.

If necessary a carrier compound that assists in condensation can be added during the condensation reaction, e.g., by controlled addition. For example, the carrier compound can be a polymer other than a nucleic acid (e.g., spermine or spermidine), pH can also be adjusted to favor condensation.

Methods for producing stable polynucleotide delivery vehicles, which incorporate a poly nucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., (1987) *Proc. Natl. Acad. Sci. USA* 8:7413-7417; U.S. Pat. Nos. 4,897,355; 5,171,678; Bangham et al., (1965) *M. Mol. Biol.* 23:238; Olson et al., (1979) *Biochim. Biophys. Acta* 557:9; Szoka et al., (1978) *Proc. Natl. Acad Sci.* 75: 4194; Mayhew et al., (1984) *Biochim. Biophys. Acta* 775:169; Kim et al., (1983) *Biochim. Biophys. Acta* 728:339; and Fukunaga et al., (1984) *Endocrinol.* 115:757. Commonly used techniques for preparing lipid aggregates of appropriate size for use as delivery vehicles include sonication and freeze-thaw plus extrusion (see, e.g., Mayer et al., (1986) *Biochim. Biophys. Acta* 858:161. Microfluidization can be used when consistently small (50 to 200 nm) and relatively uniform aggregates are desired (Mayhew et al., (1984) *Biochim. Biophys. Acta* 775:169. These methods are readily adapted to packaging RNAi agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al. (1987) *Biochem. Biophys. Res. Commun.,* 147:980-985).

Liposomes, which are pH-sensitive or negatively charged, entrap nucleic acids rather than complex with them. Since both the nucleic acid and the lipid are similarly charged, repulsion rather than complex formation occurs. Nevertheless, some nucleic acid is entrapped within the aqueous interior of these liposomes, pH sensitive liposomes have been used to deliver nucleic acids encoding the thymidine kinase gene to cell monolayers in culture. Expression of the exogenous gene was detected in the target cells (Zhou et al. (1992) *Journal of Controlled Release,* 19:269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid or phosphatidylcholine or cholesterol.

Examples of other methods to introduce liposomes into cells in vitro and in vivo include U.S. Pat. Nos. 5,283,185; 5,171,678; WO 94/00569; WO 93/24640; WO 91/16024; Felgner, (1994) *J. Biol. Chem.* 269:2550; Nabel, (1993) *Proc. Natl. Acad Sci.* 90:11307; Nabel, (1992) *Human Gene her.* 3:649; Gershon, (1993) *Biochem.* 32:7143; and Strauss, (1992) *EMBO J.* 11:417.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ I (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al., (1994) *S.T.P. Pharma. Sci.,* 4(6):466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside Gm, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., (1987) *FEBS Letters,* 223:42; Wu et al., (1993) *Cancer Research,* 53:3765).

Various liposomes comprising one or more glycolipids are known in the art. Papahadjopoulos et al. (*Ann. N Y. Acad & Sci*., (1987), 507:64) reported the ability of monosialoganglioside Gm, galactocerebroside sulfate and phosphatidylinositol to improve blood half-lives of liposomes. These findings were expounded upon by Gabizon et al. (*Proc. Natl. Acad. Sci. U.S.A*., (1988), 85,:6949). U.S. Pat. No. 4,837,028 and WO 88/04924, both to Allen et al., disclose liposomes comprising (1) sphingomyelin and (2) the ganglioside Gm, or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver RNAi agents to macrophages.

Further advantages of liposomes include: liposomes obtained from natural phospholipids are biocompatible and biodegradable; liposomes can incorporate a wide range of water and lipid soluble drugs; liposomes can protect encapsulated RNAi agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid. N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of RNAi agent (see, e.g., Felgner, P. L. et al., (1987) *Proc. Natl. Acad. Sci. USA* 8:7413-7417, and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim. Indianapolis, Indiana) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam, Promega, Madison, Wisconsin) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X, and Huang, L., (1991) *Biochim. Biophys. Res. Commun.* 179:280). Lipopolylysine, made by conjugating polylysine to DOPE, has been reported to be effective for transfection in the presence of serumn (Zhou, X. et al., (1991) *Biochim. Biophys. Acta* 1065:8). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, California) and Lipofectamine (DOSPA) (Life Technology, Inc., Gaithersburg, Maryland). Other cationic lipids suitable for the delivery of oligonucleotides are described in WO 98/39359 and WO 96f37194.

Liposomal formulations are particularly suited for topical administration; liposomes present several advantages over other formulations. Such advantages include reduced side effects related to high systemic absorption of the administered drug, increased accumulation of the administered drug at the desired target, and the ability to administer RNAi agent into the skin. In some implementations, liposomes are used for delivering RNAi agent to epidermal cells and also to enhance the penetration of RNAi agent into dermal tissues, e.g., into skin. For example, the liposomes can be applied topically. Topical delivery of drugs formulated as liposomes to the skin has been documented (see, e.g., Weiner et al., (1992) *Journal of Drug Targeting*, vol. 2, 405-410 and du Plessis et al. (1992) *Antiviral Research,* 18:259-265; Mannino, R. J. and Fould-Fogerite. S., (1998) *Biotechniques* 6:682-690; Itani. T. et al., (1987) *Gene* 56:267-276; Nicolau, C. et al. (1987) *Meth. Enzymol.* 149:157-176; Straubinger, R. M. and Papahadjopoulos, D. (1983) *Meth. Enzymol.* 101:512-527; Wang, C. Y. and Huang, L., (1987) *Proc. Natl. Acad Sci. USA* 84:7851-7855).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome 11 (glyceryl distearate/cholesterol/polyoxyethylene-10-stearyl ether) were used to deliver a drug into the dermis of mouse skin. Such formulations with RNAi agent are useful for treating a dermatological disorder.

Liposomes that include RNAi agents can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include RNAi agent can be delivered, for example, subcutaneously by infection in order to deliver RNAi agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present disclosure are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application number PCT/US2007/080331, filed Oct. 3, 2007, also describes formulations that are amenable to the present disclosure.

Transfersomes, yet another type of liposomes, are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as those described herein, particularly in emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York. N.Y., 1988, p. 285).

If the surfactant molecule is not ionized, it is classified as a nonionic surfactant. Nonionic surfactants find wide application in pharmaceutical and cosmetic products and are usable over a wide range of pH values. In general, their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides. The use of surfactants in drug products, formulations and in emulsions has been reviewed (Rieger, in Pharmaceutical Dosage Forms, Marcel Dekker, Inc., New York, N.Y., 1988, p. 285).

The RNAi agent for use in the methods of the disclosure can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol or m-cresol may be added to the mixed micellar composition to stabilize the formulation and protect against bacterial growth. Alternatively, phenol or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles

RNAi agents, e.g., dsRNAs of in the disclosure may be fully encapsulated in a lipid formulation, e.g., a LNP, or other nucleic acid-lipid particle.

As used herein, the term "LNP" refers to a stable nucleic acid-lipid particle. LNPs typically contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in WO 00/03683. The particles of the present disclosure typically have a mean diameter of about 50 nm to about 130 nm, more typically about 60 nm to about 130 nm, more typically about 70 nm to about 110 nm, most typically about 70 nm to about 90) nm, and are substantially nontoxic. In addition, the nucleic acids when present in the nucleic acid-lipid particles of the present disclosure are resistant in aqueous solution to degradation with a nuclease. Nucleic acid-lipid particles and their method of preparation are disclosed in e.g., U.S. Pat. Nos. 5,976,567; 5,981,501; 6,534,484; 6,586,410; 6,815,432; United States Patent publication No. 2010/0324120 and WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the disclosure.

Certain specific LNP formulations for delivery of RNAi agents have been described in the art, including, e.g., "LNP01" formulations as described in, e.g., WO 2008/042973, which is hereby incorporated by reference.

Additional exemplary lipid-dsRNA formulations are identified in Table 1 below.

TABLE 1

| | Ionizable/Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG- DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |

TABLE 1-continued

| | Ionizable/Cationic Lipid | cationic lipid/non-cationic lipid/cholesterol/PEG-lipid conjugate Lipid:siRNA ratio |
|---|---|---|
| LNP22 | XTC | XTC/DSPC/Chol/PEG-DSG 50/10/38.5/1.5 Lipid:siRNA: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)

SNALP (1,2-Dilinolenyloxy-N,N-dimethylaminopropane (DLinDMA)) comprising formulations are described in WO 2009/127060, which is hereby incorporated by reference.

XTC comprising formulations are described in WO 2010/088537, the entire contents of which are hereby incorporated herein by reference.

MC3 comprising formulations are described, e.g., in United States Patent Publication No. 2010/0324120, the entire contents of which are hereby incorporated by reference.

ALNY-100 comprising formulations are described in WO 2010/054406, the entire contents of which are hereby incorporated herein by reference.

C12-200 comprising formulations are described in WO 2010/129709, the entire contents of which are hereby incorporated herein by reference.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the disclosure are administered in conjunction with one or more penetration enhancer surfactants and chelators. Suitable surfactants include fatty acids or esters or salts thereof, bile acids or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, I-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the disclosure can be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906. U.S. 2003/0027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the brain when treating APP-associated diseases or disorders.

The pharmaceutical formulations of the present disclosure, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present disclosure can be formulated into any of many possible dosage forms such as, but not limited to, tablets, capsules, gel capsules, liquid syrups, soft gels, suppositories, and enemas. The compositions of the present disclosure can also be formulated as suspensions in aqueous, non-aqueous or mixed media. Aqueous suspensions can further contain substances which increase the viscosity of the suspension including, for example, sodium carboxymethylcellulose, sorbitol or dextran. The suspension can also contain stabilizers.

C. Additional Formulations i. Emulsions

The compositions of the present disclosure can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Idson, in Pharmaceutical Dosage Forms, Lieberman. Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton. Pa., 1985, p. 301). Emulsions are often biphasic systems comprising two immiscible liquid phases intimately mixed and dispersed with each other. In general, emulsions can be of either the water-in-oil (w/o) or the oil-in-water (a % w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (ow) emulsion. Emulsions can contain additional components in addition to the dispersed phases, and the active drug which can be present as a solution in either aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise, a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen. L V., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York. N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York. N.Y., volume 1, p. 285; Idson, in Pharmaceutical Dosage Forms. Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY Rieger, in Pharmaceutical Dosage Forms, Lieberman, Rieger and Banker (Eds.), 1988. Marcel Dekker. Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York. N.Y., volume 1, p. 335; Idson, in Pharmaceutical Dosage Forms, Lieberman, Rieger and Banker (Eds.), 1988, Marcel Dekker. Inc., New York. N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms. Lieberman. Rieger and Banker (Eds.), 1988. Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present disclosure, the compositions of RNAi agents and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems. Allen. L V., Popovich N G., and Ansel H C., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245). Typically, microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems. Rosoff, M., Ed., 1989. VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used, and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen. L V., Popovich N G., and Ansel H C., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker. Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300. PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs, peptides or RNAi agents. Microemulsions have also been effective in the transdermal delivery of active components in both cosmetic and pharmaceutical applications. It is expected that the microemulsion compositions and formulations of the present disclosure will facilitate the increased systemic absorption of RNAi agents and nucleic acids from the gastrointestinal tract, as well as improve the local cellular uptake of RNAi agents and nucleic acids.

Microemulsions of the present disclosure can also contain additional components and additives such as sorbitan monostearate (Grill 3), Labrasol, and penetration enhancers to improve the properties of the formulation and to enhance the absorption of the RNAi agents and nucleic acids of the present disclosure. Penetration enhancers used in the microemulsions of the present disclosure can be classified as belonging to one of five broad categories-surfactants, fatty acids, bile salts, chelating agents, and non-chelating non-surfactants (Lee et al., Critical Reviews in Therapeutic Drug Carrier Systems, 1991, p. 92). Each of these classes has been discussed above.

iii. Microparticles

An RNAi agent of the disclosure may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present disclosure employs various penetration enhancers to effect the efficient delivery of nucleic acids, particularly RNAi agents, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, NY, 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of RNAi agents through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, NY, 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, I-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou. E., et al. Enhancement in Drug Delivery, CRC Press, Danvers, MA, 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, NY, 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten. M. Surfactants and polymers in drug delivery. Informa Health Care, New York, NY, 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating agents, as used in connection with the present disclosure, can be defined as compounds that remove metallic ions from solution by forming complexes therewith, with the result that absorption of RNAi agents through the mucosa is enhanced. With regards to their use as penetration enhancers in the present disclosure, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, MA, 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

As used herein, non-chelating non-surfactant penetration enhancing compounds can be defined as compounds that demonstrate insignificant activity as chelating agents or as surfactants but that nonetheless enhance absorption of RNAi agents through the alimentary mucosa (see e.g., Muranishi, Critical Reviews in Therapeutic Drug Carrier Systems, 1990, 7, 1-33). This class of penetration enhancers includes, for example, unsaturated cyclic ureas, I-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of RNAi agents at the cellular level can also be added to the pharmaceutical and other compositions of the present disclosure. For example, cationic lipids, such as lipofectin (Junichi et al, U.S. Pat. No. 5,705,188), cationic glycerol derivatives, and polycationic molecules, such as polylysine (WO 97/30731), are also known to enhance the cellular uptake of dsRNAs.

Other agents can be utilized to enhance the penetration of the administered nucleic acids, including glycols such as ethylene glycol and propylene glycol, pyrrols such as 2-pyrrol, azones, and terpenes such as limonene and menthone.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients suitable for non-parenteral administration which do not deleteriously react with nucleic acids can also be used to formulate the compositions of the present disclosure. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present disclosure can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings or aromatic substances and the like which do not deleteriously interact with the nucleic acid(s) of the formulation.

Aqueous suspensions can contain substances which increase the viscosity of the suspension including, for example, sodium carboxymethylcellulose, sorbitol or dextran. The suspension can also contain stabilizers.

In some embodiments, pharmaceutical compositions featured in the disclosure include (a) one or more RNAi agents and (b) one or more agents which function by a non-RNAi mechanism and which are useful in treating an ADRA2A-associated disorder. Examples of such agents include, but are not limited to, cholinesterase inhibitors. N-methyl D-aspartate (NMDA) antagonists, levodopa, dopamine agonists, monoamine inhibitors, reserpine, anticonvulsants, antipsychotic agents, and antidepressants.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred.

The data obtained from cell culture assays and animal studies can be used in formulating a range of dosage for use in humans. The dosage of compositions featured herein in the disclosure lies generally within a range of circulating concentrations that include the $ED_{50}$ with little or no toxicity. The dosage can vary within this range depending upon the dosage form employed and the route of administration utilized. For any compound used in the methods featured in the disclosure, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the RNAi agents featured in the disclosure can be administered in combination with other known agents effective in treatment of pathological processes mediated by nucleotide repeat expression. In any event, the administering physician can adjust the amount and timing of RNAi agent administration on the basis of results observed using standard measures of efficacy known in the art or described herein.

VII. Kits

In certain aspects, the instant disclosure provides kits that include a suitable container containing a pharmaceutical formulation of a siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof).

Such kits include one or more dsRNA agent(s) and instructions for use, e.g., instructions for administering a prophylactically or therapeutically effective amount of a dsRNA agent(s). The dsRNA agent may be in a vial or a pre-filled syringe. The kits may optionally further comprise means for administering the dsRNA agent (e.g., an injection device, such as a pre-filled syringe or an intrathecal pump), or means for measuring the inhibition of C3 (e.g., means for measuring the inhibition of ADRA2A mRNA, ADRA2A protein, and/or ADRA2A activity). Such means for measuring the inhibition of ADRA2A may comprise a means for obtaining a sample from a subject, such as, e.g., a CSF and/or plasma sample. The kits of the invention may optionally further comprise means for determining the therapeutically effective or prophylactically effective amount.

In certain embodiments the individual components of the pharmaceutical formulation may be provided in one container. Alternatively, it may be desirable to provide the components of the pharmaceutical formulation separately in two or more containers, e.g., one container for a siRNA compound preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

VII. Methods for Inhibiting ADRA2A Expression

The present disclosure also provides methods of inhibiting expression of an ADRA2A gene in a cell. The methods include contacting a cell with an RNAi agent, e.g., double stranded RNAi agent, in an amount effective to inhibit expression and/or activity of ADRA2A in the cell, thereby inhibiting expression and/or activity of ADRA2A in the cell. In certain embodiments of the disclosure, ADRA2A expression and/or activity is inhibited by at least 30% preferentially in CNS (e.g., brain) cells. In specific embodiments. ADRA2A expression and/or activity is inhibited by at least 30%. In other embodiments of the disclosure. ADRA2A expression and/or activity is inhibited preferentially by at least 30% in ocular (e.g., eye) cells. In certain other embodiments of the disclosure, ADRA2A expression and/or activity is inhibited by at least 30% preferentially in hepatocytes.

Contacting of a cell with an RNAi agent, e.g., a double stranded RNAi agent, may be done in vitro or in vivo. Contacting a cell in vivo with the RNAi agent includes contacting a cell or group of cells within a subject, e.g., a human subject, with the RNAi agent. Combinations of in vitro and in vivo methods of contacting a cell are also possible.

Contacting a cell may be direct or indirect, as discussed above. Furthermore, contacting a cell may be accomplished via a targeting ligand, including any ligand described herein or known in the art. In some embodiments, the targeting ligand is a carbohydrate moiety, e.g., a GalNAc ligand, or any other ligand that directs the RNAi agent to a site of interest.

The term "inhibiting," as used herein, is used interchangeably with "reducing," "silencing," "downregulating," "suppressing" and other similar terms, and includes any level of inhibition. In certain embodiments, a level of inhibition, e.g., for an RNAi agent of the instant disclosure, can be assessed in cell culture conditions, e.g., wherein cells in cell culture are transfected via Lipofectamine™-mediated transfection at a concentration in the vicinity of a cell of 10 nM or less, 1 nM or less, etc. Knockdown of a given RNAi agent can be determined via comparison of pre-treated levels in cell culture versus post-treated levels in cell culture, optionally also comparing against cells treated in parallel with a scrambled or other form of control RNAi agent. Knockdown in cell culture of, e.g., at least about 30%, can thereby be identified as indicative of "inhibiting" or "reducing", "downregulating" or "suppressing", etc. having occurred. It is expressly contemplated that assessment of targeted mRNA or encoded protein levels (and therefore an extent of "inhibiting", etc. caused by an RNAi agent of the disclosure) can also be assessed in in vivo systems for the RNAi agents of the instant disclosure, under properly controlled conditions as described in the art.

The phrase "inhibiting ADRA2A," "inhibiting expression of an ADRA2A gene" or "inhibiting expression of ADRA2A," as used herein, includes inhibition of expression of any ADRA2A gene (such as, e.g., a mouse ADRA2A gene, a rat ADRA2A gene, a monkey ADRA2A gene, or a human ADRA2A gene) as well as variants or mutants of an ADRA2A gene that encode an ADRA2A protein. Thus, the ADRA2A gene may be a wild-type ADRA2A gene, a mutant ADRA2A gene, or a transgenic ADRA2A gene in the context of a genetically manipulated cell, group of cells, or organism.

"Inhibiting expression of an ADRA2A gene" includes any level of inhibition of an ADRA2A gene, e.g., at least partial suppression of the expression of an ADRA2A gene, such as an inhibition by at least 30%. In certain embodiments, inhibition is by at least 35%, at least 40%, at least 45%, by at least 50%, at least 55%, by at least 60%, by at least 65%, by at least 70%, by at least 75%, by at least 80%, by at least 85%, by at least 90%, by at least 95%, or by at least 99%. ADRA2A inhibition can be measured using the in vitro assay with, e.g., A549 cells and a 10 nM concentration of the RNA agent and the PCR assay as provided in the examples herein, are contemplated to be within the scope of the present disclosure. In some embodiments. ADRA2A inhibition can be measured using the in vitro assay with primary mouse hepatocytes. In another embodiment, ADRA2A inhibition can be measured using the in vitro assay with Cos-7 (Dual-Luciferase psiCHECK2 vector). In yet another embodiment. ADRA2A inhibition can be measured using the in vitro assay with BE(2)-C cells. In some embodiments, ADRA2A inhibition can be measured using the in vitro assay with Neuro-2a cells.

The expression of an ADRA2A gene may be assessed based on the level of any variable associated with ADRA2A gene expression, e.g., ADRA2A mRNA level (e.g., sense mRNA, antisense mRNA, and/or total ADRA2A mRNA) or ADRA2A protein level (e.g., total ADRA2A protein and/or wild-type ADRA2A protein).

Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

For example, in some embodiments of the methods of the disclosure, expression of an ADRA2A gene is inhibited by at least 30%, 40%, 50%, 60%/0, 70%, 80%, 85%, 90%, or 95%, or to below the level of detection of the assay. In certain embodiments, the methods include a clinically relevant inhibition of expression of ADRA2A, e.g. as demonstrated by a clinically relevant outcome after treatment of a subject with an agent to reduce the expression of ADRA2A.

Inhibition of the expression of an ADRA2A gene may be manifested by a reduction of the amount of mRNA expressed by a first cell or group of cells (such cells may be present, for example, in a sample derived from a subject) in which an ADRA2A gene is transcribed and which has or have been treated (e.g., by contacting the cell or cells with an RNAi agent of the disclosure, or by administering an RNAi agent of the disclosure to a subject in which the cells are or were present) such that the expression of an ADRA2A gene is inhibited, as compared to a second cell or group of cells substantially identical to the first cell or group of cells but which has not or have not been so treated (control cell(s) not treated with an RNAi agent or not treated with an RNAi agent targeted to the gene of interest). The degree of inhibition may be expressed in terms of:

$$\frac{(mRNA \text{ in control cells}) - (mRNA \text{ in treated cells})}{(mRNA \text{ in control cells})} \cdot 100\%$$

In other embodiments, inhibition of the expression of an ADRA2A gene may be assessed in terms of a reduction of a parameter that is functionally linked to an ADRA2A gene expression, e.g., ADRA2A protein expression. ADRA2A gene silencing may be determined in any cell expressing ADRA2A, either endogenous or heterologous from an expression construct, and by any assay known in the art.

Inhibition of the expression of an ADRA2A protein may be manifested by a reduction in the level of the ADRA2A protein (or functional parameter, e.g., kinase and/or GTPase activity) that is expressed by a cell or group of cells (e.g., the level of protein expressed in a sample derived from a subject). As explained above, for the assessment of mRNA suppression, the inhibition of protein expression levels in a treated cell or group of cells may similarly be expressed as a percentage of the level of protein in a control cell or group of cells. In some embodiments, the phrase "inhibiting ADRA2A", can also refer to the inhibition of the kinase and/or GTPase activity of ADRA2A, e.g., at least partial suppression of the ADRA2A kinase and/or GTPase activity, such as an inhibition by at least 30%. In certain embodiments, inhibition of the ADRA2A kinase and/or GTPase activity is by at least 35%, at least 40%, at least 45%, by at least 50%, at least 55%, by at least 60%, by at least 65%, by at least 70%, by at least 75%, by at least 80%, by at least 85%, by at least 90%, by at least 95%, or by at least 99%. ADRA2A kinase activity can be measured using the in vitro assay with, e.g., the assay described in (Smith et al. (2006) Nature Neuroscience 9(10):1231-3). ADRA2A GTPase activity can be measured using the in vitro assay with, e.g., the assay described in (Xiong et al. (2010) Plos Genet 6(4): e1000902).

A control cell or group of cells that may be used to assess the inhibition of the expression of an ADRA2A gene includes a cell or group of cells that has not yet been contacted with an RNAi agent of the disclosure. For example, the control cell or group of cells may be derived from an individual subject (e.g., a human or animal subject) prior to treatment of the subject with an RNAi agent.

The level of ADRA2A mRNA that is expressed by a cell or group of cells may be determined using any method known in the art for assessing mRNA expression. In one embodiment, the level of expression of ADRA2A in a sample is determined by detecting a transcribed polynucleotide, or portion thereof, e.g., mRNA of the ADRA2A gene. RNA may be extracted from cells using RNA extraction techniques including, for example, using acid phenol/guanidine isothiocyanate extraction (RNAzol B; Biogenesis). RNeasy™ RNA preparation kits (Qiagen®) or PAXgene (PreAnalytix, Switzerland). Typical assay formats utilizing ribonucleic acid hybridization include nuclear run-on assays, RT-PCR. RNase protection assays, northern blotting, in situ hybridization, and microarray analysis. Strand specific ADRA2A mRNAs may be detected using the quantitative RT-PCR and or droplet digital PCR methods described in, for example, Jiang, et al. supra, Lagier-Tourenne, et al., supra and Jiang, et al., supra. Circulating ADRA2A mRNA may be detected using methods the described in WO2012/177906, the entire contents of which are hereby incorporated herein by reference.

In some embodiments, the level of expression of ADRA2A is determined using a nucleic acid probe. The term "probe", as used herein, refers to any molecule that is capable of selectively binding to a specific ADRA2A nucleic acid or protein, or fragment thereof. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses and probe arrays. One method for the determination of mRNA levels involves contacting the isolated mRNA with a nucleic acid molecule (probe) that can hybridize to ADRA2A mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affy Metrix® gene chip array. A skilled artisan can readily adapt known mRNA detection methods for use in determining the level of ADRA2A mRNA.

An alternative method for determining the level of expression of ADRA2A in a sample involves the process of nucleic acid amplification or reverse transcriptase (to prepare cDNA) of for example mRNA in the sample, e.g., by RT-PCR (the experimental embodiment set forth in Mullis, 1987. U.S. Pat. No. 4,683,202), ligase chain reaction (Barany (1991) *Proc. Natl. Acad. Sci. USA* 88:189-193), self-sustained sequence replication (Guatelli et al. (1990) *Proc. Natl. Acad Sci. USA* 87:1874-1878), transcriptional amplification system (Kwoh et al. (1989) *Proc. Natl. Acad Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the disclosure, the level of expression of ADRA2A is determined by quantitative fluorogenic RT-PCR (i.e., the TaqMan™ System), by a Dual-Glo® Luciferase assay, or by other art-recognized method for measurement of ADRA2A expression or mRNA level.

The expression level of ADRA2A mRNA may be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of ADRA2A expression level may also comprise using nucleic acid probes in solution.

In some embodiments, the level of mRNA expression is assessed using branched DNA (bDNA) assays or real time PCR (qPCR). The use of this PCR method is described and exemplified in the Examples presented herein. Such methods can also be used for the detection of ADRA2A nucleic acids.

The level of ADRA2A protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like. Such assays can also be used for the detection of proteins indicative of the presence or replication of ADRA2A proteins. In some embodiments, the efficacy of the methods of the disclosure in the treatment of an ADRA2A-associated disease is assessed by a decrease in ADRA2A mRNA level (e.g., by assessment of a CSF sample and/or plasma sample for ADRA2A level, by brain biopsy, or otherwise).

In some embodiments of the methods of the disclosure, the RNAi agent is administered to a subject such that the RNAi agent is delivered to a specific site within the subject. The inhibition of expression of ADRA2A may be assessed using measurements of the level or change in the level of ADRA2A mRNA (e.g., sense mRNA, antisense mRNA, total ADRA2A mRNA) and/or ADRA2A protein (e.g., total ADRA2A protein, wild-type ADRA2A protein) in a sample derived from a specific site within the subject, e.g., CNS cells, ocular cells. In certain embodiments, the methods include a clinically relevant inhibition of expression of ADRA2A, e.g. as demonstrated by a clinically relevant outcome after treatment of a subject with an agent to reduce the expression of ADRA2A, such as, for example, stabilization or inhibition of caudate atrophy (e.g., as assessed by volumetric MRI (vMRI)), a stabilization or reduction in neurofilament light chain (Nfl) levels in a CSF sample from a subject, a reduction in mutant ADRA2A mRNA or a cleaved mutant ADRA2A protein, e.g., full-length mutant ADRA2A mRNA or protein and a cleaved mutant ADRA2A mRNA or protein, and a stabilization or improvement in Unified ADRA2A-associated disease Rating Scale (UHDRS) score.

As used herein, the terms detecting or determining a level of an analyte are understood to mean performing the steps to determine if a material, e.g., protein, RNA, is present. As used herein, methods of detecting or determining include detection or determination of an analyte level that is below the level of detection for the method used.

IX. Methods of Treating or Preventing ADRA2A-Associated Diseases

The present disclosure also provides methods of using an RNAi agent of the disclosure or a composition containing an RNAi agent of the disclosure to reduce or inhibit ADRA2A expression in a cell. The methods include contacting the cell with a dsRNA of the disclosure and maintaining the cell for a time sufficient to obtain degradation of the mRNA transcript of an ADRA2A gene, thereby inhibiting expression of the ADRA2A gene in the cell.

Reduction in gene expression can be assessed by any methods known in the art. For example, a reduction in the expression of ADRA2A may be determined by determining the mRNA expression level of ADRA2A using methods routine to one of ordinary skill in the art, e.g., northern blotting, qRT-PCR; by determining the protein level of ADRA2A using methods routine to one of ordinary skill in the art, such as western blotting, immunological techniques.

In the methods of the disclosure the cell may be contacted in vitro or in vivo, i.e., the cell may be within a subject.

A cell suitable for treatment using the methods of the disclosure may be any cell that expresses an ADRA2A gene. A cell suitable for use in the methods of the disclosure may be a mammalian cell, e.g., a primate cell (such as a human cell or a non-human primate cell, e.g., a monkey cell or a chimpanzee cell), a non-primate cell (such as a rat cell, or a mouse cell). In one embodiment, the cell is a human cell, e.g., a human CNS cell, or a human ocular cell.

ADRA2A expression (e.g., as assessed by sense mRNA, antisense mRNA, total ADRA2A mRNA, total ADRA2A protein) is inhibited in the cell by at least 30%, 40%, preferably at least 50%, 60%, 70%, 80%, 85%, 90%, or 95%, 99%, or to below the level of detection of the assay.

The in vivo methods of the disclosure may include administering to a subject a composition containing an RNAi agent, where the RNAi agent includes a nucleotide sequence that is complementary to at least a part of an RNA transcript of the ADRA2A gene of the mammal to be treated. When the organism to be treated is a mammal such as a human, the composition can be administered by any means known in the art including, but not limited to oral, intraperitoneal, or parenteral routes, including intracranial (e.g., intraventricular, intraparenchymal, and intrathecal), intravenous, intramuscular, intravitreal, subcutaneous, transdermal, airway (aerosol), nasal, rectal, and topical (including buccal and sublingual) administration. In certain embodiments, the compositions are administered by intravenous infusion or injection. In certain embodiments, the compositions are administered by subcutaneous injection. In certain embodiments, the compositions are administered by intrathecal injection.

In some embodiments, the administration is via a depot injection. A depot injection may release the RNAi agent in a consistent way over a prolonged time period. Thus, a depot injection may reduce the frequency of dosing needed to obtain a desired effect, e.g., a desired inhibition of ADRA2A, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intracranial, intravenous, subcutaneous, arterial, or epidural infusions. In preferred embodiments, the infusion pump is a subcutaneous infusion pump. In other embodiments, the pump is a surgically implanted pump that delivers the RNAi agent to the CNS.

The mode of administration may be chosen based upon whether local or systemic treatment is desired and based upon the area to be treated. The route and site of administration may be chosen to enhance targeting.

In one aspect, the present disclosure also provides methods for inhibiting the expression of an ADRA2A gene in a mammal. The methods include administering to the mammal a composition comprising a dsRNA that targets an ADRA2A gene in a cell of the mammal, thereby inhibiting expression of the ADRA2A gene in the cell. Reduction in gene expression can be assessed by any methods known it the art and by methods, e.g. qRT-PCR, described herein. Reduction in protein production can be assessed by any methods known it the art and by methods, e.g. ELISA, described herein. In one embodiment, a CNS biopsy sample or a cerebrospinal fluid (CSF) sample serves as the tissue material for monitoring the reduction in ADRA2A gene or protein expression (or of a proxy therefore).

The present disclosure further provides methods of treatment of a subject in need thereof. The treatment methods of the disclosure include administering an RNAi agent of the disclosure to a subject, e.g., a subject that would benefit from inhibition of ADRA2A expression, such as a subject having a missense and/or deletion mutations in the ADRA2A gene, in a therapeutically effective amount of an RNAi agent targeting an ADRA2A gene or a pharmaceutical composition comprising an RNAi agent targeting an ADRA2A gene.

In addition, the present disclosure provides methods of preventing, treating or inhibiting the progression of an ADRA2A-associated disease or an ADRA2A-associated disorder in a subject. The methods include administering to the subject a therapeutically effective amount of any of the RNAi agent, e.g., dsRNA agents, or the pharmaceutical composition provided herein, thereby preventing, treating or inhibiting the progression of an ADRA2A-associated disease or disorder in the subject.

An RNAi agent of the disclosure may be administered as a "free RNAi agent." A free RNAi agent is administered in the absence of a pharmaceutical composition. The naked RNAi agent may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the RNAi agent can be adjusted such that it is suitable for administering to a subject.

Alternatively, an RNAi agent of the disclosure may be administered as a pharmaceutical composition, such as a dsRNA liposomal formulation.

Subjects that would benefit from a reduction or inhibition of ADRA2A gene expression are those having an ADRA2A-associated disease. Exemplary ADRA2A-associated diseases include, but are not limited to neurodegenerative disorders such as tauopathies (including primary tauopathies and Alzheimer's disease).

Tauopathies may be difficult to diagnose, particularly early in the course of a neurodegenerative disease, and may be difficult to distinguish from other tauopathies. Symptoms of tauopathies generally coincide with the particular neurodegenerative disease to which the tauopathy contributes and may include forgetfulness (particularly for Alzheimer's disease), anomia, aphasia, impaired fluency (e.g., letter-cued fluency), cognitive impairments, neurological impairments (e.g., frequent falling, impaired ocular movements, difficulty with motorized sequences, asymmetric motor abnormalities, apraxia), executive dysfunction, etc. Subjects with Alzheimer's disease, in particular, may generally present with impaired memory, including rapid forgetting, some degree of anomia, poor visuoconstruction, and impaired category fluency, with preserved phonemic fluency. Neurodegenerative diseases, including tauopathies, may generally be diagnosed by neuropsychological and/or neurological evaluation. Neurological exam of subjects having Alzheimer's disease tends to remain normal until more advanced stages. Neuroimaging (e.g., magnetic resonance imaging (MRI), positron emission topography (PET)) may be useful in identifying tau-mediated changes in brain structure and function. Subjects with Alzheimer's disease generally display hippocampal and parietal atrophy on MRI. PET in vivo imaging with tau tracers can be used to characterize the size and/or distribution of tau deposits in the brain, which may help identify and distinguish tauopathies. Levels of total tau (e.g., in cerebrospinal fluid and/or plasma) and total phosphotau (e.g., in plasma) are strongly associated with Alzheimer's disease and mild cognitive impairment due to Alzheimer's disease.

The disclosure further provides methods for the use of an RNAi agent or a pharmaceutical composition thereof, e.g., for treating a subject that would benefit from reduction or inhibition of ADRA2A expression, e.g., a subject having an ADRA2A-associated disorder, in combination with other pharmaceuticals or other therapeutic methods, e.g., with known pharmaceuticals or known therapeutic methods, such as, for example, those which are currently employed for treating these disorders. For example, in certain embodiments, an RNAi agent targeting ADRA2A is administered in combination with, e.g., an agent useful in treating an ADRA2A-associated disorder as described elsewhere herein or as otherwise known in the art. For example, additional agents suitable for treating a subject that would benefit from reduction in ADRA2A expression, e.g., a subject having an ADRA2A-associated disorder, may include agents currently used to treat symptoms of ADRA2A-associated diseases. The RNAi agent and additional therapeutic agents may be administered at the same time or in the same combination, e.g., intrathecally, or the additional therapeutic agent can be administered as part of a separate composition or at separate times or by another method known in the art or described herein.

Existing treatments for neurodegenerative diseases, including tauopathies, are primarily symptomatic. For example, subjects having a tauopathy may benefit from speech therapy, physical therapy, and/or treatment for apathy, depression (e.g., selective serotonin reuptake inhibitors). In general, treatment of a tauopathy may be coupled with an appropriate treatment for dementia or motor dysfunction.

Exemplary additional therapeutics include, for example, a cholinesterase inhibitor, e.g., donepezil (Aricept), N-methyl D-aspartate (NMDA) antagonists, e.g., memantine (Namenda), levodopa, dopamine agonists, e.g., apriprazole (Abilify), a monoamine inhibitor, e.g., tetrabenazine (Xenazine), deutetrabenazine (Austedo), and reserpine, an anticonvulsant, e.g., valproic acid (Depakote, Depakene, Depacon), and clonazepam (Klonopin), an antipsychotic agent, e.g., risperidone (Risperdal), and haloperidol (Haldol), and an antidepressant, e.g., paroxetine (Paxil).

In one embodiment, the method includes administering a composition featured herein such that expression of the target ADRA2A gene is decreased, for at least one month. In preferred embodiments, expression is decreased for at least 2 months, 3 months, or 6 months.

Preferably, the RNAi agents useful for the methods and compositions featured herein specifically target RNAs (primary or processed) of the target ADRA2A gene. Compositions and methods for inhibiting the expression of these genes using RNAi agents can be prepared and performed as described herein.

Administration of the dsRNA according to the methods of the disclosure may result in a reduction of the severity, signs, symptoms, or markers of such diseases or disorders in a patient with an ADRA2A-associated disorder. By "reduction" in this context is meant a statistically significant or clinically significant decrease in such level. The reduction can be, for example, at least 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of an ADRA2A-associated disorder may be assessed, for example, by periodic monitoring of a subject's marker's and/or symptoms. Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an RNAi agent targeting ADRA2A or pharmaceutical composition thereof, "effective against" an ADRA2A-associated disorder indicates that administration in a clinically appropriate manner results in a beneficial effect for at least a statistically significant fraction of patients, such as an improvement of symptoms, a cure, a reduction in disease, extension of life, improvement in quality of life, or other effect generally recognized as positive by medical doctors familiar with treating ADRA2A-associated disorders and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given RNAi agent drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale. Any positive change resulting in e.g., lessening of severity of disease measured using the appropriate scale, represents adequate treatment using an RNAi agent or RNAi agent formulation as described herein.

Subjects can be administered a therapeutic amount of dsRNA, such as about 0.01 mg/kg to about 200 mg/kg.

The RNAi agent can be administered intrathecally, via intravitreal injection, or by intravenous infusion over a period of time, on a regular basis. In certain embodiments, after an initial treatment regimen, the treatments can be administered on a less frequent basis. Administration of the RNAi agent can reduce ADRA2A levels, e.g., in a cell, tissue, blood, CSF sample or other compartment of the patient.

Before administration of a full dose of the RNAi agent, patients can be administered a smaller dose, such as a 5% infusion reaction, and monitored for adverse effects, such as an allergic reaction. In another example, the patient can be monitored for unwanted immunostimulatory effects, such as increased cytokine (e.g., TNF-alpha or INF-alpha) levels.

Alternatively, the RNAi agent can be administered subcutaneously, i.e., by subcutaneous injection. One or more injections may be used to deliver the desired, e.g., monthly dose of RNAi agent to a subject. The injections may be repeated over a period of time. The administration may be repeated on a regular basis. In certain embodiments, after an initial treatment regimen, the treatments can be administered on a less frequent basis. A repeat-dose regimen may include administration of a therapeutic amount of RNAi agent on a regular basis, such as monthly or extending to once a quarter, twice per year, once per year. In certain embodiments, the RNAi agent is administered about once per month to about once per quarter (i.e., about once every three months).

Unless otherwise defined, all technical and scientific terms used herein have the same meaning as commonly understood by one of ordinary skill in the art to which this invention belongs. Although methods and materials similar or equivalent to those described herein can be used in the practice or testing of the RNAi agents and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

An informal Sequence Listing is filed herewith and forms part of the specification as filed.

EXAMPLES

Example 1. iRNA Synthesis

Source of Reagents

Where the source of a reagent is not specifically given herein, such reagent can be obtained from any supplier of reagents for molecular biology at a quality/purity standard for application in molecular biology.

siRNA Design siRNAs targeting the human ADRA2A gene (human: NCBI refseqID NM_000681; NCBI GeneID: 150) were designed using custom R and Python scripts. The human NM_000681 REFSEQ mRNA has a length of 3879 bases.

A detailed list of the unmodified ADRA2A sense and antisense strand nucleotide sequences is shown in Table 3. A detailed list of the modified ADRA2A sense and antisense strand nucleotide sequences is shown in Table 4.

It is to be understood that, throughout the application, a duplex name without a decimal is equivalent to a duplex name with a decimal which merely references the batch number of the duplex. For example, AD-1201748 is equivalent to AD-1201748.1.

siRNA Synthesis siRNAs were synthesized and annealed using routine methods known in the art.

Briefly, siRNA sequences were synthesized at 1 μmol scale on a Mermade 192 synthesizer (BioAutomation) using the solid support mediated phosphoramidite chemistry. The solid support was controlled pore glass (500 A) loaded with custom GalNAc ligand or universal solid support (AM biochemical). Ancillary synthesis reagents, 2'-F and 2'-O-Methyl RNA and deoxy phosphoramidites were obtained from Thermo-Fisher (Milwaukee, WI) and Hongene (China). 2'F 2'-O-Methyl, GNA (glycol nucleic acids), 5'phosphate and other modifications were introduced using the corresponding phosphoramidites. Synthesis of 3' GalNAc conjugated single strands was performed on a GalNAc modified CPG support. Custom CPG universal solid support was used for the synthesis of antisense single strands. Coupling time for all phosphoramidites (100 mM in acetonitrile) was 5 min employing 5-Ethylthio-1H-tetrazole (ETT) as activator (0.6 M in acetonitrile). Phosphorothioate linkages were generated using a 50 mM solution of 3-((Dimethylamino-methylidene) amino)-3H-1,2,4-dithiazole-3-thione (DDTT, obtained from Chemgenes (Wilmington, MA, USA)) in anhydrous acetonitrile/pyridine (1:1 v/v). Oxidation time was 3 minutes. All sequences were synthesized with final removal of the DMT group ("DMT off").

Upon completion of the solid phase synthesis, oligoribonucleotides were cleaved from the solid support and deprotected in sealed 96 deep well plates using 200 μL Aqueous Methylamine reagents at 60° C. for 20 minutes. For sequences containing 2' ribo residues (2'-OH) that are protected with a tert-butyl dimethyl silyl (TBDMS) group, a second step deprotection was performed using TEA.3HF (triethylamine trihydro fluoride) reagent. To the methylamine deprotection solution, 200 uL of dimethyl sulfoxide (DMSO) and 300 ul TEA.3HF reagent was added and the solution was incubated for additional 20 min at 60° C. At the end of cleavage and deprotection step, the synthesis plate was allowed to come to room temperature and was precipitated by addition of 1 mL of acetonitrile:ethanol mixture (9:1). The plates were cooled at −80 C for 2 hrs, supernatant decanted carefully with the aid of a multi-channel pipette. The oligonucleotide pellet was re-suspended in 20 mM NaOAc buffer and were desalted using a 5 mL HiTrap size exclusion column (GE Healthcare) on an AKTA Purifier System equipped with an A905 autosampler and a Frac 950 fraction collector. Desalted samples were collected in 96-well plates. Samples from each sequence were analyzed by LC-MS to confirm the identity, UV (260 nm) for quantification and a selected set of samples by IEX chromatography to determine purity.

Annealing of single strands was performed on a Tecan liquid handling robot. Equimolar mixture of sense and antisense single strands were combined and annealed in 96 well plates. After combining the complementary single strands, the 96-well plate was sealed tightly and heated in an oven at 100° C. for 10 minutes and allowed to come slowly to room temperature over a period 2-3 hours. The concentration of each duplex was normalized to 10 μM in 1×PBS and then submitted for in vitro screening assays.

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Ab | beta-L-adenosine-3'-phosphate |
| Abs | beta-L-adenosine-3'-phosphorothioate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cbs | beta-L-cytidine-3'-phosphorothioate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide, modified or unmodified |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridme-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol (Hyp-(GalNAc-alkyl)3) |
| Y34 | 2-hydroxymethyl-tetrahydrofurane-4-methoxy-3-phosphate (abasic 2'-OMe furanose) |
| Y44 | inverted abasic DNA (2-hydroxymethyl-tetrahydrofurane-5-phosphate) |
| (Agn) | Adenosine-glycol nucleic acid (GNA) |
| (Cgn) | Cytidine-glycol nucleic acid (GNA) |
| (Ggn) | Guanosine-glycol nucleic acid (GNA) |
| (Tgn) | Thymidine-glycol nucleic acid (GNA) S-Isomer |
| P | Phosphate |
| VP | Vinyl-phosphonate |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine-3'-phosphate |
| dTs | 2'-deoxythymidine-3'-phosphorothioate |
| dU | 2'-deoxyuridine |
| dUs | 2'-deoxyuridine-3'-phosphorothioate |

TABLE 3

Unmodified Sense and Antisense Strand Sequences of ADRA2A dsRNA Agents

| Duplex Name | Sense Sequence 5' to 3' | SEQ ID NO: | Range in NM_000681 | Antisense Sequence 5' to 3' | SEQ ID NO: | Range in NM_000681 |
|---|---|---|---|---|---|---|
| AD-1201748 | GGAGAGCUGAUC GUUCACCUG | 14 | 193-213 | CAGGUGAACGAUC AGCUCUCCAG | 149 | 191-213 |

TABLE 3-continued

Unmodified Sense and Antisense Strand Sequences of ADRA2A dsRNA Agents

| Duplex Name | Sense Sequence 5' to 3' | SEQ ID NO: | Range in NM_000681 | Antisense Sequence 5' to 3' | SEQ ID NO: | Range in NM_000681 |
|---|---|---|---|---|---|---|
| AD-1201749 | GCACAACUUUGGAAGUCUCGC | 15 | 323-343 | GCGAGACUUCCAAAGUUGUGCGC | 150 | 321-343 |
| AD-1201750 | AGAGAGUCGGUAAUCGCUUCG | 16 | 422-442 | CGAAGCGAUUACCGACUCUCUGG | 151 | 420-442 |
| AD-1201751 | UCGGGGAUGUAAGGCGACAGA | 17 | 440-460 | UCUGUCGCCUUACAUCCCCGAAG | 152 | 438-460 |
| AD-1201752 | CGGUAAGACCUCUUGCUUUCG | 18 | 528-548 | CGAAAGCAAGAGGUCUUACCGUG | 153 | 526-548 |
| AD-1201753 | UUGCUUUCGCUCAGGCUCAAG | 19 | 540-560 | CUUGAGCCUGAGCGAAAGCAAGA | 154 | 538-560 |
| AD-1201754 | CUCAAGAUUCAAGAUACAGAU | 20 | 555-575 | AUCUGUAUCUUGAAUCUUGAGCC | 155 | 553-575 |
| AD-1201755 | AUUUAAUUUCCUGUCAUCCUU | 21 | 594-614 | AAGGAUOACAGGAAAUUAAAUAU | 156 | 592-614 |
| AD-1201756 | UCAUCCUUCCAAGUUAUCAGG | 22 | 607-627 | CCUGAUAACUUGGAAGGAUGACA | 157 | 605-627 |
| AD-1201757 | UAUCAGGCCACCGAUGAUUUU | 23 | 621-641 | AAAAUCAUCGGUGGCCUGAUAAC | 158 | 619-641 |
| AD-1201758 | UUGUUCUCCCUUCUUGAAGAA | 24 | 641-661 | UUCUUCAAGAAGGGAGAACAAAA | 159 | 639-661 |
| AD-1201759 | AAGAAUAAAUCUCUCUUUACC | 25 | 657-677 | GGUAAAGAGAGAUUUAUUCUUCA | 160 | 655-677 |
| AD-1201760 | AUCGGCUCUCCCUACUCUCUC | 26 | 679-699 | GAGAGAGUAGGGAGAGCCGAUGG | 161 | 677-699 |
| AD-1201761 | GCCGCUUAGAAAUAAAACUUG | 27 | 702-722 | CAAGUUUUAUUUCUAAGCGGCGG | 162 | 700-722 |
| AD-1201762 | AAACUUGGCUGUAUUAGGAGC | 28 | 716-736 | GCUCCUAAUACAGCCAAGUUUUA | 163 | 714-736 |
| AD-1201763 | UUAGGAGCUCGGAGCAAGAAG | 29 | 729-749 | CUUCUUGCUCCGAGCUCCUAAUA | 164 | 727-749 |
| AD-1201764 | GUUCAUGUUCCGCCAGGAGCA | 30 | 965-985 | UGCUCCUGGCGGAACAUGAACGC | 165 | 963-985 |
| AD-1201765 | CCCCUUACUCCCUGCAGGUGA | 31 | 1090-1110 | UCACCUGCAGGGAGUAAGGGGUG | 166 | 1088-1110 |
| AD-1201766 | GCUCACCGUGUUCGGCAACGU | 32 | 1148-1168 | ACGUUGCCGAACACGGUGAGCAG | 167 | 1146-1168 |
| AD-1201767 | GUGCUCGUCAUCAUCGCCGUG | 33 | 1167-1187 | CACGGCGAUGAUGACGAGCACGU | 168 | 1165-1187 |
| AD-1201768 | CCCCAAAACCUCUUCCUGGUG | 34 | 1212-1232 | CACCAGGAAGAGGUUUUGGGGCG | 169 | 1210-1232 |
| AD-1201769 | UUCCUGGUGUCUCUGGCCUCG | 35 | 1224-1244 | CGAGGCCAGAGACACCAGGAAGA | 170 | 1222-1244 |
| AD-1201770 | CUCGUCAUCCCUUUCUCGCUG | 36 | 1266-1286 | CAGCGAGAAAGGGAUGACGAGCG | 171 | 1264-1286 |
| AD-1201771 | GCCAACGAGGUCAUGGGCUAC | 37 | 1287-1307 | GUAGCCCAUGACCUCGUUGGCCA | 172 | 1285-1307 |
| AD-1201772 | CUACUGGUACUUCGGCAAGGC | 38 | 1304-1324 | GCCUUGCCGAAGUACCAGUAGCC | 173 | 1302-1324 |
| AD-1201773 | UUGGUGCGAGAUCUACCUGGC | 39 | 1325-1345 | GCCAGGUAGAUCUCGCACCAAGC | 174 | 1323-1345 |

TABLE 3-continued

Unmodified Sense and Antisense Strand Sequences of ADRA2A dsRNA Agents

| Duplex Name | Sense Sequence 5' to 3' | SEQ ID NO: | Range in NM_000681 | Antisense Sequence 5' to 3' | SEQ ID NO: | Range in NM_000681 |
|---|---|---|---|---|---|---|
| AD-1201774 | CCUGGCGCUCGACGUGCUCUU | 40 | 13404360 | AAGAGCACGUCGAGCGCCAGGUA | 175 | 1338-1360 |
| AD-1201775 | CGUGCUCUUCUGCACGUCGUC | 41 | 1352-1372 | GACGACGUGCAGAAGAGCACGUC | 176 | 1350-1372 |
| AD-1201776 | GUCGUCCAUCGUGCACCUGUG | 42 | 1367-1387 | CACAGGUGCACGAUGGACGACGU | 177 | 1365-1387 |
| AD-1201777 | CGCUACUGGUCCAUGACACAG | 43 | 1404-1424 | CUGUGUGAUGGACCAGUAGCGGU | 178 | 1402-1424 |
| AD-1201778 | AUCACACAGGCCAUCGAGUAC | 44 | 1416-1436 | GUACUCGAUGGCCUGUGUGAUGG | 179 | 1414-1436 |
| AD-1201779 | AUCGAGUACAACCUGAAGCGC | 45 | 1428-1448 | GCGCUUCAGGUUGUACUCGAUGG | 180 | 1426-1448 |
| AD-1201780 | CAUCAAGGCCAUCAUCAUCAC | 46 | 1460-1480 | GUGAUGAUGAUGGCCUUGAUGCG | 181 | 1458-1480 |
| AD-1201781 | CACCGUGUGGGU(AUCUCGGC | 47 | 1478-1498 | GCCGAGAUGACCCACACGGUGAU | 182 | 1476-1498 |
| AD-1201782 | CUCGGCCGUCAUGUCCUUCCC | 48 | 1493-1513 | GGGAAGGAGAUGACGGCCGAGAU | 183 | 1491-1513 |
| AD-1201783 | CUCCUUCCCGCCGCUCAUCUC | 49 | 15054525 | GAGAUGAGCGGCGGGAAGGAGAU | 184 | 1503-1525 |
| AD-1201784 | GCUCAUCUCCAUCGAGAAGAA | 50 | 1517-1537 | UUCUUCUCGAUGGAGAUGAGCGG | 185 | 1515-1537 |
| AD-1201785 | UGGGAGAUCAACGACCAGAAG | 51 | 1575-1595 | CUUCUGGUCGUUGAUCUCGCAGC | 186 | 1573-1595 |
| AD-1201786 | CCAGAAGUGGUACGUCAUCUC | 52 | 1589-1609 | GAGAUGACGUACCACUUCUGGUC | 187 | 1587-1609 |
| AD-1201787 | CGUCAUCUCGUCGUGCAUCGG | 53 | 1601-1621 | CCGAUGCACGACGAGAUGACGUA | 188 | 1599-1621 |
| AD-1201788 | CGGCUCCUUCUUCGCUCCCUG | 54 | 1619-1639 | CAGGGAGCGAAGAAGGAGCCGAU | 189 | 1617-1639 |
| AD-1201789 | CUCAUCAUGAUCCUGGUCUAC | 55 | 1641-1661 | GUAGACCAGGAUCAUGAUGAGGC | 190 | 1639-1661 |
| AD-1201790 | CUGGUCUACGUGCGCAUCUAC | 56 | 1653-1673 | GUAGAUGCGCACGUAGACCAGGA | 191 | 1651-1673 |
| AD-1201791 | CGCAUCUACCAGAUCGCCAAG | 57 | 1665-1685 | CUUGGCGAUCUGGUAGAUGCGCA | 192 | 1663-1685 |
| AD-1201792 | GAGAGCUCGUCUUCCGACCAC | 58 | 1896-1916 | GUGGUCGGAAGACGAGCUCUCCU | 193 | 1894-1916 |
| AD-1201793 | CGAGAAGCGCUUCACGUUCGU | 59 | 2117-2137 | ACGAACGUGAAGCGCUUCUCGCG | 194 | 2115-2137 |
| AD-1201794 | CACGUUCGUGCUGOCCGUGGU | 60 | 2129-2149 | ACCACGGCCAGCACGAACGUGAA | 195 | 2127-2149 |
| AD-1201795 | GUGGUCAUCGOAGUGUUCGUG | 61 | 2145-2165 | CACGAACACUCCGAUGACCACGG | 196 | 2143-2165 |
| AD-1201796 | GUGGUGUGCUGGUUCCCCUUC | 62 | 2163-2183 | GAAGGGGAACCAGCACACCACGA | 197 | 2161-2183 |
| AD-1201797 | CCCCUUCUUCUUCACCUACAC | 63 | 2177-2197 | GUGUAGGUGAAGAAGAAGGGGAA | 198 | 2175-2197 |
| AD-1201798 | CACCUACACGCUCACGGCCGU | 64 | 2189-2209 | ACGGCCGUGAGCGUGUAGGUGAA | 199 | 2187-2209 |

TABLE 3-continued

Unmodified Sense and Antisense Strand Sequences of ADRA2A dsRNA Agents

| Duplex Name | Sense Sequence 5' to 3' | SEQ ID NO: | Range in NM_000681 | Antisense Sequence 5' to 3' | SEQ ID NO: | Range in NM_000681 |
|---|---|---|---|---|---|---|
| AD-1201799 | CCACGCACGCUCUUCAAAUUC | 65 | 2223-2243 | GAAUUUGAAGAGCGUGCGUGGCA | 200 | 2221-2243 |
| AD-1201800 | UUCAAAUUCUUCUUCUGGUUC | 66 | 2235-2255 | GAACCAGAAGAAGAAUUUGAAGA | 201 | 2233-2255 |
| AD-1201801 | CUACUGCAACAGCUCGUUGAA | 67 | 2258-2278 | UUCAACGAGCUGUUGCAGUAGCC | 202 | 2256-2278 |
| AD-1201802 | CCGGUCAUCUACACCAUCUUC | 68 | 2280-2300 | GAAGAUGGUGUAGAUGACCGGGU | 203 | 2278-2300 |
| AD-1201803 | ACCAUCUUCAACCACGAUUUC | 69 | 2292-2312 | GAAAUCGUGGUUGAAGAUGGUGU | 204 | 2290-2312 |
| AD-1201804 | CGAUUUCCGCCGCGCCUUCAA | 70 | 2306-2326 | UUGAAGGCGCGGCGGAAAUCGUG | 205 | 2304-2326 |
| AD-1201805 | CGCCUUCAAGAAGAUCCUCUG | 71 | 2318-2338 | CAGAGGAUCUUCUUGAAGGCGCG | 206 | 2316-2338 |
| AD-1201806 | GAUCGUGUGAGGUUUCCGCUG | 72 | 2357-2377 | CAGCGGAAACCUCACACGAUCCG | 207 | 2355-2377 |
| AD-1201807 | CGUAGACUCACGCUGACUGCA | 73 | 2385-2405 | UGCAGUCAGCGUGAGUCUACGCG | 208 | 2383-2/405 |
| AD-1201808 | UAGCCCCAGGGCACUCAGAAA | 74 | 2432-2452 | UUUCUGAGUGCCCUGGGGCUAAG | 209 | 2430-2452 |
| AD-1201809 | UGCUCUGCGUUUCCUCGUCUG | 75 | 2466-2486 | CAGACGAGGAAACGCAGAGCAGG | 210 | 2464-2486 |
| AD-1201810 | CUCCUACAAGGGAAGCUUCUU | 76 | 2525-2545 | AAGAAGCUUCCCUUGUAGGAGCA | 211 | 2523-2545 |
| AD-1201811 | AGCUUCUUGCUGCCAGGCCCA | 77 | 2538-2558 | UGGGCCUGGCAGCAAGAAGCUUC | 212 | 2536-2558 |
| AD-1201812 | CCCCAGUUGUUGGUUUGGCCA | 78 | 2564-2584 | UGGCCAAACCAACAACUGGGGAU | 213 | 2562-2584 |
| AD-1201813 | GGCCACUCUUGACCUGGAGCC | 79 | 2580-2600 | GGCUCCAGGUCAAGAGUGGCCAA | 214 | 2578-2600 |
| AD-1201814 | GGAGCCAUCUUCCUAGUGGGC | 80 | 2595-2615 | GCCCACUAGGAAGAUGGCUCCAG | 215 | 2593-2615 |
| AD-1201815 | GUGGGCCACCCCUAAUCACUA | 81 | 2610-2630 | UAGUGAUUAGGGGUGGCCCACUA | 216 | 2608-2630 |
| AD-1201816 | UAAUCACUAUUGCUUCCUAAA | 82 | 2622-2642 | UUUAGGAAGCAAUAGUGAUUAGG | 217 | 2620-2642 |
| AD-1201817 | UUCCUAAAGGUAUUUUCACCC | 83 | 2635-2655 | GGGUGAAAAUACCUUUAGGAAGC | 218 | 2633-2655 |
| AD-1201818 | UCACCCUCUUCGCCUGGUACA | 84 | 2650-2670 | UGUACCAGGCGAAGAGGGUGAAA | 219 | 2648-2670 |
| AD-1201819 | UACAGCCCUCACAGCUCUUCA | 85 | 2667-2687 | UGAAGAGCUGUGAGGGCUGUACC | 220 | 2665-2687 |
| AD-1201820 | AGCUCUUCAGAGCAAGCACUG | 86 | 2679-2699 | CAGUGCUUGCUCUGAAGAGCUGU | 221 | 2677-2699 |
| AD-1201821 | GCACUGGACUACAAGGGCAUG | 87 | 2694-2714 | CAUGCCCUUGUAGUCCAGUGCUU | 222 | 2692-2714 |
| AD-1201822 | UCACAAAAGGUUAAUGGAUGG | 88 | 2717-2737 | CCAUCCAUUAACCUUUUGUGAGC | 223 | 2715-2737 |
| AD-1201823 | CCUGGCUAAUUCCCCUUCCAU | 89 | 2750-2770 | AUGGAAGGGGAAUUAGCCAGGGC | 224 | 2748-2770 |

TABLE 3-continued

Unmodified Sense and Antisense Strand Sequences of ADRA2A dsRNA Agents

| Duplex Name | Sense Sequence 5' to 3' | SEQ ID NO: | Range in NM_000681 | Antisense Sequence 5' to 3' | SEQ ID NO: | Range in NM_000681 |
|---|---|---|---|---|---|---|
| AD-1201824 | UCCCAACUCUCUCUCUCUUUU | 90 | 2771-2791 | AAAAGAGAGAGAGAGUUGGGAAU | 225 | 2769-2791 |
| AD-1201825 | CGCUGUAAAUAUACACUAUUU | 91 | 2837-2857 | AAAUAGUGUAUAUUUACAGCGGG | 226 | 2835-2857 |
| AD-1201826 | AUAUCUCUUGGCCUUGGUUUU | 92 | 2881-2901 | AAAACCAAGGCCAAGAGAUAUGG | 227 | 2879-2901 |
| AD-1201827 | CUUGGUUUUGAUGUUGAAAUC | 93 | 2893-2913 | GAUUUCAACAUCAAAACCAAGGC | 228 | 2891-2913 |
| AD-1201828 | CUUGGGAGAGAUGCCUUCCAG | 94 | 2919-2939 | CUGGAAGGCAUCUCUCCCAAGGC | 229 | 2917-2939 |
| AD-1201829 | CCAGGCAGACACAGCUGUCUG | 95 | 2936-2956 | CAGACAGCUGUGUCUGCCUGGAA | 230 | 2934-2956 |
| AD-1201830 | AGCUGUCUGGUUCAGGCCAAG | 96 | 2948-2968 | CUUGGCCUGAACCAGACAGCUGU | 231 | 2946-2968 |
| AD-1201831 | CCUUUGCAAUGCAAGCCCUUU | 97 | 2971-2991 | AAAGGGCUUGCAUUGCAAAGGGG | 232 | 2969-2991 |
| AD-1201832 | CUUUCUGGUGUUAUGAAGUCC | 98 | 2988-3008 | GGACUUCAUAACACCAGAAAGGG | 233 | 2986-3008 |
| AD-1201833 | CUAUGUCGUCGUUUUCACCAG | 99 | 3011-3031 | CUGGUGAAAACGACGACAUAGAG | 234 | 3009-3031 |
| AD-1201834 | CACCAGCAACUGGUGACUGUC | 100 | 3026-3046 | GACAGUCACCAGUUGCUGGUGAA | 235 | 3024-3046 |
| AD-1201835 | UGUCCCUUCGACACGGACCUG | 101 | 3043-3063 | CAGGUCCGUGUCGAAGGGACAGU | 236 | 3041-3063 |
| AD-1201836 | CCUGCUUUGAGAUUUCCUGAC | 102 | 3060-3080 | GUCAGGAAAUCUCAAAGCAGGUC | 237 | 3058-3080 |
| AD-1201837 | UUUCCUGACAGGGAAAAGAUU | 103 | 3072-3092 | AAUCUUUUCCCUGUCAGGAAAUC | 238 | 3070-3092 |
| AD-1201838 | GAAAAGAUUUCUGUCCAUUUU | 104 | 3084-3104 | AAAAUGGACAGAAAUCUUUUCCC | 239 | 3082-3104 |
| AD-1201839 | AACAGCAUAAUUGCCUUUUCC | 105 | 3117-3137 | GGAAAAGGCAAUUAUGCUGUUAG | 240 | 3115-3137 |
| AD-1201840 | UUUUCCUAUGUAAAUAUUAUG | 106 | 3132-3152 | CAUAAUAUUUACAUAGGAAAAGG | 241 | 3130-3152 |
| AD-1201841 | AUUAUGAUGGUGGAUCAAGAC | 107 | 3147-3167 | GUCUUGAUCCACCAUCAUAAUAU | 242 | 3145-3167 |
| AD-1201842 | CUAAGUAAAUGAGCCUUUCU | 108 | 3167-3187 | AGAAAGGCUCAUUUACUUAUGUC | 243 | 3165-3187 |
| AD-1201843 | GCCUUUCUGCCUCACAUCAGC | 109 | 3180-3200 | GCUGAUGUGAGGCAGAAAGGCUC | 244 | 3178-3200 |
| AD-1201844 | AGCCCUGUGUAUAAAGCCAUU | 110 | 3198-3218 | AAUGGCUUUAUACACAGGGCUGA | 245 | 3196-3218 |
| AD-1201845 | AAAGCCAUUAUUCUCUGAUGC | 111 | 3210-3230 | GCAUCAGAGAAUAAUGGCUUUAU | 246 | 3208-3230 |
| AD-1201846 | CUCUGAUGCACUGUUUGCCCC | 112 | 3222-3242 | GGGGCAAACAGUGCAUCAGAGAA | 247 | 3220-3242 |
| AD-1201847 | UGCCCCAGUAACUCACUUUAA | 113 | 3237-3257 | UUAAAGUGAGUUACUGGGGCAAA | 248 | 3235-3257 |
| AD-1201848 | UCACUUUAAAACCUCUCUUUC | 114 | 3249-3269 | GAAAGAGAGGUUUUAAAGUGAGU | 249 | 3247-3269 |

TABLE 3-continued

Unmodified Sense and Antisense Strand Sequences of ADRA2A dsRNA Agents

| Duplex Name | Sense Sequence 5' to 3' | SEQ ID NO: | Range in NM_000681 | Antisense Sequence 5' to 3' | SEQ ID NO: | Range in NM_000681 |
|---|---|---|---|---|---|---|
| AD-1201849 | UCUCUUUCCAGUGUUCCCUCU | 115 | 3262-3282 | AGAGGGAACACUGGAAAGAGAGG | 250 | 3260-3282 |
| AD-1201850 | CCUCCAGGGCCACUGCUUGAA | 116 | 3286-3306 | UUCAAGCAGUGGCCCUGGAGGGA | 251 | 3284-3306 |
| AD-1201851 | CUGCUUGAAGAAGAAUAUGUA | 117 | 3298-3318 | UACAUAUUCUUCUUCAAGCAGUG | 252 | 3296-3318 |
| AD-1201852 | GUAUGUUUCUAUCUUGUAUGU | 118 | 3316-3336 | ACAUACAAGAUAGAAACAUACAU | 253 | 3314-3336 |
| AD-1201853 | UUGUAUGUCUGUGUGCCCCUC | 119 | 3329-3349 | GAGGGGCACACAGACAUACAAGA | 254 | 3327-3349 |
| AD-1201854 | CCCGAAAGUGCUGACUAUGGG | 120 | 3354-3374 | CCCAUAGUCAGCACUUUCGGGGC | 255 | 3352-3374 |
| AD-1201855 | GAAAUCUUUUAGCUGCUGUUU | 121 | 3375-3395 | AAACAGCAGCUAAAAGAUUUCCC | 256 | 3373-3395 |
| AD-1201856 | AGACUCCAAGGAGUGGAAAUU | 122 | 3398-3418 | AAUUUCCACUCCUUGGAGUCUAA | 257 | 3396-3418 |
| AD-1201857 | GUGGAAAUUAUGUGGAAGAAG | 123 | 3410-3430 | CUUCUUCCACAUAAUUUCCACUC | 258 | 3408-3430 |
| AD-1201858 | GCAAACCUGAUACAAUUUGCC | 124 | 3430-3450 | GGCAAAUUGUAUCAGGUUUGCUU | 259 | 3428-3450 |
| AD-1201859 | UUUGCCCAAGGUAAACAGUUU | 125 | 3445-3465 | AAACUGUUUACCUUGGGCAAAUU | 260 | 3443-3465 |
| AD-1201860 | AAACAGUUUGAAAAGACAAAU | 126 | 3457-3477 | AUUUGUCUUUUCAAACUGUUUAC | 261 | 3455-3477 |
| AD-1201861 | AGACAAAUGGGCCUGCCAAAC | 127 | 3470-3490 | GUUUGGCAGGCCCAUUUGUCUUU | 262 | 3468-3490 |
| AD-1201862 | CCAAACUGUACAGUUUCUUCC | 128 | 3485-3505 | GGAAGAAACUGUACAGUUUGGCA | 263 | 3483-3505 |
| AD-1201863 | GUUUCUUCCCCAAGAGCUGUU | 129 | 3497-3517 | AACAGCUCUUGGGGAAGAAACUG | 264 | 3495-3517 |
| AD-1201864 | AGAGCUGUUAGGUAUCAAAAU | 130 | 3509-3529 | AUUUUGAUACCUAACAGCUCUUG | 265 | 3507-3529 |
| AD-1201865 | UAUCAAAAUGUUGUCCUUUCC | 131 | 3521-3541 | GGAAAGGACAACAUUUUGAUACC | 266 | 3519-3541 |
| AD-1201866 | UUUCUGGUUGAGAUCAUGUCA | 132 | 3554-3574 | UGACAUGAUCUCAACCAGAAAAG | 267 | 3552-3574 |
| AD-1201867 | AUCAUGUCAUUGAUGAACUGC | 133 | 3566-3586 | GCAGUUCAUCAAUGACAUGAUCU | 268 | 3564-3586 |
| AD-1201868 | ACUGCCAAAGUCAGGGGAGGA | 134 | 3582-3602 | UCCUCCCCUGACUUUGGCAGUUC | 269 | 3580-3602 |
| AD-1201869 | GAGACUUUGUGUUUACAUCUG | 135 | 3608-3628 | CAGAUGUAAACACAAAGUCUCUG | 270 | 3606-3628 |
| AD-1201870 | UCUGCAUUUCUACAUGUUUUA | 136 | 3625-3645 | UAAAACAUGUAGAAAUGCAGAUG | 271 | 3623-3645 |
| AD-1201871 | UUUAGACAGAGACAAUUUAAG | 137 | 3642-3662 | CUUAAAUUGUCUCUGUCUAAAAC | 272 | 3640-3662 |
| AD-1201872 | CAAUUUAAGGCCUGCACUCUU | 138 | 3654-3674 | AAGAGUGCAGGCCUUAAAUUGUC | 273 | 3652-3674 |
| AD-1201873 | UGCACUCUUAUUUCACUAAAG | 139 | 3666-3686 | CUUUAGUGAAAUAAGAGUGCAGG | 274 | 3664-3686 |

TABLE 3-continued

Unmodified Sense and Antisense Strand Sequences of ADRA2A dsRNA Agents

| Duplex Name | Sense Sequence 5' to 3' | SEQ ID NO: | Range in NM_000681 | Antisense Sequence 5' to 3' | SEQ ID NO: | Range in NM_000681 |
|---|---|---|---|---|---|---|
| AD-1201874 | AUGUCAGCACAUGUUGCUAAU | 140 | 3695-3715 | AUUAGCAACAUGUGCUGACAUUA | 275 | 3693-3715 |
| AD-1201875 | UUGCUAAUGACAGUGGAUUUU | 141 | 3708-3728 | AAAAUCCACUGUCAUUAGCAACA | 276 | 3706-3728 |
| AD-1201876 | UUACAGAUCAAAUGUGAAAUA | 142 | 3746-3766 | UAUUUCACAUUUGAUCUGUAAAC | 277 | 3744-3766 |
| AD-1201877 | GUGAAAUAAAUAUGAAUGGAG | 143 | 3759-3779 | CUCCAUUCAUAUUUAUUUCACAU | 278 | 3757-3779 |
| AD-1201878 | UGAAUGGAGUGGUCCUCUUGU | 144 | 3771-3791 | ACAAGAGGACCACUCCAUUCAUA | 279 | 3769-3791 |
| AD-1201879 | UCUUGUCUGUUAUCUGAGUUU | 145 | 3786-3806 | AAACUCAGAUAACAGACAAGAGG | 280 | 3784-3806 |
| AD-1201880 | UCUGAGUUUUCAAAAGCUUUA | 146 | 3798-3818 | UAAAGCUUUUGAAAACUCAGAUA | 281 | 3796-3818 |
| AD-1201881 | AAGCUUUAAGACUCUGGGAAC | 147 | 3811-3831 | GUUCCCAGAGUCUUAAAGCUUUU | 282 | 3809-3831 |
| AD-1201882 | ACAUCUGAUUUUAUGGAUUUU | 148 | 3830-3850 | AAAAUCCAUAAAAUCAGAUGUUC | 283 | 3828-3850 |

TABLE 4

Modified Sense and Antisense Strand Sequences of ADRA2A dsRNA Agents

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-1201748 | gsgsaga(Ghd)CfuGfAfUfcguucaccsusa | 284 | VPusAfsgguGfaAfCfgaucAfgCfucuccsasg | 419 | CTGGAGAGCTGATCGTTCACCTG | 554 |
| AD-1201749 | gscsaca(Ahd)CfuUfUfGfgaagucucsgsa | 285 | VPusCfsgagAfcUfUfccaaAfgUfugugcsgsc | 420 | GCGCACAACTTTGGAAGTCTCGC | 555 |
| AD-1201750 | asgsaga(Ghd)UfcGfGfUfaaucgcuascsa | 286 | VPusGfsaagCfgAfUfuaccGfaCfucucusgsg | 421 | CCAGAGAGTCGGTAATCGCTTCG | 556 |
| AD-1201751 | uscsggg(Ghd)AfuGfUfAfaggcgacasgsa | 287 | VPusCfsuguCfgCfCfuuacAfuCfcccgasasg | 422 | CTTCGGGGATGTAAGGCGACAGA | 557 |
| AD-1201752 | csgsgua(Ahd)GfaCfCfUfcuugcuuuscsa | 288 | VPusGfsaaaGfcAfAfgaggUfcUfuaccgsusg | 423 | CACGGTAAGACCTCTTGGTTTCG | 558 |
| AD-1201753 | ususgcu(Uhd)UfcGfCfUfcaggcucasasa | 289 | VPusUfsugaGfcCfUfgagcGfaAfagcaasgsa | 424 | TCTTGCTTTCGCTCAGGCTCAAG | 559 |
| AD-1201754 | csuscaa(Ghd)AfuUfCfAfagauacagsasa | 290 | VPusUfscugUfaUfCfuugaAfuCfuugagscsc | 425 | GGCTCAAGATTCAAGATACAGAT | 560 |
| AD-1201755 | asusuua(Ahd)UfuUfCfCfugucauccsusa | 291 | VPusAfsggaUfgAfCfaggaAfaUfuaaausasu | 426 | ATATTTAATTTCCTGTCATCCTT | 561 |
| AD-1201756 | uscsauc(Chd)UfuCfCfAfaguuaucasgsa | 292 | VPusCfsugaUfaAfCfuuggAfaGfgaugascsa | 427 | TGTCATCCTTCCAAGTTATCAGG | 562 |
| AD-1201757 | usasuca(Ghd)GfcCfAfCfcgaugauususa | 293 | VPusAfsaauCfaUfCfgguGgfcCfugauasasc | 428 | GTTATCAGGCCACCGATGATTTT | 563 |
| AD-1201758 | ususguu(Chd)UfcCfCfUfucuugaagsasa | 294 | VPusUfscuuCfaAfGfaaggGfaGfaacaasasa | 429 | TTTTGTTCTCCCTTCTTGAAGAA | 564 |
| AD-1201759 | asasgaa(Uhd)AfaAfUfCfucucuuuascsa | 295 | VPusGfsuaaAfgAfGfagauUfuAfuucuuscsa | 430 | TGAAGAATAAATCTCTCTTTACC | 565 |

TABLE 4-continued

Modified Sense and Antisense Strand Sequences of ADRA2A dsRNA Agents

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-1201760 | asuscgg(Chc)UfcUfCfCfcuacucucsusa | 296 | VPusAfsgagAfgUfAfgggaGfaGfccgausgsg | 431 | CCATCGGCTCTCCCTACTCTCTC | 566 |
| AD-1201761 | gscscgc(Uhd)UfaGfAfAfauaaaacususa | 297 | VPusAfsaguUfuUfAfuuucUfaAfgcggcsgsg | 432 | CCGCCGCTTAGAAATAAAACTTG | 567 |
| AD-1201762 | asasacu(Uhd)GfgCfUfGfuauuaggasgsa | 298 | VPusCfsuccUfaAfUfacagCfcAfaguuusasa | 433 | TAAAACTTGGCTGTATTAGGAGC | 568 |
| AD-1201763 | ususagg(Ahd)GfcUfCfGfgagcaagasasa | 299 | VPusUfsucuUfgCfUfccgaGfcUfccuaasusa | 434 | TATTAGGAGCTCGGAGCAAGAAG | 569 |
| AD-1201764 | gsusuca(Uhd)GfuUfCfCfgccaggagscsa | 300 | VPusGfscucCfuGfGfcggaAfcAfugaacsgsc | 435 | GCGTTCATGTTCCGCCAGGAGCA | 570 |
| AD-1201765 | cscsccu(Uhd)AfcUfCfCfcugcaggusgsa | 301 | VPusCfsaccUfgCfAfgggaGfuAfaggggsusg | 436 | CACCCCTTACTCCCTGCAGGTGA | 571 |
| AD-1201766 | gscsuca(Chd)CfgUfGfUfucggcaacsgsa | 302 | VPusCfsguuGfcCfGfaacaCfgGfugagcsasg | 437 | CTGCTCACCGTGTTCGGCAACGT | 572 |
| AD-1201767 | gsusgcu(Chd)GfuCfAfUfcaucgccgsusa | 303 | VPusAfscggCfgAfUfgaugAfcGfagcacsgsu | 438 | ACGTGCTCGTCATCATCGCCGTG | 573 |
| AD-1201768 | cscscca(Ahd)AfaCfCfUfcuuccuggsusa | 304 | VPusAfsccaGfgAfAfgaggUfuUfuggggscsg | 439 | CGCCCCAAAACCTCTTCCTGGTG | 574 |
| AD-1201769 | ususccu(Ghd)GfuGfUfCfucuggccuscsa | 305 | VPusGfsaggCfcAfGfagacAfcCfaggaasgsa | 440 | TCTTCCTGGTGTCTCTGGCCTCG | 575 |
| AD-1201770 | csuscgu(Chd)AfuCfCfCfuuacucgcsusa | 306 | VPusAfsgcgAfgAfAfagggAfuGfacgagscsg | 441 | CGCTCGTCATCCCTTTCTCGCTG | 576 |
| AD-1201771 | gscscaa(Chd)GfaGfGfUfcaugggcusasa | 307 | VPusUfsagcCfcAfUfgaccUfcGfuuggcscsa | 442 | TGGCCAACGAGGTCATGGGCTAC | 577 |
| AD-1201772 | csusacu(Ghd)GfuAfCfUfucggcaagsgsa | 308 | VPusCfscuuGfcCfGfaaguAfcCfaguagscsc | 443 | GGCTACTGGTACTTCGGCAAGGC | 578 |
| AD-1201773 | ususggu(Ghd)CfgAfGfAfucuaccugsgsa | 309 | VPusCfscagGfuAfGfaucuCfgCfaccaasgsc | 444 | GCTTGGTGCGAGATCTACCTGGC | 579 |
| AD-1201774 | cscsugg(Chd)GfcUfCfGfacgugcacsusa | 310 | VPusAfsgagCfaCfGfucgaGfcGfccaggsasa | 445 | TACCTGGCGCTCGACGTGCTCTT | 580 |
| AD-1201775 | csgsugc(Uhd)CfuUfCfUfgcacgucgsusa | 311 | VPusAfscgaCfgUfGfcagaAfgAfgcacgsusc | 446 | GACGTGCTCTTCTGCACGTCGTC | 581 |
| AD-1201776 | gsuscgu(Chd)CfaUfCfGfugcaccugsusa | 312 | VPusAfscagGfuGfCfacgaUfgGfacgacsgsu | 447 | ACGTCGTCCATCGTGCACCTGTG | 582 |
| AD-1201777 | csgscua(Chd)UfgGfUfCfcaucacacsasa | 313 | VPusUfsgugUfgAfUfggacCfaGfuagcgsgsu | 448 | ACCGCTACTGGTCCATCACACAG | 583 |
| AD-1201778 | asuscac(Ahd)CfaGfGfCfcaucgagusasa | 314 | VPusUfsacuCfgAfUfggccUfgUfgugausgsg | 449 | CCATCACACAGGCCATCGAGTAC | 584 |
| AD-1201779 | asuscga(Ghd)UfaCfAfAfccugaagcsgsa | 315 | VPusCfsgcuUfAfGfguugUfaCfucgausgsg | 450 | CCATCGAGTACAACCTGAAGCGC | 585 |
| AD-1201780 | csasuca(Ahd)GfgCfCfAfucaucaucsasa | 316 | VPusUfsgauGfaUfGfaugGfcCfUfugaugscsg | 451 | CGCATCAAGGCCATCATCATCAC | 586 |
| AD-1201781 | csasccg(Uhd)GfuGfGfUfcaucucgsgsa | 317 | VPusCfscgaGfaUfGfaccAfcAfcggugsasu | 452 | ATCACCGTGTOGGTCATCTCGGC | 587 |
| AD-1201782 | csuscgg(Chd)CfgUfCfAfucuccuucscsa | 318 | VPusGfsgaaGfgAfGfaugaCfgGfccgagsasu | 453 | ATCTCGGCCGTCATCTCCTTCCC | 588 |
| AD-1201783 | csusccu(Uhd)CfcCfGfCfcgcucaucsusa | 319 | VPusAfsgauGfaGfCfggcgGfgAfaggagsasu | 454 | ATCTCCTTCCCGCCGCTCATCTC | 589 |
| AD-1201784 | gscsuca(Uhd)CfuCfCfAfucgagaagsasa | 320 | VPusUfscuuCfuCfGfauggAfgAfugagcsgsg | 455 | CCGCTCATCTCCATCGAGAAGAA | 590 |

TABLE 4-continued

| Modified Sense and Antisense Strand Sequences of ADRA2A dsRNA Agents | | | | | | |
|---|---|---|---|---|---|---|
| Duplex ID | Sense Sequence 5' to 3' | SEQ ID NO: | Antisense Sequence 5' to 3' | SEQ ID NO: | mRNA Target Sequence 5' to 3' | SEQ ID NO: |
| AD-1201785 | usgscga(Ghd)AfuCfAfAfcgaccagasasa | 321 | VPusUfsucuGfgUfCfguugAfaCfucgcasgsc | 456 | GCTGCGAGATCAACGACCAGAAG | 591 |
| AD-1201786 | cscsaga(Ahd)GfuGfGfUfacgucaucsusa | 322 | VPusAfsgauGfaCfGfuaccAfcUfucuggsusc | 457 | GACCAGAAGTGGTACGTCATCTC | 592 |
| AD-1201787 | csgsuca(Uhd)CfuCfGfUfcgugcaucsgsa | 323 | VPusCfsgauGfAfCfgacgAfgAfugacgsusa | 458 | TACGTCATCTCGTCGTGCATCGG | 593 |
| AD-1201788 | csgsgcu(Chd)CfuUfCfUfucgcucccsusa | 324 | VPusAfsgggAfgCfGfaagaAfgGfagccgsasu | 459 | ATCGGCTCCTTCTTCGCTCCCTG | 594 |
| AD-1201789 | csuscau(Chd)AfuGfAfUfccuggucusasa | 325 | VPusUfsagaCfcAfGfgaucAfuGfaugagsgsc | 460 | GCCTCATCATGATCCTGGTCTAC | 595 |
| AD-1201790 | csusggu(Chd)UfaCfGfUfgcgcaucusasa | 326 | VPusUfsagaUfgCfGfcacgUfaGfaccagsgsa | 461 | TCCTGGTCTACGTGCGCATCTAC | 596 |
| AD-1201791 | csgscau(Chd)UfaCfCfAfgaucgccasasa | 327 | VPusUfsuggCfgAfUfcuggUfaGfaugcgscsa | 462 | TGCGCATCTACCAGATCGCCAAG | 597 |
| AD-1201792 | gsasgag(Chd)UfcGfUfCfuuccgaccsasa | 328 | VPusUfsgguCfgGfAfagacGfaGfcucucscsu | 463 | AGGAGAGCTCGTCTTCCGACCAC | 598 |
| AD-1201793 | csgsaga(Ahd)GfcGfCfUfucacguucsgsa | 329 | VPusCfsgaaCfgUfGfaagcGfcUfucucgscsg | 464 | CGCGAGAAGCGCTTCACGTTCGT | 599 |
| AD-1201794 | csascgu(Uhd)CfgUfGfCfuggccgugsgsa | 330 | VPusCfscacGfgCfCfagcaCfgAfacgugsasa | 465 | TTCACGTTCGTGCTGGCCGTGGT | 600 |
| AD-1201795 | gsusggu(Chd)AfuCfGfGfaguguucgsusa | 331 | VPusAfscgaAfAfCfuccgAfuGfaccacsgsg | 466 | CCGTGGTCATCGGAGTGTTCGTG | 601 |
| AD-1201796 | gsusggu(Ghd)UfgCfUfGfguacccccsusa | 332 | VPusAfsaggGfgAfAfccagCfaCfaccacsgsa | 467 | TCGTGGTGTGCTGGTTCCCGTTC | 602 |
| AD-1201797 | cscsccu(Uhd)CfuUfCfUfucaccuacsasa | 333 | VPusUfsguaGfgUfGfaagaAfgAfaggggsasa | 468 | TTCCCCTTCTTCTTCACCTACAC | 603 |
| AD-1201798 | csasccu(Ahd)CfaCfGfCfucacggccsgsa | 334 | VPusCfsggcCfgUfGfagcgUfgUfaggugsasa | 469 | TTCACCTACACGCTCACGGCCGT | 604 |
| AD-1201799 | cscsacg(Chd)AfcGfCfUfcuucaaaususa | 335 | VPusAfsauuUfgAfAfgagcGfuGfcguggscsa | 470 | TGCCACGCACGCTCTTCAAATTC | 605 |
| AD-1201800 | ususcaa(Ahd)UfuCfUfUfcuucuggususa | 336 | VPusAfsaccAfgAfAfgaagAfaUfuugaasgsa | 471 | TCTTCAAATTCTTCTTCTGGTTC | 606 |
| AD-1201801 | csusacu(Ghd)CfaAfCfAfgcucguugsasa | 337 | VPusUfscaaCfgAfGfcuguUfgCfaguagscsc | 472 | GGCTACTGCAACAGCTCGTTGAA | 607 |
| AD-1201802 | cscsggu(Chd)AfuCfUfAfcaccaucususa | 338 | VPusAfsagaUfgGfUfguagAfuGfaccggsgsu | 473 | ACCCGGTCATCTACACCATCTTC | 608 |
| AD-1201803 | ascscau(Chc)UfuCfAfAfccacgauususa | 339 | VPusAfsaauCfgUfGfguugAfaGfauggusgsu | 474 | ACACCATCTTCAACCACGATTTC | 609 |
| AD-1201804 | csgsauu(Uhd)CfcGfCfCfgcgccuucsasa | 340 | VPusUfsgaaGfgCfGfcggcGfgAfaaucgsusg | 475 | CACGATTTCCGCCGCGCCTTCAA | 610 |
| AD-1201805 | csgsccu(Uhd)CfaAfGfAfagauccucsusa | 341 | VPusAfsgagGfaUfCfuucuUfgAfaggcgscsg | 476 | CGCGCCTTCAAGAAGATCCTCTG | 611 |
| AD-1201806 | gsasucg(Uhd)GfuGfAfGfguuuccgcsusa | 342 | VPusAfsgcgGfaAfAfccucAfcAfcgaucscsg | 477 | CGGATCGTGTGAGGTTTCCGCTG | 612 |
| AD-1201807 | csgsuag(Ahd)CfuCfAfCfgcugacugscsa | 343 | VPusGfscagUfcAfGfcguggAfgUfcuacgscsg | 478 | CGCGTAGACTCACGCTGACTGCA | 613 |
| AD-1201808 | usasgcc(Chd)CfaGfGfGfcacucagasasa | 344 | VPusUfsucuGfaGfUfgcccUfgGfggcuasasg | 479 | CTTAGCCCCAGGGCACTCAGAAA | 614 |

TABLE 4-continued

Modified Sense and Antisense Strand Sequences of ADRA2A dsRNA Agents

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-1201809 | usgscuc(Uhd)GfcGfUfUfuccucgucsusa | 345 | VPusAfsgacGfaGfGfaaacGfcAfgagcasgsg | 480 | CCTGCTCTGCGTTTCCTCGTCTG | 615 |
| AD-1201810 | csusccu(Ahd)CfaAfGfGfgaagcuucsusa | 346 | VPusAfsgaaGfcUfUfcccuUfgUfaggagscsa | 481 | TGCTCCTACAAGGGAAGCTTCTT | 616 |
| AD-1201811 | asgscuu(Chd)UfuGfCfUfgccaggccscsa | 347 | VPusGfsggcCfuGfGfcagcAfaGfaagcusc | 482 | GAAGCTTCTTGCTGCCAGGCCCA | 617 |
| AD-1201812 | CSCscca(Ghd)UfuGfUfUfggauuggcscsa | 348 | VPusGfsgccAfaAfCfcaacAfaCfuggggsasu | 483 | ATCCCCAGTTGTTGGTTTGGCCA | 618 |
| AD-1201813 | gsgscca(Chd)UfcUfUfGfaccuggagscsa | 349 | VPusGfscucCfaGfGfucaaGfaGfuggccsasa | 484 | TTGGCCACTCTTGACCTGGAGCC | 619 |
| AD-1201814 | gsgsagc(Chd)AfuCfUfUfccuaguggsgsa | 350 | VPusCfscccaCfuAfGfgaagAfuGfgcuccsasg | 485 | CTGGAGCCATCTTCCTAGTGGGC | 620 |
| AD-1201815 | gsusggg(Chd)CfaCfCfCfcuaaucacsusa | 351 | VPusAfsgugAfuUfAfggggUfgGfcccacsusa | 486 | TAGTGGGCCACCCCTAATCACTA | 621 |
| AD-1201816 | asasauc(Ahd)CfuAfUfUfgcuuccuasasa | 352 | VPusUfsuagGfaAfGfcaauAfgUfgaauasgsg | 487 | CCTAATCACTATTGCTTCCTAAA | 622 |
| AD-1201817 | ususccu(Ahd)AfaGfGfUfauuuucacscsa | 353 | VPusGfsgugAfaAfAfuaccUfuUfaggaasgsc | 488 | GCTTCCTAAAGGTATTTTCACCC | 623 |
| AD-1201818 | uscsacc(Chd)UfcUfUfCfgccugguascsa | 354 | VPusGfsuacCfaGfGfgaaGfaGfggugasasa | 489 | TTTCACCCTCTTCGCCTGGTACA | 624 |
| AD-1201819 | usascag(Chd)CfcUfCfAfcagcucuuscsa | 355 | VPusGfsaagAfgCfUfgugaGfgGfcuguascsc | 490 | GGTACAGCCCTCACAGCTCTTCA | 625 |
| AD-1201820 | asgscuc(Uhd)UfcAfGfAfgcaagcacsusa | 356 | VPusAfsgugCfuUfGfcucuGfaAfgagcusgsu | 491 | ACAGCTCTTCAGAGCAAGCACTG | 626 |
| AD-1201821 | gscsacu(Ghd)GfaCfUfAfcaagggcasusa | 357 | VPusAfsugcCfcUfUfguagUfcCfagugcsusu | 492 | AAGCACTGGACTACAAGGGCATG | 627 |
| AD-1201822 | uscsaca(Ahd)AfaGfGfUfuaauggausgsa | 358 | VPusCfsaucCfaUfUfaaccUfuUfugugasgsc | 493 | GCTCACAAAAGGTTAATGGATGG | 628 |
| AD-1201823 | cscsugg(Chd)UfaAfUfUfccccuuccsasa | 359 | VPusUfsggaAfgGfGfgaauUfaGfccaggsgsc | 494 | GCCCTGGCTAATTCCCCTTCCAT | 629 |
| AD-1201824 | uscscca(Ahd)CfuCfUfCfucucucuususa | 360 | VPusAfsaagAfgAfGfagagAfgUfugggasasu | 495 | ATTCCCAACTCTCTCTCTCTTTT | 630 |
| AD-1201825 | csgscug(Uhd)AfaAfUfAfuacacuaususa | 361 | VPusAfsauaGfuGfUfauauUfuAfcagcgsgsg | 496 | CCCGCTGTAAATATACACTATTT | 631 |
| AD-1201826 | asusauc(Uhd)CfuUfGfGfccuugguususa | 362 | VPusAfsaacCfaAfGfgccaAfgAfgauausgsg | 497 | CCATATCTCTTGGCCTTGGTTTT | 632 |
| AD-1201827 | csusugg(Uhd)UfuUfGfAfuguugaaasusa | 363 | VPusAfsuuuCfaAfCfaucaAfaAfccaagsgsc | 498 | GCCTTGGTTTTGATGTTGAAATC | 633 |
| AD-1201828 | csusugg(Ghd)AfgAfGfAfugccuuccsasa | 364 | VPusUfsggaAfgGfCfaucuCfuCfccaagsgsc | 499 | GCCTTGGGAGAGATGCCTTCCAG | 634 |
| AD-1201829 | cscsagg(Chd)AfgAfCfAfcagcugucsusa | 365 | VPusAfsgacAfgCfUfguguCfuGfccaggsasa | 500 | TTCCAGGCAGACACAGCTGTCTG | 635 |
| AD-1201830 | asgscug(Uhd)CfuGfGfUfucaggccasasa | 366 | VPusUfsuggCfcUfGfaaccAfgAfcagcusgsu | 501 | ACAGCTGTCTGGTPCAGGCCAAG | 636 |
| AD-1201831 | cscsuuu(Ghd)CfaAfUfGfcaagcccususa | 367 | VPusAfsaggGfcUfUfgcauUfgCfaaaggsgsg | 502 | CCCCTTTGCAATGCAAGCCCTTT | 637 |
| AD-1201832 | csusuuc(Uhd)GfgUfGfUfuaugaaguscsa | 368 | VPusGfsacuUfAfUfaacaCfCAfgaaagsgsg | 503 | CCCTTTCTGGTGTTATGAAGTCC | 638 |

TABLE 4-continued

| Modified Sense and Antisense Strand Sequences of ADRA2A dsRNA Agents | | | | | | |
|---|---|---|---|---|---|---|
| Duplex ID | Sense Sequence 5' to 3' | SEQ ID NO: | Antisense Sequence 5' to 3' | SEQ ID NO: | mRNA Target Sequence 5' to 3' | SEQ ID NO: |
| AD-1201833 | csusaug(Uhd)CfgUfCf Gfuauucaccsasa | 369 | VPusUfsgguGfaAfAfacg aCfgAfcauagsasg | 504 | CTCTATGTCGTCGT TTTCACCAG | 639 |
| AD-1201834 | csascca(Ghd)CfaAfCfU fggugacugsusa | 370 | VPusAfscagUfAfCfcag uUfgCfuggugsasa | 505 | TTCACCAGCAACT GGTGACTGTC | 640 |
| AD-1201835 | usgsucc(Chd)UfuCfGf Afcacggaccsusa | 371 | VPusAfsgguCfGfUfguc gAfaGfggacasgsu | 506 | ACTGTCCCTTCGAC ACGGACCTG | 641 |
| AD-1201836 | cscsugc(Uhd)UfuGfAf Gfauauccugsasa | 372 | VPusUfscagGfaAfAfucu cAfaAfgcaggsusc | 507 | GACCTGCTTTGAG ATTTCCTGAC | 642 |
| AD-1201837 | ususucc(Uhd)GfaCfAf Gfggaaaagasusa | 373 | VPusAfsucuUfuUfCfccu gUfcAfggaaasusc | 508 | GATTTCCTGACAG GGAAAAGATT | 643 |
| AD-1201838 | gsasaaa(Ghd)AfcUfUf Cfuguccauususa | 374 | VPusAfsaauGfgAfCfaga aAfuCfuuuucscsc | 509 | GGGAAAAGATTTC TGTCCATTTT | 644 |
| AD-1201839 | asascag(Chd)AfuAfAf Ufugccuuuuscsa | 375 | VPusGfsaaaAfgGfCfaau uAfuGfcuguusasg | 510 | CTAACAGCATAAT TGCCTTTTCC | 645 |
| AD-1201840 | asusuuc(Chd)UfaUfGf Ufaaaaauuasasa | 376 | VPusAfsuaaUfaUfUfuac aUfaGfgaaaasgsg | 511 | CCTTTTCCTATGTA AATATTATG | 646 |
| AD-1201841 | asusuau(Ghd)AfuGfGf Ufggaucaagsasa | 377 | VPusUfscuuGfaUfCfcac cAfuCfauaausasu | 512 | ATATTATGATGGT GGATCAAGAC | 647 |
| AD-1201842 | csasuaa(Ghd)UfaAfAf Ufgagccuuuscsa | 378 | VPusGfsaaaGfgCfUfcau uUfaCfuuaugsusc | 513 | GACATAAGTAAAT GAGCCTTTCT | 648 |
| AD-1201843 | gscscuu(Uhd)CfuGfCf Cfucacaucasgsa | 379 | VPusCfsugaUfgUfGfagg cAfgAfaaggcsusc | 514 | GAGCCTTTCTGCCT CACATCAGC | 649 |
| AD-1201844 | asgsccc(Uhd)GfuGfUf Afuaaagccasusa | 380 | VPusAfsuggCfuUfUfaua cAfCAfgggcusgsa | 515 | TCAGCCCTGTGTAT AAAGCCATT | 650 |
| AD-1201845 | asasagc(Chd)AfuUfAf Ufucucugausgsa | 381 | VPusCfsaucAfgAfGfaau aAfuGfgcuuusasu | 516 | ATAAAGCCATTAT TCTCTGATGC | 651 |
| AD-1201846 | csuscug(Ahd)UfgCfAf Cfuguuugccscsa | 382 | VPusGfsggcAfaAfCfagu gCfaUfcagagsasa | 517 | TTCTCTGATGCACT GTTTGCCCC | 652 |
| AD-1201847 | usgsccc(Chd)AfgUfAf Afcucacuuusasa | 383 | VPusUfsaaaGfuGfAfguu aCfuGfgggcasasa | 518 | TTTGCCCCAGTAA CTCACTTTAA | 653 |
| AD-1201848 | ascsacu(Uhd)UfaAfAf Afccucucuususa | 384 | VPusAfsaagAfgAfGfguu uUfaAfagugasgsu | 519 | ACTCACTTTAAAA CCTCTCTTTC | 654 |
| AD-1201849 | ascsucu(Uhd)UfcCfAf Gfuguucccuscsa | 385 | VPusGfsaggGfaAfCfacu gGfaAfagagasgsg | 520 | CCTCTCTTTCCAGT GTTCCCTCT | 655 |
| AD-1201850 | cscsucc(Ahd)GfgGfCf Cfacugcuugsasa | 386 | VPusUfscaaGfAfGfugg cCfcUfggaggsgsa | 521 | TCCCTCCAGGGCC ACTGCTTGAA | 656 |
| AD-1201851 | csusgcu(Uhd)GfaAfGf Afagaauaugsusa | 387 | VPusAfscauAfuUfCfuuc uUfCAfagcagsusg | 522 | CACTGCTTGAAGA AGAATATGTA | 657 |
| AD-1201852 | gsusaug(Uhd)UfuCfUf Afucuuguausgsa | 388 | VPusCfsauaCfaAfGfaua gAfaAfcauacsasu | 523 | ATGTATGTTTCTAT CTTGTATGT | 658 |
| AD-1201853 | ususgua(Uhd)GfuCfUf Gfugugccccsusa | 389 | VPusAfsgggGfAfCfaca gAfcAfuacaasgsa | 524 | TCTTGTATGTCTGT GTGCCCCTC | 659 |
| AD-1201854 | cscscga(Ahd)AfgUfGf Cfugacuaugsgsa | 390 | VPusCfscauAfgUfCfagc aCfuUfucgggsgsc | 525 | GCCCCGAAAGTGC TGACTATGGG | 660 |
| AD-1201855 | gsasaau(Chd)UfuUfUf Afgcugcagususa | 391 | VPusAfsacaGfcAfGfcua aAfaGfauaucscsc | 526 | GGGAAATCTTTTA GCTGCTGTTT | 661 |
| AD-1201856 | asgsacu(Chd)CfaAfGf Gfaguggaaasusa | 392 | VPusAfsuuuCfcAfCfucc uUfgGfagacusasa | 527 | TTAGACTCCAAGG AGTGGAAATT | 662 |

TABLE 4-continued

Modified Sense and Antisense Strand Sequences of ADRA2A dsRNA Agents

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-1201857 | gsusgga(Ahd)AfuUfAfUfgaggaagasasa | 393 | VPusUfsucuUfcCfAfcauaAfuUfuccacsusc | 528 | GAGTGGAAATTATGTGGAAGAAG | 663 |
| AD-1201858 | gscsaaa(Chd)CfuGfAfUfacaauuugscsa | 394 | VPusGfscaaAfuUfGfuaucAfgGfuuagcsusu | 529 | AAGCAAACCTGATACAATTTGCC | 664 |
| AD-1201859 | ususugc(Chd)CfaAfGfGfuaaacagususa | 395 | VPusAfsacuGfuUfUfaccuUfgGfgcaaasusu | 530 | AATTTGCCCAAGGTAAACAGTTT | 665 |
| AD-1201860 | asasaca(Ghd)UfuUfGfAfaaagacaasasa | 396 | VPusUfsuugUfUfUfucaAfaCfuguuusasc | 531 | GTAAACAGTTTGAAAAGACAAAT | 666 |
| AD-1201861 | asgsaca(Ahd)AfuGfGfGfccugccaasasa | 397 | VPusUfsuugGfAfGfgcccAfuUfugucusus u | 532 | AAAGACAAATGGGCCTGCCAAAC | 667 |
| AD-1201862 | cscsaaa(Chd)UfgUfAfCfagauucuuscsa | 398 | VPusGfsaagAfaAfCfuguaCfaGfuuuggscsa | 533 | TGCCAAACTGTACAGTTTCTTCC | 668 |
| AD-1201863 | gsusuuc(Uhd)UfcCfCfCfaagagcugsusa | 399 | VPusAfscagCfuCfUfugggGfaAfgaaacsusg | 534 | CAGTTTCTTCCCCAAGAGCTGTT | 669 |
| AD-1201864 | asgsagc(Uhd)GfuUfAfGfguaucaaasasa | 400 | VPusUfsuuuGfaUfAfccuaAfCAfgcucusug | 535 | CAAGAGCTGTTAGGTATCAAAAT | 670 |
| AD-1201865 | usasuca(Ahd)AfaUfGfUfuguccuuuscsa | 401 | VPusGfsaaaGfgAfCfaacaUfuUfugauascsc | 536 | GGTATCAAAATGTTGTCCTTTCC | 671 |
| AD-1201866 | ususucu(Ghd)GfuUfGfAfgaucaugucsa | 402 | VPusGfsacaUfgAfUfcucaAfcCfagaaasasg | 537 | CTTTTCTGGTTGAGATCATGTCA | 672 |
| AD-1201867 | asuscau(Ghd)UfcAfUfUfgaugaacusgsa | 403 | VPusCfsaguUfcAfUfcaauGfaCfaugauscsu | 538 | AGATCATGTCATTGATGAACTGC | 673 |
| AD-1201868 | ascsugc(Chd)AfaAfGfUfcaggggagsgsa | 404 | VPusCfscucCfcCfUfgacuUfuGfgcagusus c | 539 | GAACTGCCAAAGTCAGGGGAGGA | 674 |
| AD-1201869 | gsasgac(Uhd)UfuGfUfGfuuqacaucsusa | 405 | VPusAfsgauGfuAfAfacacAfaAfgucucsusg | 540 | CAGAGACTTTGTGTTTACATCTG | 675 |
| AD-1201870 | uscsugc(Ahd)UfuUfCfUfacauguaususa | 406 | VPusAfsaaaCfaUfGfuagaAfaUlgcagasusg | 541 | CATCTGCATTTCTACATGTTtTA | 676 |
| AD-1201871 | ususuag(Ahd)CfaGfAfGfacaauuuasasa | 407 | VPusUfsuaaAfuUfGfucucUfgUfcuaaasasc | 542 | GTTTTAGACAGAGACAATTTAAG | 677 |
| AD-1201872 | csasauu(Uhd)AfaGfGfCfcugcacucsusa | 408 | VPusAfsgagUfgCfAfggccUfuAfaauugsusc | 543 | GACAATTTAAGGCCTGCACTCTT | 678 |
| AD-1201873 | usgscac(Uhd)CfuUfAfUfuacacuaasasa | 409 | VPusUfsuuaGfuGfAfaauaAfgAfgugcasgsg | 544 | CCTGCACTCTTATTTCACTAAAG | 679 |
| AD-1201874 | asusguc(Ahd)GfcAfCfAfuguugcuasasa | 410 | VPusUfsuagCfaAfCfauguGfCUfgacausus a | 545 | TAATGTCAGCACATGTTGCTAAT | 680 |
| AD-1201875 | ususgcu(Ahd)AfuGfAfCfaguggauususa | 411 | VPusAfsaauCfcAfCfuguCAfuUfagcaascsa | 546 | TGTTGCTAATGACAGTGGATTTT | 681 |
| AD-1201876 | asusaca(Ghd)AfuCfAfAfaugugaaasusa | 412 | VPusAfsuuuCfaCfAfuuugAfuCfuguaasasc | 547 | GTTTACAGATCAAATGTGAAATA | 682 |
| AD-1201877 | gsusgaa(Ahd)UfaAfAfUfaugaauggsasa | 413 | VPusUfsccaUfuCfAfuauuUfaUfuucacsasu | 548 | ATGTGAAATAAATATGAATGGAG | 683 |
| AD-1201878 | asgsaau(Ghd)GfaGfUfGfguccacuusgsa | 414 | VPusCfsaagAfgGfAfccacCUfcCfauucasusa | 549 | TATGAATGGAGTGGTCCTCTTGT | 684 |
| AD-1201879 | uscsuug(Uhd)CfuGfUfUfaucugagususa | 415 | VPusAfsacuCfaGfAfuaacAfgAfcaagasgsg | 550 | CCTCTTGTCTGTTAPCTGAGTTT | 685 |
| AD-1201880 | uscsuga(Ghd)UfuUfUfCfaaaagcuususa | 416 | VPusAfsaagCfuUfUfugaaAfaCfucagasusa | 551 | TATCTGAGTTTTCAAAAGGTTTA | 686 |
| AD-1201881 | asasgcu(Uhd)UfaAfGfAfcucugggasasa | 417 | VPusUfsuccCfaGfAfgucuUfaAfagcuususa | 552 | AAAAGCTTTAAGACTCTGGGAAC | 687 |

TABLE 4-continued

Modified Sense and Antisense Strand Sequences of ADRA2A dsRNA Agents

| Duplex ID | Sense Sequence 5' to 3' | SEQ ID NO: | Antisense Sequence 5' to 3' | SEQ ID NO: | mRNA Target Sequence 5' to 3' | SEQ ID NO: |
|---|---|---|---|---|---|---|
| AD-1201882 | ascsauc(Uhd)GfaUfUfUfuaaggauasusa | 418 | VPusAfsaauCfcAfUfaaaaUfAfgaugususc | 553 | GAACATCTGATTTTATGGATTTT | 688 |

Example 2. In Vitro Screening Methods

Cell Culture and 384-Well Transfections

Cos-7 (ATCC) were transfected by adding 5 μl of 2 ng/ul, diluted in Opti-MEM, ADRA2A psiCHECK2 vector (Blue Heron Biotechnology), 4.9 μl of Opti-MEM plus 0.10 μl of Lipofectamine 2000 per well (Invitrogen, Carlsbad CA. cat #11668-019) to 5 μl of siRNA duplexes per well, with 4 replicates of each siRNA duplex, into a 384-well plate, and incubated at room temperature for 15 minutes. Thirty-five μl of Dulbecco's Modified Eagle Medium (ThermoFisher) containing ~$5\times10^3$ cells were then added to the siRNA mixture. Cells were incubated for 48 hours followed by Firefly (transfection control) and *Renilla* (fused to target sequence) luciferase measurements. Three dose experiments were performed at 10 nM, 1 nM, and 0.1 nM.

BE(2)-C (ATCC) are transfected by adding 4.904 of Opti-MEM plus 0.1 μl of RNAiMAX per well (Invitrogen, Carlsbad CA. cat #13778-150) to 5 μl of siRNA duplexes per well, with 4 replicates of each siRNA duplex, into a 384-well plate, and incubated at room temperature for 15 minutes. Forty μl of 1:1 mixture of Minimum Essential Medium and F12 Medium (ThermoFisher) containing ~$5\times10^3$ cells are then added to the siRNA mixture. Cells are incubated for 48 hours prior to RNA purification. Three dose experiments are performed at 10 nM, 1 nM, and 0.1 nM.

Neuro-2a (ATCC) are transfected by adding 4.9 μl of Opti-MEM plus 0.1 μl of RNAiMAX per well (Invitrogen, Carlsbad CA. cat #13778-150) to 5 μl of siRNA duplexes per well, with 4 replicates of each siRNA duplex, into a 384-well plate, and incubated at room temperature for 15 minutes. Forty μl of Minimum Essential Medium (ThermoFisher) containing ~$5\times10^3$ cells are then added to the siRNA mixture. Cells are incubated for 48 hours prior to RNA purification. Three dose experiments are performed at 10 nM, 1 nM, and 0.1 nM.

HeLa (ATCC) were transfected by adding 4.9 μl of Opti-MEM plus 0.1 μl of RNAiMAX per well (Invitrogen, Carlsbad CA. cat #13778-150) to 51 of siRNA duplexes per well, with 4 replicates of each siRNA duplex, into a 384-well plate, and incubated at room temperature for 15 minutes. Forty μl of Minimum Essential Medium (ThermoFisher) containing ~$5\times10^3$ cells were then added to the siRNA mixture. Cells were incubated for 24 hours prior to RNA purification. Two dose experiments were performed at 10 nM and 0.1 nM.

Total RNA Isolation Using DYNABEADS mRNA Isolation Kit (Invitrogen™, Part #: 610-12)

Cells are lysed in 75 μl of Lysis/Binding Buffer containing 3 μL of beads per well and are mixed for 10 minutes on an electrostatic shaker. The washing steps are automated on a Biotek EL406, using a magnetic plate support. Beads are washed (in 90 μL) once in Buffer A, once in Buffer B, and twice in Buffer E, with aspiration steps in between. Following a final aspiration, complete 10 μL RT mixture is added to each well, as described below.

cDNA Synthesis Using ABI High Capacity cDNA Reverse Transcription Kit (Applied Biosystems, Foster City, CA, Cat #4368813)

A master mix of 1 μl 10× Buffer, 0.4 μl 25× dNTPs, 1 μl Random primers, 0.5 μl Reverse Transcriptase, 0.5 μl RNase inhibitor and 6.6 μl of Hz per reaction is added per well. Plates are sealed, are agitated for 10 minutes on an electrostatic shaker, and then are incubated at 37 degrees C. for 2 hours. Following this, the plates are agitated at 80 degrees C. for 8 minutes.

Real Time PCR

Two microliter (μl) of cDNA is added to a master mix containing 0.5 μl of human GAPDH TaqMan Probe and 0.5 μl human ADRA2A probe, or 0.5 μl mouse GAPDH TaqMan Probe and 0.5 μl mouse ADRA2A probe, or 0.5 μl cynomolgus monkey GAPDH TaqMan Probe and 0.5 μl cynomolgus monkey ADRA2A probe, 2 μl nuclease-free water and 5 μl Lightcycler 480 probe master mix (Roche Cat #04887301001) per well in a 384 well plates (Roche cat #04887301001). Real time PCR is done in a LightCycler480 Real Time PCR system (Roche). Each duplex is tested at least two times and data are normalized to cells transfected with a non-targeting control siRNA. To calculate relative fold change, real time data are analyzed using the ΔΔCt method and are normalized to assays performed with cells transfected with a non-targeting control siRNA.

Results

The results of the two-dose screen in HeLa cells with exemplary human ADRA2A siRNAs are shown in Table 5. The experiments were performed at 10 nM and 0.1 nM final duplex concentrations and the data are expressed as percent message remaining relative to non-targeting control. The results of the three-dose screen in Cos-7 cells with exemplary human ADRA2A siRNAs are shown in Table 6. The experiments were performed at 10 nM, 1 nM and 0.1 nM final duplex concentrations and the data are expressed as percent message remaining relative to non-targeting control.

TABLE 5

ADRA2A Two-Dose Screen in HeLa Cells

| | 10 nM Dose | | 0.1 nM Dose | |
|---|---|---|---|---|
| Duplex | Avg % ADRA2A mRNA Remaining | SD | Avg % ADRA2A mRNA Remaining | SD |
| AD-1201748.1 | 61 | 18 | 93 | 20 |
| AD-1201749.1 | 34 | 10 | 59 | 9 |
| AD-1201750.1 | 105 | 31 | 102 | 32 |
| AD-1201751.1 | 54 | 10 | 81 | 12 |
| AD-1201752.1 | 22 | 5 | 42 | 11 |
| AD-1201753.1 | 75 | 13 | 52 | 15 |
| AD-1201754.1 | 26 | 8 | 36 | 5 |
| AD-1201755.1 | 19 | 7 | 43 | 14 |
| AD-1201756.1 | 22 | 4 | 34 | 8 |

TABLE 5-continued

ADRA2A Two-Dose Screen in HeLa Cells

| Duplex | 10 nM Dose Avg % ADRA2A mRNA Remaining | 10 nM Dose SD | 0.1 nM Dose Avg % ADRA2A mRNA Remaining | 0.1 nM Dose SD |
|---|---|---|---|---|
| AD-1201757.1 | 53 | 18 | 65 | 14 |
| AD-1201758.1 | 40 | 4 | 45 | 7 |
| AD-1201759.1 | 13 | 1 | 29 | 8 |
| AD-1201760.1 | 20 | 1 | 49 | 12 |
| AD-1201761.1 | 17 | 6 | 47 | 11 |
| AD-1201762.1 | 33 | 6 | 65 | 10 |
| AD-1201763.1 | | | 88 | 17 |
| AD-1201764.1 | 145 | 14 | 103 | 11 |
| AD-1201765.1 | 82 | 25 | 83 | 17 |
| AD-1201766.1 | 55 | 10 | 102 | 25 |
| AD-1201767.1 | 76 | 23 | 78 | 26 |
| AD-1201768.1 | 30 | 5 | 54 | 11 |
| AD-1201769.1 | 84 | 26 | 111 | 15 |
| AD-1201770.1 | 65 | 16 | 48 | 11 |
| AD-1201771.1 | 135 | 23 | 90 | 32 |
| AD-1201772.1 | 36 | 8 | 70 | 24 |
| AD-1201773.1 | 42 | 9 | 62 | 17 |
| AD-1201774.1 | 71 | 7 | 78 | 30 |
| AD-1201775.1 | 73 | 24 | 85 | 19 |
| AD-1201776.1 | 77 | 18 | 79 | 27 |
| AD-1201777.1 | 92 | 16 | 123 | 49 |
| AD-1201778.1 | 133 | 14 | 99 | 17 |
| AD-1201779.1 | 119 | 11 | 86 | 26 |
| AD-1201780.1 | 61 | 6 | 41 | 9 |
| AD-1201781.1 | 30 | 5 | 30 | 11 |
| AD-1201782.1 | | | 73 | 47 |
| AD-1201783.1 | 89 | 18 | 105 | 40 |
| AD-1201784.1 | 131 | 6 | 100 | 34 |
| AD-1201785.1 | 200 | 38 | 145 | 38 |
| AD-1201786.1 | 87 | 11 | 113 | 37 |
| AD-1201787.1 | 55 | 11 | 66 | 7 |
| AD-1201788.1 | 54 | 14 | 41 | 16 |
| AD-1201789.1 | 41 | 8 | 47 | 14 |
| AD-1201790.1 | 44 | 9 | 63 | 19 |
| AD-1201791.1 | | | 68 | 12 |
| AD-1201792.1 | 107 | 31 | 109 | 53 |
| AD-1201793.1 | 36 | 7 | 71 | 22 |
| AD-1201794.1 | 52 | 9 | 69 | 13 |
| AD-1201795.1 | 45 | 8 | 48 | 13 |
| AD-1201796.1 | 83 | 24 | 87 | 18 |
| AD-1201797.1 | 39 | 6 | 51 | 16 |
| AD-1201798.1 | 97 | 16 | 92 | 38 |
| AD-1201799.1 | 108 | 39 | 95 | 33 |
| AD-1201800.1 | 42 | 14 | 58 | 22 |
| AD-1201801.1 | 40 | 11 | 59 | 31 |
| AD-1201802.1 | 42 | 7 | 53 | 22 |
| AD-1201803.1 | 35 | 10 | 35 | 14 |
| AD-1201804.1 | 68 | 7 | 84 | 35 |
| AD-1201805.1 | 26 | 6 | 53 | 27 |
| AD-1201806.1 | 71 | 26 | 66 | 29 |
| AD-1201807.1 | 123 | 11 | 96 | 37 |
| AD-1201808.1 | 91 | 14 | 117 | 23 |
| AD-1201809.1 | 38 | 11 | 71 | 32 |
| AD-1201810.1 | 50 | 12 | 51 | 19 |
| AD-1201811.1 | 80 | 8 | 87 | 26 |
| AD-1201812.1 | 37 | 10 | 67 | 32 |
| AD-1201813.1 | 59 | 14 | 83 | 31 |
| AD-1201814.1 | 62 | 15 | 79 | 39 |
| AD-1201815.1 | 88 | 6 | 72 | 22 |
| AD-1201816.1 | 30 | 11 | 30 | 12 |
| AD-1201817.1 | 19 | 2 | 26 | 12 |
| AD-1201818.1 | 28 | 4 | 76 | 42 |
| AD-1201819.1 | 24 | 6 | 31 | 7 |
| AD-1201820.1 | 15 | 5 | 55 | 29 |
| AD-1201821.1 | 78 | 25 | 84 | 34 |
| AD-1201822.1 | 30 | 7 | 44 | 10 |
| AD-1201823.1 | 33 | 5 | 83 | 23 |
| AD-1201824.1 | 16 | 8 | 21 | 10 |
| AD-1201825.1 | 16 | 2 | 26 | 6 |
| AD-1201826.1 | 39 | 9 | 77 | 20 |
| AD-1201827.1 | 33 | 18 | 47 | 26 |
| AD-1201828.1 | 59 | 18 | 88 | 43 |
| AD-1201829.1 | 44 | 16 | 84 | 6 |

TABLE 5-continued

ADRA2A Two-Dose Screen in HeLa Cells

| Duplex | 10 nM Dose Avg % ADRA2A mRNA Remaining | 10 nM Dose SD | 0.1 nM Dose Avg % ADRA2A mRNA Remaining | 0.1 nM Dose SD |
|---|---|---|---|---|
| AD-1201830.1 | 86 | 19 | 111 | 24 |
| AD-1201831.1 | 30 | 9 | 36 | 16 |
| AD-1201832.1 | 32 | 10 | 34 | 16 |
| AD-1201833.1 | 26 | 5 | 58 | 27 |
| AD-1201834.1 | 36 | 10 | 51 | 22 |
| AD-1201835.1 | 56 | 7 | 87 | 25 |
| AD-1201836.1 | 23 | 11 | 37 | 9 |
| AD-1201837.1 | 24 | 1 | 58 | 22 |
| AD-1201838.1 | 15 | 7 | 49 | 15 |
| AD-1201839.1 | 13 | 4 | 31 | 7 |
| AD-1201840.1 | 20 | 9 | 39 | 13 |
| AD-1201841.1 | 21 | 8 | 57 | 10 |
| AD-1201842.1 | 22 | 10 | 42 | 10 |
| AD-1201843.1 | 23 | 10 | 39 | 14 |
| AD-1201844.1 | 17 | 3 | 36 | 8 |
| AD-1201845.1 | 33 | 12 | 43 | 17 |
| AD-1201846.1 | 21 | 8 | 40 | 13 |
| AD-1201847.1 | 46 | 13 | 28 | 5 |
| AD-1201848.1 | 14 | 3 | 32 | 11 |
| AD-1201849.1 | 20 | 6 | 42 | 11 |
| AD-1201850.1 | 49 | 7 | 52 | 10 |
| AD-1201851.1 | 25 | 10 | 34 | 14 |
| AD-1201852.1 | 45 | 19 | 38 | 14 |
| AD-1201853.1 | 47 | 6 | 59 | 16 |
| AD-1201854.1 | 23 | 11 | 66 | 17 |
| AD-1201855.1 | 22 | 9 | 28 | 6 |
| AD-1201856.1 | 39 | 18 | 45 | 16 |
| AD-1201857.1 | 19 | 4 | 34 | 11 |
| AD-1201858.1 | 17 | 5 | 28 | 9 |
| AD-1201859.1 | 18 | 2 | 51 | 16 |
| AD-1201860.1 | 15 | 4 | 62 | 18 |
| AD-1201861.1 | 34 | 12 | 75 | 13 |
| AD-1201862.1 | 25 | 11 | 51 | 11 |
| AD-1201863.1 | 25 | 5 | 39 | 15 |
| AD-1201864.1 | 22 | 10 | 27 | 9 |
| AD-1201865.1 | 17 | 9 | 23 | 9 |
| AD-1201866.1 | 19 | 10 | 21 | 8 |
| AD-1201867.1 | 42 | 18 | 36 | 12 |
| AD-1201868.1 | 88 | 29 | 93 | 33 |
| AD-1201869.1 | 10 | 6 | 27 | 9 |
| AD-1201870.1 | 13 | 7 | 48 | 15 |
| AD-1201871.1 | 10 | 4 | 39 | 14 |
| AD-1201872.1 | 19 | 15 | 31 | 12 |
| AD-1201873.1 | 13 | 6 | 34 | 14 |
| AD-1201874.1 | 24 | 14 | 52 | 18 |
| AD-1201875.1 | 19 | 6 | 34 | 9 |
| AD-1201876.1 | 59 | 23 | 37 | 10 |
| AD-1201877.1 | 58 | 20 | 49 | 17 |
| AD-1201878.1 | 60 | 18 | 62 | 16 |
| AD-1201879.1 | 64 | 22 | 52 | 8 |
| AD-1201880.1 | 74 | 24 | 61 | 17 |
| AD-1201881.1 | 58 | 7 | 64 | 21 |
| AD-1201882.1 | 53 | 30 | 59 | 19 |

TABLE 6

| ADRA2A Three-Dose Screen in COS-7 Cells | | | | | | |
|---|---|---|---|---|---|---|
| | 10 nM Dose | | 1 nM Dose | | 0.1 nM Dose | |
| Duplex | Avg % ADRA2A mRNA Remaining | SD | Avg % ADRA2A mRNA Remaining | SD | Avg % ADRA2A mRNA Remaining | SD |
| AD-1201748.1 | 34.2 | 11.0 | 38.1 | 3.0 | 46.2 | 13.2 |
| AD-1201749.1 | 82.2 | 16.0 | 103.9 | 18.0 | 107.7 | 25.0 |
| AD-1201750.1 | 113.9 | 16.9 | 96.3 | 24.3 | 113.5 | 30.1 |
| AD-1201751.1 | 89.6 | 15.2 | 107.6 | 17.8 | 114.3 | 11.9 |
| AD-1201752.1 | 16.2 | 4.4 | 35.3 | 10.3 | 48.2 | 15.9 |
| AD-1201753.1 | 66.9 | 15.6 | 67.9 | 7.4 | 63.2 | 10.2 |
| AD-1201754.1 | 20.2 | 2.7 | 25.3 | 3.3 | 47.7 | 5.8 |
| AD-1201755.1 | 9.8 | 2.6 | 11.8 | 3.3 | 23.1 | 4.8 |
| AD-1201756.1 | 17.1 | 4.5 | 18.6 | 3.2 | 28.8 | 9.2 |
| AD-1201757.1 | 28.6 | 3.6 | 46.6 | 5.7 | 52.3 | 7.3 |
| AD-1201758.1 | 10.5 | 3.8 | 14.3 | 4.5 | 23.8 | 6.5 |
| AD-1201759.1 | 11.4 | 2.2 | 15.0 | 3.6 | 19.0 | 5.6 |
| AD-1201760.1 | 58.7 | 14.9 | 75.9 | 12.8 | 75.5 | 13.5 |
| AD-1201761.1 | 41.4 | 6.8 | 73.1 | 9.2 | 75.2 | 19.2 |
| AD-1201762.1 | 83.5 | 14.4 | 89.6 | 14.2 | 102.8 | 8.0 |
| AD-1201763.1 | 135.0 | 19.6 | 136.4 | 44.4 | 125.1 | 25.0 |
| AD-1201764.1 | 132.2 | 21.7 | 151.0 | 25.1 | 135.4 | 20.2 |
| AD-1201765.1 | 66.5 | 8.9 | 88.8 | 20.9 | 102.6 | 18.5 |
| AD-1201766.1 | 84.7 | 16.6 | 100.2 | 18.2 | 98.4 | 26.0 |
| AD-1201767.1 | 86.9 | 25.1 | 78.6 | 7.9 | 111.7 | 36.7 |
| AD-1201768.1 | 65.0 | 13.0 | 92.1 | 15.0 | 79.8 | 15.4 |
| AD-1201769.1 | 134.8 | 33.3 | 143.5 | 25.1 | 115.0 | 30.4 |
| AD-1201770.1 | 33.3 | 4.5 | 57.6 | 9.2 | 83.1 | 27.3 |
| AD-1201771.1 | 115.9 | 14.6 | 121.9 | 19.5 | 130.2 | 33.1 |
| AD-1201772.1 | 108.3 | 34.4 | 120.4 | 21.4 | 110.1 | 19.2 |
| AD-1201773.1 | 63.1 | 12.3 | 87.3 | 11.6 | 85.8 | 17.5 |
| AD-1201774.1 | 77.2 | 21.4 | 78.4 | 13.4 | 86.4 | 16.4 |
| AD-1201775.1 | 107.4 | 9.4 | 89.9 | 16.0 | 97.0 | 20.5 |
| AD-1201776.1 | 64.9 | 15.1 | 76.1 | 11.3 | 86.4 | 23.1 |
| AD-1201777.1 | 115.1 | 34.1 | 112.3 | 16.4 | 89.8 | 16.2 |
| AD-1201778.1 | 141.4 | 13.8 | 108.4 | 16.6 | 96.5 | 9.2 |
| AD-1201779.1 | 88.0 | 24.3 | 84.0 | 13.7 | 84.8 | 11.4 |
| AD-1201780.1 | 86.2 | 4.1 | 104.6 | 12.4 | 114.7 | 13.9 |
| AD-1201781.1 | 42.7 | 11.8 | 65.2 | 11.3 | 84.5 | 26.3 |
| AD-1201782.1 | 55.8 | 6.2 | 95.1 | 21.9 | 89.8 | 9.2 |
| AD-1201783.1 | 116.7 | 30.7 | 113.2 | 8.9 | 100.7 | 5.3 |
| AD-1201784.1 | 47.2 | 20.8 | 55.8 | 2.0 | 70.3 | 6.7 |
| AD-1201785.1 | 114.0 | 26.6 | 101.1 | 9.9 | 120.2 | 27.8 |
| AD-1201786.1 | 75.8 | 7.0 | 98.3 | 12.0 | 91.2 | 13.1 |
| AD-1201787.1 | 100.5 | 19.9 | 88.6 | 13.6 | 93.1 | 11.2 |
| AD-1201788.1 | 51.0 | 11.9 | 67.7 | 13.9 | 92.9 | 12.0 |
| AD-1201789.1 | 81.2 | 14.2 | 80.5 | 5.9 | 88.7 | 21.5 |
| AD-1201790.1 | 85.9 | 32.7 | 80.1 | 26.7 | 93.7 | 12.7 |
| AD-1201791.1 | 94.8 | 11.4 | 95.5 | 17.2 | 103.0 | 10.3 |
| AD-1201792.1 | 71.4 | 7.8 | 85.3 | 6.9 | 101.0 | 33.0 |
| AD-1201793.1 | 106.7 | 14.3 | 93.1 | 4.3 | 101.8 | 19.3 |
| AD-1201794.1 | 91.6 | 22.9 | 102.8 | 26.0 | 83.7 | 14.8 |
| AD-1201795.1 | 99.9 | 10.5 | 134.5 | 26.3 | 119.4 | 17.8 |
| AD-1201796.1 | 98.5 | 27.8 | 91.3 | 15.3 | 84.1 | 14.7 |
| AD-1201797.1 | 58.7 | 11.7 | 59.2 | 9.6 | 71.5 | 16.9 |
| AD-1201798.1 | 86.0 | 7.7 | 97.6 | 7.6 | 91.5 | 26.3 |
| AD-1201799.1 | 96.6 | 16.8 | 94.1 | 9.4 | 107.7 | 10.9 |
| AD-1201800.1 | 106.2 | 36.6 | 88.7 | 13.1 | 113.8 | 33.8 |
| AD-1201801.1 | 118.2 | 11.0 | 109.6 | 12.3 | 122.6 | 14.6 |
| AD-1201802.1 | 72.1 | 14.9 | 68.1 | 11.2 | 100.7 | 3.0 |
| AD-1201803.1 | 75.8 | 18.5 | 72.9 | 11.7 | 97.7 | 34.3 |
| AD-1201804.1 | 74.0 | 14.1 | 81.8 | 14.7 | 96.1 | 7.9 |
| AD-1201805.1 | 61.9 | 17.2 | 65.2 | 13.3 | 77.8 | 20.0 |
| AD-1201806.1 | 77.5 | 5.7 | 65.7 | 4.8 | 71.2 | 15.5 |
| AD-1201807.1 | 116.3 | 19.5 | 98.1 | 9.3 | 93.0 | 10.9 |
| AD-1201808.1 | 91.7 | 23.9 | 92.6 | 18.8 | 95.2 | 9.6 |
| AD-1201809.1 | 88.9 | 6.3 | 103.3 | 15.4 | 101.7 | 24.2 |
| AD-1201810.1 | 78.1 | 16.6 | 67.2 | 7.1 | 78.9 | 12.0 |
| AD-1201811.1 | 85.7 | 7.5 | 79.0 | 8.7 | 105.9 | 18.5 |
| AD-1201812.1 | 82.0 | 1.2 | 108.6 | 16.3 | 120.9 | 15.5 |
| AD-1201813.1 | 83.9 | 19.4 | 100.5 | 16.7 | 98.9 | 37.9 |
| AD-1201814.1 | 89.2 | 3.3 | 80.3 | 7.8 | 90.9 | 26.3 |
| AD-1201815.1 | 85.3 | 9.3 | 81.8 | 8.6 | 81.4 | 8.0 |
| AD-1201816.1 | 84.8 | 8.0 | 83.6 | 18.6 | 76.3 | 6.0 |
| AD-1201817.1 | 45.6 | 24.6 | 58.9 | 6.8 | 80.9 | 25.0 |
| AD-1201818.1 | 93.2 | 25.4 | 97.7 | 20.7 | 97.6 | 39.2 |
| AD-1201819.1 | 52.4 | 9.0 | 55.2 | 7.2 | 80.5 | 20.5 |
| AD-1201820.1 | 134.0 | 26.3 | 124.0 | 18.3 | 115.5 | 8.9 |

TABLE 6-continued

| ADRA2A Three-Dose Screen in COS-7 Cells | | | | | | |
|---|---|---|---|---|---|---|
| | 10 nM Dose | | 1 nM Dose | | 0.1 nM Dose | |
| Duplex | Avg % ADRA2A mRNA Remaining | SD | Avg % ADRA2A mRNA Remaining | SD | Avg % ADRA2A mRNA Remaining | SD |
| AD-1201821.1 | 91.5 | 29.5 | 94.3 | 8.1 | 90.9 | 13.2 |
| AD-1201822.1 | 83.0 | 20.6 | 108.5 | 19.5 | 121.1 | 15.9 |
| AD-1201823.1 | 76.3 | 19.9 | 84.2 | 13.4 | 108.2 | 21.7 |
| AD-1201824.1 | 39.1 | 4.6 | 51.9 | 5.3 | 67.9 | 19.6 |
| AD-1201825.1 | 51.6 | 7.2 | 57.1 | 10.6 | 91.9 | 8.6 |
| AD-1201826.1 | 91.7 | 13.5 | 98.8 | 13.4 | 103.6 | 11.7 |
| AD-1201827.1 | 75.4 | 13.7 | 69.4 | 22.1 | 82.4 | 15.9 |
| AD-1201828.1 | 82.7 | 26.0 | 102.1 | 11.9 | 145.8 | 41.1 |
| AD-1201829.1 | 72.3 | 21.7 | 101.0 | 2.4 | 100.8 | 26.6 |
| AD-1201830.1 | 126.2 | 11.2 | 123.7 | 26.5 | 124.9 | 26.0 |
| AD-1201831.1 | 118.6 | 19.9 | 139.3 | 18.7 | 153.4 | 12.0 |
| AD-1201832.1 | 100.3 | 9.2 | 120.3 | 18.2 | 118.7 | 24.6 |
| AD-1201833.1 | 72.8 | 13.3 | 108.4 | 30.0 | 103.9 | 10.7 |
| AD-1201834.1 | 68.6 | 10.9 | 93.4 | 6.1 | 112.8 | 11.4 |
| AD-1201835.1 | 102.5 | 10.5 | 101.9 | 30.4 | 104.9 | 18.0 |
| AD-1201836.1 | 83.1 | 11.1 | 88.9 | 19.9 | 91.5 | 9.5 |
| AD-1201837.1 | 79.7 | 17.9 | 99.9 | 7.5 | 118.1 | 29.8 |
| AD-1201838.1 | 75.3 | 21.5 | 70.5 | 14.8 | 88.2 | 21.2 |
| AD-1201839.1 | 69.0 | 14.8 | 108.5 | 24.8 | 75.5 | 11.7 |
| AD-1201840.1 | 64.0 | 18.9 | 85.7 | 20.0 | 74.5 | 11.1 |
| AD-1201841.1 | 110.5 | 26.1 | 93.2 | 34.8 | 83.2 | 17.1 |
| AD-1201842.1 | 51.5 | 14.7 | 73.4 | 18.2 | 58.7 | 6.2 |
| AD-1201843.1 | 80.7 | 10.9 | 103.9 | 19.7 | 80.8 | 22.2 |
| AD-1201844.1 | 82.9 | 18.5 | 89.4 | 29.5 | 74.6 | 11.0 |
| AD-1201845.1 | 53.7 | 42.8 | 73.5 | 15.4 | 70.6 | 21.7 |
| AD-1201846.1 | 64.0 | 9.5 | 84.7 | 7.3 | 87.6 | 32.6 |
| AD-1201847.1 | 52.4 | 14.5 | 100.0 | 33.1 | 63.8 | 5.1 |
| AD-1201848.1 | 72.1 | 19.2 | 64.7 | 14.6 | 53.2 | 13.9 |
| AD-1201849.1 | 53.7 | 13.8 | 61.7 | 19.0 | 64.7 | 17.9 |
| AD-1201850.1 | 70.8 | 13.5 | 72.9 | 18.7 | 55.4 | 13.6 |
| AD-1201851.1 | 56.9 | 13.0 | 70.9 | 16.8 | 59.2 | 9.8 |
| AD-1201852.1 | 91.2 | 9.0 | 83.1 | 27.2 | 71.9 | 16.4 |
| AD-1201853.1 | 87.2 | 39.0 | 94.0 | 33.4 | 81.4 | 9.9 |
| AD-1201854.1 | 88.3 | 5.5 | 121.2 | 14.3 | 95.1 | 23.9 |
| AD-1201855.1 | 43.6 | 4.9 | 43.5 | 10.6 | 43.1 | 5.9 |
| AD-1201856.1 | 123.6 | 23.1 | 114.5 | 14.2 | 82.8 | 23.6 |
| AD-1201857.1 | 68.8 | 20.7 | 81.5 | 16.3 | 70.9 | 16.5 |
| AD-1201858.1 | 56.3 | 7.0 | 61.5 | 14.5 | 74.3 | 12.7 |
| AD-1201859.1 | 83.0 | 18.1 | 72.7 | 24.5 | 75.1 | 17.0 |
| AD-1201860.1 | 78.2 | 5.0 | 95.5 | 24.1 | 92.0 | 17.5 |
| AD-1201861.1 | 109.0 | 8.4 | 90.8 | 23.5 | 96.4 | 8.4 |
| AD-1201862.1 | 71.7 | 4.9 | 62.6 | 10.4 | 76.4 | 16.8 |
| AD-1201863.1 | 49.6 | 17.2 | 56.7 | 11.2 | 64.8 | 5.8 |
| AD-1201864.1 | 60.4 | 25.9 | 64.8 | 17.0 | 66.2 | 11.2 |
| AD-1201865.1 | 42.1 | 15.2 | 55.9 | 25.0 | 59.9 | 14.7 |
| AD-1201866.1 | 65.1 | 4.5 | 67.4 | 6.3 | 61.7 | 7.1 |
| AD-1201867.1 | 78.5 | 18.1 | 67.9 | 9.7 | 85.8 | 11.3 |
| AD-1201868.1 | 78.9 | 7.8 | 98.0 | 18.8 | 91.1 | 20.3 |
| AD-1201869.1 | 71.9 | 6.2 | 62.2 | 12.7 | 79.9 | 11.9 |
| AD-1201870.1 | 67.8 | 21.2 | 66.0 | 6.5 | 62.4 | 16.4 |
| AD-1201871.1 | 58.5 | 3.9 | 63.4 | 8.8 | 64.5 | 8.5 |
| AD-1201872.1 | 65.0 | 18.7 | 82.5 | 16.8 | 93.6 | 28.2 |
| AD-1201873.1 | 71.5 | 12.3 | 62.1 | 7.1 | 80.2 | 15.0 |
| AD-1201874.1 | 50.6 | 14.2 | 72.3 | 15.2 | 75.5 | 10.1 |
| AD-1201875.1 | 104.2 | 16.3 | 101.0 | 19.3 | 90.2 | 25.5 |
| AD-1201876.1 | 90.3 | 29.5 | 70.3 | 4.1 | 70.7 | 10.7 |
| AD-1201877.1 | 66.3 | 29.2 | 64.1 | 21.3 | 78.5 | 7.9 |
| AD-1201878.1 | 46.8 | 10.2 | 57.2 | 12.1 | 65.2 | 16.3 |
| AD-1201879.1 | 58.1 | 23.2 | 76.2 | 7.6 | 100.2 | 20.6 |
| AD-1201880.1 | 54.1 | 15.2 | 56.1 | 24.0 | 63.3 | 23.1 |
| AD-1201881.1 | 70.4 | 6.0 | 70.2 | 10.8 | 89.6 | 18.7 |
| AD-1201882.1 | 74.4 | 24.8 | 76.0 | 12.1 | 86.6 | 16.1 |

EQUIVALENTS

Those skilled in the art will recognize, or be able to ascertain using no more than routine experimentation, many equivalents to the specific embodiments and methods described herein. Such equivalents are intended to be encompassed by the scope of the following claims.

ADRA2A SEQUENCES

SEQ ID NO: 1
> NM_000681.4 *Home sapiens* alpha-2A adrenergic receptor (ADRA2A), mRNA
GAGCAGCAGCAGCTCCAGCTCGGTGCAGAAGCCCAGCAGCCGGCGTGCCGCCGCCCGGCCACTCCAGCGCCTTCTT
CCCCGCCTTGCGCTCCTGCCCCAACTCGCGCTGTCGTCGGACCCCGGCCCATCCAGCAGCGCTCGGCGCCCACCAG
GCGGACGCCCAGGAGAACCCCTGCCTCCGTCGCGGCTCCTGGAGAGCTGATCGTTCACCTGCCCCGGCCCGCCTGA
GGACGGGGGTGCCTTCATGCGGCCCCCACACTCCTCACCCCGCCGCCGCCGCCGTCCCGGAGCTCCGCACAGTGTG
CCCCAGCCCCAGCAGGGCGCACAACTTTGGAAGTCTCGCGGCGCTCCGAGAGGCGGCAGAGTCCGCGCCCCAGCCC
CGGGCCGGGCCGGGCCAGAACCGCAGCGTCTGGGGGAAGCCAGAGAGTCGGTAATCGCTTCGGGGATGTAAGGCGA
CAGACATAGGACCCCCGAGCTCGCATCAGCACCCTTCGGCTGCCTCCCGGGGTGGGGGCGGGCCCCGCACACGGTA
AGACCTCTTGCTTTCGCTCAGGCTCAAGATTCAAGATACAGATATTGATATGTATATATATATTTAATTTCCTGTC
ATCCTTCCAAGTTATCAGGCCACCGATGATTTTTGTTCTCCCTTCTTGAAGAATAAATCTCTCTTTACCCATCGGC
TCTCCCTACTCTCTCCCGCCGCTTAGAAATAAAACTTGGCTGTATTAGGAGCTCGGAGCAAGAAGGCGCCCACCGA
GAGCGTCTGAAGCGCGAGCCAGGCGCAGTTCGCGGGACCCGGGCCATGGGCCGCTAGCGGTCCTCCAGTTCGGGCC
CGGCCTCCCTGCGGCCCCCTCCCTATGTGAGCCGCAGCCAGGCGAGCGGGGCGCCGGAGGAAGAGGAGGACCCACG
GGCGCCGGGCCGGAAGGCAGCTGGCAGCAGGCCCAGGCCAGCGGGCGCCCGCGTTCATGTTCCGCCAGGAGCAGCC
GTTGGCCGAGGGCAGCTTTGCGCCCATGGGCTCCCTGCAGCCGGACGCGGGCAACGCGAGCTGGAACGGGACCGAG
GCGCCGGGGGGCGGCGCCCGGGCCACCCCTTACTCCCTGCAGGTGACGCTGACGCTGGTGTGCCTGGCCGGCCTGC
TCATGCTGCTCACCGTGTTCGGCAACGTGCTCGTCATCATCGCCGTGTTCACGAGCCGCGCGCTCAAGGCGCCCCA
AAACCTCTTCCTGGTGTCTCTGGCCTCGGCCGACATCCTGGTGGCCACGCTCGTCATCCCTTTCTCGCTGGCCAAC
GAGGTCATGGGCTACTGGTACTTCGGCAAGGCTTGGTGCGAGATCTACCTGGCGCTCGACGTGCTCTTCTGCACGT
CGTCCATCGTGCACCTGTGCGCCATCAGCCTGGACCGCTACTGGTCCATCACACAGGCCATCGAGTACAACCTGAA
GCGCACGCCGCGCCGCATCAAGGCCATCATCATCACCGTGTGGGTCATCTCGGCCGTCATCTCCTTCCCGCCGCTC
ATCTCCATCGAGAAGAAGGGCGGCGGCGGCGGCCCGCAGCCGGCCGAGCCGCGCTGCGAGATCAACGACCAGAAGT
GGTACGTCATCTCGTCGTGCATCGGCTCCTTCTTCGCTCCCTGCCTCATCATGATCCTGGTCTACGTGCGCATCTA
CCAGATCGCCAAGCGTCGCACCCGCGTGCCACCCAGCCGCCGGGGTCCGGACGCCGTCGCCGCGCCGCCGGGGGGC
ACCGAGCGCAGGCCCAACGGTCTGGGCCCCGAGCGCAGCGCGGGCCCGGGGGGCGCAGAGGCCGAACCGCTGCCCA
CCCAGCTCAACGGCGCCCCTGGCGAGCCCGCGCCGGCCGGGCCGCGCGACACCGACGCGCTGGACCTGGAGGAGAG
CTCGTCTTCCGACCACGCCGAGCGGCCTCCAGGGCCCCGCAGACCCGAGCGCGGTCCCCGGGGCAAAGGCAAGGCC
CGAGCGAGCCAGGTGAAGCCGGGCGACAGCCTGCCGCGGCGCGGGCCGGGGGCGACGGGGATCGGGACGCCGGCTG
CAGGGCCGGGGGAGGAGCGCGTCGGGGCTGCCAAGGCGTCGCGCTGGCGCGGGCGGCAGAACCGCGAGAAGCGCTT
CACGTTCGTGCTGGCCGTGGTCATCGGAGTGTTCGTGGTGTGCTGGTTCCCCTTCTTCTTCACCTACACGCTCACG
GCCGTCGGGTGCTCCGTGCCACGCACGCTCTTCAAATTCTTCTTCTGGTTCGGCTACTGCAACAGCTCGTTGAACC
CGGTCATCTACACCATCTTCAACCACGATTTCCGCCGCGCCTTCAAGAAGATCCTCTGTCGGGGGGACAGGAAGCG
GATCGTGTGAGGTTTCCGCTGGCGCCCGCGTAGACTCACGCTGACTGCAGGCAGCGGGGGGCATCGAGGGGTGCTT
AGCCCCAGGGCACTCAGAAACCCGGGCGCTGCCTGCTCTGCGTTTCCTCGTCTGGGGTGGCTCTGCAGCCTCCTGC
GGGCGGGCGTCTGCTGCTCCTACAAGGGAAGCTTCTTGCTGCCAGGCCCACACATCCCCAGTTGTTGGTTTGGCCA
CTCTTGACCTGGAGCCATCTTCCTAGTGGGCCACCCCTAATCACTATTGCTTCCTAAAGGTATTTTCACCCTCTTC
GCCTGGTACAGCCCTCACAGCTCTTCAGAGCAAGCACTGGACTACAAGGGCATGGCTCACAAAAGGTTAATGGATG
GGGGTTACCTAGCCCTGGCTAATTCCCCTTCCATTCCCAACTCTCTCTCTCTTTTTAAAGAAAAATGCTAAGGGCA
GCCCTGCCTGCCCTCCCCATCCCCCGCTGTAAATATACACTATTTTTGATAGCACACATGGGGCCCCCATATCTCT
TGGCCTTGGTTTTGATGTTGAAATCCTGGCCTTGGGAGAGATGCCTTCCAGGCAGACACAGCTGTCTGGTTCAGGC
CAAGCCCCTTTGCAATGCAAGCCCTTTCTGGTGTTATGAAGTCCCTCTATGTCGTCGTTTTCACCAGCAACTGGTG
ACTGTCCCTTCGACACGGACCTGCTTTGAGATTTCCTGACAGGGAAAAGATTTCTGTCCATTTTTTTCCTGTGCCT
AACAGCATAATTGCCTTTTCCTATGTAAATATTATGATGGTGGATCAAGACATAAGTAAATGAGCCTTTCTGCCTC
ACATCAGCCCTGTGTATAAAGCCATTATTCTCTGATGCACTGTTTGCCCCAGTAACTCACTTTAAAACCTCTCTTT
CCAGTGTTCCCTCTCTCCCTCCAGGGCCACTGCTTGAAGAAGAATATGTATGTTTCTATCTTGTATGTCTGTGTGC
CCCTCCTGCCCCGAAAGTGCTGACTATGGGGAAATCTTTTAGCTGCTGTTTTTAGACTCCAAGGAGTGGAAATTAT
GTGGAAGAAGCAAACCTGATACAATTTGCCCAAGGTAAACAGTTTGAAAAGACAAATGGGCCTGCCAAACTGTACA
GTTTCTTCCCCAAGAGCTGTTAGGTATCAAAATGTTGTCCTTTCCCCCCTCCGTGCTTTTCTGGTTGAGATCATGT
CATTGATGAACTGCCAAAGTCAGGGGAGGAGGGCAGAGACTTTGTGTTTACATCTGCATTTCTACATGTTTTAGAC
AGAGACAATTTAAGGCCTGCACTCTTATTTCACTAAAGAAAAACTAATGTCAGCACATGTTGCTAATGACAGTGGA
TTTTTTTTTAAATAAAAAAGTTTACAGATCAAATGTGAAATAAATATGAATGGAGTGGTCCTCTTGTCTGTTATCT
GAGTTTTCAAAAGCTTTAAGACTCTGGGAACATCTGATTTTATGGATTTTTTAAAAATAAAAAATGTACATTATAA
AAA SEQ ID NO: 2
>Reverse Complement of SEQ ID NO: 1
TTTTTATAATGTACATTTTTTATTTTTAAAAAATCCATAAAATCAGATGTTCCCAGAGTCTTAAAGCTTTTGAAAA
CTCAGATAACAGACAAGAGGACCACTCCATTCATATTTATTTCACATTTGATCTGTAAACTTTTTTATTTAAAAAA
AAATCCACTGTCATTAGCAACATGTGCTGACATTAGTTTTTCTTTAGTGAAATAAGAGTGCAGGCCTTAAATTGTC
TCTGTCTAAAACATGTAGAAATGCAGATGTAAACACAAAGTCTCTGCCCTCCTCCCCTGACTTTGGCAGTTCATCA
ATGACATGATCTCAACCAGAAAAGCACGGAGGGGGGAAAGGACAACATTTTGATACCTAACAGCTCTTGGGGAAGA
AACTGTACAGTTTGGCAGGCCCATTTGTCTTTTCAAACTGTTTACCTTGGGCAAATTGTATCAGGTTTGCTTCTTC
CACATAATTTCCACTCCTTGGAGTCTAAAAACAGCAGCTAAAAGATTTCCCCATAGTCAGCACTTTCGGGGCAGGA
GGGGCACACAGACATACAAGATAGAAACATACATATTCTTCTTCAAGCAGTGGCCCTGGAGGGAGAGAGGGAACAC
TGGAAAGAGAGGTTTTAAAGTGAGTTACTGGGGCAAACAGTGCATCAGAGAATAATGGCTTTATACACAGGGCTGA
TGTGAGGCAGAAAGGCTCATTTACTTATGTCTTGATCCACCATCATAATATTTACATAGGAAAAGGCAATTATGCT
GTTAGGCACAGGAAAAAAATGGACAGAAATCTTTTCCCTGTCAGGAAATCTCAAAGCAGGTCCGTGTCGAAGGGAC
AGTCACCAGTTGCTGGTGAAAACGACGACATAGAGGGACTTCATAACACCAGAAAGGGCTTGCATTGCAAAGGGGC
TTGGCCTGAACCAGACAGCTGTGTCTGCCTGGAAGGCATCTCTCCCAAGGCCAGGATTTCAACATCAAAACCAAGG -continued

ADRA2A SEQUENCES

CCAAGAGATATGGGGGCCCCATGTGTGCTATCAAAAATAGTGTATATTTACAGCGGGGATGGGGAGGGCAGGCAG
GGCTGCCCTTAGCATTTTTCTTTAAAAAGAGAGAGAGAGTTGGGAATGGAAGGGGAATTAGCCAGGGCTAGGTAAC
CCCCATCCATTAACCTTTTGTGAGCCATGCCCTTGTAGTCCAGTGCTTGCTCTGAAGAGCTGTGAGGGCTGTACCA
GGCGAAGAGGGTGAAAATACCTTTAGGAAGCAATAGTGATTAGGGGTGGCCCACTAGGAAGATGGCTCCAGGTCAA
GAGTGGCCAAACCAACAACTGGGGATGTGTGGGCCTGGCAGCAAGAAGCTTCCCTTGTAGGAGCAGCAGACGCCCG
CCCGCAGGAGGCTGCAGAGCCACCCCAGACGAGGAAACGCAGAGCAGGCAGCGCCCGGGTTTCTGAGTGCCCTGGG
GCTAAGCACCCCTCGATGCCCCCCGCTGCCTGCAGTCAGCGTGAGTCTACGCGGGCGCCAGCGGAAACCTCACACG
ATCCGCTTCCTGTCCCCCCGACAGAGGATCTTCTTGA+GGCGCGGCGGAAATCGTGGTTGAAGATGGTGTAGATGA
CCGGGTTCAACGAGCTGTTGCAGTAGCCGAACCAGAAGAAGAATTTGAAGAGCGTGCGTGGCACGGAGCACCCGAC
GGCCGTGAGCGTGTAGGTGAAGAAGAAGGGGAACCAGCACACCACGAACACTCCGATGACCACGGCCAGCACGAAC
GTGAAGCGCTTCTCGCGGTTCTGCCGCCCGCGCCAGCGCGACGCCTTGGCAGCCCCGACGCGCTCCTCCCCCGGCC
CTGCAGCCGGCGTCCCGATCCCCGTCGCCCCCGGCCCGCGCCGCGGCAGGCTGTCGCCCGGCTTCACCTGGCTCGC
TCGGGCCTTGCCTTTGCCCCGGGGACCGCGCTCGGGTCTGCGGGGCCCTGGAGGCCGCTCGGCGTGGTCGGAAGAC
GAGCTCTCCTCCAGGTCCAGCGCGTCGGTGTCGCGCGGCCCGGCCGGCGCGGGCTCGCCAGGGGCGCCGTTGAGCT
GGGTGGGCAGCGGTTCGGCCTCTGCGCCCCCCGGGCCCGCGCTGCGCTCGGGGCCCAGACCGTTGGGCCTGCGCTC
GGTGCCCCCCGGCGGCGCGGCGACGGCGTCCGGACCCCGGCGGCTGGGTGGCACGCGGGTGCGACGCTTGGCGATC
TGGTAGATGCGCACGTAGACCAGGATCATGATGAGGCAGGGAGCGAAGAAGGAGCCGATGCACGACGAGATGACGT
ACCACTTCTGGTCGTTGATCTCGCAGCGCGGCTCGGCCGGCTGCGGGCCGCCGCCGCCGCCCTTCTTCTCGATGGA
GATGAGCGGCGGGAAGGAGATGACGGCCGAGATGACCCACACGGTGATGATGATGGCCTTGATGCGGCGCGGCGTG
CGCTTCAGGTTGTACTCGATGGCCTGTGTGATGGACCAGTAGCGGTCCAGGCTGATGGCGCACAGGTGCACGATGG
ACGACGTGCAGAAGAGCACGTCGAGCGCCAGGTAGATCTCGCACCAAGCCTTGCCGAAGTACCAGTAGCCCATGAC
CTCGTTGGCCAGCGAGAAAGGGATGACGAGCGTGGCCACCAGGATGTCGGCCGAGGCCAGAGACACCAGGAAGAGG
TTTTGGGGCGCCTTGAGCGCGCGGCTCGTGAACACGGCGATGATGACGAGCACGTTGCCGAACACGGTGAGCAGCA
TGAGCAGGCCGGCCAGGCACACCAGCGTCAGCGTCACCTGCAGGGAGTAAGGGGTGGCCCGGGCGCCGCCCCCCGG
CGCCTCGGTCCCGTTCCAGCTCGCGTTGCCCGCGTCCGGCTGCAGGGAGCCCATGGGCGCAAAGCTGCCCTCGGCC
AACGGCTGCTCCTGGCGGAACATGAACGCGGGCGCCCGCTGGCCTGGGCCTGCTGCCAGCTGCCTTCCGGCCCGGC
GCCCGTGGGTCCTCCTCTTCCTCCGGCGCCCCGCTCGCCTGGCTGCGGCTCACATAGGGAGGGGGCCGCAGGGAGG
CCGGGCCCGAACTGGAGGACCGCTAGCGGCCCATGGCCCGGGTCCCGCGAACTGCGCCTGGCTCGCGCTTCAGACG
CTCTCGGTGGGCGCCTTCTTGCTCCGAGCTCCTAATACAGCCAAGTTTTATTTCTAAGCGGCGGGAGAGAGTAGGG
AGAGCCGATGGGTAAAGAGAGATTTATTCTTCAAGAAGGGAGAACAAAAATCATCGGTGGCCTGATAACTTGGAAG
GATGACAGGAAATTAAATATATATATACATATCAATATCTGTATCTTGAATCTTGAGCCTGAGCGAAAGCAAGAGG
TCTTACCGTGTGCGGGGCCCGCCCCCACCCCGGGAGGCAGCCGAAGGGTGCTGATGCGAGCTCGGGGGTCCTATGT
CTGTCGCCTTACATCCCCGAAGCGATTACCGACTCTCTGGCTTCCCCCAGACGCTGCGGTTCTGGCCCGGCCCGGC
CCGGGGCTGGGGCGCGGACTCTGCCGCCTCTCGGAGCGCCGCGAGACTTCCAAAGTTGTGCGCCCTGCTGGGGCTG
GGGCACACTGTGCGGAGCTCCGGGACGGCGGCGGCGGCGGGGTGAGGAGTGTGGGGGCCGCATGAAGGCACCCCCG
TCCTCAGGCGGGCCGGGGCAGGTGAACGATCAGCTCTCCAGGAGCCGCGACGGAGGCAGGGGTTCTCCTGGGCGTC
CGCCTGGTGGGCGCCGAGCGCTGCTGGATGGGCCGGGGTCCGACGACAGCGCGAGTTGGGGCAGGAGCGCAAGGCG
GGGAAGAAGGCGCTGGAGTGGCCGGGCGGCGGCACGCCGGCTGCTGGGCTTCTGCACCGAGCTGGAGCTGCTGCTG
CTC

SEQ ID NO: 3
>XM_XM_015148184.2 PREDICTED: *Macaca mulatta* alpha-2A adrenergic receptor
(ADRA2A), mRNA
ACGCCGGCTTGATCCTGGGGCTATAAAACGAGTCCACCGTGAGCGCAGCGGAGCAGTAGCAGCTGCGGCTCCGTGC
AGACGCCCAGCAGCCGGCGTGCCGCCGCCCGGCAGCTCCAGCGCCTTCTTCCCCCAACCTTGCGCTCCAAGCCCAA
CTCGCGCTGTCGTCGGACCCCGGCCCATCCAGTCGCGCTCGGCGCCCACCTGGCGGACGCCCAGGAGACACCCTGG
CTTCGTCGCAGCTCCTGCAGAGCTGATCGTTCACCTACCCCGGCCCGCCTGAGGACGGGGGTGCCTTCATGCGGTG
CCCACACTCCTCACCCCGCCGCCGCCGCCGCCCCCGAGCTCCGCACAGTGCGCCCCAGCCTCAGCAGGGCGCACAA
CTTTGGAAGTCTCGCGGCGCTCCGAGAGGCGGCAGGGTCCGCGCCCCAGCCCCGGGCCGGGCCCGGCCAGAAGCGC
AGCGTCTGGGGGAAGCCAGAGAGTCGGTAATCGCTTCGGGGATATAAGGAGACAGACATAGGACCCCAAGCTCGCA
TCAGCACCCCTCGGCTGCCTCCCGGGGTGGGGGCGGGCCCCGCACACGGTAAGACCTCTTGCTTTCGCTCAGGCTC
AAGAGTCAAGATATAGATATCGATATGTATATATATATTTAATTTCCTGTCATCCTTCCAAGTTATCAGGCCACCG
ATGATTTTTGTTCTCCCTTCTTGAAGAATAAATCTCTTTACCCATCGGCTCTCCCTACTCTCTCCCGCCGCTTAGA
AATAAAACTTGGCTGTGTTAGGAGCTCGGAGCGAGAAGGCGCCCACCGAGAGCGTCCGAAGCGCGAGCCAGGCGCA
GTTCGCGGGACCCGGGCCATGGGCCGCTAGCGGTCCCCCAGCTCGGGCCCGGCCTCCCTGCGGCCCCCTCCCTATG
TGAGCTGCAGCCAGGCGAGCGGGGCGCCGGAGGAAGAGGAGGACCCACGGGCGCCGGGCCGGAAGGCAGCTGGCAG
CAGGCCCAGGCGAGCGGGCGCCCGCGTTCATGTTCCGCCAGGAGCAGCCGCTGGCCGAGGGCAGCTTTGCGCCCAT
GGGCTCCCTGCAGCCGGACGCGGGCAATGCGAGCTGGAACGGGACCGAGGCGCCGGGGGGCGGCGCCCGGGCCACC
CCTTACTCCCTGCAGGTGACGCTGACGCTGGTGTGCCTGGCCGGCCTGCTCATGCTGCTCACCGTGTTCGGCAACG
TGCTCGTCATCATCGCGGTGTTCACGAGCCGCGCGCTCAAGGCGCCCCAAAACCTCTTCCTGGTGTCTCTGGCCTC
GGCCGACATCCTGGTGGCCACGCTTGTCATCCCTTTCTCGCTGGCCAACGAGGTCATGGGCTACTGGTACTTTGGC
AAGGCTTGGTGCGAGATCTACCTGGCGCTCGACGTGCTCTTCTGCACGTCGTCCATCGTGCACCTGTGCGCCATCA
GCCTGGACCGCTACTGGTCCATCACACAGGCCATCGAGTACAATCTGAAGCGCACGCCGCGCCGCATCAAGGCCAT
CATCATCACCGTGTGGGTCATCTCGGCCGTCATCTCCTTCCCGCCGCTCATCTCCTTCGAGAAGAAGCGCGGCCAG
GGCGGCCCGCAGCCGGCCGAGCCGCGCTGCGAGATCAACGACCAGAAGTGGTACGTCATCTCGTCGTGCATCGGCT
CCTTCTTCGCTCCCTGCCTCATCATGATCCTGGTCTACGTGCGCATCTACCAGATCGCCAAGCGTCGCACCCGCGT
GCCACCTAGCCGCCGGGGTCCGGACGCCGCCGCCGTGCCGCAGGGGGGCGCCGAGCGCAGGCCCAACGGTCTGGGC
CCAGAGCGCGGCGCGGGCCCGGGGGGCGCGGAGGCCGAGCCGCTGCCCACCCAGCTCAACGGCGCCCCTGGCGAGC
CCGCGCCGGCCGGGCCGCGCGACGCCGACGCGCTGGACCTGGAGGAGAGCTCGTCGTCCGACCACGCCGAGCGGCC
TCCCGGGCCCCGCAGACCCGAGCGCGGCCTCCGGGGCAAGGGCAAGGCCCGGGCGAGCCAGTTGAAGCCGGGGGAC
AGCCTGCCACGGCGCGGGCTGGGGGAGACCGGGATCGGGACGGCTGCGGCAGGGCCGGGGGTGGAGCGCGCTGGGG
CCGCCAAGGCGTCGCGCTGGCGCGGGCGGCAGAACCGCGAGAAACGCTTCACGTTCGTGCTGGCCGTGGTCATCGG
AGTGTTCGTGGTGTGCTGGTTCCCCTTCTTCTTCACCTACACGCTCACAGCCGTCGGGTGCTCAGTGCCGCGCACG
CTCTTCAAGTTCTTCTTCTGGTTCGGCTACTGCAACAGCTCGCTGAACCCGGTCATCTACACCATCTTCAACCACG
ACTTCCGCCGCGCCTTCAAGAAGATCCTCTGCCGCGGGGACAGGAAGCGGATCGTGTGAGGTTTCCGCCGGCGCCC
GCGTAGACTCACGCCGACTGCAGGCAGCAAGGCACCAAGGAGTGCTCAGCCCCAGGGCACTCAGAAACCCGGGCCC
TGTCTGCTCTGCGTTTCCTCCTCTGGGGTGGCTCTGCAGCCTCCTGCGGGCGGGCGTCTGCTGCTCCTACAAGGGA -continued

ADRA2A SEQUENCES

AGCGTTCTTGCTGCCAGACCCACGCATCCCCAGTTGTTGGTTTGGCCACTCTTGACCTGGAGCCATCTTCCCGGTG
GGCCACCCCAATCAGTATTGCTTCCTGAAGGTATTTTCACCTTCTTCCCCTGGTATAGCCCTCACAGCTCTTCAGA
GCAAGCACTGGACTACAAGGACATGGCTCACAAAAGGTTAATGGATGGTTACCTAGAGGATTACCTAGCCCTGGCT
AATTCCCCTTCCATCCCCAGCTCTCTCTCTCTCTTTTTAAAACCCACTCAGGGCAGCCCTGACTGCCCTCCCCAC
CACCCCCTCCACAATGTAAATATACACTATTTTTGATAGTACACATGGGGACCCCATATCTCTTGACCTTGGTTTT
GACGGTGAAATCCTGGCCTTGGGAGAGATGCCTTCTAGGCAGACACAGCTGTGTGGTTCAGGCCAAGCCCCATTTG
CAATGCAAGCCCTTTCTGGTGTTATGATGTCCCTCTATGTCGTCCTTTTCACCAGCAACTGGTGACTGTCCCTTTG
ACACGGACCTGCTTTGAGATTTCCTGACGGGGAAAAGATTTCTGTCCATTTTTTTTTCCTGTGCCTAACAGCATAA
TTGCCTTTTCCTATGTAAATATTATGATGATGGATCAAGACATAAGTAAATGAACCTTTCTGCCTCACATCAGCCC
TGTGTATAAAGCCATTATTCTCTGATGCACTGTTCACCCCAGTAACTCACTTTAAAACCTCTCTTTCCAGTGTTCC
CTCTCTCCCTGCAGGGCCACTGCTTGAAGAAGAATATGTATGTTTCTATCTTGTATGTATGTGCGCCCCTCCTGCC
CCCAAAGTGCTGACTATGGGAAAATCTTTTAGCTGCTGTTTTTAGACACCAAGGAGTGGAAATTATGTGGAAGAAG
CAAACCTGATACAATTTGCCCAAGGTAAACAGTTTGAAAAGACAAATGGGCCTGCCAAACTGTACAGTTCCTGCCC
CAAGAGCTGTTAGGTATCAAAGTGTGGTccTTTCCCCCCTCCCTGCTTTTCTGGTTGAGATCATGTCATTGATGAA
CTGCCAAAGTCAGGGGAGGAGGGCGGAGACCTTGTGTTTACATCTGCGTTTCTACATGTTTTAGACAGAGACAATT
TAAGGCCTGCACTCTTATTTCACTAAAGAAAAACTAATGTCAGCACATGTTGCTAATGACAGTGGATTTTTTTTAA
ATAAAAAAGTTTACAGATCAAATGTGAAATAAATATGAATGAAGTGGTCCTCTTGTCTGTTACCTGAGTTTTCAAA
AGCTTTAAGGCTCTGGGAACATCTGATTTTGTGGATTTTTTAAAAATAAAAAATGTACATTATAAA

SEQ ID NO: 4
>Reverse Complement of SEQ ID NO: 3
TTTATAATGTACATTTTTTATTTTTAAAAAATCCACAAAATCAGATGTTCCCAGAGCCTTAAAGCTTTTGAAAACT
CAGGTAACAGACAAGAGGACCACTTCATTCATATTTATTTCACATTTGATCTGTAAACTTTTTTATTTAAAAAAAA
TCCACTGTCATTAGCAACATGTGCTGACATTAGTTTTTCTTTAGTGAAATAAGAGTGCAGGCCTTAAATTGTCTCT
GTCTAAAACATGTAGAAACGCAGATGTAAACACAAGGTCTCCGCCCTCCTCCCCTGACTTTGGCAGTTCATCAATG
ACATGATCTCAACCAGAAAAGCAGGGAGGGGGGAAAGGACCACACTTTGATACCTAACAGCTCTTGGGGCAGGAAC
TGTACAGTTTGGCAGGCCCATTTGTCTTTTCAAACTGTTTACCTTGGGCAAATTGTATCAGGTTTGCTTCTTCCAC
ATAATTTCCACTCCTTGGTGTCTAAAAACAGCAGCTAAAAGATTTTCCCATAGTCAGCACTTTGGGGGCAGGAGGG
GCGCACATACATACAAGATAGAAACATACATATTCTTCTTCAAGCAGTGGCCCTGCAGGGAGAGAGGGAACACTGG
AAAGAGAGGTTTTAAAGTGAGTTACTGGGGTGAACAGTGCATCAGAGAATAATGGCTTTATACACAGGGCTGATGT
GAGGCAGAAAGGTTCATTTACTTATGTCTTGATCCATCATCATAATATTTACATAGGAAAAGGCAATTATGCTGTT
AGGCACAGGAAAAAAAAATGGACAGAAATCTTTTCCCCGTCAGGAAATCTCAAAGCAGGTCCGTGTCAAAGGGACA
GTCACCAGTTGCTGGTGAAAAGGACGACATAGAGGGACATCATAACACCAGAAAGGGCTTGCATTGCAAATGGGGC
TTGGCCTGAACCACACAGCTGTGTCTGCCTAGAAGGCATCTCTCCCAAGGCCAGGATTTCACCGTCAAAACCAAGG
TCAAGAGATATGGGGTCCCCATGTGTACTATCAAAAATAGTGTATATTTACATTGTGGAGGGGGTGGTGGGGAGGG
CAGTCAGGGCTGCCCTGAGTGGGTTTTAAAAAAGAGAGAGAGAGAGCTGGGGATGGAAGGGGAATTAGCCAGGGCT
AGGTAATCCTCTAGGTAACCATCCATTAACCTTTTGTGAGCCATGTCCTTGTAGTCCAGTGCTTGCTCTGAAGAGC
TGTGAGGGCTATACCAGGGGAAGAAGGTGAAAATACCTTCAGGAAGCAATACTGATTGGGGTGGCCCACCGGGAAG
ATGGCTCCAGGTCAAGAGTGGCCAAACCAACAACTGGGGATGCGTGGGTCTGGCAGCAAGAACGCTTCCCTTGTAG
GAGCAGCAGACGCCCGCCCGCAGGAGGCTGCAGAGCCACCCCAGAGGAGGAAACGCAGAGCAGACAGGGCCCGGGT
TTCTGAGTGCCCTGGGGCTGAGCACTCCTTGGTGCCTTGCTGCCTGCAGTCGGCGTGAGTCTACGCGGGCGCCGGC
GGAAACCTCACACGATCCGCTTCCTGTCCCCGCGGCAGAGGATCTTCTTGAAGGCGCGGCGGAAGTCGTGGTTGAA
GATGGTGTAGATGACCGGGTTCAGCGAGCTGTTGCAGTAGCCGAACCAGAAGAAGAACTTGAAGAGCGTGCGCGGC
ACTGAGCACCCGACGGCTGTGAGCGTGTAGGTGAAGAAGAAGGGGAACCAGCACACCACGAACACTCCGATGACCA
CGGCCAGCACGAACGTGAAGCGTTTCTCGCGGTTCTGCCGCCCGCGCCAGCGCGACGCCTTGGCGGCCCCAGCGCG
CTCCACCCCCGGCCCTGCCGCAGCCGTCCCGATCCCGGTCTCCCCCAGCCCGCGCCGTGGCAGGCTGTCCCCCGGC
TTCAACTGGCTCGCCCGGGCCTTGCCCTTGCCCCGGAGGCCGCGCTCGGGTCTGCGGGGCCCGGGAGGCCGCTCGG
CGTGGTCGGACGACGAGCTCTCCTCCAGGTCCAGCGCGTCGGCGTCGCGCGGCCCGGCCGGCGCGGGCTCGCCAGG
GGCGCCGTTGAGCTGGGTGGGCAGCGGCTCGGCCTCCGCGCCCCCCGGGCCCGCGCCGCGCTCTGGGCCCAGACCG
TTGGGCCTGCGCTCGGCGCCCCCCTGCGGCACGGCGGCGGCGTCCGGACCCCGGCGGCTAGGTGGCACGCGGGTGC
GACGCTTGGCGATCTGGTAGATGCGCACGTAGACCAGGATCATGATGAGGCAGGGAGCGAAGAAGGAGCCGATGCA
CGACGAGATGACGTACCACTTCTGGTCGTTGATCTCGCAGCGCGGCTCGGCCGGCTGCGGGCCGCCGTGGCCGCGC
TTCTTCTCGAAGGAGATGAGCGGCGGGAAGGAGATGACGGCCGAGATGACCCACACGGTGATGATGATGGCCTTGA
TGCGGCGCGGCGTGCGCTTCAGATTGTACTCGATGGCCTGTGTGATGGACCAGTAGCGGTCCAGGCTGATGGCGCA
CAGGTGCACGATGGACGACGTGCAGAAGAGCACGTCGAGCGCCAGGTAGATCTCGCACCAAGCCTTGCCAAAGTAC
CAGTAGCCCATGACCTCGTTGGCCAGCGAGAAAGGGATGACAAGCGTGGCCACCAGGATGTCGGCCGAGGCCAGAG
ACACCAGGAAGAGGTTTTGGGGCGCCTTGAGCGCGCGGCTCGTGAACACCGCGATGATGACGAGCACGTTGCCGAA
CACGGTGAGCAGCATGAGCAGGCCGGCCAGGCACACCAGCGTCAGCGTCACCTGCAGGGAGTAAGGGGTGGCCCGG
GCGCCGCCCCCCGGCGCCTCGGTCCCGTTCCAGCTCGCATTGCCCGCGTCCGGCTGCAGGGAGCCCATGGGCGCAA
AGCTGCCCTCGGCCAGCGGCTGCTCCTGGCGGAACATGAACGCGGGCGCCCGCTCGCCTGGGCCTGCTGCCAGCTG
CCTTCCGGCCCGGCGCCCGTGGGTCCTCCTCTTCCTCCGGCGCCCCGCTCGCCTGGCTGCAGCTCACATAGGGAGG
GGGCCGCAGGGAGGCCGGGCCCGAGCTGGGGGACCGCTAGCGGCCCATGGCCCGGGTCCCGCGAACTGCGCCTGGC
TCGCGCTTCGGACGCTCTCGGTGGGCGCCTTCTCGCTCCGAGCTCCTAACACAGCCAAGTTTTATTTCTAAGCGGC
GGGAGAGAGTAGGGAGAGCCGATGGGTAAAGAGATTTATTCTTCAAGAAGGGAGAACAAAAATCATCGGTGGCCTG
ATAACTTGGAAGGATGACAGGAAATTAAATATATATATACATATCGATATCTATATCTTGACTCTTGAGCCTGAGC
GAAAGCAAGAGGTCTTACCGTGTGCGGGGCCCGCCCCCACCCCGGGAGGCAGCCGAGGGGTGCTGATGCGAGCTTG
GGGTCCTATGTCTGTCTCCTTATATCCCCGAAGCGATTACCGACTCTCTGGCTTCCCCCAGACGCTGCGCTTCTGG
CCGGGCCCGGCCCGGGGCTGGGGCGCGGACCCTGCCGCCTCTCGGAGCGCCGCGAGACTTCCAAAGTTGTGCGCCC
TGCTGAGGCTGGGGCGCACTGTGCGGAGCTCGGGGGCGGCGGCGGCGGCGGGGTGAGGAGTGTGGGCACCGCATGA
AGGCACCCCCGTCCTCAGGCGGGCCGGGGTAGGTGAACGATCAGCTCTGCAGGAGCTGCGACGPAGGCAGGGTGTC
TCCTGGGCGTCCGCCAGGTGGGCGCCGAGCGCGACTGGATGGGCCGGGGTCCGACGACAGCGCGAGTTGGGCTTGG
AGCGCAAGGTTGGGGGAAGAAGGCGCTGGAGCTGCCGGGCGGCGGCACGCCGGCTGCTGGGCGTCTGCACGGAGCC
GCAGCTGCTACTGCTCCGCTGCGCTCACGGTGGACTCGTTTTATAGCCCCAGGATCAAGCCGGCGT -continued

| ADRA2A SEQUENCES |
|---|

SEQ ID NO: 5
> NM_007417.5 *Mus musculus* alpha-2A adrenergic receptor (ADRA2A), mRNA
AGCAGCCTCGGCTCCCGCTTCCGTGCAGACGCCCAGCAGCCGGCGCACACCGCCCAGCCACCCAGCGCCTCCAGCT
CCAAGTCCTGCGGTCCTGCGAAAACTCACGCGGCCCTCCGACCCCCGCCGGGTCTGTGGCGCTCAGCGCCCACCCA
GATCGCGGCTAGCAGCCACCCTTGGCTCCGCCGCGGCTCCTGGAGAGCCGGTCGCTCACCTAGCTTGGCCCTGAGG
ACCGAGGTGGTGGTGGTGGGGGTGCGGCTTCATGCGGCCCCCACACCCTTCACCCCACCGCCGCCGCCCCCGAGCT
CTGTGTACAGAGTCCCAGCCCCAGCAGAGCGCACAACTTTGGAAGTCCCGTGGGGCTCCTAGAGGAGGCAGAGTCC
GCGCCTTCGCCGGAGGTCCGGCCCAGCCCTCGCCACCCCGCCTGGAGGGTAGCGACGGAGTTGGAAATCTCTTCGA
GGGTATAAGAAGACAGACCTAGGACTCCGAGCCCACACCAACACCCCTCCGCTGCCTCTTGGGGTAAGACTTCATG
CTTTCGCTCAGCTTAAGAATCAAGGTATAGATGACTAGCTAAATGCATTTGTATAAATTTCTGACATCTTTCCAAA
TCATCAGGCCACCGATAATTTCTTTTCTCTTTTCTTGAAGAATAAAATCTCTAACCACCAGCTGGCCCTACTCGAT
CCTGCCGCTTAGAAATAAAACTTGGCTGTGTTTGAGGAGCTGGGAGAGAGAAAGCACCCACCCGGAGCGTCGGAAG
GACGAACCGGTGCCAGTTCGCGGGCTCCAGTCCATGGACCACTAGCGGTCCCCAGCTTGGGCCCGAGCTCCCTGCG
GCCCTCTTCCTTATGTGAGGCGCGGCGGGACGAACCCCGCACCGGAGGAAGAGGAGGACCCACGGACGCGGGGCCG
GAAGGCAGCTGGCAGCAGGCCCACGAGAACCAGCACCCGCGTTCATGTTCCGCCAGGAGCAGCCGCTGGCCGAGGG
CAGCTTTGCGCCCATGGGCTCACTGCAGCCGGATGCCGGCAACAGCAGCTGGAACGGGACCGAAGCGCCCGGAGGC
GGCACCCGAGCCACCCCTTACTCCCTGCAGGTGACACTGACGCTGGTTTGCCTGGCTGGCCTGCTCATGCTGTTCA
CAGTATTTGGCAACGTGCTGGTTATTATCGCGGTGTTCACCAGTCGCGCGCTCAAAGCTCCCCAAAACCTCTTCCT
GGTGTCCCTGGCCTCAGCGGACATCCTGGTGGCCACGCTGGTCATTCCCTTTTCTTTGGCCAACGAGGTTATGGGT
TACTGGTACTTTGGTAAGGTGTGGTGTGAGATCTATTTGGCTCTCGACGTGCTCTTTTGCACGTCGTCCATAGTGG
ACCTGTGCGCCATCAGCCTTGACCGCTACTGGTCCATCACGCAGGCCATCGAGTACAACCTGAAGCGCACGCCGCG
TCGCATCAAGGCCATCATTGTCACCGTGTGGGTCATCTCGGCTGTCATCTCCTTCCCGCCACTCATCTCCATAGAG
AAGAAGGGCGCTGGCGGCGGGCAGCAGCCGGCCGAGCCAAGCTGCAAGATCAACGACCAGAAGTGGTATGTCATCT
CCTCGTCCATCGGTTCCTTCTTCGCGCCTTGCCTCATCATGATCCTGGTCTACGTGCGTATTTACCAGATCGCCAA
GCGTCGCACCCGCGTGCCTCCCAGCCGCCGGGGTCCGGACGCCTGTTCCGCGCCGCCGGGGGGCGCCGATCGCAGG
CCCAACGGGCTGGGCCCGGAGCGCGGCGCGGGTCCCACGGGCGCTGAGGCGGAGCCGCTGCCCACCCAGCTTAACG
GTGCCCCGGGGGAGCCCGCGCCCGCCGGGCCCCGCGATGGGGATGCGCTGGACCTAGAGGAGAGTTCGTCGTCCGA
GCACGCCGAGCGGCCCCCGGGGCCCCGCAGACCCGACCGCGGCCCCCGAGCCAAGGGCAAGACCCGGGCGAGTCAG
GTGAAGCCGGGGGACAGTCTGCCGCGGCGCGGGCCCGGGGCCGCGGGGCCGGGGGCTTCGGGGTCCGGGCACGGAG
AGGAGCGCGGCGGGGGCGCCAAAGCGTCGCGCTGGCGCGGGAGGCAAAACCGGGAGAAACGCTTCACGTTCGTGCT
GGCGGTGGTGATCGGCGTGTTCGTGGTGTGTTGGTTTCCGTTCTTTTTCACCTACACGCTCATAGCGGTCGGCTGC
CCGGTGCCCAGCCAGCTCTTCAAATTCTTCTTCTGGTTCGGCTACTGCAACAGCTCGCTGAACCCTGTTATCTACA
CCATCTTCAACCACGACTTCCGACGCGCCTTCAAGAAGATCCTCTGCCGTGGGGACAGAAAACGCATCGTGTGAGC
GCATGGGCCTTGCCCTGCGTGCAGACAATGGTCAGACGCAGGCCCTGGGCTTCGAGGGGGTGCGTCTACGCATGCA
GCCCCTAGCACTCTGAAACCCCGGACCTACCCAGCTGGGAGGGAGCTCCGTGGCCTTTGAGACCTTTTGTTACAAT
GTGTAAAGTTCTGGCTGAGAGGGACACATGAGCCCTTTTGCTGGTTGTTGTGGTTGTTCCCAGCCCACAGCCAGTT
TCCTGGTGGGCTACCCCTGATCAGTATGGTTTCCTGATGATATTGTCATATCCCCAAGTCTGACTCTCCCAAGCTC
TTCAGAGCAAGCACAGTACTAGAGAGGGCATGGCTGCCAAAGGGTTAATGAACCAAGGTTTCCTCTAGTCCTGGCT
AATTATCTCCTCCACACCCCCTTCCTTAAATAAATAAATAAAGATCATTCAGGGCGGTCCTGCCTGCCCTCCCTTC
TCCCCACTGTAAATATACATTATTTTTGATAGCATACTTTGGGTTCTTCAGTGTCGGCCTTGATGCATATTGGAAT
CATGGCTGTGsAGATGCCCTCCAGTCAGACAGTGGGCTATCTGGTCCAGACCACGCTCCTTTGCAATGCAAGCCCC
TTTCTAGTGTTAAGTTGCTCTCAGTGCTTTTCAGCAGTAACTGGTGACTGTCCCCTGGACACGGACCTGCTTTGAC
ATTTCCTGACAGGGAAGGGATTTCTGCTCATTTTCCCCTGTGCCTAACTGCATAATTGCCTTTTCCTATGTAAATA
TTACAGCGATGGACCAAGGCAGAAGGAAATGAAGCCTCTGCCTTGCATCAGCCCCGTGTATAAAGCCATTATCTGC
TGAGGCACCGCTTGCCCCAGTAACTCACTTTAGAACTGACTTTTCTTCCGTTCTCCCCTCCTCTGGGGCTTGAAGA
AGAGCGTGTATGTTTCTATCTTGTCTGTGCGCCGCCCCCTCCCCCAGAAAGTGCTGACTAAGGGGAATCTTTTAGC
TGCTGTTTTTAGACACCCAGGAGGGGAAATTATGTGGAAGAAACCAACCCGATACAATTTGCCAAGGTAAACAGTG
TGAGGAGACAAATGGGCTGCCACACTGTATGGAGCCAGCCCCAAGAGCTCTTGGGTATCAAAGTGTTACCTCCCCT
TGCTGTCCTGGCTGAGATCATGTGACTACTGAATTGCCAAAGTCAGGGGGTAGGCGGAGACTTCGTGTTTACAACC
TGGTTTCTACTTATTTTAGGCAGACTGTGGAAGGCCTGTGATCTGATTTCACGAGAGAAAAACTAAATGTCAGCAC
TTGTTGCTCGTGACGGTGGATTTTTTTAAATAAAAGTTTACAGATCAAATGTGAAATAAACATGAATTAAGTGGG SEQ ID NO: 6
>Reverse Complement of SEQ ID NO: 5
CCCACTTAATTCATGTTTATTTCACATTTGATCTGTAAACTTTTATTTAAAAAAATCCACCGTCACGAGCAACAA
GTGCTGACATTTAGTTTTTCTCTCGTGAAATCAGATCACAGGCCTTCCACAGTCTGCCTAAAATAAGTAGAAACCA
GGTTGTAAACACGAAGTCTCCGCCTACCCCCTGACTTTGGCAATTCAGTAGTCACATGATCTCAGCCAGGACAGCA
AGGGGAGGTAACACTTTGATACCCAAGAGCTCTTGGGGCTGGCTCCATACAGTGTGGCAGCCCATTTGTCTCCTCA
CACTGTTTACCTTGGCAAATTGTATCGGGTTGGTTTCTTCCACATAATTTCCCCTCCTGGGTGTCTAAAAACAGCA
GCTAAAAGATTCCCCTTAGTCAGCACTTTCTGGGGGAGGGGGCGGCGCACAGACAAGATAGAAACATACACGCTCT
TCTTCAAGCCCCAGAGGAGGGGAGAACGGAAGAAAAGTCAGTTCTAAAGTGAGTTACTGGGGCAAGCGGTGCCTCA
GCAGATAATGGCTTTATACACGGGGCTGATGCAAGGCAGAGGcTTCATTTCCTTCTGCCTTGGTCCATCGCTGTAA
TATTTACATAGGAAAAGGCAATTATGCAGTTAGGCACAGGGGAAAATGAGCAGAAATCCCTTCCCTGTCAGGAAAT
GTCAAAGCAGGTCCGTGTCCAGGGGACAGTCACCAGTTACTGCTGAAAAGCACTGAGAGCAACTTAACACTAGAAA
GGGGCTTGCATTGCAAAGGAGCGTGGTCTGGACCAGATAGCCCACTGTCTGACTGGAGGGCATCTCCACAGCCATG
ATTCCAATATGCATCAAGGCCGACACTGAAGAACCCAAAGTATGCTATCAAAAATAATGTATATTTACAGTGGGGA
GAAGGGAGGGCAGGCAGGACCGCCCTGAATGATCTTTATTTATTTATTTAAGGAAGGGGGTG1GGAGGAGATAATT
AGCCAGGACTAGAGGAAACCTTGGTTCATTAACCCTTTGGCAGCCATGCCCTCTCTAGTACTGTGCTTGCTCTGAA
GAGCTTGGGAGAGTCAGACTTGGGGATATGACAATATCATCAGGAAACCATACTGATCAGGGGTAGCCCACCAGGA
AACTGGCTGTGGGCTGGGAACAACCACAACAACCAGCAAAAGGGCTCATGTGTCCCTCTCAGCCAGAACTTTACAC
ATTGTAACAAAAGGTCTCAAAGGCCACGGAGCTCCCTCCCAGCTGGGTAGGTCCGGGGTTTCAGAGTGCTAGGGGC
TGCATGCGTAGACGCACCCCCTCGAAGCCCAGGGCCTGCGTCTGACCATTGTCTGCACGCAGGGCAAGGCCCATGC
GCTCACACGATGCGTTTTCTGTCCCCACGGCAGAGGATCTTCTTGAAGGCGCGTCGGAAGTCGTGGTTGAAGATGG
TGTAGATAACAGGGTTCAGCGAGCTGTTGCAGTAGCCGAACCAGAAGAAGAAGTTGAAGAGCTGGCTGGGCACCGG
GCAGCCGACCGCTATGAGCGTGTAGGTGAAAAAGAACGGAAACCAACACACCACGAACACGCCGATCACCACCGCC
AGCACGAACGTGAAGCGTTTCTCCCGGTTTTGCCTCCCGCGCCAGCGCGACGCTTTGGCGCCCCCGCCGCGCTCCT -continued

| ADRA2A SEQUENCES |
| --- |

CTCCGTGCCCGGACCCCGAAGCCCCCGGCCCCGCGGCCCCGGGCCCGCGCCGCGGCAGACTGTCCCCCGGCTTCAC
CTGACTCGCCCGGGTCTTGCCCTTGGCTCGGGGGCCGCGGTCGGGTCTGCGGGGCCCCGGGGGCCGCTCGGCGTGC
TCGGACGACGAACTCTCCTCTAGGTCCAGCGCATCCCCATCGCGGGGCCCGGCGGGCGCGGGCTCCCCCGGGGCAC
CGTTAAGCTGGGTGGGCAGCGGCTCCGCCTCAGCGCCCGTGGGACCCGCGCCGCGCTCCGGGCCCAGCCCGTTGGG
CCTGCGATCGGCGCCCCCGGCGGCGCGGAACAGGCGTCCGGACCCCGGCGGCTGGGAGGCACGCGGGTGCGACGC
TTGGCGATCTGGTAAATACGCACGTAGACCAGGATCATGATGAGGCAAGGCGCGAAGAAGGAACCGATGGACGAGG
AGATGACATACCACTTCTGGTCGTTGATCTTGCAGCTTGGCTCGGCCGGCTGCTGCCCGCCGCCAGCGCCCTTCTT
CTCTATGGAGATGAGTGGCGGGAAGGAGATGACAGCCGAGATGACCCACACGGTGACAATGATGGCCTTGATGCGA
CGCGGCGTGCGCTTCAGGTTGTACTCGATGGCCTGCGTGATGGACCAGTAGCGGTCAAGGCTGATGGCGCACAGGT
GCACTATGGACGACGTGCAAAAGAGCACGTCGAGAGCCAAATAGATCTCACACCACACCTTACCAAAGTACCAGTA
ACCCATAACCTCGTTGGCCAAAGAAAAGGGAATGACCAGCGTGGCCACCAGGATGTCCGCTGAGGCCAGGGACACC
AGGAAGAGGTTTTGGGGAGCTTTGAGCGCGCGACTGGTGAACACCGCGATAATAACCAGCACGTTGCCAAATACTG
TGAACAGCATGAGCAGGCCAGCCAGGCAAACCAGCGTCAGTGTCACCTGCAGGGAGTAAGGGGTGGCTCGGGTGCC
GCCTCCGGGCGCTTCGGTCCCGTTCCAGCTGCTGTTGCCGGCATCCGGCTGCAGTGAGCCCATGGGCGCAAAGCTG
CCCTCGGCCAGCGGCTGCTCCTGGCGGAACATGAACGCGGGTGCTGGTTCTCGTGGGCCTGCTGCCAGCTGCCTTC
CGGCCCCGCGTCCGTGGGTCCTCCTCTTCCTCCGGTGCGGGGTTCGTCCCGCCGCGCCTCACATAAGGAAGAGGGC
CGCAGGGAGCTCGGGCCCAAGCTGGGGACCGCTAGTGGTCCATGGACTGGAGCCCGCGAACTGGCACCGGTTCGTC
CTTCCGACGCTCCGGGTGGGTGCTTTCTCTCTCCCAGCTCCTCAAACACAGCCAAGTTTTATTTCTAAGCGGCAGG
ATCGAGTAGGGCCAGCTGGTGGTTAGAGATTTTATTCTTCAAGAAAAGAGAAAAGAAATTATCGGTGGCCTGATGA
TTTGGAAAGATGTCAGAAATTTATACAAATGCATTTAGCTAGTCATCTATACCTTGATTCTTAAGCTGAGCGAAAG
CATGAAGTCTTACCCCAAGAGGCAGCGGAGGGGTGTTGGTGTGGGCTCGGAGTCCTAGGTCTGTCTTCTTATACCC
TCGAAGAGATTTCCAACTCCGTCGCTACCCTCCAGGCGGGGTGGCGAGGGCTGGGCCGGACCTCCGGCGAAGGCGC
GGACTCTGCCTCCTCTAGGAGCCCCACGGGACTTCCAAAGTTGTGCGCTCTGCTGGGGCTGGGACTCTGTACACAG
AGCTCGGGGGCGGCGGCGGTGGGGTGAAGGGTGTGGGGGCCGCATGAAGCCGCACCCCCACCACCACCACCTCGGT
CCTCAGGGCCAAGCTAGGTGAGCGACCGGCTCTCCAGGAGCCGCGGCGGAGCCAAGGGTGGCTGCTAGCCGCGATC
TGGGTGGGCGCTGAGCGCCACAGACCCGGCGGGGGTCGGAGGGCCGCGTGAGTTTTCGCAGGACCGCAGGACTTGG
AGCTGGAGGCGCTGGGTGGCTGGGCGGTGTGCGCCGGCTGCTGGGCGTCTGCACGGAAGCGGGAGCCGAGGCTGCT

SEQ ID NO: 7
> NM_012739.3 *Rattus norvegicus* alpha-2A adrenergic receptor (ADRA2A), mRNA
ATGTTCCGCCAGGAGCAGCCGCTGGCCGAGGGCAGCTTTGCGCCCATGGGCTCCCTGCAGCCGGATGCCGGCAATA
GCAGCTGGAACGGCACCGAGGCGCCCGGAGGCGGCACCCGGGCCACCCCTTACTCCCTGCAGGTGACGCTGACGCT
GGTGTGCCTGGCTGGCCTGCTCATGCTGTTCACCGTGTTTGGCAACGTGCTGGTTATTATCGCAGTGTTCACCAGC
CGCGCGCTCAAAGCGCCCCAGAACCTCTTCCTGGTGTCTCTGGCCTCAGCGGACATCCTGGTGGCCACGCTGGTCA
TTCCCTTTTCTTTGGCCAACGAGGTTATGGGCTACTGGTACTTTGGTAAGGTGTGGTGCGAGATCTACTTGGCCCT
CGACGTGCTCTTTTGCACGTCGTCCATAGTGCACCTGTGCGCCATCAGCCTTGACCGCTACTGGTCCATCACGCAG
GCCATCGAGTACAACCTGAAGCGCACGCCGCGGCGCATCAAGGCCATCATTGTCACTGTGTGGGTCATCTCGGCCG
TCATCTCCTTCCCGCCACTCATCTCCATAGAGAAGAAGGGCGCTGGCGGCGGGCAGCAGCCGGCCGAGCCGAGCTG
CAAGATTAACGACCAGAAGTGGTATGTCATCTCGTCGTCCATCGGCTCCTTCTTCGCGCCTTGCCTCATCATGATC
CTGGTCTACGTGCGTATCTACCAGATCGCCAAGCGTCGCACCCGCGTGCCGCCCAGTCGCCGGGGTCCGGACGCCT
GTTCCGCGCCGCCGGGGGGCGCCGATCGCAGGCCCAACGGGCTGGGCCCGGAGCGCGGCGCTGGTACCGCGGGCGC
GGAGGCCGAGCCGCTGCCCACCCAGCTTAACGGCGCCCCGGGGGAGCCCGCGCCCACCCGGCCGCGCGACGGGGAT
GCGCTGGACCTAGAGGAGAGTTCGTCGTCCGAGCACGCCGAGCGGCCCCAGGGGCCCGGCAAACCCGAGCGCGGTC
CCCGGGCCAAGGGCAAGACCAAGGCGAGCCAGGTGAAACCGGGGGACAGTCTGCCGCGGCGCGGGCCCGGGGCTGC
GGGGCCGGGGGCTTCGGGGTCCGGGCAGGGAGAGGAGCGTGCCGGGGGCGCCAAAGCGTCGCGCTGGCGCGGGAGG
CAGAACCGCGAGAAACGCTTCACGTTCGTGCTGGCGGTGGTGATCGGCGTGTTCGTGGTGTGTTGGTTCCCGTTCT
TTTTCACCTACACGCTCATAGCGGTCGGcTGCCCGGTGCCCTACCAGCTCTTCAACTTCTTCTTCTGGTTCGGCTA
CTGCAACAGCTCGCTGAACCCTGTTATCTACACCATTTTCAACCACGACTTCCGCCGCGCCTTCAAGAAGATCCTC
TGCCGTGGGGACAGAAAGCGCATCGTGTGAGCGCTCGGGCTGTGCCCTGCTTACAGACCCTGGTCAGATGCAGGCC
CTGGGCTTCGAGGGGGCGCGTCTACGCATGCAGCCCCTAGCACTCTGAAACCCTGGACCTTCCTGCTCTGTGTAAT
ACCCAGTTTGGAGGGGACTTGGTGGCTTTTGAGACCTTTTGTTACCATGTGTAAAGTTCTGGCTGAGAGGGACATA
TGCGCCTTTTTGCTGGTTGTTGTGGTTGTTCCCAGCCCACAGCCAGTTTCCTGGTGGGCTACCCCCGATCAGTATT
GTTTCCTGACGATATTGCCATCTTCTCCCCGAGTCTGACTCTCCCAAGCTCTTCAGAGCAAGCACAGTACTAGAGA
GGGCATGACTGCCAAAGGGTTAATGAACCAAGGTTTCCTAGCCCTGGCTAATTGTCACTTCCCTCCTTCCCCCCCT
TTAAAAATATCATTCAGGGCAGCCCTGCCTGCCCTCCGTACCCTCCACTGTAAATATACATTATTTTTGATAGCAC
ACTTTGTGTTCCTCAGAATTGGCCTTGTCGCGATATTGGAATCCCGGCTGTGGGGATGCCCTCCAGTCACAGACAG
TGGGCTATCTGGTCCAGACCAACGTCCTTTGCAATGCAAGTCCCTTTCTAGTGTTATTACATCGTCGCTCTCAGTA
CTTTTCAGCAGTAACTGGTAACTGTCCCCTGGACACGGACCTGCTTTGACATTTCCTGAGAGGGAAGGGATTTCTG
TTCATTTTCCCCCTGTGCCTAACAGCATAATTGCCTTTTCCTATGTAAATATTACAGCGATGGACCAAGACAGAAG
GAAATGAACCTTCTGCCTGGCCCCAGCCCTGTGTATAAAGCCATTATTCGCTGAGGCACCACTTGCCCCAGTAACT
CACTTTAGAACTGACGCTGCGGTTCTCCTCTCCTCTGGGGCCAAGGCTTGAAGAAGAACGGGTGGGTGTGCTTGTT
TCTGTCTTGTGTGTGTGCCGCCCCTCATCCAGAAAGTGCTGAGTAAGGGGAATCTTTTAGCAGCTGTTTTTAGACA
CACAGGAGGGGAAATTATGTGGAAGAAACCTACCCGATACAATTTGCCAAGGTAAACAGTGTGAGGAGACAAACAG
TCCGCCACACTGTTCAGCGCCAGCCCCAAGAGCTCTTGGGTATCAAAGTGTTACCTCCCCTTGCTTTTCTGGCTGA
GATCACGTCACCAGTGAATTGCCAAAGTCAGGGAGTAGGCGGAGAATTGGTGTTTACAACCTGGTTTCTACTTAGT
TTAGGCGGACTGTGGAAGGCCTGCGATCTGTTTTTCCTGAGAGAAAAACCTAAATGTCAGCACTTGTTGCTCATGA
TGGTGGATTTTTTTTTAAAATAAAAGTTTACAGATCAAATGTGAAATAAACATGAATTAAGTGATAAAAAAAAAAA
AA SEQ ID NO: 8
>Reverse Complement of SEQ ID NO: 7
TTTTTTTTTTTTTATCACTTAATTCATGTTTATTTCACATTTGATCTGTAAACTTTTATTTTAAAAAAAATCCAC
CATCATGAGCAACAAGTGCTGACATTTAGGTTTTTCTCTCAGGAAAAACAGATCGCAGGCCTTCCACAGTCCGCCT
AAACTAAGTAGAAACCAGGTTGTAAACACCAATTCTCCGCCTACTCCCTGACTTTGGCAATTCACTGGTGACGTGA
TCTCAGCCAGAAAAGCAAGGGGAGGTAACACTTTGATACCCAAGAGCTCTTGGGGCTGGCGCTGAACAGTGTGGCG
GACTGTTTGTCTCCTCACACTGTTTACCTTGGCAAATTGTATCGGGTAGGTTTCTTCCACATAATTTCCCCTCCTG
TGTGTCTAAAAACAGCTGCTAAAAGATTCCCCTTACTCAGCACTTTCTGGATGAGGGGCGGCACACACACAAGACA -continued

| ADRA2A SEQUENCES |
| --- |
| GAAACAAGCACACCCACCCGTTCTTCTTCAAGCCTTGGCCCCAGAGGAGAGGAGAACCGCAGCGTCAGTTCTAAAG<br>TGAGTTACTGGGGCAAGTGGTGCCTCAGCGAATAATGGCTTTATACACAGGGCTGGGGCCAGGCAGAAGGTTCATT<br>TCCTTCTGTCTTGGTCCATCGCTGTAATATTTACATAGGAAAAGGCAATTATGCTGTTAGGCACAGGGGGAAAATG<br>AACAGAAATCCCTTCCCTCTCAGGAAATGTCAAAGCAGGTCCGTGTCCAGGGGACAGTTACCAGTTACTGCTGAAA<br>AGTACTGAGAGCGACGATGTAATAACACTAGAAAGGGACTTGCATTGCAAAGGACGTTGGTCTGGACCAGATAGCC<br>CACTGTCTGTGACTGGAGGGCATCCCCACAGCCGGGATTCCAATATCGCGACAAGGCCAATTCTGAGGAACACAAA<br>GTGTGCTATCAAAAATAATGTATATTTACAGTGGAGGGTACGGAGGGCAGGCAGGGCTGCCCTGAATGATATTTTT<br>AAAGGGGGGGAAGGAGGGAAGTGACAATTAGCCAGGGCTAGGAAACCTTGGTTCATTAACCCTTTGGCAGTCATGC<br>CCTCTCTAGTACTGTGCTTGCTCTGAAGAGCTTGGGAGAGTCAGACTCGGGGAGAAGATGGCAATATCGTCAGGAA<br>ACAATACTGATCGGGGGTAGCCCACCAGGAAACTGGCTGTGGGCTGGGAACAACCACAACAACCAGCAAAAAGGCG<br>CATATGTCCCTCTCAGCCAGAACTTTACACATGGTAACAAAAGGTCTCAAAAGCCACCAAGTCCCCTCCAAACTGG<br>GTATTACACAGAGCAGGAAGGTCCAGGGTTTCAGAGTGCTAGGGGCTGCATGCGTAGACGCGCCCCCTCGAAGCCC<br>AGGGCCTGCATCTGACCAGGGTCTGTAAGCAGGGCACAGCCCGAGCGCTCACACGATGCGCTTTCTGTCCCCACGG<br>CAGAGGATCTTCTTGAAGGCGCGGCGGAAGTCGTGGTTGAAAATGGTGTAGATAACAGGGTTCAGCGAGCTGTTGC<br>AGTAGCCGAACCAGAAGAAGAAGTTGAAGAGCTGGTAGGGCACCGGGCAGCCGACCGCTATGAGCGTGTAGGTGAA<br>AAAGAACGGGAACCAACACACCACGAACACGCCGATCACCACCGCCAGCACGAACGTGAAGCGTTTCTCGCGGTTC<br>TGCCTCCCGCGCCAGCGCGACGCTTTGGCGCCCCCGGCACGCTCCTCTCCCTGCCCGGACCCCGAAGCCCCCGGCC<br>CCGCAGCCCCGGGCCCGCGCCGCGGCAGACTGTCCCCCGGTTTCACCTGGCTCGCCTTGGTCTTGCCCTTGGCCCG<br>GGGACCGCGCTCGGGTTTGCCGGGCCCCTGGGGCCGCTCGGCGTGCTCGGACGACGAACTCTCCTCTAGGTCCAGC<br>GCATCCCCGTCGCGCGGCCGGGTGGGCGCGGGCTCCCCCGGGGCGCCGTTAAGCTGGGTGGGCAGCGGCTCGGCCT<br>CCGCGCCCGCGGTACCAGCGCCGCGCTCCGGGCCCAGCCCGTTGGGCCTGCGATCGGCGCCCCCCGGCGGCGCGGA<br>ACAGGCGTCCGGACCCCGGCGACTGGGCGGCACGCGGGTGCGACGCTTGGCGATCTGGTAGATACGCACGTAGACC<br>AGGATCATGATGAGGCAAGGCGCGAAGAAGGAGCCGATGGACGACGAGATGACATACCACTTCTGGTCGTTAATCT<br>TGCAGCTCGGCTCGGCCGGCTGCTGCCCGCCGCCAGCGCCCTTCTTCTCTATGGAGATGAGTGGCGGGAAGGAGAT<br>GACGGCCGAGATGACCCACACAGTGACAATGATGGCCTTGATGCGCCGCGGCGTGCGCTTCAGGTTGTACTCGATG<br>GCCTGCGTGATGGACCAGTAGCGGTCAAGGCTGATGGCGCACAGGTGCACTATGGACGACGTGCAAAAGAGCACGT<br>CGAGGGCCAAGTAGATCTCGCACCACACCTTACCAAAGTACCAGTAGCCCATAACCTCGTTGGCCAAAGAAAAGGG<br>AATGACCAGCGTGGCCACCAGGATGTCCGCTGAGGCCAGAGACACCAGGAAGAGGTTCTGGGGCGCTTTGAGCGCG<br>CGGCTGGTGAACACTGCGATAATAACCAGCACGTTGCCAAACACGGTGAACAGCATGAGCAGGCCAGCCAGGCACA<br>CCAGCGTCAGCGTCACCTGCAGGGAGTAAGGGGTGGCCCGGGTGCCGCCTCCGGGCGCCTCGGTGCCGTTCCAGCT<br>GCTATTGCCGGCATCCGGCTGCAGGGAGCCCATGGGCGCAAAGCTGCCCTCGGCCAGCGGCTGCTCCTGGCGGAAC<br>AT |

We claim:

1. A double stranded ribonucleic acid (dsRNA) agent for inhibiting expression of ADRA2A, wherein the dsRNA agent comprises a sense strand and an antisense strand forming a double stranded region, wherein the antisense strand comprises a region of complementarity to an mRNA encoding ADRA2A, and wherein the region of complementarity comprises at least 15 contiguous nucleotides differing by no more than 3 nucleotides from SEQ ID NO: 153 or 423.

2. The dsRNA agent of claim 1, wherein the sense strand comprises at least 15 contiguous nucleotides differing by no more than three nucleotides from any one of the nucleotide sequence of nucleotides 528-548 of SEQ ID NO: 1, and the antisense strand comprises at least 15 contiguous nucleotides from the corresponding nucleotide sequence of SEQ ID NO: 2; and/or the antisense strand comprises at least 15 contiguous nucleotides differing by no more than three nucleotides from the antisense strand nucleotide sequences of a duplex AD-1201752.

3. The dsRNA agent of claim 1, wherein the sense strand comprises SEQ ID NO: 18 and the antisense strand comprises SEQ ID NO: 153, or the sense strand comprises SEQ ID NO: 288 and the antisense strand comprises SEQ ID NO: 423.

4. The dsRNA agent of claim 1, wherein the sense strand, the antisense strand, or both the sense strand and the antisense strand is conjugated to one or more lipophilic moieties, optionally wherein:

the lipophilic moiety is conjugated to one or more internal positions in the double stranded region of the dsRNA agent;

the lipophilic moiety is conjugated via a linker or carrier; and/or lipophilicity of the lipophilic moiety, measured by logKow, exceeds 0.

5. The dsRNA agent of claim 4, wherein the one or more lipophilic moieties are conjugated to one or more internal positions in the double stranded region of the dsRNA agent on at least one strand, optionally wherein:

(i) the one or more lipophilic moieties are conjugated to the one or more internal positions on at least one strand via a linker or carrier, optionally wherein:

(a) the internal positions include all positions except the terminal two or three positions from each end of the at least one strand; and/or (b) the internal positions exclude a cleavage site region of the sense strand, optionally wherein the internal positions include (i) all positions except positions 9-12, counting from the 5'-end of the sense strand or (ii) all positions except positions 11-13, counting from the 3'-end of the sense strand;

the internal positions exclude a cleavage site region of the antisense strand, optionally wherein the internal positions include all positions except positions 12-14, counting from the 5'-end of the antisense strand; and/or the internal positions include all positions except positions 11-13 on the sense strand, counting from the 3'-end, and positions 12-14 on the antisense strand, counting from the 5'-end;

(ii) the one or more lipophilic moieties are conjugated to one or more of the internal positions selected from the group consisting of positions 4-8 and 13-18 on the sense strand, and positions 6-10 and 15-18 on the antisense strand, counting from the 5'end of each strand, optionally wherein the one or more lipophilic moieties are conjugated to one or more of the internal positions selected from the group consisting of positions 5, 6, 7, 15, and 17 on the sense strand, and positions 15 and 17 on the antisense strand, counting from the 5'-end of each strand; and/or (iii) the internal positions in the double stranded region exclude a cleavage site region of the sense strand.

6. The dsRNA agent claim 4, wherein the sense strand is 21 nucleotides in length, the antisense strand is 23 nucleotides in length, and the lipophilic moiety is conjugated to position 21, position 20, position 15, position 1, position 7, position 6, or position 2 of the sense strand or position 16 of the antisense strand, optionally wherein:

the lipophilic moiety is conjugated to position 21, position 20, position 15, position 1, or position 7 of the sense strand;

the lipophilic moiety is conjugated to position 21, position 20, or position 15 of the sense strand;

the lipophilic moiety is conjugated to position 20 or position 15 of the sense strand; or the lipophilic moiety is conjugated to position 16 of the antisense strand.

7. The dsRNA agent of claim 4, wherein the lipophilic moiety is an aliphatic, alicyclic, or polyalicyclic compound, optionally wherein:

the lipophilic moiety is selected from the group consisting of lipid, cholesterol, retinoic acid, cholic acid, adamantane acetic acid, 1-pyrene butyric acid, dihydrotestosterone, 1,3-bis-O (hexadecyl) glycerol, geranyloxyhexyanol, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine; and/or the lipophilic moiety contains a saturated or unsaturated C4-C30 hydrocarbon chain, and an optional functional group selected from the group consisting of hydroxyl, amine, carboxylic acid, sulfonate, phosphate, thiol, azide, and alkyne, optionally wherein the lipophilic moiety contains a saturated or unsaturated C6-C18 hydrocarbon chain or a saturated or unsaturated C16 hydrocarbon chain, optionally wherein the C16 hydrocarbon chain is conjugated to position 6, counting from the 5'-end of the strand.

8. The dsRNA agent of claim 4, wherein:

the lipophilic moiety is conjugated via a carrier that replaces one or more nucleotide(s) in the internal position(s) or the double stranded region, optionally wherein the carrier is a cyclic group selected from the group consisting of pyrrolidinyl, pyrazolinyl, pyrazolidinyl, imidazolinyl, imidazolidinyl, piperidinyl, piperazinyl, [1,3] dioxolanyl, oxazolidinyl, isoxazolidinyl, morpholinyl, thiazolidinyl, isothiazolidinyl, quinoxalinyl, pyridazinonyl, tetrahydrofuranyl, and decalinyl; or is an acyclic moiety based on a serinol backbone or a diethanolamine backbone;

the lipophilic moiety is conjugated to the double-stranded iRNA agent via a linker containing an ether, thioether, urea, carbonate, amine, amide, maleimide-thioether, disulfide, phosphodiester, sulfonamide linkage, a product of a click reaction, or carbamate;

the lipophilic moiety is conjugated to a nucleobase, sugar moiety, or internucleosidic linkage;

the lipophilic moiety is conjugated via a bio-clevable linker selected from the group consisting of DNA, RNA, disulfide, amide, funtionalized monosaccharides or oligosaccharides of galactosamine, glucosamine, glucose, galactose, mannose, and combinations thereof;

the 3' end of the sense strand is protected via an end cap which is a cyclic group having an amine, said cyclic group being selected from the group consisting of pyrrolidinyl, pyrazolinyl, pyrazolidinyl, imidazolinyl, imidazolidinyl, piperidinyl, piperazinyl, [1,3] dioxolanyl, oxazolidinyl, isoxazolidinyl, morpholinyl, thiazolidinyl, isothiazolidinyl, quinoxalinyl, pyridazinonyl, tetrahydrofuranyl, and decalinyl; and/or the dsRNA agent further comprises a targeting ligand that targets a neuronal cell, optionally wherein the targeting ligand is a GalNAc conjugate.

9. The dsRNA agent of claim 1, wherein the hydrophobicity of the double-stranded RNA agent, measured by the unbound fraction in a plasma protein binding assay of the double-stranded RNA agent, exceeds 0.2, optionally wherein the plasma protein binding assay is an electrophoretic mobility shift assay using human serum albumin protein.

10. The dsRNA agent of claim 1, wherein the dsRNA agent comprises at least one modified nucleotide, optionally wherein:

(i) no more than five of the sense strand nucleotides and no more than five of the nucleotides of the antisense strand are unmodified nucleotides, or all of the nucleotides of the sense strand and all of the nucleotides of the antisense strand are modified nucleotides; and/or (ii) at least one of the modified nucleotides is selected from the group a deoxy-nucleotide, a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxly-modified nucleotide, a 2'-methoxyethyl modified nucleotide, a 2'-O-alkyl-modified nucleotide, a morpholino nucleotide, a phosphoramidate, a non-natural base comprising nucleotide, a tetrahydropyran modified nucleotide, a 1,5-anhydrohexitol modified nucleotide, a cyclohexenyl modified nucleotide, a nucleotide comprising a 5'-phosphorothioate group, a nucleotide comprising a 5'-methylphosphonate group, a nucleotide comprising a 5' phosphate or 5' phosphate mimic, a nucleotide comprising vinyl phosphonate, a nucleotide comprising adenosine-glycol nucleic acid (GNA), a nucleotide comprising thymidine-glycol nucleic acid (GNA) S-Isomer, a nucleotide comprising 2-hydroxymethyl-tetrahydrofurane-5-phosphate, a nucleotide comprising 2'-deoxythymidine-3'phosphate, a nucleotide comprising 2'-deoxyguanosine-3'-phosphate, and a terminal nucleotide linked to a cholesteryl derivative and a dodecanoic acid bisdecylamide group; and combinations thereof, optionally wherein:

(a) the modified nucleotide is selected from the group consisting of a 2'-deoxy-2'-fluoro modified nucleotide, a 2'-deoxy-modified nucleotide, 3'-terminal deoxy-thymine nucleotides (dT), a locked nucleotide, an abasic nucleotide, a 2'-amino-modified nucleotide, a 2'-alkyl-modified nucleotide, a morpholino nucleotide, a phosphoramidate, and a non-natural base comprising nucleotide;

(b) the modified nucleotide comprises a short sequence of 3'-terminal deoxy-thymine nucleotides (dT); and/or (c) the modifications on the nucleotides are 2'-O-methyl, GNA and 2'fluoro modifications.

11. The dsRNA agent of claim 1, further comprising at least one phosphorothioate internucleotide linkage, optionally wherein the dsRNA agent comprises 6-8 phosphorothioate internucleotide linkages.

12. The dsRNA agent of claim 1, wherein each strand is no more than 30 nucleotides in length, optionally wherein:

at least one strand comprises a 3' overhang of at least 1 nucleotide;

at least one strand comprises a 3' overhang of at least 2 nucleotides;

the double stranded region is 15-30, 17-23, 17-25, 23-27, 19-21, or 21-23 nucleotide pairs in length; and/or each strand has 19-30, 19-23, or 21-23 nucleotides.

13. The dsRNA agent of claim 1, further comprising:

(i) a terminal, chiral modification occurring at the first internucleotide linkage at the 3' end of the antisense strand, having the linkage phosphorus atom in Sp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp configuration or Sp configuration;

(ii) a terminal, chiral modification occurring at the first and second internucleotide linkages at the 3' end of the antisense strand, having the linkage phosphorus atom in Sp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration;

(iii) a terminal, chiral modification occurring at the first, second and third internucleotide linkages at the 3' end of the antisense strand, having the linkage phosphorus atom in Sp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration;

(iv) a terminal, chiral modification occurring at the first, and second internucleotide linkages at the 3' end of the antisense strand, having the linkage phosphorus atom in Sp configuration, a terminal, chiral modification occurring at the third internucleotide linkages at the 3' end of the antisense strand, having the linkage phosphorus atom in Rp configuration, a terminal, chiral modification occurring at the first internucleotide linkage at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration; or (v) a terminal, chiral modification occurring at the first, and second internucleotide linkages at the 3' end of the antisense strand, having the linkage phosphorus atom in Sp configuration, a terminal, chiral modification occurring at the first, and second internucleotide linkages at the 5' end of the antisense strand, having the linkage phosphorus atom in Rp configuration, and a terminal, chiral modification occurring at the first internucleotide linkage at the 5' end of the sense strand, having the linkage phosphorus atom in either Rp or Sp configuration.

14. The dsRNA agent of claim 1, wherein:

the dsRNA further comprises a phosphate or phosphate mimic at the 5'-end of the antisense strand, optionally wherein the phosphate mimic is a 5'-vinyl phosphonate (VP);

the base pair at the 1 position of the 5'-end of the antisense strand of the duplex is an AU base pair; and/or the sense strand has a total of 21 nucleotides and the antisense strand has a total of 23 nucleotides.

15. A pharmaceutical composition for inhibiting expression of a gene encoding ADRA2A, comprising the dsRNA agent of claim 1, optionally wherein:

the pharmaceutical composition further comprises a lipid formulation;

the dsRNA agent is in an unbuffered solution, optionally wherein the unbuffered solution is saline or water; and/or the dsRNA agent is in a buffer solution, optionally wherein the buffer solution comprises acetate, citrate, prolamine, carbonate, or phosphate or any combination thereof, or the buffer solution is phosphate buffered saline (PBS).

16. An isolated cell containing the dsRNA agent of claim 1.

17. A kit or a container comprising the dsRNA agent of claim 1 or a pharmaceutical composition comprising the dsRNA agent of claim 1, optionally wherein the container is a vial, a syringe, or an intrathecal pump.

18. A method of inhibiting expression of an ADRA2A gene in a cell, the method comprising contacting the cell with the dsRNA agent of claim 1, or a pharmaceutical composition comprising the dsRNA agent of claim 1, thereby inhibiting expression of the ADRA2A gene in the cell.

19. The method of claim 18, wherein:

(i) the cell is within a subject;

optionally wherein the subject is human;

optionally wherein the subject has an ADRA2A-associated disorder;

optionally wherein the ADRA2A-associated disorder is a neurodegenerative disorder, optionally wherein the neurodegenerative disorder is a tauopathy, Alzheimer's disease, or a primary tauopathy; and/or optionally wherein the primary tauopathy is selected from the group of disorders consisting of: frontotemporal dementia (FTD), frontotemporal dementia and parkinsonism linked to chromosome 17 (FTDP-17), frontotemporal lobar degeneration (FTLD), progressive supranuclear palsy (PSP), corticobasal degeneration (CBD), chronic traumatic encephalopathy (CTE), Pick's disease (PiD), globular glial tauopathies (GGTs), argyrophilic grain disease (AGD), and primary age-related tauopathy (PART);

(ii) contacting the cell with the dsRNA agent inhibits the expression of ADRA2A by at least 30%; and/or (iii) inhibiting expression of ADRA2A decreases ADRA2A protein level in serum of the subject by at least 30%.

20. A method of treating a subject having a disorder that would benefit from reduction in ADRA2A expression, or preventing at least one symptom in the subject, the method comprising administering to the subject a therapeutically effective amount of the dsRNA agent of claim 1, or a pharmaceutical composition comprising the dsRNA agent of claim 1, thereby treating the subject having the disorder that would benefit from reduction in ADRA2A expression, optionally wherein:

the disorder is an ADRA2A-associated disorder, optionally wherein the ADRA2A-associated disorder is selected from the group consisting of Alzheimer's disease, a primary tauopathy, frontotemporal dementia (FTD), frontotemporal dementia and parkinsonism linked to chromosome 17 (FTDP-17), frontotemporal lobar degeneration (FTLD), progressive supranuclear palsy (PSP), corticobasal degeneration (CBD), chronic traumatic encephalopathy (CTE), Pick's disease (PiD), globular glial tauopathies (GGTs), argyrophilic grain disease (AGD), and primary age-related tauopathy (PART);

the subject is human;

the administration of the agent to the subject causes a decrease in ADRA2A protein accumulation;

the dsRNA agent is administered to the subject at a dose of about 0.01 mg/kg to about 50 mg/kg;

the dsRNA agent is administered to the subject intrathecally;

the method further comprises determining the level of ADRA2A in a sample(s) from the subject, optionally wherein the level of ADRA2A in the subject sample(s) is an ADRA2A protein level in a blood, serum, or cerebrospinal fluid sample(s); and/or the method further comprises administering to the subject an additional therapeutic agent.

* * * * *

SEQUENCE LISTING

<160> NUMBER OF SEQ ID NOS: 688

<210> SEQ ID NO 1
<211> LENGTH: 3879
<212> TYPE: DNA
<213> ORGANISM: Homo sapiens

<400> SEQUENCE: 1
gagcagcagc agctccagct cggtgcagaa gcccagcagc cggcgtgccg ccgcccggcc 60
actccagcgc cttcttcccc gccttgcgct cctgccccaa ctcgcgctgt cgtcggaccc 120
cggcccatcc agcagcgctc ggcgcccacc aggcggacgc ccaggagaac ccctgcctcc 180
gtcgcggctc ctggagagct gatcgttcac ctgccccggc ccgcctgagg acgggggtgc 240
cttcatgcgg cccccacact cctcaccccg ccgccgccgc cgtcccggag ctccgcacag 300
tgtgccccag ccccagcagg gcgcacaact ttggaagtct cgcggcgctc cgagaggcgg 360
cagagtccgc gccccagccc cgggccgggc cgggccagaa ccgcagcgtc tgggggaagc 420
cagagagtcg gtaatcgctt cggggatgta aggcgacaga cataggaccc ccgagctcgc 480
atcagcaccc ttcggctgcc tcccggggtg ggggcgggcc ccgcacacgg taagacctct 540
tgctttcgct caggctcaag attcaagata cagatattga tatgtatata tatatttaat 600
ttcctgtcat ccttccaagt tatcaggcca ccgatgattt ttgttctccc ttcttgaaga 660
ataaatctct ctttacccat cggctctccc tactctctcc cgccgcttag aaataaaact 720
tggctgtatt aggagctcgg agcaagaagg cgcccaccga gagcgtctga agcgcgagcc 780
aggcgcagtt cgcgggaccc gggccatggg ccgctagcgg tcctccagtt cgggcccggc 840
ctccctgcgg ccccctccct atgtgagccg cagccaggcg agcggggcgc cggaggaaga 900

-continued

```
ggaggaccca cgggcgccgg gccggaaggc agctggcagc aggcccaggc cagcgggcgc    960
ccgcgttcat gttccgccag gagcagccgt tggccgaggg cagctttgcg cccatgggct   1020
ccctgcagcc ggacgcgggc aacgcgagct ggaacgggac cgaggcgccg gggggcggcg   1080
cccgggccac cccttactcc ctgcaggtga cgctgacgct ggtgtgcctg gccggcctgc   1140
tcatgctgct caccgtgttc ggcaacgtgc tcgtcatcat cgccgtgttc acgagccgcg   1200
cgctcaaggc gccccaaaac ctcttcctgg tgtctctggc ctcggccgac atcctggtgg   1260
ccacgctcgt catccctttc tcgctggcca acgaggtcat gggctactgg tacttcggca   1320
aggcttggtg cgagatctac ctggcgctcg acgtgctctt ctgcacgtcg tccatcgtgc   1380
acctgtgcgc catcagcctg gaccgctact ggtccatcac acaggccatc gagtacaacc   1440
tgaagcgcac gccgcgccgc atcaaggcca tcatcatcac cgtgtgggtc atctcggccg   1500
tcatctcctt cccgccgctc atctccatcg agaagaaggg cggcggcggc ggcccgcagc   1560
cggccgagcc gcgctgcgag atcaacgacc agaagtggta cgtcatctcg tcgtgcatcg   1620
gctccttctt cgctccctgc ctcatcatga tcctggtcta cgtgcgcatc taccagatcg   1680
ccaagcgtcg cacccgcgtg ccacccagcc gccggggtcc ggacgccgtc gccgcgccgc   1740
cgggggcac cgagcgcagg cccaacggtc tgggccccga gcgcagcgcg ggcccggggg    1800
gcgcagaggc cgaaccgctg cccacccagc tcaacggcgc ccctggcgag cccgcgccgg   1860
ccgggccgcg cgacaccgac gcgctggacc tggaggagag ctcgtcttcc gaccacgccg   1920
agcggcctcc agggccccgc agacccgagc gcggtccccg gggcaaaggc aaggcccgag   1980
cgagccaggt gaagccgggc gacagcctgc cgcggcgcgg gccgggggcg acggggatcg   2040
ggacgccggc tgcagggccg ggggaggagc gcgtcggggc tgccaaggcg tcgcgctggc   2100
gcgggcggca gaaccgcgag aagcgcttca cgttcgtgct ggccgtggtc atcggagtgt   2160
tcgtggtgtg ctggttcccc ttcttcttca cctacacgct cacggccgtc gggtgctccg   2220
tgccacgcac gctcttcaaa ttcttcttct ggttcggcta ctgcaacagc tcgttgaacc   2280
cggtcatcta caccatcttc aaccacgatt tccgccgcgc cttcaagaag atcctctgtc   2340
ggggggacag gaagcggatc gtgtgaggtt tccgctggcg cccgcgtaga ctcacgctga   2400
ctgcaggcag cggggggcat cgaggggtgc ttagccccag ggcactcaga aacccgggcg   2460
ctgcctgctc tgcgtttcct cgtctggggt ggctctgcag cctcctgcgg gcgggcgtct   2520
gctgctccta caagggaagc ttcttgctgc caggcccaca catccccagt tgttggtttg   2580
gccactcttg acctggagcc atcttcctag tgggccaccc ctaatcacta ttgcttccta   2640
aaggtatttt caccctcttc gcctggtaca gccctcacag ctcttcagag caagcactgg   2700
actacaaggg catggctcac aaaaggttaa tggatggggg ttacctagcc ctggctaatt   2760
ccccttccat tcccaactct ctctctcttt ttaaagaaaa atgctaaggg cagccctgcc   2820
tgccctcccc atcccccgct gtaaatatac actatttttg atagcacaca tggggccccc   2880
atatctcttg gccttggttt tgatgttgaa atcctggcct tgggagagat gccttccagg   2940
cagacacagc tgtctggttc aggccaagcc cctttgcaat gcaagccctt tctggtgtta   3000
tgaagtccct ctatgtcgtc gttttcacca gcaactggtg actgtccctt cgacacggac   3060
ctgctttgag atttcctgac agggaaaaga tttctgtcca tttttttcct gtgcctaaca   3120
gcataattgc cttttcctat gtaaatatta tgatggtgga tcaagacata agtaaatgag   3180
cctttctgcc tcacatcagc cctgtgtata aagccattat tctctgatgc actgtttgcc   3240
```

-continued

```
ccagtaactc actttaaaac ctctctttcc agtgttccct ctctccctcc agggccactg   3300

cttgaagaag aatatgtatg tttctatctt gtatgtctgt gtgcccctcc tgccccgaaa   3360

gtgctgacta tggggaaatc ttttagctgc tgtttttaga ctccaaggag tggaaattat   3420

gtggaagaag caaacctgat acaatttgcc caaggtaaac agtttgaaaa gacaaatggg   3480

cctgccaaac tgtacagttt cttccccaag agctgttagg tatcaaaatg ttgtcctttc   3540

ccccctccgt gcttttctgg ttgagatcat gtcattgatg aactgccaaa gtcaggggag   3600

gagggcagag actttgtgtt tacatctgca tttctacatg ttttagacag agacaattta   3660

aggcctgcac tcttatttca ctaaagaaaa actaatgtca gcacatgttg ctaatgacag   3720

tggatttttt tttaaataaa aaagtttaca gatcaaatgt gaaataaata tgaatggagt   3780

ggtcctcttg tctgttatct gagttttcaa aagctttaag actctgggaa catctgattt   3840

tatggatttt ttaaaaataa aaaatgtaca ttataaaaaa                         3879
```

```
<210> SEQ ID NO 2
<211> LENGTH: 3879
<212> TYPE: DNA
<213> ORGANISM: Homo sapiens

<400> SEQUENCE: 2
```

```
tttttataat gtacattttt tatttttaaa aaatccataa aatcagatgt tcccagagtc     60

ttaaagcttt tgaaaactca gataacagac aagaggacca ctccattcat atttatttca    120

catttgatct gtaaactttt ttatttaaaa aaaaatccac tgtcattagc aacatgtgct    180

gacattagtt tttctttagt gaaataagag tgcaggcctt aaattgtctc tgtctaaaac    240

atgtagaaat gcagatgtaa acacaaagtc tctgccctcc tcccctgact ttggcagttc    300

atcaatgaca tgatctcaac cagaaaagca cggagggggg aaaggacaac attttgatac    360

ctaacagctc ttggggaaga aactgtacag tttggcaggc ccatttgtct tttcaaactg    420

tttaccttgg gcaaattgta tcaggtttgc ttcttccaca taatttccac tccttggagt    480

ctaaaaacag cagctaaaag atttccccat agtcagcact ttcggggcag gaggggcaca    540

cagacataca agatagaaac atacatattc ttcttcaagc agtggccctg gagggagaga    600

gggaacactg gaaagagagg ttttaaagtg agttactggg gcaaacagtg catcagagaa    660

taatggcttt atacacaggg ctgatgtgag gcagaaaggc tcatttactt atgtcttgat    720

ccaccatcat aatatttaca taggaaaagg caattatgct gttaggcaca ggaaaaaaat    780

ggacagaaat cttttccctg tcaggaaatc tcaaagcagg tccgtgtcga agggacagtc    840

accagttgct ggtgaaaacg acgacataga gggacttcat aacaccagaa agggcttgca    900

ttgcaaaggg gcttggcctg aaccagacag ctgtgtctgc ctggaaggca tctctcccaa    960

ggccaggatt tcaacatcaa aaccaaggcc aagagatatg gggccccat gtgtgctatc    1020

aaaaatagtg tatatttaca gcgggggatg gggagggcag gcagggctgc ccttagcatt   1080

tttctttaaa aagagagaga gagttgggaa tggaaggggga attagccagg gctaggtaac   1140

ccccatccat taacctttg tgagccatgc ccttgtagtc cagtgcttgc tctgaagagc   1200

tgtgagggct gtaccaggcg aagagggtga aaataccttt aggaagcaat agtgattagg   1260

ggtggcccac taggaagatg gctccaggtc aagagtggcc aaaccaacaa ctggggatgt   1320

gtgggcctgg cagcaagaag cttcccttgt aggagcagca gacgcccgcc cgcaggaggc   1380

tgcagagcca ccccagacga ggaaacgcag agcaggcagc gcccgggttt ctgagtgccc   1440

tggggctaag caccccctcga tgcccccgc tgcctgcagt cagcgtgagt ctacgcgggc   1500
```

-continued

```
gccagcggaa acctcacacg atccgcttcc tgtcccccg acagaggatc ttcttgaagg   1560
cgcggcggaa atcgtggttg aagatggtgt agatgaccgg gttcaacgag ctgttgcagt   1620
agccgaacca gaagaagaat ttgaagagcg tgcgtggcac ggagcacccg acggccgtga   1680
gcgtgtaggt gaagaagaag gggaaccagc acaccacgaa cactccgatg accacggcca   1740
gcacgaacgt gaagcgcttc tcgcggttct gccgcccgcg ccagcgcgac gccttggcag   1800
ccccgacgcg ctcctccccc ggccctgcag ccggcgtccc gatccccgtc gcccccggcc   1860
cgcgccgcgg caggctgtcg cccggcttca cctggctcgc tcgggccttg cctttgcccc   1920
ggggaccgcg ctcgggtctg cggggccctg gaggccgctc ggcgtggtcg gaagacgagc   1980
tctcctccag gtccagcgcg tcggtgtcgc gcggcccggc cggcgcgggc tcgccagggg   2040
cgccgttgag ctgggtgggc agcggttcgg cctctgcgcc ccccgggccc gcgctgcgct   2100
cggggcccag accgttgggc ctgcgctcgg tgccccccgg cggcgcggcg acggcgtccg   2160
gaccccggcg gctgggtggc acgcgggtgc gacgcttggc gatctggtag atgcgcacgt   2220
agaccaggat catgatgagg cagggagcga agaaggagcc gatgcacgac gagatgacgt   2280
accacttctg gtcgttgatc tcgcagcgcg gctcggccgg ctgcgggccg ccgccgccgc   2340
ccttcttctc gatggagatg agcggcggga aggagatgac ggccgagatg acccacacgg   2400
tgatgatgat ggccttgatg cggcgcggcg tgcgcttcag gttgtactcg atggcctgtg   2460
tgatggacca gtagcggtcc aggctgatgg cgcacaggtg cacgatggac gacgtgcaga   2520
agagcacgtc gagcgccagg tagatctcgc accaagcctt gccgaagtac cagtagccca   2580
tgacctcgtt ggccagcgag aaagggatga cgagcgtggc caccaggatg tcggccgagg   2640
ccagagacac caggaagagg ttttggggcg ccttgagcgc gcggctcgtg aacacggcga   2700
tgatgacgag cacgttgccg aacacggtga gcagcatgag caggccggcc aggcacacca   2760
gcgtcagcgt cacctgcagg gagtaagggg tggcccgggc gccgcccccc ggcgcctcgg   2820
tcccgttcca gctcgcgttg cccgcgtccg gctgcaggga gcccatgggc gcaaagctgc   2880
cctcggccaa cggctgctcc tggcggaaca tgaacgcggg cgcccgctgg cctgggcctg   2940
ctgccagctg ccttccggcc cggcgcccgt gggtcctcct cttcctccgg cgccccgctc   3000
gcctggctgc ggctcacata gggagggggc cgcagggagg ccgggcccga actggaggac   3060
cgctagcggc ccatggcccg ggtcccgcga actgcgcctg gctcgcgctt cagacgctct   3120
cggtgggcgc cttcttgctc cgagctccta atacagccaa gttttatttc taagcggcgg   3180
gagagagtag ggagagccga tgggtaaaga gagatttatt cttcaagaag ggagaacaaa   3240
aatcatcggt ggcctgataa cttggaagga tgacaggaaa ttaaatatat atatacatat   3300
caatatctgt atcttgaatc ttgagcctga gcgaaagcaa gaggtcttac cgtgtgcggg   3360
gcccgccccc accccgggag gcagccgaag ggtgctgatg cgagctcggg ggtcctatgt   3420
ctgtcgcctt acatccccga agcgattacc gactctctgg cttcccccag acgctgcggt   3480
tctggcccgg cccggcccgg ggctggggcg cggactctgc cgcctctcgg agcgccgcga   3540
gacttccaaa gttgtgcgcc ctgctggggc tggggcacac tgtgcggagc tccgggacgg   3600
cggcggcggc ggggtgagga gtgtgggggc cgcatgaagg cacccccgtc ctcaggcggg   3660
ccggggcagg tgaacgatca gctctccagg agccgcgacg gaggcagggg ttctcctggg   3720
cgtccgcctg gtgggcgccg agcgctgctg gatgggccgg ggtccgacga cagcgcgagt   3780
```

tggggcagga gcgcaaggcg gggaagaagg cgctggagtg gccgggcggc ggcacgccgg 3840
ctgctgggct tctgcaccga gctggagctg ctgctgctc 3879

<210> SEQ ID NO 3
<211> LENGTH: 3942
<212> TYPE: DNA
<213> ORGANISM: Macaca mulatta

<400> SEQUENCE: 3
acgccggctt gatcctgggg ctataaaacg agtccaccgt gagcgcagcg gagcagtagc 60
agctgcggct ccgtgcagac gcccagcagc cggcgtgccg ccgcccggca gctccagcgc 120
cttcttcccc caaccttgcg ctccaagccc aactcgcgct gtcgtcggac cccggcccat 180
ccagtcgcgc tcggcgccca cctggcggac gcccaggaga caccctgcct tcgtcgcagc 240
tcctgcagag ctgatcgttc acctaccccg gcccgcctga ggacgggggt gccttcatgc 300
ggtgcccaca ctcctcaccc cgccgccgcc gccgcccccg agctccgcac agtgcgcccc 360
agcctcagca gggcgcacaa ctttggaagt ctcgcggcgc tccgagaggc ggcagggtcc 420
gcgccccagc cccgggccgg gcccggccag aagcgcagcg tctgggggaa gccagagagt 480
cggtaatcgc ttcggggata taaggagaca gacataggac cccaagctcg catcagcacc 540
cctcggctgc ctcccggggt gggggcgggc cccgcacacg gtaagacctc ttgctttcgc 600
tcaggctcaa gagtcaagat atagatatcg atatgtatat atatatttaa tttcctgtca 660
tccttccaag ttatcaggcc accgatgatt tttgttctcc cttcttgaag aataaatctc 720
tttacccatc ggctctccct actctctccc gccgcttaga aataaaactt ggctgtgtta 780
ggagctcgga gcgagaaggc gcccaccgag agcgtccgaa gcgcgagcca ggcgcagttc 840
gcgggacccg ggccatgggc cgctagcggt cccccagctc gggcccggcc tccctgcggc 900
cccctcccta tgtgagctgc agccaggcga gcggggcgcc ggaggaagag gaggacccac 960
gggcgccggg ccggaaggca gctggcagca ggcccaggcg agcgggcgcc cgcgttcatg 1020
ttccgccagg agcagccgct ggccgagggc agctttgcgc ccatgggctc cctgcagccg 1080
gacgcgggca atgcgagctg gaacgggacc gaggcgccgg ggggcggcgc ccgggccacc 1140
ccttactccc tgcaggtgac gctgacgctg gtgtgcctgg ccggcctgct catgctgctc 1200
accgtgttcg gcaacgtgct cgtcatcatc gcggtgttca cgagccgcgc gctcaaggcg 1260
ccccaaaacc tcttcctggt gtctctggcc tcggccgaca tcctggtggc cacgcttgtc 1320
atccctttct cgctggccaa cgaggtcatg ggctactggt actttggcaa ggcttggtgc 1380
gagatctacc tggcgctcga cgtgctcttc tgcacgtcgt ccatcgtgca cctgtgcgcc 1440
atcagcctgg accgctactg gtccatcaca caggccatcg agtacaatct gaagcgcacg 1500
ccgcgccgca tcaaggccat catcatcacc gtgtgggtca tctcggccgt catctccttc 1560
ccgccgctca tctccttcga gaagaagcgc ggccacggcg gcccgcagcc ggccgagccg 1620
cgctgcgaga tcaacgacca gaagtggtac gtcatctcgt cgtgcatcgg ctccttcttc 1680
gctccctgcc tcatcatgat cctggtctac gtgcgcatct accagatcgc caagcgtcgc 1740
acccgcgtgc cacctagccg ccggggtccg gacgccgccg ccgtgccgca ggggggcgcc 1800
gagcgcaggc ccaacggtct gggcccagag cgcggcgcgg gcccgggggg cgcggaggcc 1860
gagccgctgc ccacccagct caacggcgcc cctggcgagc ccgcgccggc cgggccgcgc 1920
gacgccgacg cgctggacct ggaggagagc tcgtcgtccg accacgccga gcggcctccc 1980

-continued

```
gggccccgca gacccgagcg cggcctccgg ggcaagggca aggcccgggc gagccagttg   2040
aagccggggg acagcctgcc acggcgcggg ctgggggaga ccgggatcgg gacggctgcg   2100
gcagggccgg gggtggagcg cgctggggcc gccaaggcgt cgcgctggcg cgggcggcag   2160
aaccgcgaga aacgcttcac gttcgtgctg gccgtggtca tcggagtgtt cgtggtgtgc   2220
tggttcccct tcttcttcac ctacacgctc acagccgtcg ggtgctcagt gccgcgcacg   2280
ctcttcaagt tcttcttctg gttcggctac tgcaacagct cgctgaaccc ggtcatctac   2340
accatcttca accacgactt ccgccgcgcc ttcaagaaga tcctctgccg cggggacagg   2400
aagcggatcg tgtgaggttt ccgccggcgc ccgcgtagac tcacgccgac tgcaggcagc   2460
aaggcaccaa ggagtgctca gccccagggc actcagaaac ccgggccctg tctgctctgc   2520
gtttcctcct ctggggtggc tctgcagcct cctgcgggcg ggcgtctgct gctcctacaa   2580
gggaagcgtt cttgctgcca gacccacgca tccccagttg ttggtttggc cactcttgac   2640
ctggagccat cttcccggtg ggccacccca atcagtattg cttcctgaag gtattttcac   2700
cttcttcccc tggtatagcc ctcacagctc ttcagagcaa gcactggact acaaggacat   2760
ggctcacaaa aggttaatgg atggttacct agaggattac ctagccctgg ctaattcccc   2820
ttccatcccc agctctctct ctctcttttt taaaacccac tcagggcagc cctgactgcc   2880
ctccccacca ccccctccac aatgtaaata tacactattt ttgatagtac acatggggac   2940
cccatatctc ttgaccttgg ttttgacggt gaaatcctgg ccttgggaga gatgccttct   3000
aggcagacac agctgtgtgg ttcaggccaa gccccatttg caatgcaagc cctttctggt   3060
gttatgatgt ccctctatgt cgtccttttc accagcaact ggtgactgtc cctttgacac   3120
ggacctgctt tgagatttcc tgacggggaa aagatttctg tccatttttt tttcctgtgc   3180
ctaacagcat aattgccttt tcctatgtaa atattatgat gatggatcaa gacataagta   3240
aatgaacctt tctgcctcac atcagccctg tgtataaagc cattattctc tgatgcactg   3300
ttcaccccag taactcactt taaaacctct ctttccagtg ttccctctct ccctgcaggg   3360
ccactgcttg aagaagaata tgtatgtttc tatcttgtat gtatgtgcgc ccctcctgcc   3420
cccaaagtgc tgactatggg aaaatctttt agctgctgtt tttagacacc aaggagtgga   3480
aattatgtgg aagaagcaaa cctgatacaa tttgcccaag gtaaacagtt tgaaaagaca   3540
aatgggcctg ccaaactgta cagttcctgc cccaagagct gttaggtatc aaagtgtggt   3600
cctttccccc ctccctgctt ttctggttga gatcatgtca ttgatgaact gccaaagtca   3660
ggggaggagg gcggagacct tgtgtttaca tctgcgtttc tacatgtttt agacagagac   3720
aatttaaggc ctgcactctt atttcactaa agaaaaacta atgtcagcac atgttgctaa   3780
tgacagtgga tttttttaa ataaaaaagt ttacagatca aatgtgaaat aaatatgaat   3840
gaagtggtcc tcttgtctgt tacctgagtt ttcaaaagct ttaaggctct gggaacatct   3900
gattttgtgg attttttaaa aataaaaaat gtacattata aa                      3942
```

<210> SEQ ID NO 4
<211> LENGTH: 3942
<212> TYPE: DNA
<213> ORGANISM: Macaca mulatta

<400> SEQUENCE: 4

```
tttataatgt acatttttta tttttaaaaa atccacaaaa tcagatgttc ccagagcctt     60
aaagcttttg aaaactcagg taacagacaa gaggaccact tcattcatat ttatttcaca    120
tttgatctgt aaactttttt atttaaaaaa aatccactgt cattagcaac atgtgctgac    180
```

-continued

```
attagttttt ctttagtgaa ataagagtgc aggccttaaa ttgtctctgt ctaaaacatg    240
tagaaacgca gatgtaaaca caaggtctcc gccctcctcc cctgactttg gcagttcatc    300
aatgacatga tctcaaccag aaaagcaggg aggggggaaa ggaccacact ttgataccta    360
acagctcttg gggcaggaac tgtacagttt ggcaggccca tttgtctttt caaactgttt    420
accttgggca aattgtatca ggtttgcttc ttccacataa tttccactcc ttggtgtcta    480
aaaacagcag ctaaaagatt ttcccatagt cagcactttg ggggcaggag gggcgcacat    540
acatacaaga tagaaacata catattcttc ttcaagcagt ggccctgcag ggagagaggg    600
aacactggaa agagaggttt taaagtgagt tactggggtg aacagtgcat cagagaataa    660
tggctttata cacagggctg atgtgaggca gaaaggttca tttacttatg tcttgatcca    720
tcatcataat atttacatag gaaaaggcaa ttatgctgtt aggcacagga aaaaaaaatg    780
gacagaaatc ttttccccgt caggaaatct caaagcaggt ccgtgtcaaa gggacagtca    840
ccagttgctg gtgaaaagga cgacatagag ggacatcata acaccagaaa gggcttgcat    900
tgcaaatggg gcttggcctg aaccacacag ctgtgtctgc ctagaaggca tctctcccaa    960
ggccaggatt tcaccgtcaa aaccaaggtc aagagatatg gggtccccat gtgtactatc   1020
aaaaatagtg tatatttaca ttgtggaggg ggtggtgggg agggcagtca gggctgccct   1080
gagtgggttt taaaaaagag agagagagag ctggggatgg aaggggaatt agccagggct   1140
aggtaatcct ctaggtaacc atccattaac cttttgtgag ccatgtcctt gtagtccagt   1200
gcttgctctg aagagctgtg agggctatac caggggaaga aggtgaaaat accttcagga   1260
agcaatactg attggggtgg cccaccggga agatggctcc aggtcaagag tggccaaacc   1320
aacaactggg gatgcgtggg tctggcagca agaacgcttc ccttgtagga gcagcagacg   1380
cccgcccgca ggaggctgca gagccacccc agaggaggaa acgcagagca gacagggccc   1440
gggtttctga gtgccctggg gctgagcact ccttggtgcc ttgctgcctg cagtcggcgt   1500
gagtctacgc gggcgccggc ggaaacctca cacgatccgc ttcctgtccc cgcggcagag   1560
gatcttcttg aaggcgcggc ggaagtcgtg gttgaagatg gtgtagatga ccgggttcag   1620
cgagctgttg cagtagccga accagaagaa gaacttgaag agcgtgcgcg gcactgagca   1680
cccgacggct gtgagcgtgt aggtgaagaa gaaggggaac cagcacacca cgaacactcc   1740
gatgaccacg gccagcacga acgtgaagcg tttctcgcgg ttctgccgcc cgcgccagcg   1800
cgacgccttg gcggccccag cgcgctccac ccccggccct gccgcagccg tcccgatccc   1860
ggtctccccc agcccgcgcc gtggcaggct gtcccccggc ttcaactggc tcgcccgggc   1920
cttgcccttg ccccggaggc cgcgctcggg tctgcggggc ccgggaggcc gctcggcgtg   1980
gtcggacgac gagctctcct ccaggtccag cgcgtcggcg tcgcgcggcc cggccggcgc   2040
gggctcgcca ggggcgccgt tgagctgggt gggcagcggc tcggcctccg cgcccccccgg   2100
gcccgcgccg cgctctgggc ccagaccgtt gggcctgcgc tcggcgcccc cctgcggcac   2160
ggcggcggcg tccggacccc ggcggctagg tggcacgcgg gtgcgacgct tggcgatctg   2220
gtagatgcgc acgtagacca ggatcatgat gaggcaggga gcgaagaagg agccgatgca   2280
cgacgagatg acgtaccact tctggtcgtt gatctcgcag cgcggctcgg ccggctgcgg   2340
gccgccgtgg ccgcgcttct tctcgaagga gatgagcggc gggaaggaga tgacggccga   2400
gatgacccac acggtgatga tgatggcctt gatgcggcgc ggcgtgcgct tcagattgta   2460
ctcgatggcc tgtgtgatgg accagtagcg gtccaggctg atggcgcaca ggtgcacgat   2520
```

ggacgacgtg cagaagagca cgtcgagcgc caggtagatc tcgcaccaag ccttgccaaa 2580
gtaccagtag cccatgacct cgttggccag cgagaaaggg atgacaagcg tggccaccag 2640
gatgtcggcc gaggccagag acaccaggaa gaggttttgg ggcgccttga gcgcgcggct 2700
cgtgaacacc gcgatgatga cgagcacgtt gccgaacacg gtgagcagca tgagcaggcc 2760
ggccaggcac accagcgtca gcgtcacctg cagggagtaa ggggtggccc gggcgccgcc 2820
ccccggcgcc tcggtcccgt tccagctcgc attgcccgcg tccggctgca gggagcccat 2880
gggcgcaaag ctgccctcgg ccagcggctg ctcctggcgg aacatgaacg cgggcgcccg 2940
ctcgcctggg cctgctgcca gctgccttcc ggcccggcgc ccgtgggtcc tcctcttcct 3000
ccggcgcccc gctcgcctgg ctgcagctca catagggagg gggccgcagg gaggccgggc 3060
ccgagctggg ggaccgctag cggcccatgg cccgggtccc gcgaactgcg cctggctcgc 3120
gcttcggacg ctctcggtgg gcgccttctc gctccgagct cctaacacag ccaagtttta 3180
tttctaagcg gcgggagaga gtagggagag ccgatgggta aagagattta ttcttcaaga 3240
agggagaaca aaaatcatcg gtggcctgat aacttggaag gatgacagga aattaaatat 3300
atatatacat atcgatatct atatcttgac tcttgagcct gagcgaaagc aagaggtctt 3360
accgtgtgcg gggcccgccc ccaccccggg aggcagccga ggggtgctga tgcgagcttg 3420
gggtcctatg tctgtctcct tatatccccg aagcgattac cgactctctg gcttccccca 3480
gacgctgcgc ttctggccgg gcccggcccg gggctggggc gcggaccctg ccgcctctcg 3540
gagcgccgcg agacttccaa agttgtgcgc cctgctgagg ctggggcgca ctgtgcggag 3600
ctcgggggcg gcggcggcgg cggggtgagg agtgtgggca ccgcatgaag gcacccccgt 3660
cctcaggcgg gccggggtag gtgaacgatc agctctgcag gagctgcgac gaaggcaggg 3720
tgtctcctgg gcgtccgcca ggtgggcgcc gagcgcgact ggatgggccg gggtccgacg 3780
acagcgcgag ttgggcttgg agcgcaaggt tgggggaaga aggcgctgga gctgccgggc 3840
ggcggcacgc cggctgctgg gcgtctgcac ggagccgcag ctgctactgc tccgctgcgc 3900
tcacggtgga ctcgttttat agccccagga tcaagccggc gt 3942

<210> SEQ ID NO 5
<211> LENGTH: 3724
<212> TYPE: DNA
<213> ORGANISM: Mus musculus

<400> SEQUENCE: 5
agcagcctcg gctcccgctt ccgtgcagac gcccagcagc cggcgcacac cgcccagcca 60
cccagcgcct ccagctccaa gtcctgcggt cctgcgaaaa ctcacgcggc cctccgaccc 120
ccgccgggtc tgtggcgctc agcgcccacc cagatcgcgg ctagcagcca cccttggctc 180
cgccgcggct cctggagagc cggtcgctca cctagcttgg ccctgaggac cgaggtggtg 240
gtggtggggg tgcggcttca tgcggccccc acacccttca ccccaccgcc gccgcccccg 300
agctctgtgt acagagtccc agccccagca gagcgcacaa ctttggaagt cccgtggggc 360
tcctagagga ggcagagtcc gcgccttcgc cggaggtccg gcccagccct cgccaccccg 420
cctggagggt agcgacggag ttggaaatct cttcgagggt ataagaagac agacctagga 480
ctccgagccc acaccaacac ccctccgctg cctcttgggg taagacttca tgctttcgct 540
cagcttaaga atcaaggtat agatgactag ctaaatgcat ttgtataaat ttctgacatc 600
tttccaaatc atcaggccac cgataatttc ttttctcttt tcttgaagaa taaaatctct 660
aaccaccagc tggccctact cgatcctgcc gcttagaaat aaaacttggc tgtgtttgag 720

-continued gagctgggag agagaaagca cccacccgga gcgtcggaag gacgaaccgg tgccagttcg 780
cgggctccag tccatggacc actagcggtc cccagcttgg gcccgagctc cctgcggccc 840
tcttccttat gtgaggcgcg gcgggacgaa ccccgcaccg gaggaagagg aggacccacg 900
gacgcggggc cggaaggcag ctggcagcag gcccacgaga accagcaccc gcgttcatgt 960
tccgccagga gcagccgctg gccgagggca gctttgcgcc catgggctca ctgcagccgg 1020
atgccggcaa cagcagctgg aacgggaccg aagcgcccgg aggcggcacc cgagccaccc 1080
cttactccct gcaggtgaca ctgacgctgg tttgcctggc tggcctgctc atgctgttca 1140
cagtatttgg caacgtgctg gttattatcg cggtgttcac cagtcgcgcg ctcaaagctc 1200
cccaaaacct cttcctggtg tccctggcct cagcggacat cctggtggcc acgctggtca 1260
ttccctttc tttggccaac gaggttatgg gttactggta ctttggtaag gtgtggtgtg 1320
agatctattt ggctctcgac gtgctctttt gcacgtcgtc catagtgcac ctgtgcgcca 1380
tcagccttga ccgctactgg tccatcacgc aggccatcga gtacaacctg aagcgcacgc 1440
cgcgtcgcat caaggccatc attgtcaccg tgtgggtcat ctcggctgtc atctccttcc 1500
cgccactcat ctccatagag aagaagggcg ctggcggcgg gcagcagccg gccgagccaa 1560
gctgcaagat caacgaccag aagtggtatg tcatctcctc gtccatcggt tccttcttcg 1620
cgccttgcct catcatgatc ctggtctacg tgcgtattta ccagatcgcc aagcgtcgca 1680
cccgcgtgcc tcccagccgc cggggtccgg acgcctgttc cgcgccgccg gggggcgccg 1740
atcgcaggcc caacgggctg ggcccggagc gcggcgcggg tcccacgggc gctgaggcgg 1800
agccgctgcc cacccagctt aacggtgccc cgggggagcc cgcgcccgcc gggccccgcg 1860
atggggatgc gctggaccta gaggagagtt cgtcgtccga gcacgccgag cggcccccgg 1920
ggccccgcag acccgaccgc ggcccccgag ccaagggcaa gacccgggcg agtcaggtga 1980
agccggggga cagtctgccg cggcgcgggc ccggggccgc ggggccgggg gcttcggggt 2040
ccgggcacgg agaggagcgc ggcgggggcg ccaaagcgtc gcgctggcgc gggaggcaaa 2100
accgggagaa acgcttcacg ttcgtgctgg cggtggtgat cggcgtgttc gtggtgtgtt 2160
ggtttccgtt ctttttcacc tacacgctca tagcggtcgg ctgcccggtg cccagccagc 2220
tcttcaactt cttcttctgg ttcggctact gcaacagctc gctgaaccct gttatctaca 2280
ccatcttcaa ccacgacttc cgacgcgcct tcaagaagat cctctgccgt ggggacagaa 2340
aacgcatcgt gtgagcgcat gggccttgcc ctgcgtgcag acaatggtca gacgcaggcc 2400
ctgggcttcg agggggtgcg tctacgcatg cagcccctag cactctgaaa ccccggacct 2460
acccagctgg gagggagctc cgtggccttt gagacctttt gttacaatgt gtaaagttct 2520
ggctgagagg gacacatgag ccctttgct ggttgttgtg gttgttccca gcccacagcc 2580
agtttcctgg tgggctaccc ctgatcagta tggtttcctg atgatattgt catatcccca 2640
agtctgactc tcccaagctc ttcagagcaa gcacagtact agagagggca tggctgccaa 2700
agggttaatg aaccaaggtt tcctctagtc ctggctaatt atctcctcca cacccccttc 2760
cttaaataaa taaataaaga tcattcaggg cggtcctgcc tgccctccct tctccccact 2820
gtaaatatac attatttttg atagcatact ttgggttctt cagtgtcggc cttgatgcat 2880
attggaatca tggctgtgga gatgccctcc agtcagacag tgggctatct ggtccagacc 2940
acgctccttt gcaatgcaag cccctttcta gtgttaagtt gctctcagtg cttttcagca 3000
gtaactggtg actgtcccct ggacacggac ctgctttgac atttcctgac agggaaggga 3060
tttctgctca ttttccccctg tgcctaactg cataattgcc ttttcctatg taaatattac 3120
agcgatggac caaggcagaa ggaaatgaag cctctgcctt gcatcagccc cgtgtataaa 3180
gccattatct gctgaggcac cgcttgcccc agtaactcac tttagaactg acttttcttc 3240
cgttctcccc tcctctgggg cttgaagaag agcgtgtatg tttctatctt gtctgtgcgc 3300
cgccccctcc cccagaaagt gctgactaag gggaatcttt tagctgctgt ttttagacac 3360
ccaggagggg aaattatgtg gaagaaacca acccgataca atttgccaag gtaaacagtg 3420
tgaggagaca aatgggctgc cacactgtat ggagccagcc ccaagagctc ttgggtatca 3480
aagtgttacc tccccttgct gtcctggctg agatcatgtg actactgaat tgccaaagtc 3540
agggggtagg cggagacttc gtgtttacaa cctggtttct acttatttta ggcagactgt 3600
ggaaggcctg tgatctgatt tcacgagaga aaaactaaat gtcagcactt gttgctcgtg 3660
acggtggatt ttttttaaat aaaagtttac agatcaaatg tgaaataaac atgaattaag 3720
tggg 3724

<210> SEQ ID NO 6
<211> LENGTH: 3724
<212> TYPE: DNA
<213> ORGANISM: Mus musculus

<400> SEQUENCE: 6
cccacttaat tcatgtttat ttcacatttg atctgtaaac ttttatttaa aaaaaatcca 60
ccgtcacgag caacaagtgc tgacatttag tttttctctc gtgaaatcag atcacaggcc 120
ttccacagtc tgcctaaaat aagtagaaac caggttgtaa acacgaagtc tccgcctacc 180
ccctgacttt ggcaattcag tagtcacatg atctcagcca ggacagcaag gggaggtaac 240
actttgatac ccaagagctc ttggggctgg ctccatacag tgtggcagcc catttgtctc 300
ctcacactgt ttaccttggc aaattgtatc gggttggttt cttccacata atttcccctc 360
ctgggtgtct aaaaacagca gctaaaagat tccccttagt cagcactttc tgggggaggg 420
ggcggcgcac agacaagata gaaacataca cgctcttctt caagccccag aggaggggag 480
aacggaagaa aagtcagttc taaagtgagt tactggggca agcggtgcct cagcagataa 540
tggctttata cacggggctg atgcaaggca gaggcttcat ttccttctgc cttggtccat 600
cgctgtaata tttacatagg aaaaggcaat tatgcagtta ggcacagggg aaaatgagca 660
gaaatccctt ccctgtcagg aaatgtcaaa gcaggtccgt gtccagggga cagtcaccag 720
ttactgctga aaagcactga gagcaactta acactagaaa ggggcttgca ttgcaaagga 780
gcgtggtctg gaccagatag cccactgtct gactggaggg catctccaca gccatgattc 840
caatatgcat caaggccgac actgaagaac ccaaagtatg ctatcaaaaa taatgtatat 900
ttacagtggg gagaagggag ggcaggcagg accgccctga atgatcttta tttatttatt 960
taaggaaggg ggtgtggagg agataattag ccaggactag aggaaacctt ggttcattaa 1020
ccctttggca gccatgccct ctctagtact gtgcttgctc tgaagagctt gggagagtca 1080
gacttgggga tatgacaata tcatcaggaa accatactga tcaggggtag cccaccagga 1140
aactggctgt gggctgggaa caaccacaac aaccagcaaa agggctcatg tgtccctctc 1200
agccagaact ttacacattg taacaaaagg tctcaaaggc cacggagctc cctcccagct 1260
gggtaggtcc ggggtttcag agtgctaggg gctgcatgcg tagacgcacc ccctcgaagc 1320
ccagggcctg cgtctgacca ttgtctgcac gcagggcaag gcccatgcgc tcacacgatg 1380
cgttttctgt ccccacggca gaggatcttc ttgaaggcgc gtcggaagtc gtggttgaag 1440

-continued

```
atggtgtaga taacagggtt cagcgagctg ttgcagtagc cgaaccagaa gaagaagttg   1500
aagagctggc tgggcaccgg gcagccgacc gctatgagcg tgtaggtgaa aaagaacgga   1560
aaccaacaca ccacgaacac gccgatcacc accgccagca cgaacgtgaa gcgtttctcc   1620
cggttttgcc tcccgcgcca gcgcgacgct ttggcgcccc cgccgcgctc ctctccgtgc   1680
ccggaccccg aagcccccgg ccccgcggcc ccgggcccgc gccgcggcag actgtccccc   1740
ggcttcacct gactcgcccg ggtcttgccc ttggctcggg ggccgcggtc gggtctgcgg   1800
ggccccgggg gccgctcggc gtgctcggac gacgaactct cctctaggtc cagcgcatcc   1860
ccatcgcggg gcccggcggg cgcgggctcc cccggggcac cgttaagctg ggtgggcagc   1920
ggctccgcct cagcgcccgt gggacccgcg ccgcgctccg ggcccagccc gttgggcctg   1980
cgatcggcgc cccccggcgg cgcggaacag gcgtccggac cccggcggct gggaggcacg   2040
cgggtgcgac gcttggcgat ctggtaaata cgcacgtaga ccaggatcat gatgaggcaa   2100
ggcgcgaaga aggaaccgat ggacgaggag atgacatacc acttctggtc gttgatcttg   2160
cagcttggct cggccggctg ctgcccgccg ccagcgccct tcttctctat ggagatgagt   2220
ggcgggaagg agatgacagc cgagatgacc cacacggtga caatgatggc cttgatgcga   2280
cgcggcgtgc gcttcaggtt gtactcgatg gcctgcgtga tggaccagta gcggtcaagg   2340
ctgatggcgc acaggtgcac tatggacgac gtgcaaaaga gcacgtcgag agccaaatag   2400
atctcacacc acaccttacc aaagtaccag taacccataa cctcgttggc caaagaaaag   2460
ggaatgacca gcgtggccac caggatgtcc gctgaggcca gggacaccag gaagaggttt   2520
tggggagctt tgagcgcgcg actggtgaac accgcgataa taaccagcac gttgccaaat   2580
actgtgaaca gcatgagcag gccagccagg caaaccagcg tcagtgtcac ctgcagggag   2640
taaggggtgg ctcgggtgcc gcctccgggc gcttcggtcc cgttccagct gctgttgccg   2700
gcatccggct gcagtgagcc catgggcgca aagctgccct cggccagcgg ctgctcctgg   2760
cggaacatga acgcgggtgc tggttctcgt gggcctgctg ccagctgcct tccggccccg   2820
cgtccgtggg tcctcctctt cctccggtgc ggggttcgtc ccgccgcgcc tcacataagg   2880
aagagggccg cagggagctc gggcccaagc tggggaccgc tagtggtcca tggactggag   2940
cccgcgaact ggcaccggtt cgtccttccg acgctccggg tgggtgcttt ctctctccca   3000
gctcctcaaa cacagccaag ttttatttct aagcggcagg atcgagtagg gccagctggt   3060
ggttagagat tttattcttc aagaaaagag aaaagaaatt atcggtggcc tgatgatttg   3120
gaaagatgtc agaaatttat acaaatgcat ttagctagtc atctatacct tgattcttaa   3180
gctgagcgaa agcatgaagt cttaccccaa gaggcagcgg aggggtgttg gtgtgggctc   3240
ggagtcctag gtctgtcttc ttataccctc gaagagattt ccaactccgt cgctaccctc   3300
caggcggggt ggcgagggct gggccggacc tccggcgaag gcgcggactc tgcctcctct   3360
aggagcccca cgggacttcc aaagttgtgc gctctgctgg ggctgggact ctgtacacag   3420
agctcggggg cggcggcggt ggggtgaagg gtgtgggggc cgcatgaagc cgcaccccca   3480
ccaccaccac ctcggtcctc agggccaagc taggtgagcg accggctctc caggagccgc   3540
ggcggagcca agggtggctg ctagccgcga tctgggtggg cgctgagcgc cacagacccg   3600
gcgggggtcg gagggccgcg tgagttttcg caggaccgca ggacttggag ctggaggcgc   3660
tgggtggctg ggcggtgtgc gccggctgct gggcgtctgc acggaagcgg gagccgaggc   3720
tgct                                                                 3724
```

<210> SEQ ID NO 7
<211> LENGTH: 2814
<212> TYPE: DNA
<213> ORGANISM: Rattus norvegicus

<400> SEQUENCE: 7
atgttccgcc aggagcagcc gctggccgag ggcagctttg cgcccatggg ctccctgcag 60
ccggatgccg gcaatagcag ctggaacggc accgaggcgc ccggaggcgg cacccgggcc 120 acccccttact ccctgcaggt gacgctgacg ctggtgtgcc tggctggcct gctcatgctg 180
ttcaccgtgt ttggcaacgt gctggttatt atcgcagtgt tcaccagccg cgcgctcaaa 240
gcgccccaga acctcttcct ggtgtctctg gcctcagcgg acatcctggt ggccacgctg 300
gtcattccct tttctttggc caacgaggtt atgggctact ggtactttgg taaggtgtgg 360
tgcgagatct acttggccct cgacgtgctc ttttgcacgt cgtccatagt gcacctgtgc 420
gccatcagcc ttgaccgcta ctggtccatc acgcaggcca tcgagtacaa cctgaagcgc 480
acgccgcggc gcatcaaggc catcattgtc actgtgtggg tcatctcggc cgtcatctcc 540
ttcccgccac tcatctccat agagaagaag ggcgctggcg gcgggcagca gccggccgag 600
ccgagctgca agattaacga ccagaagtgg tatgtcatct cgtcgtccat cggctccttc 660
ttcgcgcctt gcctcatcat gatcctggtc tacgtgcgta tctaccagat cgccaagcgt 720
cgcacccgcg tgccgcccag tcgccggggt ccggacgcct gttccgcgcc gccgggggc 780 gccgatcgca ggcccaacgg gctgggcccg gagcgcggcg ctggtaccgc gggcgcggag 840
gccgagccgc tgcccaccca gcttaacggc gccccggggg agcccgcgcc cacccggccg 900
cgcgacgggg atgcgctgga cctagaggag agttcgtcgt ccgagcacgc cgagcggccc 960
caggggcccg gcaaacccga gcgcggtccc cgggccaagg gcaagaccaa ggcgagccag 1020
gtgaaaccgg gggacagtct gccgcggcgc gggcccgggg ctgcggggcc gggggcttcg 1080
gggtccgggc agggagagga gcgtgccggg ggcgccaaag cgtcgcgctg gcgcgggagg 1140
cagaaccgcg agaaacgctt cacgttcgtg ctggcggtgg tgatcggcgt gttcgtggtg 1200
tgttggttcc cgttcttttt cacctacacg ctcatagcgg tcggctgccc ggtgccctac 1260
cagctcttca acttcttctt ctggttcggc tactgcaaca gctcgctgaa ccctgttatc 1320
tacaccattt tcaaccacga cttccgccgc gccttcaaga agatcctctg ccgtggggac 1380
agaaagcgca tcgtgtgagc gctcgggctg tgccctgctt acagaccctg gtcagatgca 1440
ggccctgggc ttcgaggggg cgcgtctacg catgcagccc ctagcactct gaaaccctgg 1500
accttcctgc tctgtgtaat acccagtttg gaggggactt ggtggctttt gagacctttt 1560
gttaccatgt gtaaagttct ggctgagagg gacatatgcg ccttttttgct ggttgttgtg 1620 gttgttccca gcccacagcc agtttcctgg tgggctaccc ccgatcagta ttgtttcctg 1680
acgatattgc catcttctcc ccgagtctga ctctcccaag ctcttcagag caagcacagt 1740
actagagagg gcatgactgc caaagggtta atgaaccaag gtttcctagc cctggctaat 1800
tgtcacttcc ctccttcccc ccctttaaaa atatcattca gggcagccct gcctgccctc 1860
cgtaccctcc actgtaaata tacattattt ttgatagcac actttgtgtt cctcagaatt 1920
ggccttgtcg cgatattgga atcccggctg tggggatgcc ctccagtcac agacagtggg 1980
ctatctggtc cagaccaacg tcctttgcaa tgcaagtccc tttctagtgt tattacatcg 2040
tcgctctcag tacttttcag cagtaactgg taactgtccc ctggacacgg acctgctttg 2100
acatttcctg agagggaagg gatttctgtt cattttcccc ctgtgcctaa cagcataatt 2160

-continued

```
gccttttcct atgtaaatat tacagcgatg gaccaagaca gaaggaaatg aaccttctgc   2220
ctggccccag ccctgtgtat aaagccatta ttcgctgagg caccacttgc cccagtaact   2280
cactttagaa ctgacgctgc ggttctcctc tcctctgggg ccaaggcttg aagaagaacg   2340
ggtgggtgtg cttgtttctg tcttgtgtgt gtgccgcccc tcatccagaa agtgctgagt   2400
aaggggaatc ttttagcagc tgtttttaga cacacaggag gggaaattat gtggaagaaa   2460
cctacccgat acaatttgcc aaggtaaaca gtgtgaggag acaaacagtc cgccacactg   2520
ttcagcgcca gccccaagag ctcttgggta tcaaagtgtt acctcccctt gcttttctgg   2580
ctgagatcac gtcaccagtg aattgccaaa gtcagggagt aggcggagaa ttggtgttta   2640
caacctggtt tctacttagt ttaggcggac tgtggaaggc ctgcgatctg tttttcctga   2700
gagaaaaacc taaatgtcag cacttgttgc tcatgatggt ggattttttt ttaaaataaa   2760
agtttacaga tcaaatgtga aataaacatg aattaagtga taaaaaaaaa aaaa         2814
```

<210> SEQ ID NO 8
<211> LENGTH: 2814
<212> TYPE: DNA
<213> ORGANISM: Rattus norvegicus

<400> SEQUENCE: 8

```
ttttttttt tttatcactt aattcatgtt tatttcacat ttgatctgta aacttttatt     60
ttaaaaaaaa atccaccatc atgagcaaca agtgctgaca tttaggtttt tctctcagga    120
aaaacagatc gcaggccttc cacagtccgc ctaaactaag tagaaaccag gttgtaaaca    180
ccaattctcc gcctactccc tgactttggc aattcactgg tgacgtgatc tcagccagaa    240
aagcaagggg aggtaacact ttgataccca agagctcttg gggctggcgc tgaacagtgt    300
ggcggactgt ttgtctcctc acactgttta ccttggcaaa ttgtatcggg taggtttctt    360
ccacataatt tcccctcctg tgtgtctaaa aacagctgct aaaagattcc ccttactcag    420
cactttctgg atgaggggcg gcacacacac aagacagaaa caagcacacc cacccgttct    480
tcttcaagcc ttggccccag aggagaggag aaccgcagcg tcagttctaa agtgagttac    540
tggggcaagt ggtgcctcag cgaataatgg ctttatacac agggctgggg ccaggcagaa    600
ggttcatttc cttctgtctt ggtccatcgc tgtaatattt acataggaaa aggcaattat    660
gctgttaggc acagggggaa aatgaacaga aatcccttcc ctctcaggaa atgtcaaagc    720
aggtccgtgt ccaggggaca gttaccagtt actgctgaaa agtactgaga gcgacgatgt    780
aataacacta gaaagggact tgcattgcaa aggacgttgg tctggaccag atagcccact    840
gtctgtgact ggagggcatc cccacagccg ggattccaat atcgcgacaa ggccaattct    900
gaggaacaca aagtgtgcta tcaaaaaataa tgtatattta cagtggaggg tacggagggc   960
aggcagggct gccctgaatg atatttttaa agggggggaa ggagggaagt gacaattagc   1020
cagggctagg aaaccttggt tcattaaccc tttggcagtc atgccctctc tagtactgtg   1080
cttgctctga agagcttggg agagtcagac tcggggagaa gatggcaata tcgtcaggaa   1140
acaatactga tcgggggtag cccaccagga aactggctgt gggctgggaa caaccacaac   1200
aaccagcaaa aaggcgcata tgtccctctc agccagaact ttacacatgg taacaaaagg   1260
tctcaaaagc caccaagtcc cctccaaact gggtattaca cagagcagga aggtccaggg   1320
tttcagagtg ctaggggctg catgcgtaga cgcgcccccct cgaagcccag ggcctgcatc  1380
tgaccagggt ctgtaagcag ggcacagccc gagcgctcac acgatgcgct ttctgtcccc   1440
```

```
acggcagagg atcttcttga aggcgcggcg gaagtcgtgg ttgaaaatgg tgtagataac   1500

agggttcagc gagctgttgc agtagccgaa ccagaagaag aagttgaaga gctggtaggg   1560

caccgggcag ccgaccgcta tgagcgtgta ggtgaaaaag aacgggaacc aacacaccac   1620

gaacacgccg atcaccaccg ccagcacgaa cgtgaagcgt ttctcgcggt tctgcctccc   1680

gcgccagcgc gacgctttgg cgccccggc acgctcctct ccctgcccgg accccgaagc   1740

ccccggcccc gcagccccgg gcccgcgccg cggcagactg tcccccggtt tcacctggct   1800

cgccttggtc ttgcccttgg cccggggacc gcgctcgggt ttgccgggcc cctggggccg   1860

ctcggcgtgc tcggacgacg aactctcctc taggtccagc gcatccccgt cgcgcggccg   1920

ggtgggcgcg ggctcccccg gggcgccgtt aagctgggtg ggcagcggct cggcctccgc   1980

gcccgcggta ccagcgccgc gctccgggcc cagcccgttg ggcctgcgat cggcgccccc   2040

cggcggcgcg gaacaggcgt ccggaccccg gcgactgggc ggcacgcggg tgcgacgctt   2100

ggcgatctgg tagatacgca cgtagaccag gatcatgatg aggcaaggcg cgaagaagga   2160

gccgatggac gacgagatga cataccactt ctggtcgtta atcttgcagc tcggctcggc   2220

cggctgctgc ccgccgccag cgcccttctt ctctatggag atgagtggcg ggaaggagat   2280

gacggccgag atgacccaca cagtgacaat gatggccttg atgcgccgcg gcgtgcgctt   2340

caggttgtac tcgatggcct gcgtgatgga ccagtagcgg tcaaggctga tggcgcacag   2400

gtgcactatg gacgacgtgc aaaagagcac gtcgagggcc aagtagatct cgcaccacac   2460

cttaccaaag taccagtagc ccataacctc gttggccaaa gaaaagggaa tgaccagcgt   2520

ggccaccagg atgtccgctg aggccagaga caccaggaag aggttctggg gcgctttgag   2580

cgcgcggctg gtgaacactg cgataataac cagcacgttg ccaaacacgg tgaacagcat   2640

gagcaggcca gccaggcaca ccagcgtcag cgtcacctgc agggagtaag gggtggcccg   2700

ggtgccgcct ccgggcgcct cggtgccgtt ccagctgcta ttgccggcat ccggctgcag   2760

ggagcccatg ggcgcaaagc tgccctcggc cagcggctgc tcctggcgga acat         2814
```

<210> SEQ ID NO 9
<211> LENGTH: 16
<212> TYPE: PRT
<213> ORGANISM: Unknown
<220> FEATURE:
<223> OTHER INFORMATION: Description of Unknown:
RFGF peptide

<400> SEQUENCE: 9

```
Ala Ala Val Ala Leu Leu Pro Ala Val Leu Leu Ala Leu Leu Ala Pro
1               5                   10                  15
```

<210> SEQ ID NO 10
<211> LENGTH: 11
<212> TYPE: PRT
<213> ORGANISM: Unknown
<220> FEATURE:
<223> OTHER INFORMATION: Description of Unknown:
RFGF analogue peptide

<400> SEQUENCE: 10

```
Ala Ala Leu Leu Pro Val Leu Leu Ala Ala Pro
1               5                   10
```

<210> SEQ ID NO 11
<211> LENGTH: 13
<212> TYPE: PRT
<213> ORGANISM: Human immunodeficiency virus

<400> SEQUENCE: 11

Gly Arg Lys Lys Arg Arg Gln Arg Arg Arg Pro Pro Gln
1 5 10

<210> SEQ ID NO 12
<211> LENGTH: 16
<212> TYPE: PRT
<213> ORGANISM: Drosophila sp.

<400> SEQUENCE: 12

Arg Gln Ile Lys Ile Trp Phe Gln Asn Arg Arg Met Lys Trp Lys Lys
1 5 10 15

<210> SEQ ID NO 13

<400> SEQUENCE: 13

000

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 14
ggagagcuga ucguucaccu g 21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 15
gcacaacuuu ggaagucucg c 21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 16
agagagucgg uaaucgcuuc g 21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 17
ucggggaugu aaggcgacag a 21

<210> SEQ ID NO 18
<211> LENGTH: 21

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 18
cgguaagacc ucuugcuuuc g 21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 19
uugcuuucgc ucaggcucaa g 21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 20
cucaagauuc aagauacaga u 21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 21
auuuaauuuc cugucauccu u 21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 22
ucauccuucc aaguuaucag g 21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 23
uaucaggcca ccgaugauuu u 21

<210> SEQ ID NO 24
<211> LENGTH: 21
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 24
uuguucuccc uucuugaaga a 21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
aagaauaaau cucucuuuac c 21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aucggcucuc ccuacucucu c 21

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
gccgcuuaga aauaaaacuu g 21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
aaacuuggcu guauuaggag c 21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
uuaggagcuc ggagcaagaa g 21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
guucauguuc cgccaggagc a 21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ccccuuacuc ccugcaggug a 21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
gcucaccgug uucggcaacg u 21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gugcucguca ucaucgccgu g 21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ccccaaaacc ucuuccuggu g 21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
uuccuggugu cucuggccuc g 21

<210> SEQ ID NO 36
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 36
cucgucaucc cuuucucgcu g 21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 37
gccaacgagg ucaugggcua c 21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 38
cuacugguac uucggcaagg c 21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 39
uuggugcgag aucuaccugg c 21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 40
ccuggcgcuc gacgugcucu u 21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 41
cgugcucuuc ugcacgucgu c 21

<210> SEQ ID NO 42
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 42
gucguccauc gugcaccugu g 21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 43
cgcuacuggu ccaucacaca g 21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 44
aucacacagg ccaucgagua c 21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 45
aucgaguaca accugaagcg c 21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 46
caucaaggcc aucaucauca c 21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 47
caccgugugg gucaucucgg c 21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 48
cucggccguc aucuccuucc c 21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 49
cuccuucccg ccgcucaucu c 21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 50
gcucaucucc aucgagaaga a 21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 51
ugcgagauca acgaccagaa g 21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 52
ccagaagugg uacgucaucu c 21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 53
cgucaucucg ucgugcaucg g 21

<210> SEQ ID NO 54
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 54

cggcuccuuc uucgcucccu g                                             21


<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55

cucaucauga uccuggucua c                                             21


<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56

cuggucuacg ugcgcaucua c                                             21


<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57

cgcaucuacc agaucgccaa g                                             21


<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58

gagagcucgu cuuccgacca c                                             21


<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59

cgagaagcgc uucacguucg u                                             21


<210> SEQ ID NO 60
<211> LENGTH: 21
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 60
cacguucgug cuggccgugg u                                                21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
guggucaucg gaguguucgu g                                                21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
guggugugcu gguuccccuu c                                                21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ccccuucuuc uucaccuaca c                                                21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
caccuacacg cucacggccg u                                                21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
ccacgcacgc ucuucaaauu c                                                21

<210> SEQ ID NO 66
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 66
uucaaauucu ucuucugguu c                                                 21

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
cuacugcaac agcucguuga a                                                 21

<210> SEQ ID NO 68
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ccggucaucu acaccaucuu c                                                 21

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
accaucuuca accacgauuu c                                                 21

<210> SEQ ID NO 70
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
cgauuuccgc cgcgccuuca a                                                 21

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
cgccuucaag aagauccucu g                                                 21

<210> SEQ ID NO 72
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 72
gaucguguga gguuuccgcu g 21

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
cguagacuca cgcugacugc a 21

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uagccccagg gcacucagaa a 21

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ugcucugcgu uuccucgucu g 21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
cuccuacaag ggaagcuucu u 21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
agcuucuugc ugccaggccc a 21

<210> SEQ ID NO 78
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 78
ccccaguugu ugguuuggcc a 21

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
ggccacucuu gaccuggagc c 21

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
ggagccaucu uccuaguggg c 21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gugggccacc ccuaaucacu a 21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
uaaucacuau ugcuuccuaa a 21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
uuccuaaagg uauuuucacc c 21

<210> SEQ ID NO 84
<211> LENGTH: 21
<212> TYPE: RNA
<213> ORGANISM: Artificial Sequence
<220> FEATURE:

-continued

<223> OTHER INFORMATION: Description of Artificial Sequence: Synthetic
      oligonucleotide

<400> SEQUENCE: 84
ucacccucuu cgccugguac a 21

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
uacagcccuc acagcucuuc a 21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
agcucuucag agcaagcacu g 21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
gcacuggacu acaagggcau g 21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ucacaaaagg uuaauggaug g 21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ccuggcuaau uccccuucca u 21

<210> SEQ ID NO 90
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 90
ucccaacucu cucucucuuu u 21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
cgcuguaaau auacacuauu u 21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
auaucucuug gccuugguuu u 21

<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
cuugguuuug auguugaaau c 21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
cuugggagag augccuucca g 21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
ccaggcagac acagcugucu g 21

<210> SEQ ID NO 96
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 96
agcugucugg uucaggccaa g                                            21

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ccuuugcaau gcaagcccuu u                                            21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
cuuucuggug uuaugaaguc c                                            21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
cuaugucguc guuuucacca g                                            21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
caccagcaac uggugacugu c                                            21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
ugucccuucg acacggaccu g                                            21

<210> SEQ ID NO 102
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 102
ccugcuuuga gauuuccuga c                                              21

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
uuuccugaca gggaaaagau u                                              21

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
gaaaagauuu cuguccauuu u                                              21

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
aacagcauaa uugccuuuuc c                                              21

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
uuuuccuaug uaaauauuau g                                              21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
auuaugaugg uggaucaaga c                                              21

<210> SEQ ID NO 108
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 108
cauaaguaaa ugagccuuuc u 21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
gccuuucugc cucacaucag c 21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
agcccugugu auaaagccau u 21

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
aaagccauua uucucugaug c 21

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
cucugaugca cuguuugccc c 21

<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
ugccccagua acucacuuua a 21

<210> SEQ ID NO 114
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 114
ucacuuuaaa accucucuuu c 21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 115
ucucuuucca guguucccuc u 21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 116
ccuccagggc cacugcuuga a 21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 117
cugcuugaag aagaauaugu a 21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 118
guauguuucu aucuuguaug u 21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 119
uuguaugucu gugugccccu c 21

<210> SEQ ID NO 120
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 120
cccgaaagug cugacuaugg g 21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
gaaaucuuuu agcugcuguu u 21

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
agacuccaag gaguggaaau u 21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
guggaaauua uguggaagaa g 21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gcaaaccuga uacaauuugc c 21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
uuugcccaag guaaacaguu u 21

<210> SEQ ID NO 126
<211> LENGTH: 21
<212> TYPE: RNA
<213> ORGANISM: Artificial Sequence
<220> FEATURE:

-continued

<223> OTHER INFORMATION: Description of Artificial Sequence: Synthetic
      oligonucleotide

<400> SEQUENCE: 126
aaacaguuug aaaagacaaa u 21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
agacaaaugg gccugccaaa c 21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
ccaaacugua caguuucuuc c 21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
guuucuuccc caagagcugu u 21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
agagcuguua gguaucaaaa u 21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
uaucaaaaug uuguccuuuc c 21

<210> SEQ ID NO 132
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 132
uuucugguug agaucauguc a 21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
aucaugucau ugaugaacug c 21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
acugccaaag ucaggggagg a 21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
gagacuuugu guuuacaucu g 21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ucugcauuuc uacauguuuu a 21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
uuuagacaga gacaauuuaa g 21

<210> SEQ ID NO 138
<211> LENGTH: 21
<212> TYPE: RNA
<213> ORGANISM: Artificial Sequence
<220> FEATURE:

-continued

<223> OTHER INFORMATION: Description of Artificial Sequence: Synthetic
      oligonucleotide

<400> SEQUENCE: 138
caauuuaagg ccugcacucu u 21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
ugcacucuua uuucacuaaa g 21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
augucagcac auguugcuaa u 21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
uugcuaauga caguggauuu u 21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
uuacagauca aaugugaaau a 21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
gugaaauaaa uaugaaugga g 21

<210> SEQ ID NO 144
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 144
ugaauggagu gguccucuug u                                                21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
ucuugucugu uaucugaguu u                                                21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
ucugaguuuu caaaagcuuu a                                                21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
aagcuuuaag acucugggaa c                                                21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
acaucugauu uuauggauuu u                                                21

<210> SEQ ID NO 149
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
caggugaacg aucagcucuc cag                                              23

<210> SEQ ID NO 150
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 150
gcgagacuuc caaaguugug cgc 23

<210> SEQ ID NO 151
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 151
cgaagcgauu accgacucuc ugg 23

<210> SEQ ID NO 152
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 152
ucugucgccu uacauccccg aag 23

<210> SEQ ID NO 153
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 153
cgaaagcaag aggucuuacc gug 23

<210> SEQ ID NO 154
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 154
cuugagccug agcgaaagca aga 23

<210> SEQ ID NO 155
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 155
aucuguaucu ugaaucuuga gcc 23

<210> SEQ ID NO 156
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 156
aaggaugaca ggaaauuaaa uau                                                23

<210> SEQ ID NO 157
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
ccugauaacu uggaaggaug aca                                                23

<210> SEQ ID NO 158
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
aaaaucaucg guggccugau aac                                                23

<210> SEQ ID NO 159
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
uucuucaaga agggagaaca aaa                                                23

<210> SEQ ID NO 160
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
gguaaagaga gauuuauucu uca                                                23

<210> SEQ ID NO 161
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
gagagaguag ggagagccga ugg                                                23

<210> SEQ ID NO 162
<211> LENGTH: 23
<212> TYPE: RNA
<213> ORGANISM: Artificial Sequence
<220> FEATURE:

-continued

<223> OTHER INFORMATION: Description of Artificial Sequence: Synthetic
      oligonucleotide

<400> SEQUENCE: 162
caaguuuuau uucuaagcgg cgg 23

<210> SEQ ID NO 163
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
gcuccuaaua cagccaaguu uua 23

<210> SEQ ID NO 164
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
cuucuugcuc cgagcuccua aua 23

<210> SEQ ID NO 165
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
ugcuccuggc ggaacaugaa cgc 23

<210> SEQ ID NO 166
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
ucaccugcag ggaguaaggg gug 23

<210> SEQ ID NO 167
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
acguugccga acacggugag cag 23

<210> SEQ ID NO 168
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 168
cacggcgaug augacgagca cgu 23

<210> SEQ ID NO 169
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 169
caccaggaag agguuuuggg gcg 23

<210> SEQ ID NO 170
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 170
cgaggccaga gacaccagga aga 23

<210> SEQ ID NO 171
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 171
cagcgagaaa gggaugacga gcg 23

<210> SEQ ID NO 172
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 172
guagcccaug accucguugg cca 23

<210> SEQ ID NO 173
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 173
gccuugccga aguaccagua gcc 23

<210> SEQ ID NO 174
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 174
gccagguaga ucucgcacca agc 23

<210> SEQ ID NO 175
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 175
aagagcacgu cgagcgccag gua 23

<210> SEQ ID NO 176
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 176
gacgacgugc agaagagcac guc 23

<210> SEQ ID NO 177
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 177
cacaggugca cgauggacga cgu 23

<210> SEQ ID NO 178
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 178
cugugugaug gaccaguagc ggu 23

<210> SEQ ID NO 179
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 179
guacucgaug gccuguguga ugg 23

<210> SEQ ID NO 180
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 180
gcgcuucagg uuguacucga ugg                                              23

<210> SEQ ID NO 181
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
gugaugauga uggccuugau gcg                                              23

<210> SEQ ID NO 182
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
gccgagauga cccacacggu gau                                              23

<210> SEQ ID NO 183
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
gggaaggaga ugacggccga gau                                              23

<210> SEQ ID NO 184
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
gagaugagcg gcgggaagga gau                                              23

<210> SEQ ID NO 185
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
uucuucucga uggagaugag cgg                                              23

<210> SEQ ID NO 186
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 186
cuucuggucg uugaucucgc agc 23

<210> SEQ ID NO 187
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
gagaugacgu accacuucug guc 23

<210> SEQ ID NO 188
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
ccgaugcacg acgagaugac gua 23

<210> SEQ ID NO 189
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
cagggagcga agaaggagcc gau 23

<210> SEQ ID NO 190
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
guagaccagg aucaugauga ggc 23

<210> SEQ ID NO 191
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
guagaugcgc acguagacca gga 23

<210> SEQ ID NO 192
<211> LENGTH: 23
<212> TYPE: RNA
<213> ORGANISM: Artificial Sequence
<220> FEATURE:

-continued

<223> OTHER INFORMATION: Description of Artificial Sequence: Synthetic
      oligonucleotide

<400> SEQUENCE: 192
cuuggcgauc ugguagaugc gca 23

<210> SEQ ID NO 193
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
guggucggaa gacgagcucu ccu 23

<210> SEQ ID NO 194
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
acgaacguga agcgcuucuc gcg 23

<210> SEQ ID NO 195
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
accacggcca gcacgaacgu gaa 23

<210> SEQ ID NO 196
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
cacgaacacu ccgaugacca cgg 23

<210> SEQ ID NO 197
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
gaaggggaac cagcacacca cga 23

<210> SEQ ID NO 198
<211> LENGTH: 23
<212> TYPE: RNA
<213> ORGANISM: Artificial Sequence
<220> FEATURE:

-continued

<223> OTHER INFORMATION: Description of Artificial Sequence: Synthetic
      oligonucleotide

<400> SEQUENCE: 198
guguagguga agaagaaggg gaa 23

<210> SEQ ID NO 199
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
acggccguga gcguguaggu gaa 23

<210> SEQ ID NO 200
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
gaauuugaag agcgugcgug gca 23

<210> SEQ ID NO 201
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
gaaccagaag aagaauuuga aga 23

<210> SEQ ID NO 202
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
uucaacgagc uguugcagua gcc 23

<210> SEQ ID NO 203
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
gaagauggug uagaugaccg ggu 23

<210> SEQ ID NO 204
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 204
gaaaucgugg uugaagaugg ugu 23

<210> SEQ ID NO 205
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 205
uugaaggcgc ggcggaaauc gug 23

<210> SEQ ID NO 206
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 206
cagaggaucu ucuugaaggc gcg 23

<210> SEQ ID NO 207
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 207
cagcggaaac cucacacgau ccg 23

<210> SEQ ID NO 208
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 208
ugcagucagc gugagucuac gcg 23

<210> SEQ ID NO 209
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 209
uuucugagug cccuggggcu aag 23

<210> SEQ ID NO 210
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 210
cagacgagga aacgcagagc agg 23

<210> SEQ ID NO 211
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
aagaagcuuc ccuuguagga gca 23

<210> SEQ ID NO 212
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
ugggccuggc agcaagaagc uuc 23

<210> SEQ ID NO 213
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
uggccaaacc aacaacuggg gau 23

<210> SEQ ID NO 214
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
ggcuccaggu caagaguggc caa 23

<210> SEQ ID NO 215
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
gcccacuagg aagauggcuc cag 23

<210> SEQ ID NO 216
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 216
uagugauuag ggguggccca cua                                              23

<210> SEQ ID NO 217
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
uuuaggaagc aauagugauu agg                                              23

<210> SEQ ID NO 218
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
gggugaaaau accuuuagga agc                                              23

<210> SEQ ID NO 219
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
uguaccaggc gaagagggug aaa                                              23

<210> SEQ ID NO 220
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
ugaagagcug ugagggcugu acc                                              23

<210> SEQ ID NO 221
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
cagugcuugc ucugaagagc ugu                                              23

<210> SEQ ID NO 222
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 222
caugcccuug uaguccagug cuu 23

<210> SEQ ID NO 223
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
ccauccauua accuuuugug agc 23

<210> SEQ ID NO 224
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
auggaagggg aauuagccag ggc 23

<210> SEQ ID NO 225
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
aaaagagaga gagaguuggg aau 23

<210> SEQ ID NO 226
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
aaauagugua uauuuacagc ggg 23

<210> SEQ ID NO 227
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
aaaaccaagg ccaagagaua ugg 23

<210> SEQ ID NO 228
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 228
gauuucaaca ucaaaaccaa ggc 23

<210> SEQ ID NO 229
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
cuggaaggca ucucucccaa ggc 23

<210> SEQ ID NO 230
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
cagacagcug ugucugccug gaa 23

<210> SEQ ID NO 231
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
cuuggccuga accagacagc ugu 23

<210> SEQ ID NO 232
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
aaagggcuug cauugcaaag ggg 23

<210> SEQ ID NO 233
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
ggacuucaua acaccagaaa ggg 23

<210> SEQ ID NO 234
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 234
cuggugaaaa cgacgacaua gag 23

<210> SEQ ID NO 235
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
gacagucacc aguugcuggu gaa 23

<210> SEQ ID NO 236
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
cagguccgug ucgaagggac agu 23

<210> SEQ ID NO 237
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
gucaggaaau cucaaagcag guc 23

<210> SEQ ID NO 238
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
aaucuuuucc cugucaggaa auc 23

<210> SEQ ID NO 239
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
aaaauggaca gaaaucuuuu ccc 23

<210> SEQ ID NO 240
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 240
ggaaaaggca auuaugcugu uag 23

<210> SEQ ID NO 241
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
cauaauauuu acauaggaaa agg 23

<210> SEQ ID NO 242
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
gucuugaucc accaucauaa uau 23

<210> SEQ ID NO 243
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
agaaaggcuc auuuacuuau guc 23

<210> SEQ ID NO 244
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
gcugauguga ggcagaaagg cuc 23

<210> SEQ ID NO 245
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
aauggcuuua uacacagggc uga 23

<210> SEQ ID NO 246
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 246
gcaucagaga auaauggcuu uau 23

<210> SEQ ID NO 247
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
ggggcaaaca gugcaucaga gaa 23

<210> SEQ ID NO 248
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
uuaaagugag uuacuggggc aaa 23

<210> SEQ ID NO 249
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
gaaagagagg uuuuaaagug agu 23

<210> SEQ ID NO 250
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
agagggaaca cuggaaagag agg 23

<210> SEQ ID NO 251
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
uucaagcagu ggcccuggag gga 23

<210> SEQ ID NO 252
<211> LENGTH: 23
<212> TYPE: RNA
<213> ORGANISM: Artificial Sequence
<220> FEATURE:

-continued

<223> OTHER INFORMATION: Description of Artificial Sequence: Synthetic
      oligonucleotide

<400> SEQUENCE: 252
uacauauucu ucuucaagca gug 23

<210> SEQ ID NO 253
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
acauacaaga uagaaacaua cau 23

<210> SEQ ID NO 254
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
gaggggcaca cagacauaca aga 23

<210> SEQ ID NO 255
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
cccauaguca gcacuuucgg ggc 23

<210> SEQ ID NO 256
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
aaacagcagc uaaaagauuu ccc 23

<210> SEQ ID NO 257
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
aauuuccacu ccuuggaguc uaa 23

<210> SEQ ID NO 258
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 258
cuucuuccac auaauuucca cuc 23

<210> SEQ ID NO 259
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
ggcaaauugu aucagguuug cuu 23

<210> SEQ ID NO 260
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
aaacuguuua ccuugggcaa auu 23

<210> SEQ ID NO 261
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
auuugucuuu ucaaacuguu uac 23

<210> SEQ ID NO 262
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
guuuggcagg cccauuuguc uuu 23

<210> SEQ ID NO 263
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
ggaagaaacu guacaguuug gca 23

<210> SEQ ID NO 264
<211> LENGTH: 23
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 264
aacagcucuu ggggaagaaa cug 23

<210> SEQ ID NO 265
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 265
auuuugauac cuaacagcuc uug 23

<210> SEQ ID NO 266
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 266
ggaaaggaca acauuuugau acc 23

<210> SEQ ID NO 267
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 267
ugacaugauc ucaaccagaa aag 23

<210> SEQ ID NO 268
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 268
gcaguucauc aaugacauga ucu 23

<210> SEQ ID NO 269
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 269
uccuccccug acuuuggcag uuc 23

<210> SEQ ID NO 270
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 270
cagauguaaa cacaaagucu cug 23

<210> SEQ ID NO 271
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
uaaaacaugu agaaaugcag aug 23

<210> SEQ ID NO 272
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
cuuaaauugu cucugucuaa aac 23

<210> SEQ ID NO 273
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
aagagugcag gccuuaaauu guc 23

<210> SEQ ID NO 274
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
cuuuagugaa auaagagugc agg 23

<210> SEQ ID NO 275
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
auuagcaaca ugugcugaca uua 23

<210> SEQ ID NO 276
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 276
aaaauccacu gucauuagca aca 23

<210> SEQ ID NO 277
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
uauuucacau uugaucugua aac 23

<210> SEQ ID NO 278
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
cuccauucau auuuauuuca cau 23

<210> SEQ ID NO 279
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
acaagaggac cacuccauuc aua 23

<210> SEQ ID NO 280
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
aaacucagau aacagacaag agg 23

<210> SEQ ID NO 281
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
uaaagcuuuu gaaaacucag aua 23

<210> SEQ ID NO 282
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 282
guucccagag ucuuaaagcu uuu 23

<210> SEQ ID NO 283
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
aaaauccaua aaaucagaug uuc 23

<210> SEQ ID NO 284
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
ggagagcuga ucguucaccu a 21

<210> SEQ ID NO 285
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
gcacaacuuu ggaagucucg a 21

<210> SEQ ID NO 286
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
agagagucgg uaaucgcuuc a 21

<210> SEQ ID NO 287
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
ucggggaugu aaggcgacag a 21

<210> SEQ ID NO 288
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 288
cgguaagacc ucuugcuuuc a 21

<210> SEQ ID NO 289
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
uugcuuucgc ucaggcucaa a 21

<210> SEQ ID NO 290
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
cucaagauuc aagauacaga a 21

<210> SEQ ID NO 291
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
auuuaauuuc cugucauccu a 21

<210> SEQ ID NO 292
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
ucauccuucc aaguuaucag a 21

<210> SEQ ID NO 293
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
uaucaggcca ccgaugauuu a 21

<210> SEQ ID NO 294
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 294
uuguucuccc uucuugaaga a 21

<210> SEQ ID NO 295
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
aagaauaaau cucucuuuac a 21

<210> SEQ ID NO 296
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
aucggcucuc ccuacucucu a 21

<210> SEQ ID NO 297
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
gccgcuuaga aauaaaacuu a 21

<210> SEQ ID NO 298
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
aaacuuggcu guauuaggag a 21

<210> SEQ ID NO 299
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
uuaggagcuc ggagcaagaa a 21

<210> SEQ ID NO 300
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 300
guucauguuc cgccaggagc a 21

<210> SEQ ID NO 301
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 301
ccccuuacuc ccugcaggug a 21

<210> SEQ ID NO 302
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 302
gcucaccgug uucggcaacg a 21

<210> SEQ ID NO 303
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 303
gugcucguca ucaucgccgu a 21

<210> SEQ ID NO 304
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 304
ccccaaaacc ucuuccuggu a 21

<210> SEQ ID NO 305
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 305
uuccuggugu cucuggccuc a 21

<210> SEQ ID NO 306
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 306
cucgucaucc cuuucucgcu a 21

<210> SEQ ID NO 307
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
gccaacgagg ucaugggcua a 21

<210> SEQ ID NO 308
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
cuacugguac uucggcaagg a 21

<210> SEQ ID NO 309
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
uuggugcgag aucuaccugg a 21

<210> SEQ ID NO 310
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
ccuggcgcuc gacgugcucu a 21

<210> SEQ ID NO 311
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
cgugcucuuc ugcacgucgu a 21

<210> SEQ ID NO 312
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 312
gucguccauc gugcaccugu a 21

<210> SEQ ID NO 313
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
cgcuacuggu ccaucacaca a 21

<210> SEQ ID NO 314
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
aucacacagg ccaucgagua a 21

<210> SEQ ID NO 315
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
aucgaguaca accugaagcg a 21

<210> SEQ ID NO 316
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
caucaaggcc aucaucauca a 21

<210> SEQ ID NO 317
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
caccgugugg gucaucucgg a 21

<210> SEQ ID NO 318
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 318
cucggccguc aucuccuucc a 21

<210> SEQ ID NO 319
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 319
cuccuucccg ccgcucaucu a 21

<210> SEQ ID NO 320
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 320
gcucaucucc aucgagaaga a 21

<210> SEQ ID NO 321
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 321
ugcgagauca acgaccagaa a 21

<210> SEQ ID NO 322
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 322
ccagaagugg uacgucaucu a 21

<210> SEQ ID NO 323
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 323
cgucaucucg ucgugcaucg a 21

<210> SEQ ID NO 324
<211> LENGTH: 21
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 324
cggcuccuuc uucgcucccu a 21

<210> SEQ ID NO 325
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 325
cucaucauga uccuggucua a 21

<210> SEQ ID NO 326
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 326
cuggucuacg ugcgcaucua a 21

<210> SEQ ID NO 327
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 327
cgcaucuacc agaucgccaa a 21

<210> SEQ ID NO 328
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 328
gagagcucgu cuuccgacca a 21

<210> SEQ ID NO 329
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 329
cgagaagcgc uucacguucg a 21

<210> SEQ ID NO 330
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 330
cacguucgug cuggccgugg a 21

<210> SEQ ID NO 331
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
guggucaucg gaguguucgu a 21

<210> SEQ ID NO 332
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
guggugugcu gguuccccuu a 21

<210> SEQ ID NO 333
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
ccccuucuuc uucaccuaca a 21

<210> SEQ ID NO 334
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
caccuacacg cucacggccg a 21

<210> SEQ ID NO 335
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
ccacgcacgc ucuucaaauu a 21

<210> SEQ ID NO 336
<211> LENGTH: 21
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 336
uucaaauucu ucuucugguu a 21

<210> SEQ ID NO 337
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 337
cuacugcaac agcucguuga a 21

<210> SEQ ID NO 338
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 338
ccggucaucu acaccaucuu a 21

<210> SEQ ID NO 339
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 339
accaucuuca accacgauuu a 21

<210> SEQ ID NO 340
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 340
cgauuuccgc cgcgccuuca a 21

<210> SEQ ID NO 341
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 341
cgccuucaag aagauccucu a 21

<210> SEQ ID NO 342
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 342
gaucguguga gguuuccgcu a 21

<210> SEQ ID NO 343
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
cguagacuca cgcugacugc a 21

<210> SEQ ID NO 344
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
uagccccagg gcacucagaa a 21

<210> SEQ ID NO 345
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
ugcucugcgu uuccucgucu a 21

<210> SEQ ID NO 346
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
cuccuacaag ggaagcuucu a 21

<210> SEQ ID NO 347
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
agcuucuugc ugccaggccc a 21

<210> SEQ ID NO 348
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 348
ccccaguugu ugguuuggcc a                                                21

<210> SEQ ID NO 349
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
ggccacucuu gaccuggagc a                                                21

<210> SEQ ID NO 350
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
ggagccaucu uccuaguggg a                                                21

<210> SEQ ID NO 351
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
gugggccacc ccuaaucacu a                                                21

<210> SEQ ID NO 352
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
uaaucacuau ugcuuccuaa a                                                21

<210> SEQ ID NO 353
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
uuccuaaagg uauuuucacc a                                                21

<210> SEQ ID NO 354
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 354
ucacccucuu cgccugguac a                                              21

<210> SEQ ID NO 355
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
uacagcccuc acagcucuuc a                                              21

<210> SEQ ID NO 356
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
agcucuucag agcaagcacu a                                              21

<210> SEQ ID NO 357
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
gcacuggacu acaagggcau a                                              21

<210> SEQ ID NO 358
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
ucacaaaagg uuaauggaug a                                              21

<210> SEQ ID NO 359
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
ccuggcuaau uccccuucca a                                              21

<210> SEQ ID NO 360
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 360
ucccaacucu cucucucuuu a 21

<210> SEQ ID NO 361
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 361
cgcuguaaau auacacuauu a 21

<210> SEQ ID NO 362
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 362
auaucucuug gccuugguuu a 21

<210> SEQ ID NO 363
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 363
cuugguuuug auguugaaau a 21

<210> SEQ ID NO 364
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 364
cuugggagag augccuucca a 21

<210> SEQ ID NO 365
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 365
ccaggcagac acagcugucu a 21

<210> SEQ ID NO 366
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 366
agcugucugg uucaggccaa a                                              21

<210> SEQ ID NO 367
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
ccuuugcaau gcaagcccuu a                                              21

<210> SEQ ID NO 368
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
cuuucuggug uuaugaaguc a                                              21

<210> SEQ ID NO 369
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
cuaugucguc guuuucacca a                                              21

<210> SEQ ID NO 370
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
caccagcaac uggugacugu a                                              21

<210> SEQ ID NO 371
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
ugucccuucg acacggaccu a                                              21

<210> SEQ ID NO 372
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 372
ccugcuuuga gauuuccuga a 21

<210> SEQ ID NO 373
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
uuuccugaca gggaaaagau a 21

<210> SEQ ID NO 374
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
gaaaagauuu cuguccauuu a 21

<210> SEQ ID NO 375
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
aacagcauaa uugccuuuuc a 21

<210> SEQ ID NO 376
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
uuuuccuaug uaaauauuau a 21

<210> SEQ ID NO 377
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
auuaugaugg uggaucaaga a 21

<210> SEQ ID NO 378
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 378
cauaaguaaa ugagccuuuc a 21

<210> SEQ ID NO 379
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
gccuuucugc cucacaucag a 21

<210> SEQ ID NO 380
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
agcccugugu auaaagccau a 21

<210> SEQ ID NO 381
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
aaagccauua uucucugaug a 21

<210> SEQ ID NO 382
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
cucugaugca cuguuugccc a 21

<210> SEQ ID NO 383
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
ugccccagua acucacuuua a 21

<210> SEQ ID NO 384
<211> LENGTH: 21
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 384
ucacuuuaaa accucucuuu a 21

<210> SEQ ID NO 385
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 385
ucucuuucca guguucccuc a 21

<210> SEQ ID NO 386
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 386
ccuccagggc cacugcuuga a 21

<210> SEQ ID NO 387
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 387
cugcuugaag aagaauaugu a 21

<210> SEQ ID NO 388
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 388
guauguuucu aucuuguaug a 21

<210> SEQ ID NO 389
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 389
uuguaugucu gugugccccu a 21

<210> SEQ ID NO 390
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 390
cccgaaagug cugacuaugg a 21

<210> SEQ ID NO 391
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 391
gaaaucuuuu agcugcuguu a 21

<210> SEQ ID NO 392
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 392
agacuccaag gaguggaaau a 21

<210> SEQ ID NO 393
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 393
guggaaauua uguggaagaa a 21

<210> SEQ ID NO 394
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 394
gcaaaccuga uacaauuugc a 21

<210> SEQ ID NO 395
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 395
uuugcccaag guaaacaguu a 21

<210> SEQ ID NO 396
<211> LENGTH: 21
<212> TYPE: RNA
<213> ORGANISM: Artificial Sequence
<220> FEATURE:

-continued

<223> OTHER INFORMATION: Description of Artificial Sequence: Synthetic
      oligonucleotide

<400> SEQUENCE: 396
aaacaguuug aaaagacaaa a 21

<210> SEQ ID NO 397
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
agacaaaugg gccugccaaa a 21

<210> SEQ ID NO 398
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
ccaaacugua caguuucuuc a 21

<210> SEQ ID NO 399
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
guuucuuccc caagagcugu a 21

<210> SEQ ID NO 400
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
agagcuguua gguaucaaaa a 21

<210> SEQ ID NO 401
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
uaucaaaaug uuguccuuuc a 21

<210> SEQ ID NO 402
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 402
uuucugguug agaucauguc a 21

<210> SEQ ID NO 403
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
aucaugucau ugaugaacug a 21

<210> SEQ ID NO 404
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
acugccaaag ucaggggagg a 21

<210> SEQ ID NO 405
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
gagacuuugu guuuacaucu a 21

<210> SEQ ID NO 406
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
ucugcauuuc uacauguuuu a 21

<210> SEQ ID NO 407
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
uuuagacaga gacaauuuaa a 21

<210> SEQ ID NO 408
<211> LENGTH: 21
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 408
caauuuaagg ccugcacucu a 21

<210> SEQ ID NO 409
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
ugcacucuua uuucacuaaa a 21

<210> SEQ ID NO 410
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
augucagcac auguugcuaa a 21

<210> SEQ ID NO 411
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
uugcuaauga caguggauuu a 21

<210> SEQ ID NO 412
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
uuacagauca aaugugaaau a 21

<210> SEQ ID NO 413
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
gugaaauaaa uaugaaugga a 21

<210> SEQ ID NO 414
<211> LENGTH: 21
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 414
ugaauggagu gguccucuug a 21

<210> SEQ ID NO 415
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 415
ucuugucugu uaucugaguu a 21

<210> SEQ ID NO 416
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 416
ucugaguuuu caaaagcuuu a 21

<210> SEQ ID NO 417
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 417
aagcuuuaag acucugggaa a 21

<210> SEQ ID NO 418
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 418
acaucugauu uuauggauuu a 21

<210> SEQ ID NO 419
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 419
uaggugaacg aucagcucuc cag 23

<210> SEQ ID NO 420
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 420
ucgagacuuc caaaguugug cgc 23

<210> SEQ ID NO 421
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
ugaagcgauu accgacucuc ugg 23

<210> SEQ ID NO 422
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
ucugucgccu uacauccccg aag 23

<210> SEQ ID NO 423
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
ugaaagcaag aggucuuacc gug 23

<210> SEQ ID NO 424
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
uuugagccug agcgaaagca aga 23

<210> SEQ ID NO 425
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
uucuguaucu ugaaucuuga gcc 23

<210> SEQ ID NO 426
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 426
uaggaugaca ggaaauuaaa uau 23

<210> SEQ ID NO 427
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 427
ucugauaacu uggaaggaug aca 23

<210> SEQ ID NO 428
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 428
uaaaucaucg guggccugau aac 23

<210> SEQ ID NO 429
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 429
uucuucaaga agggagaaca aaa 23

<210> SEQ ID NO 430
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 430
uguaaagaga gauuuauucu uca 23

<210> SEQ ID NO 431
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 431
uagagaguag ggagagccga ugg 23

<210> SEQ ID NO 432
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 432
uaaguuuuau uucuaagcgg cgg 23

<210> SEQ ID NO 433
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
ucuccuaaua cagccaaguu uua 23

<210> SEQ ID NO 434
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
uuucuugcuc cgagcuccua aua 23

<210> SEQ ID NO 435
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
ugcuccuggc ggaacaugaa cgc 23

<210> SEQ ID NO 436
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
ucaccugcag ggaguaaggg gug 23

<210> SEQ ID NO 437
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
ucguugccga acacggugag cag 23

<210> SEQ ID NO 438
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 438
uacggcgaug augacgagca cgu 23

<210> SEQ ID NO 439
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 439
uaccaggaag agguuuuggg gcg 23

<210> SEQ ID NO 440
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 440
ugaggccaga gacaccagga aga 23

<210> SEQ ID NO 441
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 441
uagcgagaaa gggaugacga gcg 23

<210> SEQ ID NO 442
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 442
uuagcccaug accucguugg cca 23

<210> SEQ ID NO 443
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 443
uccuugccga aguaccagua gcc 23

<210> SEQ ID NO 444
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 444
uccagguaga ucucgcacca agc 23

<210> SEQ ID NO 445
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
uagagcacgu cgagcgccag gua 23

<210> SEQ ID NO 446
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
uacgacgugc agaagagcac guc 23

<210> SEQ ID NO 447
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
uacaggugca cgauggacga cgu 23

<210> SEQ ID NO 448
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
uugugugaug gaccaguagc ggu 23

<210> SEQ ID NO 449
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
uuacucgaug gccuguguga ugg 23

<210> SEQ ID NO 450
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 450
ucgcuucagg uuguacucga ugg 23

<210> SEQ ID NO 451
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
uugaugauga uggccuugau gcg 23

<210> SEQ ID NO 452
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
uccgagauga cccacacggu gau 23

<210> SEQ ID NO 453
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
uggaaggaga ugacggccga gau 23

<210> SEQ ID NO 454
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
uagaugagcg gcgggaagga gau 23

<210> SEQ ID NO 455
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
uucuucucga uggagaugag cgg 23

<210> SEQ ID NO 456
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 456
uuucuggucg uugaucucgc agc 23

<210> SEQ ID NO 457
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 457
uagaugacgu accacuucug guc 23

<210> SEQ ID NO 458
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 458
ucgaugcacg acgagaugac gua 23

<210> SEQ ID NO 459
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 459
uagggagcga agaaggagcc gau 23

<210> SEQ ID NO 460
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 460
uuagaccagg aucaugauga ggc 23

<210> SEQ ID NO 461
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 461
uuagaugcgc acguagacca gga 23

<210> SEQ ID NO 462
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 462
uuuggcgauc ugguagaugc gca 23

<210> SEQ ID NO 463
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 463
uuggucggaa gacgagcucu ccu 23

<210> SEQ ID NO 464
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 464
ucgaacguga agcgcuucuc gcg 23

<210> SEQ ID NO 465
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 465
uccacggcca gcacgaacgu gaa 23

<210> SEQ ID NO 466
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 466
uacgaacacu ccgaugacca cgg 23

<210> SEQ ID NO 467
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 467
uaaggggaac cagcacacca cga 23

<210> SEQ ID NO 468
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 468
uuguagguga agaagaaggg gaa 23

<210> SEQ ID NO 469
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
ucggccguga gcguguaggu gaa 23

<210> SEQ ID NO 470
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
uaauuugaag agcgugcgug gca 23

<210> SEQ ID NO 471
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
uaaccagaag aagaauuuga aga 23

<210> SEQ ID NO 472
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
uucaacgagc uguugcagua gcc 23

<210> SEQ ID NO 473
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
uaagauggug uagaugaccg ggu 23

<210> SEQ ID NO 474
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 474
uaaaucgugg uugaagaugg ugu 23

<210> SEQ ID NO 475
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 475
uugaaggcgc ggcggaaauc gug 23

<210> SEQ ID NO 476
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 476
uagaggaucu ucuugaaggc gcg 23

<210> SEQ ID NO 477
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 477
uagcggaaac cucacacgau ccg 23

<210> SEQ ID NO 478
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 478
ugcagucagc gugagucuac gcg 23

<210> SEQ ID NO 479
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 479
uuucugagug cccuggggcu aag 23

<210> SEQ ID NO 480
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 480
uagacgagga aacgcagagc agg 23

<210> SEQ ID NO 481
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
uagaagcuuc ccuuguagga gca 23

<210> SEQ ID NO 482
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
ugggccuggc agcaagaagc uuc 23

<210> SEQ ID NO 483
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
uggccaaacc aacaacuggg gau 23

<210> SEQ ID NO 484
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
ugcuccaggu caagaguggc caa 23

<210> SEQ ID NO 485
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
ucccacuagg aagauggcuc cag 23

<210> SEQ ID NO 486
<211> LENGTH: 23
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 486
uagugauuag ggguggccca cua 23

<210> SEQ ID NO 487
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 487
uuuaggaagc aauagugauu agg 23

<210> SEQ ID NO 488
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 488
uggugaaaau accuuuagga agc 23

<210> SEQ ID NO 489
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 489
uguaccaggc gaagagggug aaa 23

<210> SEQ ID NO 490
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 490
ugaagagcug ugagggcugu acc 23

<210> SEQ ID NO 491
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 491
uagugcuugc ucugaagagc ugu 23

<210> SEQ ID NO 492
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 492
uaugcccuug uaguccagug cuu 23

<210> SEQ ID NO 493
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
ucauccauua accuuuugug agc 23

<210> SEQ ID NO 494
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
uuggaagggg aauuagccag ggc 23

<210> SEQ ID NO 495
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
uaaagagaga gagaguuggg aau 23

<210> SEQ ID NO 496
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
uaauagugua uauuuacagc ggg 23

<210> SEQ ID NO 497
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
uaaaccaagg ccaagagaua ugg 23

<210> SEQ ID NO 498
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 498
uauuucaaca ucaaaaccaa ggc 23

<210> SEQ ID NO 499
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
uuggaaggca ucucucccaa ggc 23

<210> SEQ ID NO 500
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
uagacagcug ugucugccug gaa 23

<210> SEQ ID NO 501
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
uuuggccuga accagacagc ugu 23

<210> SEQ ID NO 502
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
uaagggcuug cauugcaaag ggg 23

<210> SEQ ID NO 503
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
ugacuucaua acaccagaaa ggg 23

<210> SEQ ID NO 504
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 504
uuggugaaaa cgacgacaua gag 23

<210> SEQ ID NO 505
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
uacagucacc aguugcuggu gaa 23

<210> SEQ ID NO 506
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
uagguccgug ucgaagggac agu 23

<210> SEQ ID NO 507
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
uucaggaaau cucaaagcag guc 23

<210> SEQ ID NO 508
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508
uaucuuuucc cugucaggaa auc 23

<210> SEQ ID NO 509
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
uaaauggaca gaaaucuuuu ccc 23

<210> SEQ ID NO 510
<211> LENGTH: 23
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 510
ugaaaaggca auuaugcugu uag 23

<210> SEQ ID NO 511
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 511
uauaauauuu acauaggaaa agg 23

<210> SEQ ID NO 512
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 512
uucuugaucc accaucauaa uau 23

<210> SEQ ID NO 513
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 513
ugaaaggcuc auuuacuuau guc 23

<210> SEQ ID NO 514
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 514
ucugauguga ggcagaaagg cuc 23

<210> SEQ ID NO 515
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 515
uauggcuuua uacacagggc uga 23

<210> SEQ ID NO 516
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 516
ucaucagaga auaauggcuu uau 23

<210> SEQ ID NO 517
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
ugggcaaaca gugcaucaga gaa 23

<210> SEQ ID NO 518
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
uuaaagugag uuacuggggc aaa 23

<210> SEQ ID NO 519
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
uaaagagagg uuuuaaagug agu 23

<210> SEQ ID NO 520
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
ugagggaaca cuggaaagag agg 23

<210> SEQ ID NO 521
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 521
uucaagcagu ggcccuggag gga 23

<210> SEQ ID NO 522
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 522
uacauauucu ucuucaagca gug                                              23

<210> SEQ ID NO 523
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
ucauacaaga uagaaacaua cau                                              23

<210> SEQ ID NO 524
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
uaggggcaca cagacauaca aga                                              23

<210> SEQ ID NO 525
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
uccauaguca gcacuuucgg ggc                                              23

<210> SEQ ID NO 526
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
uaacagcagc uaaaagauuu ccc                                              23

<210> SEQ ID NO 527
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
uauuuccacu ccuuggaguc uaa                                              23

<210> SEQ ID NO 528
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 528
uuucuuccac auaauuucca cuc 23

<210> SEQ ID NO 529
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
ugcaaauugu aucagguuug cuu 23

<210> SEQ ID NO 530
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
uaacuguuua ccuugggcaa auu 23

<210> SEQ ID NO 531
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
uuuugucuuu ucaaacuguu uac 23

<210> SEQ ID NO 532
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 532
uuuuggcagg cccauuuguc uuu 23

<210> SEQ ID NO 533
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
ugaagaaacu guacaguuug gca 23

<210> SEQ ID NO 534
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 534
uacagcucuu ggggaagaaa cug 23

<210> SEQ ID NO 535
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 535
uuuuugauac cuaacagcuc uug 23

<210> SEQ ID NO 536
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
ugaaaggaca acauuuugau acc 23

<210> SEQ ID NO 537
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 537
ugacaugauc ucaaccagaa aag 23

<210> SEQ ID NO 538
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 538
ucaguucauc aaugacauga ucu 23

<210> SEQ ID NO 539
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539
uccuccccug acuuuggcag uuc 23

<210> SEQ ID NO 540
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 540
uagauguaaa cacaaagucu cug 23

<210> SEQ ID NO 541
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 541
uaaaacaugu agaaaugcag aug 23

<210> SEQ ID NO 542
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 542
uuuaaauugu cucugucuaa aac 23

<210> SEQ ID NO 543
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
uagagugcag gccuuaaauu guc 23

<210> SEQ ID NO 544
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
uuuuagugaa auaagagugc agg 23

<210> SEQ ID NO 545
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545
uuuagcaaca ugugcugaca uua 23

<210> SEQ ID NO 546
<211> LENGTH: 23
<212> TYPE: RNA
<213> ORGANISM: Artificial Sequence
<220> FEATURE:

<223> OTHER INFORMATION: Description of Artificial Sequence: Synthetic oligonucleotide

<400> SEQUENCE: 546
uaaauccacu gucauuagca aca 23

<210> SEQ ID NO 547
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 547
uauuucacau uugaucugua aac 23

<210> SEQ ID NO 548
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 548
uuccauucau auuuauuuca cau 23

<210> SEQ ID NO 549
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 549
ucaagaggac cacuccauuc aua 23

<210> SEQ ID NO 550
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 550
uaacucagau aacagacaag agg 23

<210> SEQ ID NO 551
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 551
uaaagcuuuu gaaaacucag aua 23

<210> SEQ ID NO 552
<211> LENGTH: 23
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 552
uuucccagag ucuuaaagcu uuu 23

<210> SEQ ID NO 553
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
uaaauccaua aaaucagaug uuc 23

<210> SEQ ID NO 554
<211> LENGTH: 23
<212> TYPE: DNA
<213> ORGANISM: Homo sapiens

<400> SEQUENCE: 554
ctggagagct gatcgttcac ctg 23

<210> SEQ ID NO 555
<211> LENGTH: 23
<212> TYPE: DNA
<213> ORGANISM: Homo sapiens

<400> SEQUENCE: 555
gcgcacaact ttggaagtct cgc 23

<210> SEQ ID NO 556
<211> LENGTH: 23
<212> TYPE: DNA
<213> ORGANISM: Homo sapiens

<400> SEQUENCE: 556
ccagagagtc ggtaatcgct tcg 23

<210> SEQ ID NO 557
<211> LENGTH: 23
<212> TYPE: DNA
<213> ORGANISM: Homo sapiens

<400> SEQUENCE: 557
cttcggggat gtaaggcgac aga 23

<210> SEQ ID NO 558
<211> LENGTH: 23
<212> TYPE: DNA
<213> ORGANISM: Homo sapiens

<400> SEQUENCE: 558
cacggtaaga cctcttgctt tcg 23

<210> SEQ ID NO 559
<211> LENGTH: 23
<212> TYPE: DNA
<213> ORGANISM: Homo sapiens

<400> SEQUENCE: 559
tcttgctttc gctcaggctc aag 23

<210> SEQ ID NO 560
<211> LENGTH: 23
<212> TYPE: DNA
<213> ORGANISM: Homo sapiens

<400> SEQUENCE: 560
ggctcaagat tcaagataca gat 23

<210> SEQ ID NO 561
<211> LENGTH: 23
<212> TYPE: DNA
<213> ORGANISM: Homo sapiens

<400> SEQUENCE: 561
atatttaatt tcctgtcatc ctt 23

<210> SEQ ID NO 562
<211> LENGTH: 23
<212> TYPE: DNA
<213> ORGANISM: Homo sapiens

<400> SEQUENCE: 562
tgtcatcctt ccaagttatc agg 23

<210> SEQ ID NO 563
<211> LENGTH: 23
<212> TYPE: DNA
<213> ORGANISM: Homo sapiens

<400> SEQUENCE: 563
gttatcaggc caccgatgat ttt 23

<210> SEQ ID NO 564
<211> LENGTH: 23
<212> TYPE: DNA
<213> ORGANISM: Homo sapiens

<400> SEQUENCE: 564
ttttgttctc ccttcttgaa gaa 23

<210> SEQ ID NO 565
<211> LENGTH: 23
<212> TYPE: DNA
<213> ORGANISM: Homo sapiens

<400> SEQUENCE: 565
tgaagaataa atctctcttt acc 23

<210> SEQ ID NO 566
<211> LENGTH: 23
<212> TYPE: DNA
<213> ORGANISM: Homo sapiens

<400> SEQUENCE: 566
ccatcggctc tccctactct ctc 23

<210> SEQ ID NO 567
<211> LENGTH: 23
<212> TYPE: DNA
<213> ORGANISM: Homo sapiens

<400> SEQUENCE: 567
ccgccgctta gaaataaaac ttg 23

<210> SEQ ID NO 568
<211> LENGTH: 23
<212> TYPE: DNA
<213> ORGANISM: Homo sapiens

<400> SEQUENCE: 568
taaaacttgg ctgtattagg agc 23

<210> SEQ ID NO 569
<211> LENGTH: 23
<212> TYPE: DNA
<213> ORGANISM: Homo sapiens

<400> SEQUENCE: 569
tattaggagc tcggagcaag aag 23

<210> SEQ ID NO 570
<211> LENGTH: 23
<212> TYPE: DNA
<213> ORGANISM: Homo sapiens

<400> SEQUENCE: 570
gcgttcatgt tccgccagga gca 23

<210> SEQ ID NO 571
<211> LENGTH: 23
<212> TYPE: DNA
<213> ORGANISM: Homo sapiens

<400> SEQUENCE: 571
caccccttac tccctgcagg tga 23

<210> SEQ ID NO 572
<211> LENGTH: 23
<212> TYPE: DNA
<213> ORGANISM: Homo sapiens

<400> SEQUENCE: 572
ctgctcaccg tgttcggcaa cgt 23

<210> SEQ ID NO 573
<211> LENGTH: 23
<212> TYPE: DNA
<213> ORGANISM: Homo sapiens

<400> SEQUENCE: 573
acgtgctcgt catcatcgcc gtg 23

<210> SEQ ID NO 574
<211> LENGTH: 23
<212> TYPE: DNA
<213> ORGANISM: Homo sapiens

<400> SEQUENCE: 574
cgccccaaaa cctcttcctg gtg 23

<210> SEQ ID NO 575
<211> LENGTH: 23
<212> TYPE: DNA

<213> ORGANISM: Homo sapiens

<400> SEQUENCE: 575
tcttcctggt gtctctggcc tcg 23

<210> SEQ ID NO 576
<211> LENGTH: 23
<212> TYPE: DNA
<213> ORGANISM: Homo sapiens

<400> SEQUENCE: 576
cgctcgtcat ccctttctcg ctg 23

<210> SEQ ID NO 577
<211> LENGTH: 23
<212> TYPE: DNA
<213> ORGANISM: Homo sapiens

<400> SEQUENCE: 577
tggccaacga ggtcatgggc tac 23

<210> SEQ ID NO 578
<211> LENGTH: 23
<212> TYPE: DNA
<213> ORGANISM: Homo sapiens

<400> SEQUENCE: 578
ggctactggt acttcggcaa ggc 23

<210> SEQ ID NO 579
<211> LENGTH: 23
<212> TYPE: DNA
<213> ORGANISM: Homo sapiens

<400> SEQUENCE: 579
gcttggtgcg agatctacct ggc 23

<210> SEQ ID NO 580
<211> LENGTH: 23
<212> TYPE: DNA
<213> ORGANISM: Homo sapiens

<400> SEQUENCE: 580
tacctggcgc tcgacgtgct ctt 23

<210> SEQ ID NO 581
<211> LENGTH: 23
<212> TYPE: DNA
<213> ORGANISM: Homo sapiens

<400> SEQUENCE: 581
gacgtgctct tctgcacgtc gtc 23

<210> SEQ ID NO 582
<211> LENGTH: 23
<212> TYPE: DNA
<213> ORGANISM: Homo sapiens

<400> SEQUENCE: 582
acgtcgtcca tcgtgcacct gtg 23

<210> SEQ ID NO 583
<211> LENGTH: 23

<212> TYPE: DNA
<213> ORGANISM: Homo sapiens

<400> SEQUENCE: 583
accgctactg gtccatcaca cag 23

<210> SEQ ID NO 584
<211> LENGTH: 23
<212> TYPE: DNA
<213> ORGANISM: Homo sapiens

<400> SEQUENCE: 584
ccatcacaca ggccatcgag tac 23

<210> SEQ ID NO 585
<211> LENGTH: 23
<212> TYPE: DNA
<213> ORGANISM: Homo sapiens

<400> SEQUENCE: 585
ccatcgagta caacctgaag cgc 23

<210> SEQ ID NO 586
<211> LENGTH: 23
<212> TYPE: DNA
<213> ORGANISM: Homo sapiens

<400> SEQUENCE: 586
cgcatcaagg ccatcatcat cac 23

<210> SEQ ID NO 587
<211> LENGTH: 23
<212> TYPE: DNA
<213> ORGANISM: Homo sapiens

<400> SEQUENCE: 587
atcaccgtgt gggtcatctc ggc 23

<210> SEQ ID NO 588
<211> LENGTH: 23
<212> TYPE: DNA
<213> ORGANISM: Homo sapiens

<400> SEQUENCE: 588
atctcggccg tcatctcctt ccc 23

<210> SEQ ID NO 589
<211> LENGTH: 23
<212> TYPE: DNA
<213> ORGANISM: Homo sapiens

<400> SEQUENCE: 589
atctccttcc cgccgctcat ctc 23

<210> SEQ ID NO 590
<211> LENGTH: 23
<212> TYPE: DNA
<213> ORGANISM: Homo sapiens

<400> SEQUENCE: 590
ccgctcatct ccatcgagaa gaa 23

<210> SEQ ID NO 591

<211> LENGTH: 23
<212> TYPE: DNA
<213> ORGANISM: Homo sapiens

<400> SEQUENCE: 591
gctgcgagat caacgaccag aag 23

<210> SEQ ID NO 592
<211> LENGTH: 23
<212> TYPE: DNA
<213> ORGANISM: Homo sapiens

<400> SEQUENCE: 592
gaccagaagt ggtacgtcat ctc 23

<210> SEQ ID NO 593
<211> LENGTH: 23
<212> TYPE: DNA
<213> ORGANISM: Homo sapiens

<400> SEQUENCE: 593
tacgtcatct cgtcgtgcat cgg 23

<210> SEQ ID NO 594
<211> LENGTH: 23
<212> TYPE: DNA
<213> ORGANISM: Homo sapiens

<400> SEQUENCE: 594
atcggctcct tcttcgctcc ctg 23

<210> SEQ ID NO 595
<211> LENGTH: 23
<212> TYPE: DNA
<213> ORGANISM: Homo sapiens

<400> SEQUENCE: 595
gcctcatcat gatcctggtc tac 23

<210> SEQ ID NO 596
<211> LENGTH: 23
<212> TYPE: DNA
<213> ORGANISM: Homo sapiens

<400> SEQUENCE: 596
tcctggtcta cgtgcgcatc tac 23

<210> SEQ ID NO 597
<211> LENGTH: 23
<212> TYPE: DNA
<213> ORGANISM: Homo sapiens

<400> SEQUENCE: 597
tgcgcatcta ccagatcgcc aag 23

<210> SEQ ID NO 598
<211> LENGTH: 23
<212> TYPE: DNA
<213> ORGANISM: Homo sapiens

<400> SEQUENCE: 598
aggagagctc gtcttccgac cac 23

<210> SEQ ID NO 599
<211> LENGTH: 23
<212> TYPE: DNA
<213> ORGANISM: Homo sapiens

<400> SEQUENCE: 599
cgcgagaagc gcttcacgtt cgt 23

<210> SEQ ID NO 600
<211> LENGTH: 23
<212> TYPE: DNA
<213> ORGANISM: Homo sapiens

<400> SEQUENCE: 600
ttcacgttcg tgctggccgt ggt 23

<210> SEQ ID NO 601
<211> LENGTH: 23
<212> TYPE: DNA
<213> ORGANISM: Homo sapiens

<400> SEQUENCE: 601
ccgtggtcat cggagtgttc gtg 23

<210> SEQ ID NO 602
<211> LENGTH: 23
<212> TYPE: DNA
<213> ORGANISM: Homo sapiens

<400> SEQUENCE: 602
tcgtggtgtg ctggttcccc ttc 23

<210> SEQ ID NO 603
<211> LENGTH: 23
<212> TYPE: DNA
<213> ORGANISM: Homo sapiens

<400> SEQUENCE: 603
ttccccttct tcttcaccta cac 23

<210> SEQ ID NO 604
<211> LENGTH: 23
<212> TYPE: DNA
<213> ORGANISM: Homo sapiens

<400> SEQUENCE: 604
ttcacctaca cgctcacggc cgt 23

<210> SEQ ID NO 605
<211> LENGTH: 23
<212> TYPE: DNA
<213> ORGANISM: Homo sapiens

<400> SEQUENCE: 605
tgccacgcac gctcttcaaa ttc 23

<210> SEQ ID NO 606
<211> LENGTH: 23
<212> TYPE: DNA
<213> ORGANISM: Homo sapiens

<400> SEQUENCE: 606
tcttcaaatt cttcttctgg ttc 23

<210> SEQ ID NO 607
<211> LENGTH: 23
<212> TYPE: DNA
<213> ORGANISM: Homo sapiens

<400> SEQUENCE: 607
ggctactgca acagctcgtt gaa 23

<210> SEQ ID NO 608
<211> LENGTH: 23
<212> TYPE: DNA
<213> ORGANISM: Homo sapiens

<400> SEQUENCE: 608
acccggtcat ctacaccatc ttc 23

<210> SEQ ID NO 609
<211> LENGTH: 23
<212> TYPE: DNA
<213> ORGANISM: Homo sapiens

<400> SEQUENCE: 609
acaccatctt caaccacgat ttc 23

<210> SEQ ID NO 610
<211> LENGTH: 23
<212> TYPE: DNA
<213> ORGANISM: Homo sapiens

<400> SEQUENCE: 610
cacgatttcc gccgcgcctt caa 23

<210> SEQ ID NO 611
<211> LENGTH: 23
<212> TYPE: DNA
<213> ORGANISM: Homo sapiens

<400> SEQUENCE: 611
cgcgccttca agaagatcct ctg 23

<210> SEQ ID NO 612
<211> LENGTH: 23
<212> TYPE: DNA
<213> ORGANISM: Homo sapiens

<400> SEQUENCE: 612
cggatcgtgt gaggtttccg ctg 23

<210> SEQ ID NO 613
<211> LENGTH: 23
<212> TYPE: DNA
<213> ORGANISM: Homo sapiens

<400> SEQUENCE: 613
cgcgtagact cacgctgact gca 23

<210> SEQ ID NO 614
<211> LENGTH: 23
<212> TYPE: DNA
<213> ORGANISM: Homo sapiens

<400> SEQUENCE: 614
cttagcccca gggcactcag aaa 23

<210> SEQ ID NO 615
<211> LENGTH: 23
<212> TYPE: DNA
<213> ORGANISM: Homo sapiens

<400> SEQUENCE: 615
cctgctctgc gtttcctcgt ctg 23

<210> SEQ ID NO 616
<211> LENGTH: 23
<212> TYPE: DNA
<213> ORGANISM: Homo sapiens

<400> SEQUENCE: 616
tgctcctaca agggaagctt ctt 23

<210> SEQ ID NO 617
<211> LENGTH: 23
<212> TYPE: DNA
<213> ORGANISM: Homo sapiens

<400> SEQUENCE: 617
gaagcttctt gctgccaggc cca 23

<210> SEQ ID NO 618
<211> LENGTH: 23
<212> TYPE: DNA
<213> ORGANISM: Homo sapiens

<400> SEQUENCE: 618
atccccagtt gttggtttgg cca 23

<210> SEQ ID NO 619
<211> LENGTH: 23
<212> TYPE: DNA
<213> ORGANISM: Homo sapiens

<400> SEQUENCE: 619
ttggccactc ttgacctgga gcc 23

<210> SEQ ID NO 620
<211> LENGTH: 23
<212> TYPE: DNA
<213> ORGANISM: Homo sapiens

<400> SEQUENCE: 620
ctggagccat cttcctagtg ggc 23

<210> SEQ ID NO 621
<211> LENGTH: 23
<212> TYPE: DNA
<213> ORGANISM: Homo sapiens

<400> SEQUENCE: 621
tagtgggcca cccctaatca cta 23

<210> SEQ ID NO 622
<211> LENGTH: 23
<212> TYPE: DNA
<213> ORGANISM: Homo sapiens

<400> SEQUENCE: 622
cctaatcact attgcttcct aaa 23

<210> SEQ ID NO 623
<211> LENGTH: 23
<212> TYPE: DNA
<213> ORGANISM: Homo sapiens

<400> SEQUENCE: 623
gcttcctaaa ggtattttca ccc 23

<210> SEQ ID NO 624
<211> LENGTH: 23
<212> TYPE: DNA
<213> ORGANISM: Homo sapiens

<400> SEQUENCE: 624
tttcaccctc ttcgcctggt aca 23

<210> SEQ ID NO 625
<211> LENGTH: 23
<212> TYPE: DNA
<213> ORGANISM: Homo sapiens

<400> SEQUENCE: 625
ggtacagccc tcacagctct tca 23

<210> SEQ ID NO 626
<211> LENGTH: 23
<212> TYPE: DNA
<213> ORGANISM: Homo sapiens

<400> SEQUENCE: 626
acagctcttc agagcaagca ctg 23

<210> SEQ ID NO 627
<211> LENGTH: 23
<212> TYPE: DNA
<213> ORGANISM: Homo sapiens

<400> SEQUENCE: 627
aagcactgga ctacaagggc atg 23

<210> SEQ ID NO 628
<211> LENGTH: 23
<212> TYPE: DNA
<213> ORGANISM: Homo sapiens

<400> SEQUENCE: 628
gctcacaaaa ggttaatgga tgg 23

<210> SEQ ID NO 629
<211> LENGTH: 23
<212> TYPE: DNA
<213> ORGANISM: Homo sapiens

<400> SEQUENCE: 629
gccctggcta attccccttc cat 23

<210> SEQ ID NO 630
<211> LENGTH: 23
<212> TYPE: DNA

<213> ORGANISM: Homo sapiens

<400> SEQUENCE: 630
attcccaact ctctctctct ttt 23

<210> SEQ ID NO 631
<211> LENGTH: 23
<212> TYPE: DNA
<213> ORGANISM: Homo sapiens

<400> SEQUENCE: 631
cccgctgtaa atatacacta ttt 23

<210> SEQ ID NO 632
<211> LENGTH: 23
<212> TYPE: DNA
<213> ORGANISM: Homo sapiens

<400> SEQUENCE: 632
ccatatctct tggccttggt ttt 23

<210> SEQ ID NO 633
<211> LENGTH: 23
<212> TYPE: DNA
<213> ORGANISM: Homo sapiens

<400> SEQUENCE: 633
gccttggttt tgatgttgaa atc 23

<210> SEQ ID NO 634
<211> LENGTH: 23
<212> TYPE: DNA
<213> ORGANISM: Homo sapiens

<400> SEQUENCE: 634
gccttgggag agatgccttc cag 23

<210> SEQ ID NO 635
<211> LENGTH: 23
<212> TYPE: DNA
<213> ORGANISM: Homo sapiens

<400> SEQUENCE: 635
ttccaggcag acacagctgt ctg 23

<210> SEQ ID NO 636
<211> LENGTH: 23
<212> TYPE: DNA
<213> ORGANISM: Homo sapiens

<400> SEQUENCE: 636
acagctgtct ggttcaggcc aag 23

<210> SEQ ID NO 637
<211> LENGTH: 23
<212> TYPE: DNA
<213> ORGANISM: Homo sapiens

<400> SEQUENCE: 637
cccctttgca atgcaagccc ttt 23

<210> SEQ ID NO 638
<211> LENGTH: 23

<212> TYPE: DNA
<213> ORGANISM: Homo sapiens

<400> SEQUENCE: 638
ccctttctgg tgttatgaag tcc 23

<210> SEQ ID NO 639
<211> LENGTH: 23
<212> TYPE: DNA
<213> ORGANISM: Homo sapiens

<400> SEQUENCE: 639
ctctatgtcg tcgttttcac cag 23

<210> SEQ ID NO 640
<211> LENGTH: 23
<212> TYPE: DNA
<213> ORGANISM: Homo sapiens

<400> SEQUENCE: 640
ttcaccagca actggtgact gtc 23

<210> SEQ ID NO 641
<211> LENGTH: 23
<212> TYPE: DNA
<213> ORGANISM: Homo sapiens

<400> SEQUENCE: 641
actgtccctt cgacacggac ctg 23

<210> SEQ ID NO 642
<211> LENGTH: 23
<212> TYPE: DNA
<213> ORGANISM: Homo sapiens

<400> SEQUENCE: 642
gacctgcttt gagatttcct gac 23

<210> SEQ ID NO 643
<211> LENGTH: 23
<212> TYPE: DNA
<213> ORGANISM: Homo sapiens

<400> SEQUENCE: 643
gatttcctga cagggaaaag att 23

<210> SEQ ID NO 644
<211> LENGTH: 23
<212> TYPE: DNA
<213> ORGANISM: Homo sapiens

<400> SEQUENCE: 644
gggaaaagat ttctgtccat ttt 23

<210> SEQ ID NO 645
<211> LENGTH: 23
<212> TYPE: DNA
<213> ORGANISM: Homo sapiens

<400> SEQUENCE: 645
ctaacagcat aattgccttt tcc 23

<210> SEQ ID NO 646

<211> LENGTH: 23
<212> TYPE: DNA
<213> ORGANISM: Homo sapiens

<400> SEQUENCE: 646 cctttttccta tgtaaatatt atg 23

<210> SEQ ID NO 647
<211> LENGTH: 23
<212> TYPE: DNA
<213> ORGANISM: Homo sapiens

<400> SEQUENCE: 647
atattatgat ggtggatcaa gac 23

<210> SEQ ID NO 648
<211> LENGTH: 23
<212> TYPE: DNA
<213> ORGANISM: Homo sapiens

<400> SEQUENCE: 648
gacataagta aatgagcctt tct 23

<210> SEQ ID NO 649
<211> LENGTH: 23
<212> TYPE: DNA
<213> ORGANISM: Homo sapiens

<400> SEQUENCE: 649
gagcctttct gcctcacatc agc 23

<210> SEQ ID NO 650
<211> LENGTH: 23
<212> TYPE: DNA
<213> ORGANISM: Homo sapiens

<400> SEQUENCE: 650
tcagccctgt gtataaagcc att 23

<210> SEQ ID NO 651
<211> LENGTH: 23
<212> TYPE: DNA
<213> ORGANISM: Homo sapiens

<400> SEQUENCE: 651
ataaagccat tattctctga tgc 23

<210> SEQ ID NO 652
<211> LENGTH: 23
<212> TYPE: DNA
<213> ORGANISM: Homo sapiens

<400> SEQUENCE: 652
ttctctgatg cactgtttgc ccc 23

<210> SEQ ID NO 653
<211> LENGTH: 23
<212> TYPE: DNA
<213> ORGANISM: Homo sapiens

<400> SEQUENCE: 653
tttgccccag taactcactt taa 23

<210> SEQ ID NO 654
<211> LENGTH: 23
<212> TYPE: DNA
<213> ORGANISM: Homo sapiens

<400> SEQUENCE: 654
actcacttta aaacctctct ttc 23

<210> SEQ ID NO 655
<211> LENGTH: 23
<212> TYPE: DNA
<213> ORGANISM: Homo sapiens

<400> SEQUENCE: 655
cctctctttc cagtgttccc tct 23

<210> SEQ ID NO 656
<211> LENGTH: 23
<212> TYPE: DNA
<213> ORGANISM: Homo sapiens

<400> SEQUENCE: 656
tccctccagg gccactgctt gaa 23

<210> SEQ ID NO 657
<211> LENGTH: 23
<212> TYPE: DNA
<213> ORGANISM: Homo sapiens

<400> SEQUENCE: 657
cactgcttga agaagaatat gta 23

<210> SEQ ID NO 658
<211> LENGTH: 23
<212> TYPE: DNA
<213> ORGANISM: Homo sapiens

<400> SEQUENCE: 658
atgtatgttt ctatcttgta tgt 23

<210> SEQ ID NO 659
<211> LENGTH: 23
<212> TYPE: DNA
<213> ORGANISM: Homo sapiens

<400> SEQUENCE: 659
tcttgtatgt ctgtgtgccc ctc 23

<210> SEQ ID NO 660
<211> LENGTH: 23
<212> TYPE: DNA
<213> ORGANISM: Homo sapiens

<400> SEQUENCE: 660
gccccgaaag tgctgactat ggg 23

<210> SEQ ID NO 661
<211> LENGTH: 23
<212> TYPE: DNA
<213> ORGANISM: Homo sapiens

<400> SEQUENCE: 661
gggaaatctt ttagctgctg ttt 23

<210> SEQ ID NO 662
<211> LENGTH: 23
<212> TYPE: DNA
<213> ORGANISM: Homo sapiens

<400> SEQUENCE: 662
ttagactcca aggagtggaa att 23

<210> SEQ ID NO 663
<211> LENGTH: 23
<212> TYPE: DNA
<213> ORGANISM: Homo sapiens

<400> SEQUENCE: 663
gagtggaaat tatgtggaag aag 23

<210> SEQ ID NO 664
<211> LENGTH: 23
<212> TYPE: DNA
<213> ORGANISM: Homo sapiens

<400> SEQUENCE: 664
aagcaaacct gatacaattt gcc 23

<210> SEQ ID NO 665
<211> LENGTH: 23
<212> TYPE: DNA
<213> ORGANISM: Homo sapiens

<400> SEQUENCE: 665
aatttgccca aggtaaacag ttt 23

<210> SEQ ID NO 666
<211> LENGTH: 23
<212> TYPE: DNA
<213> ORGANISM: Homo sapiens

<400> SEQUENCE: 666
gtaaacagtt tgaaaagaca aat 23

<210> SEQ ID NO 667
<211> LENGTH: 23
<212> TYPE: DNA
<213> ORGANISM: Homo sapiens

<400> SEQUENCE: 667
aaagacaaat gggcctgcca aac 23

<210> SEQ ID NO 668
<211> LENGTH: 23
<212> TYPE: DNA
<213> ORGANISM: Homo sapiens

<400> SEQUENCE: 668
tgccaaactg tacagtttct tcc 23

<210> SEQ ID NO 669
<211> LENGTH: 23
<212> TYPE: DNA
<213> ORGANISM: Homo sapiens

<400> SEQUENCE: 669
cagtttcttc cccaagagct gtt 23

<210> SEQ ID NO 670
<211> LENGTH: 23
<212> TYPE: DNA
<213> ORGANISM: Homo sapiens

<400> SEQUENCE: 670
caagagctgt taggtatcaa aat 23

<210> SEQ ID NO 671
<211> LENGTH: 23
<212> TYPE: DNA
<213> ORGANISM: Homo sapiens

<400> SEQUENCE: 671
ggtatcaaaa tgttgtcctt tcc 23

<210> SEQ ID NO 672
<211> LENGTH: 23
<212> TYPE: DNA
<213> ORGANISM: Homo sapiens

<400> SEQUENCE: 672
cttttctggt tgagatcatg tca 23

<210> SEQ ID NO 673
<211> LENGTH: 23
<212> TYPE: DNA
<213> ORGANISM: Homo sapiens

<400> SEQUENCE: 673
agatcatgtc attgatgaac tgc 23

<210> SEQ ID NO 674
<211> LENGTH: 23
<212> TYPE: DNA
<213> ORGANISM: Homo sapiens

<400> SEQUENCE: 674
gaactgccaa agtcagggga gga 23

<210> SEQ ID NO 675
<211> LENGTH: 23
<212> TYPE: DNA
<213> ORGANISM: Homo sapiens

<400> SEQUENCE: 675
cagagacttt gtgtttacat ctg 23

<210> SEQ ID NO 676
<211> LENGTH: 23
<212> TYPE: DNA
<213> ORGANISM: Homo sapiens

<400> SEQUENCE: 676
catctgcatt tctacatgtt tta 23

<210> SEQ ID NO 677
<211> LENGTH: 23
<212> TYPE: DNA
<213> ORGANISM: Homo sapiens

<400> SEQUENCE: 677
gttttagaca gagacaattt aag 23

<210> SEQ ID NO 678
<211> LENGTH: 23
<212> TYPE: DNA
<213> ORGANISM: Homo sapiens

<400> SEQUENCE: 678
gacaatttaa ggcctgcact ctt 23

<210> SEQ ID NO 679
<211> LENGTH: 23
<212> TYPE: DNA
<213> ORGANISM: Homo sapiens

<400> SEQUENCE: 679
cctgcactct tatttcacta aag 23

<210> SEQ ID NO 680
<211> LENGTH: 23
<212> TYPE: DNA
<213> ORGANISM: Homo sapiens

<400> SEQUENCE: 680
taatgtcagc acatgttgct aat 23

<210> SEQ ID NO 681
<211> LENGTH: 23
<212> TYPE: DNA
<213> ORGANISM: Homo sapiens

<400> SEQUENCE: 681
tgttgctaat gacagtggat ttt 23

<210> SEQ ID NO 682
<211> LENGTH: 23
<212> TYPE: DNA
<213> ORGANISM: Homo sapiens

<400> SEQUENCE: 682
gtttacagat caaatgtgaa ata 23

<210> SEQ ID NO 683
<211> LENGTH: 23
<212> TYPE: DNA
<213> ORGANISM: Homo sapiens

<400> SEQUENCE: 683
atgtgaaata aatatgaatg gag 23

<210> SEQ ID NO 684
<211> LENGTH: 23
<212> TYPE: DNA
<213> ORGANISM: Homo sapiens

<400> SEQUENCE: 684
tatgaatgga gtggtcctct tgt 23

<210> SEQ ID NO 685
<211> LENGTH: 23
<212> TYPE: DNA

-continued

```
<213> ORGANISM: Homo sapiens

<400> SEQUENCE: 685

cctcttgtct gttatctgag ttt                                             23


<210> SEQ ID NO 686
<211> LENGTH: 23
<212> TYPE: DNA
<213> ORGANISM: Homo sapiens

<400> SEQUENCE: 686

tatctgagtt ttcaaaagct tta                                             23


<210> SEQ ID NO 687
<211> LENGTH: 23
<212> TYPE: DNA
<213> ORGANISM: Homo sapiens

<400> SEQUENCE: 687

aaaagcttta agactctggg aac                                             23


<210> SEQ ID NO 688
<211> LENGTH: 23
<212> TYPE: DNA
<213> ORGANISM: Homo sapiens

<400> SEQUENCE: 688

gaacatctga ttttatggat ttt                                             23
```